(12) United States Patent
Hadida-Ruah et al.

(10) Patent No.: US 10,385,070 B2
(45) Date of Patent: Aug. 20, 2019

(54) CHROMAN-SPIROCYCLIC PIPERIDINE AMIDES AS MODULATORS OF ION CHANNELS

(75) Inventors: Sara Sabina Hadida-Ruah, La Jolla, CA (US); Mark Thomas Miller, San Diego, CA (US); Edward Adam Kallel, Escondido, CA (US); Brian Richard Bear, Oceanside, CA (US); Vijayalaksmi Arumugam, San Marcos, CA (US); Michael Paul Deninno, San Diego, CA (US); Jinglan Zhou, San Diego, CA (US); Johnny Uy, San Diego, CA (US); Bryan A. Frieman, La Jolla, CA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 294 days.

(21) Appl. No.: 13/398,184

(22) Filed: Feb. 16, 2012

(65) Prior Publication Data

US 2012/0245136 A1  Sep. 27, 2012

Related U.S. Application Data

(60) Provisional application No. 61/444,250, filed on Feb. 18, 2011, provisional application No. 61/540,121, filed on Sep. 28, 2011.

(51) Int. Cl.
| | |
|---|---|
| *C07D 519/00* | (2006.01) |
| *C07D 495/10* | (2006.01) |
| *C07D 491/10* | (2006.01) |
| *C07D 491/20* | (2006.01) |
| *C07D 498/08* | (2006.01) |
| *C07D 491/107* | (2006.01) |

(52) U.S. Cl.
CPC ....... *C07D 519/00* (2013.01); *C07D 491/107* (2013.01); *C07D 491/20* (2013.01); *C07D 495/10* (2013.01); *C07D 498/08* (2013.01)

(58) Field of Classification Search
CPC ... C07D 495/10; C07D 491/20; A61K 31/438
USPC .......... 546/17; 514/210.1, 278; 544/230, 70
See application file for complete search history.

(56) References Cited

U.S. PATENT DOCUMENTS

| | | | |
|---|---|---|---|
| 3,939,159 A | 2/1976 | Dornauer et al. | |
| 4,353,901 A | 10/1982 | Clark | |
| 5,206,240 A | 4/1993 | Baldwin et al. | |
| 5,633,247 A * | 5/1997 | Baldwin .............. | C07D 221/20 514/210.2 |
| 7,674,803 B2 * | 3/2010 | Guedat et al. .................. | 514/326 |
| 2002/0013325 A1 | 1/2002 | Fisher et al. | |
| 2002/0082264 A1 | 6/2002 | Nikolic et al. | |
| 2002/0151712 A1 | 10/2002 | Lin et al. | |
| 2004/0014744 A1 | 1/2004 | Haviv et al. | |
| 2004/0266802 A1 | 12/2004 | Calvet et al. | |
| 2005/0209262 A1 | 9/2005 | Tomori et al. | |
| 2006/0052597 A1 | 3/2006 | Best et al. | |
| 2007/0066584 A1 | 3/2007 | Yao et al. | |
| 2007/0078120 A1 | 4/2007 | Ban et al. | |
| 2007/0117824 A1 | 5/2007 | Berk et al. | |
| 2008/0255154 A1 | 10/2008 | Yao et al. | |
| 2009/0169567 A1 | 7/2009 | Kokubo et al. | |
| 2009/0186901 A1 * | 7/2009 | Reiser ................ | C07D 491/107 514/253.03 |
| 2009/0192182 A1 | 7/2009 | Kusumi et al. | |
| 2009/0215742 A1 * | 8/2009 | Funk ..................... | C07C 235/60 514/211.1 |
| 2009/0325992 A1 | 12/2009 | Hanada et al. | |
| 2010/0113418 A1 | 5/2010 | Fukatsu et al. | |
| 2011/0306607 A1 | 12/2011 | Hadida-Ruah et al. | |
| 2012/0196869 A1 | 8/2012 | Hadida-Ruah et al. | |
| 2012/0264749 A1 | 10/2012 | Hadida-Ruah et al. | |

FOREIGN PATENT DOCUMENTS

| | | |
|---|---|---|
| CA | 2489255 | 12/2003 |
| EP | 0 002 937 | 7/1979 |
| EP | 0 370 732 | 5/1990 |
| EP | 0 431 943 | 6/1991 |
| EP | 2 123 652 | 11/2009 |
| GB | 1 590 155 | 5/1981 |
| JP | 4 297458 | 10/1992 |
| WO | WO 92/15304 | 9/1992 |
| WO | WO 95/15327 | 6/1995 |
| WO | WO 95/30642 | 11/1995 |
| WO | WO 97/02248 | 1/1997 |
| WO | WO 97/11940 | 4/1997 |
| WO | WO 97/16729 | 5/1997 |
| WO | WO 02/20509 | 3/2002 |
| WO | WO 03/095427 | 11/2003 |
| WO | WO 03/104240 | 12/2003 |

(Continued)

OTHER PUBLICATIONS

Hong Shen et al , 2009. Discovery of spirocyclic secondary amine-derived tertiary ureas as highly potent, selective and bioavailable soluble epoxide hydrolase inhibitors.*
FEDERAL Registry pp. 53651-53659, 2010.*
Bioisosterism, George Patani et al. 1996.*
Artico, M., et al. "One-Pot Synthesis of Novel Spiro-Annelated Pyrrole-Containing Heterocyclic Systems from Suitable Synthons", J. Heterocyclic Chem., 1992, p. 241-245, vol. 29.
Fletcher, Stephen, et al., "4-(Phenylsulfonyl)piperidines: Novel, Selective, and Bioavailable 5-HT$_{2A}$ Receptor Antagonists", J. Med. Chem, 2002, p. 492-503, vol. 45.

(Continued)

*Primary Examiner* — Rita J Desai
(74) *Attorney, Agent, or Firm* — Brinks Gilson & Lione

(57) ABSTRACT

The invention relates to chroman spirocyclic piperidine amide derivatives useful as inhibitors of ion channels. The invention also provides pharmaceutically acceptable compositions comprising the compounds of the invention and methods of using the compositions in the treatment of various disorders.

43 Claims, No Drawings

(56) References Cited

FOREIGN PATENT DOCUMENTS

| WO | WO 2004/037800 | 5/2004 |
| WO | WO 2004/037828 | 5/2004 |
| WO | WO 2004/054974 | 7/2004 |
| WO | WO 2004/076418 | 9/2004 |
| WO | WO 2004/092179 | 10/2004 |
| WO | WO 2005/003128 | 1/2005 |
| WO | WO 2005/0330730 | 4/2005 |
| WO | WO 2005/110992 | 11/2005 |
| WO | WO 2005/121090 | 12/2005 |
| WO | WO 2006/105442 | 10/2006 |
| WO | WO 2006/117669 | 11/2006 |
| WO | WO 2007/011809 | 1/2007 |
| WO | WO 2007/011811 | 1/2007 |
| WO | WO 2007/050124 | 5/2007 |
| WO | WO 2007/124045 | 11/2007 |
| WO | WO 2007/128782 | 11/2007 |
| WO | WO 2007/136605 | 11/2007 |
| WO | 2008033299 * | 3/2008 |
| WO | WO 2008/045564 | 4/2008 |
| WO | 2008065508 * | 6/2008 |
| WO | WO 2008/065508 | 6/2008 |
| WO | WO 2008/088688 | 7/2008 |
| WO | WO 2008/088692 | 7/2008 |
| WO | WO 2009/127609 | 10/2009 |
| WO | WO 2009/144554 | 12/2009 |
| WO | WO 2010/002010 | 1/2010 |
| WO | WO 2010/009195 | 1/2010 |
| WO | WO 2010/027567 | 3/2010 |
| WO | WO 2010/051476 | 5/2010 |
| WO | WO 2010/051497 | 5/2010 |
| WO | WO 2010/114957 | 10/2010 |
| WO | WO 2010/151595 | 12/2010 |
| WO | WO 2010/151597 | 12/2010 |
| WO | WO 2011/025690 | 3/2011 |
| WO | WO 2011/092198 | 8/2011 |
| WO | WO 2011/140425 | 11/2011 |
| WO | WO 2012/106499 | 8/2012 |
| WO | WO 2012/125613 | 9/2012 |

OTHER PUBLICATIONS

Shen, Hong C., et al. "Discovery of spirocyclic secondary amine-derived ureas as highly potent, selective and bioavailable soluble epoxide hydrolase inhibitors", Bioorganic & Medicinal Chemistry Letters, 2009, p. 3398-3404, vol. 19.

International Search Report completed Mar. 28, 2012, in International Application No. PCT/US2012/025374, filed Feb. 16, 2012.

Office Action dated Dec. 19, 2013 in U.S. Appl. No. 13/418,737, filed Mar. 13, 2012.

Office Action dated Apr. 15, 2014, in U.S. Appl. No. 13/364,586, filed Feb. 2, 2012.

Office Action dated Oct. 8, 2013, in U.S. Appl. No. 13/364,586, filed Feb. 2, 2012.

Office Action dated Jun. 24, 2013, in U.S. Appl. No. 12/364,586, filed Feb. 2, 2012.

Hackam, Daniel G., "Translation of Research Evidence From Animals to Humans", JAMA, 2006, p. 1731-1732, vol. 296, No. 14.

Jordan, V. Craig, "Tamoxifen: A most unlikely Pioneering Medicine", Nature Reviews, Mar. 2003, p. 205-213, vol. 2.

Office Action dated Mar. 17, 2015 from U.S. Appl. No. 14/454,227, filed Aug. 7, 2014.

* cited by examiner

CHROMAN-SPIROCYCLIC PIPERIDINE AMIDES AS MODULATORS OF ION CHANNELS

CROSS REFERENCE TO RELATED APPLICATIONS

This application claims priority to U.S. provisional patent application Ser. Nos. 61/444,250, filed Feb. 18, 2011, and 61/540,121, filed Sep. 28, 2011, the entire contents of all applications are incorporated herein by reference.

TECHNICAL FIELD OF THE INVENTION

The invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Pain is a protective mechanism that allows healthy animals to avoid tissue damage and to prevent further damage to injured tissue. Nonetheless there are many conditions where pain persists beyond its usefulness, or where patients would benefit from inhibition of pain. Voltage-gated sodium channels are believed to play a critical role in pain signaling. This belief is based on the known roles of these channels in normal physiology, pathological states arising from mutations in sodium channel genes, preclinical work in animal models of disease, and the clinical usefulness of known sodium channel modulating agents (Cummins, T. R., Sheets, P. L., and Waxman, S. G., The roles of sodium channels in nociception: Implications for mechanisms of pain. *Pain* 131 (3), 243 (2007); England, S., Voltage-gated sodium channels: the search for subtype-selective analgesics. *Expert Opin Investig Drugs* 17 (12), 1849 (2008); Krafte, D. S, and Bannon, A. W., Sodium channels and nociception: recent concepts and therapeutic opportunities. *Curr Opin Pharmacol* 8 (1), 50 (2008)).

Voltage-gated sodium channels (NaV's) are key biological mediators of electrical signaling. NaV's are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role NaV's play in the initiation and propagation of neuronal signals, antagonists that reduce NaV currents can prevent or reduce neural signaling. Thus NaV channels are considered likely targets in pathologic states where reduced excitability is predicted to alleviate the clinical symptoms, such as pain, epilepsy, and some cardiac arrhythmias (Chahine, M., Chatelier, A., Babich, O., and Krupp, J. J., Voltage-gated sodium channels in neurological disorders. *CNS Neurol Disord Drug Targets* 7 (2), 144 (2008)).

The NaV's form a subfamily of the voltage-gated ion channel super-family and comprises 9 isoforms, designated NaV 1.1-NaV 1.9. The tissue localizations of the nine isoforms vary greatly. NaV 1.4 is the primary sodium channel of skeletal muscle, and NaV 1.5 is primary sodium channel of cardiac myocytes. NaV's 1.7, 1.8 and 1.9 are primarily localized to the peripheral nervous system, while NaV's 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), 397 (2005)).

NaV channels have been identified as the primary target for some clinically useful pharmaceutical agents that reduce pain (Cummins, T. R., Sheets, P. L., and Waxman, S. G., The roles of sodium channels in nociception: Implications for mechanisms of pain. *Pain* 131 (3), 243 (2007)). The local anesthetic drugs such as lidocaine block pain by inhibiting NaV channels. These compounds provide excellent local pain reduction but suffer the drawback of abolishing normal acute pain and sensory inputs. Systemic administration of these compounds results in dose limiting side effects that are generally ascribed to block of neural channels in the CNS (nausea, sedation, confusion, ataxia). Cardiac side effects can also occur, and indeed these compounds are also used as class 1 anti-arrhythmics, presumably due to block of NaV 1.5 channels in the heart. Other compounds that have proven effective at reducing pain have also been suggested to act by sodium channel blockade including carbamazepine, lamotragine, and tricyclic antidepressants (Soderpalm, B., Anti-convulsants: aspects of their mechanisms of action. *Eur J Pain* 6 Suppl A, 3 (2002); Wang, G. K., Mitchell, J., and Wang, S. Y., Block of persistent late Na$^+$ currents by antidepressant sertraline and paroxetine. *J Membr Biol* 222 (2), 79 (2008)). These compounds are likewise dose limited by adverse effects similar to those seen with the local anesthetics. Antagonists that specifically block only the isoform(s) critical for nociception are expected to have increased efficacy since the reduction of adverse effects caused by block of off-target channels should enable higher dosing and thus more complete block of target channels isoforms.

Four NaV isoforms, NaV 1.3, 1.7, 1.8, and 1.9, have been specifically indicated as likely pain targets. NaV 1.3 is normally found in the pain sensing neurons of the dorsal root ganglia (DRG) only early in development and is lost soon after birth both in humans and in rodents. Nonetheless, nerve damaging injuries have been found to result in a return of the NaV 1.3 channels to DRG neurons and this may contribute to the abnormal pain signaling in various chronic pain conditions resulting from nerve damage (neuropathic pain). These data have led to the suggestion that pharmaceutical block of NaV 1.3 could be an effective treatment for neuropathic pain. In opposition to this idea, global genetic knockout of NaV 1.3 in mice does not prevent the development of allodynia in mouse models of neuropathic pain (Nassar, M. A. et al., Nerve injury induces robust allodynia and ectopic discharges in NaV 1.3 null mutant mice. *Mol Pain* 2, 33 (2006)). It remains unknown whether compensatory changes in other channels allow for normal neuropathic pain in NaV 1.3 knockout mice, though it has been reported that knockout of NaV 1.1 results in drastic upregulation of NaV 1.3. The converse effect in NaV 1.3 knockouts might explain these results.

NaV 1.7, 1.8, and 1.9 are highly expressed in DRG neurons, including the neurons whose axons make up the C-fibers and Aδ nerve fibers that are believed to carry most pain signals from the nociceptive terminals to the central nervous. Like NaV 1.3, NaV 1.7 expression increases after nerve injury and may contribute to neuropathic pain states. The localization of NaV 1.7, 1.8, and 1.9 in nociceptors led to the hypothesis that reducing the sodium currents through these channels might alleviate pain. Indeed, specific interventions that reduce the levels of these channels have proven effective in animal models of pain.

Specific reduction of NaV 1.7 in rodents by multiple different techniques has resulted in the reduction of observable pain behaviors in model animals. Injection of a viral antisense NaV 1.7 cDNA construct greatly reduces normal pain responses due to inflammation or mechanical injury (Yeomans, D. C. et al., Decrease in inflammatory hyperalgesia by herpes vector-mediated knockdown of NaV 1.7 sodium channels in primary afferents. Hum Gene Ther 16 (2), 271 (2005)). Likewise, a genetic knockout of NaV 1.7 in a subset of nociceptor neurons reduced acute and inflammatory pain in mouse models (Nassar, M. A. et al., Nociceptor-specific gene deletion reveals a major role for NaV 1.7 (PN1) in acute and inflammatory pain. Proc Natl Acad Sci USA 101 (34), 12706 (2004)). Global knockouts of NaV 1.7 in mice lead to animals that die on the first day after birth. These mice fail to feed and this is the presumed cause of death.

Treatments that specifically reduce NaV 1.8 channels in rodent models effectively reduce pain sensitivity. Knockdown of NaV 1.8 in rats by intrathecal injection of antisense oligodeoxynucleotides reduces neuropathic pain behaviors, while leaving acute pain sensation intact (Lai, J. et al., Inhibition of neuropathic pain by decreased expression of the tetrodotoxin-resistant sodium channel, NaV1.8. Pain 95 (1-2), 143 (2002); Porreca, F. et al., A comparison of the potential role of the tetrodotoxin-insensitive sodium channels, PN3/SNS and NaN/SNS2, in rat models of chronic pain. Proc Natl Acad Sci USA 96 (14), 7640 (1999)). Global genetic knockout of NaV 1.8 in mice or specific destruction of NaV 1.8 expressing neurons greatly reduces perception of acute mechanical, inflammatory, and visceral pain (Akopian, A. N. et al., The tetrodotoxin-resistant sodium channel SNS has a specialized function in pain pathways. Nat Neurosci 2 (6), 541 (1999); Abrahamsen, B. et al., The cell and molecular basis of mechanical, cold, and inflammatory pain. Science 321 (5889), 702 (2008); Laird, J. M., Souslova, V., Wood, J. N., and Cervero, F., Deficits in visceral pain and referred hyperalgesia in NaV 1.8 (SNS/PN3)-null mice. J Neurosci 22 (19), 8352 (2002)). In contrast to the antisense experiments in rats, genetic knockout mice appear to develop neuropathic pain behaviors normally after nerve injury (Lai, J. et al., Inhibition of neuropathic pain by decreased expression of the tetrodotoxin-resistant sodium channel, NaV1.8. Pain 95 (1-2), 143 (2002); Akopian, A. N. et al., The tetrodotoxin-resistant sodium channel SNS has a specialized function in pain pathways. Nat Neurosci 2 (6), 541 (1999); Abrahamsen, B. et al., The cell and molecular basis of mechanical, cold, and inflammatory pain. Science 321 (5889), 702 (2008); Laird, J. M., Souslova, V., Wood, J. N., and Cervero, F., Deficits in visceral pain and referred hyperalgesia in NaV 1.8 (SNS/PN3)-null mice. J Neurosci 22 (19), 8352 (2002)).

NaV 1.9 global knock out mice have decreased sensitivity to inflammation induced pain, despite normal acute, and neuropathic pain behaviors (Amaya, F. et al., The voltage-gated sodium channel Na(v)1.9 is an effector of peripheral inflammatory pain hypersensitivity. J Neurosci 26 (50), 12852 (2006); Priest, B. T. et al., Contribution of the tetrodotoxin-resistant voltage-gated sodium channel NaV 1.9 to sensory transmission and nociceptive behavior. Proc Natl Acad Sci USA 102 (26), 9382 (2005)). Spinal knockdown of NaV 1.9 had no apparent effect on pain behavior in rats (Porreca, F. et al., A comparison of the potential role of the tetrodotoxin-insensitive sodium channels, PN3/SNS and NaN/SNS2, in rat models of chronic pain. Proc Natl Acad Sci USA 96 (14), 7640 (1999)).

The understanding of the role of NaV channels in human physiology and pathology has been greatly advanced by the discovery and analysis of naturally occurring human mutations. NaV 1.1 and NaV 1.2 mutations result in various forms of epilepsy (Fujiwara, T., Clinical spectrum of mutations in SCN1A gene: severe myoclonic epilepsy in infancy and related epilepsies. Epilepsy Res 70 Suppl 1, S223 (2006); George, A. L., Jr., Inherited disorders of voltage-gated sodium channels. J Clin Invest 115 (8), 1990 (2005); Misra, S, N., Kahlig, K. M., and George, A. L., Jr., Impaired NaV 1.2 function and reduced cell surface expression in benign familial neonatal-infantile seizures. Epilepsia 49 (9), 1535 (2008)). Mutations of the NaV 1.4 cause muscular disorders like paramyotonia congenital (Vicart, S., Sternberg, D., Fontaine, B., and Meola, G., Human skeletal muscle sodium channelopathies. Neurol Sci 26 (4), 194 (2005)). NaV 1.5 mutations result in cardiac abnormalities like Brugada Syndrome and long QT syndrome (Bennett, P. B., Yazawa, K., Makita, N., and George, A. L., Jr., Molecular mechanism for an inherited cardiac arrhythmia. Nature 376 (6542), 683 (1995); Darbar, D. et al., Cardiac sodium channel (SCN5A) variants associated with atrial fibrillation. Circulation 117 (15), 1927 (2008); Wang, Q. et al., SCN5A mutations associated with an inherited cardiac arrhythmia, long QT syndrome. Cell 80 (5), 805 (1995)).

Recent discoveries have demonstrated that mutations in the gene that encodes the NaV 1.7 channel (SCN9A) can cause both enhanced and reduced pain syndromes. Work by Waxman's group and others have identified at least 15 mutations that result in enhanced current through NaV 1.7 and are linked to dominant congenital pain syndromes. Mutations that lower the threshold for NaV 1.7 activation cause inherited erythromelalgia (IEM). IEM patients exhibit abnormal burning pain in their extremities. Mutations that interfere with the normal inactivation properties of NaV 1.7 lead to prolonged sodium currents and cause paroxysmal extreme pain disorder (PEPD). PEPD patients exhibit periocular, perimandibular, and rectal pain symptoms that progresses throughout life (Drenth, J. P. et al., SCN9A mutations define primary erythermalgia as a neuropathic disorder of voltage gated sodium channels. J Invest Dermatol 124 (6), 1333 (2005); Estacion, M. et al., NaV 1.7 gain-of-function mutations as a continuum: A1632E displays physiological changes associated with erythromelalgia and paroxysmal extreme pain disorder mutations and produces symptoms of both disorders. J Neurosci 28 (43), 11079 (2008)).

NaV 1.7 null mutations in human patients were recently described by several groups (Ahmad, S. et al., A stop codon mutation in SCN9A causes lack of pain sensation. Hum Mol Genet. 16 (17), 2114 (2007); Cox, J. J. et al., An SCN9A channelopathy causes congenital inability to experience pain. Nature 444 (7121), 894 (2006); Goldberg, Y. P. et al., Loss-of-function mutations in the NaV 1.7 gene underlie congenital indifference to pain in multiple human populations. Clin Genet. 71 (4), 311 (2007)). In all cases patients exhibit congenital indifference to pain. These patients report no pain under any circumstances. Many of these patients suffer dire injuries early in childhood since they do not have the protective, normal pain that helps to prevent tissue damage and develop appropriate protective behaviors. Aside from the striking loss of pain sensation and reduced or absent of smell (Goldberg, Y. P. et al., Loss-of-function mutations in the NaV 1.7 gene underlie congenital indifference to pain in multiple human populations. Clin Genet. 71

(4), 311 (2007)), these patients appear completely normal. Despite the normally high expression of NaV 1.7 in sympathetic neurons (Toledo-Aral, J. J. et al., Identification of PN1, a predominant voltage-dependent sodium channel expressed principally in peripheral neurons. *Proc Natl Acad Sci USA* 94 (4), 1527 (1997)) and adrenal chromafin cells (Klugbauer, N., Lacinova, L., Flockerzi, V., and Hofmann, F., Structure and functional expression of a new member of the tetrodotoxin-sensitive voltage-activated sodium channel family from human neuroendocrine cells. EMBO J 14 (6), 1084 (1995)), these NaV 1.7-null patients show no sign of neuroendocrine or sympathetic nervous dysfunction.

The gain of NaV 1.7 function mutations that cause pain, coupled with the loss of NaV 1.7 function mutations that abolish pain, provide strong evidence that NaV 1.7 plays an important role in human pain signaling. The relative good health of NaV 1.7-null patients indicates that ablation of NaV 1.7 is well tolerated in these patients.

Unfortunately, the efficacy of currently used sodium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels. These compounds have the general formula I:

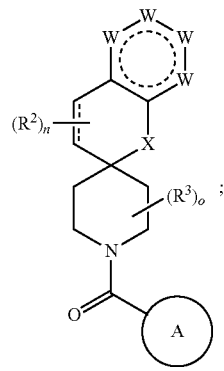

or a pharmaceutically acceptable salt thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

In one aspect, the invention provides compounds of formula I:

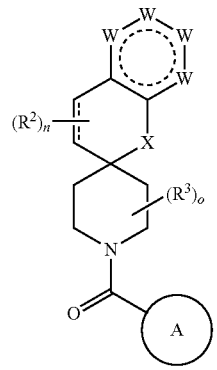

or a pharmaceutically acceptable salt thereof,
wherein, independently for each occurrence:
W is N or $CR^1$, or 1 W is a bond and the remaining W are N, $NR^1$, or $CR^1$, wherein up to 2 W are N or $NR^1$;
a dashed line or circle denotes unsaturation;
R' is H, C1-C6 alkyl, or an optionally substituted aryl, heteroaryl, cycloalkyl, or heterocycloalkyl;
$R^1$ is H, C1-C6 alkyl, C1-C6 haloalkyl, halo, CN, $NR^7$, $SO_2R^7$, $SO_2R^7$, $SR^7$, $SOR^7$, $NR^7COR^7$, $NR^7CO_2R^7$, $CON(R^7)_2$, $SO_2N(R^7)_2$, $CF_3$, $OCF_3$, $OCHF_2$, an optionally substituted aryl, heteroaryl, cycloalkyl, or heterocycloalkyl, or a straight chain, branched, or cyclic (C1-C8)-$R^8$ wherein up to two $CH_2$ units may be replaced with O, CO, S, SO, $SO_2$, $CF_2$, or $NR^7$;
$R^2$ is C1-C6 alkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $CH_2OCHF_2$, $CH_2OCH_2CHF_2$, an optionally substituted aryl, heteroaryl, C3-C8 cycloalkyl, or heterocycloalkyl, or a straight chain, branched, or cyclic (C1-C8)-$R^8$ wherein up to two $CH_2$ units may be replaced with O, CO, S, SO, $SO_2$ or $NR^7$;
$R^3$ is C1-C6 alkyl or C3-C8 cycloalkyl, wherein up to two $CH_2$ units may be replaced by O, $NR^8$, SO, $SO_2$, or 2 occurrences of $R^3$ taken together form a C3-C8 cycloalkyl group;
$R^7$ is H, C1-C6 alkyl or fluoroalkyl, C3-C8 cycloalkyl, or 2 $R^7$ taken together with the atoms to which they are attached form a ring;
$R^8$ is H, $CF_3$, $CO_2R^7$, OH, an optionally substituted aryl, heteroaryl, C3-C8 cycloalkyl, or heterocycloalkyl, $N(R^7)_2$, $NR^7COR^7$, $CON(R^7)_2$, CN, or $SO_2R^7$;
A is aryl, heteroaryl or heterocyclic;
X is O, S, SO, or $SO_2$;
n is an integer from 0 to 4 inclusive; and
o is an integer from 0 to 4 inclusive;
provided that:
a) when $R^2$ is OH, another $R^2$ is not C1-C6 alkyl;
b) the following compounds are excluded:

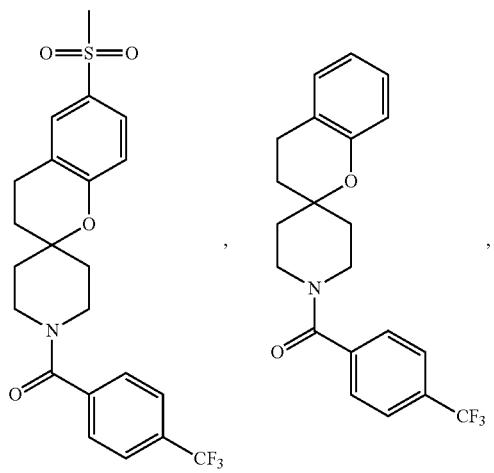

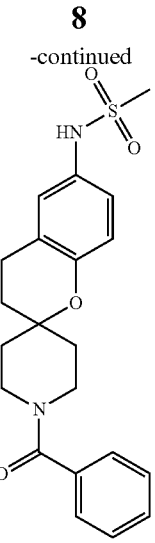

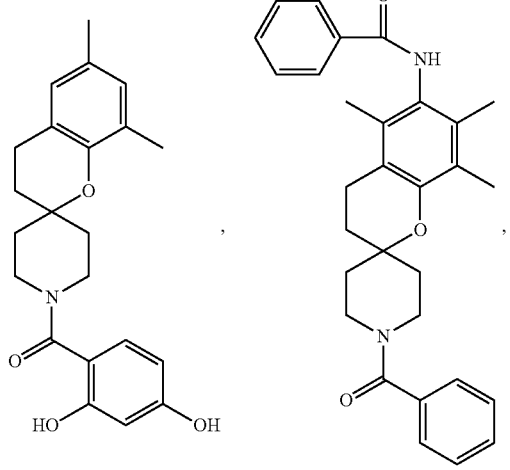

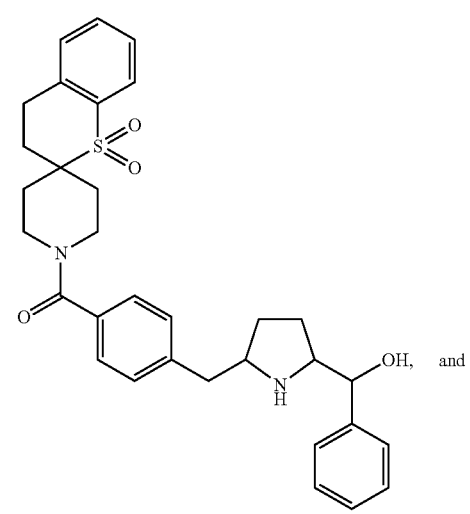

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention can optionally be substituted with one or more substituents, such as are illustrated generally above, or as exemplified by particular classes, subclasses, and species of the invention. The phrase "optionally substituted" is used interchangeably with the phrase "substituted or unsubstituted." As described herein, the variables $R^1$-$R^8$ in formula I encompass specific groups, such as, for example, alkyl and aryl. Unless otherwise noted, each of the specific groups for the variables $R^1$-$R^8$ can be optionally substituted with one or more substituents of halo, cyano, oxoalkoxy, hydroxy, amino, nitro, aryl, haloalkyl, and alkyl. For instance, an alkyl group can be optionally substituted with one or more of halo, cyano, oxoalkoxy, hydroxy, amino, nitro, aryl, haloalkyl, and alkyl. As an additional example, an aryl group can be optionally substituted with one or more of halo, cyano, alkoxy, hydroxy, nitro, haloalkyl, and alkyl. As one of ordinary skill in the art will recognize, combinations of substituents envisioned by this invention are those combinations that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The term "aliphatic", "aliphatic group" or "alkyl" as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, alkynyl groups. The term "cycloaliphatic" or "cycloalkyl" mean a monocyclic hydrocarbon, bicyclic, or tricyclic hydrocarbon that is completely saturated or that contains one or more units of unsaturation, but which is not aromatic and has a single point of attachment to the rest of the molecule. In some embodiments, "cycloaliphatic" refers to a monocyclic C3-C8 hydrocarbon or bicyclic C8-C12 hydrocarbon that is completely saturated or that contains one or more units of unsaturation, but which is not aromatic, that has a single point of attachment to the rest of the molecule wherein any individual ring in said bicyclic ring system has 3-7 members.

The term "electron withdrawing group", as used herein means an atom or a group that is electronegative relative to hydrogen. See, e.g., "Advanced Organic Chemistry: Reactions, Mechanisms, and Structure," Jerry March, 4$^{th}$ Ed., John Wiley & Sons (1992), e.g., pp. 14-16, 18-19, etc. Exemplary such substituents include halo such as Cl, Br, or F, CN, COOH, CF$_3$, etc.

Unless otherwise specified, the term "heterocycle", "heterocyclyl", "heterocycloaliphatic", "heterocycloalkyl" or "heterocyclic" as used herein means non-aromatic, monocyclic, bicyclic, or tricyclic ring systems in which one or more ring atoms in one or more ring members is an independently selected heteroatom. Heterocyclic ring can be saturated or can contain one or more unsaturated bonds. In some embodiments, the "heterocycle", "heterocyclyl", "heterocycloaliphatic", "heterocycloalkyl" or "heterocyclic" group has three to fourteen ring members in which one or more ring members is a heteroatom independently selected from oxygen, sulfur, nitrogen, or phosphorus, and each ring in the ring system contains 3 to 7 ring members.

The term "heteroatom" means oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation but is not aromatic.

The term "alkoxy", or "thioalkyl", as used herein, refers to an alkyl group, as previously defined, attached to the principal carbon chain through an oxygen ("alkoxy") or sulfur ("thioalkyl") atom.

The term "aryl" used alone or as part of a larger moiety as in "aralkyl", "aralkoxy", or "aryloxyalkyl", refers to monocyclic, bicyclic, and tricyclic ring systems having a total of five to fourteen ring carbon atoms, wherein at least one ring in the system is aromatic and wherein each ring in the system contains 3 to 7 ring carbon atoms. The term "aryl" may be used interchangeably with the term "aryl ring".

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

The term "alkylidene chain" refers to a straight or branched carbon chain that may be fully saturated or have one or more units of unsaturation and has two points of attachment to the rest of the molecule.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I.

Additionally, unless otherwise stated, structures depicted herein are also meant to include compounds that differ only in the presence of one or more isotopically enriched atoms. For example, compounds of formula I, wherein one or more hydrogen atoms are replaced deuterium or tritium, or one or more carbon atoms are replaced by a $^{13}$C- or $^{14}$C-enriched carbon are within the scope of this invention. Such compounds are useful, for example, as analytical tools, probes in biological assays, or sodium channel blockers with improved therapeutic profile.

In the formulas and drawings, a line transversing a ring and bonded to an R group such as in

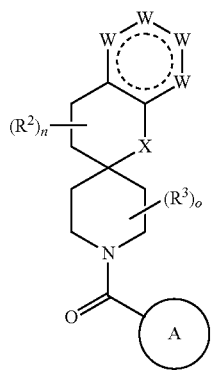

means that the R group can be bonded to any carbon, or if applicable, heteroatom such as N, of that ring as valency allows.

Within a definition of a term as, for example, $R^1$, $R^2$, $R^3$, $R^4$, $R^5$ or $R^6$, when a $CH_2$ unit or, interchangeably, methylene unit may be replaced by O, CO, S, SO, $SO_2$ or $NR^7$, it is meant to include any $CH_2$ unit, including a $CH_2$ within a terminal methyl group. For example, —$CH_2CH_2CH_2SH$ is within the definition of C1-C6 alkyl wherein up to two $CH_2$ units may be replaced by S because the $CH_2$ unit of the terminal methyl group has been replaced by S. In another example, —O-Ph is within the definition of (C1-C8)-$R^8$ wherein up to two $CH_2$ units may be replaced with O, CO, S, SO, $SO_2$ or $NR^7$, because is —$CH_2$-Ph, where the —$CH_2$— unit has been replaced by O, and $R^8$ can be aryl.

The dotted circle of formula I denotes aromaticity, such that, by the definition of W, the moiety is a fused aromatic or heteroaromatic ring.

In another embodiment, the invention features a compound of formula I and the attendant definitions, wherein all W's are $CR^1$. In another embodiment, all W's are CH. In another embodiment, one W is N.

In another embodiment, W is NR'. In another embodiment, R' is a C1-C6 alkyl.

In another embodiment, R' is $CH_3$ or tBu.

In another embodiment, the invention features a compound of formula I and the attendant definitions, wherein X is O. In another embodiment, X is $SO_2$.

In another embodiment, the invention features a compound of formula I and the attendant definitions, wherein $R^1$ is C1-C6 alkyl, halo, CN, $CON(R^7)_2$, $R^8$, or a straight chain, branched, or cyclic (C1-C8)-$R^8$ wherein up to two $CH_2$ units may be replaced with O, CO, S, SO, $SO_2$, or $NR^7$. In another embodiment, $R^1$ is F or CN.

In another embodiment, the invention features a compound of formula I and the attendant definitions, wherein $R^2$ is C1-C6 alkyl, C1-C6 alkoxy, OH, $OR^7$, $N(R^7)_2$, heterocycloalkoxy, aryl, or a straight chain, branched, or cyclic (C1-C8)-$R^8$ wherein up to two $CH_2$ units may be replaced with O, S, SO, $SO_2$ or $NR^7$. In another embodiment, $R^2$ is $OCH_3$, $OCH_2CH=CH_2$, $CH_2OCH(CH_3)_2$, $CH_2OCHF_2$, $CH_2OCH_3$, $OCH_2CH_3$, OH, $CH_3$, $CH(CH_3)_2$, $OCH(CH_3)_2$, $CH_2OCH_2CH_3$, $CH(CH_3)OCH_3$, $CH_2SCH_3$,

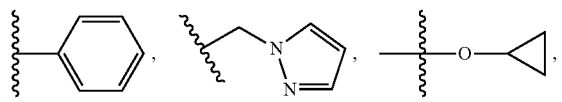

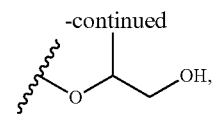

$OCH_2CH_2SO_2CH_3$, $NHCH(CH_3)_2$, OtBu,

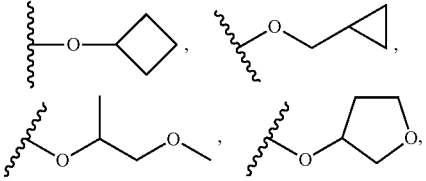

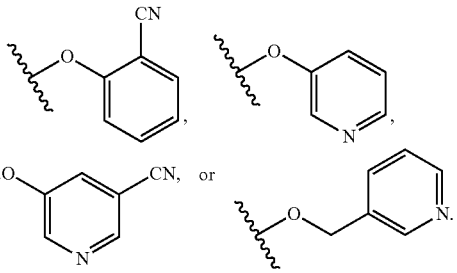

$OCH_2CH_2N(C2H_5)_2$, $OCH_2Ph$,

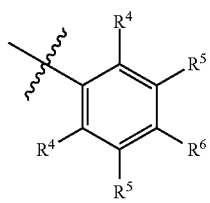

In another embodiment, the invention features a compound of formula I and the attendant definitions, wherein n is 0. In another embodiment, o is 0.

In another embodiment, the invention features a compound of formula I and the attendant definitions, wherein A is wherein:
$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CHF_2$, $CF_3$, $OCF_3$, $OCHF_2$, $R^8$, heterocycloalkyl, heterocycloalkoxy, aryl, heteroaryl, or a straight chain, branched, or cyclic (C1-C8)-$R^8$ wherein up to three $CH_2$ units may be replaced with O, CO, S, SO, $SO_2$, or $NR^7$;
$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $R^8$, heterocycloalkyl, heterocycloalkoxy, aryl, heteroaryl, or a straight chain, branched, or cyclic (C1-C8)-$R^8$ wherein up to three $CH_2$ units may be replaced with O, CO, S, SO, $SO_2$, or $NR^7$;
$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $R^8$, heterocycloalkyl, heterocycloalkoxy, aryl, heteroaryl, or a straight chain, branched, or cyclic (C1-C8)-$R^8$ wherein up to three $CH_2$ units may be replaced with O, CO, S, SO, $SO_2$, or $NR^7$; or two occurrences of $R^4$ and $R^5$, or $R^5$ and $R^6$ together with the carbons to which they are attached form an optionally substituted ring comprising up to 2 heteroatoms.

In another embodiment, $R^4$ is H, C1-C6 alkyl, C1-C6 alkoxy, halo, CN, OH, $CHF_2$, $CF_3$, $OCHF_2$, $OCF_3$, $R^8$, or a straight chain, branched, or cyclic (C1-C8)-$R^8$ wherein up to three $CH_2$ units may be replaced with O, CO, S, SO, $SO_2$, or $NR^7$. In another embodiment, $R^4$ is H, $OCH_3$, $OCHF_2$, $OCF_3$, F, $CH_3$, or $CH_2OCH_3$.

In another embodiment, $R^5$ is H, C1-C6 alkyl, C1-C6 alkoxy, CN, $R^8$, or a straight chain, branched, or cyclic (C1-C8)-$R^8$ wherein up to three $CH_2$ units may be replaced with O, CO, S, SO, $SO_2$, or $NR^7$. In another embodiment, $R^5$ is H, F, $CH_3$, $OCH_3$, $CH_2OH$, OH, $CH_2NH_2$, $CH_2NHCH_3$, $CH_2N(CH_3)_2$, or CN.

In another embodiment, $R^6$ is H, C1-C6 alkyl, C1-C6 alkoxy, $SO_2R^7$, $SO_2N(R^7)_2$, $R^8$, or a straight chain, branched, or cyclic (C1-C8)-$R^8$, wherein up to three $CH_2$ units may be replaced with O, S, SO, $SO_2$, or $NR^7$. In another embodiment, $R^6$ is H, $OCH_3$, OH, $OCH(CH_3)_2$,

$C(CH_3)_2OH$,

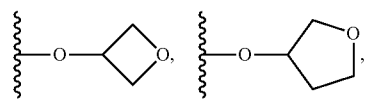

$SO_2CH_3$, $OCH_2CH_2OH$, $OCH_2CH_2CH_2OH$, $SO_2CH_3$, $SO_2CH_2CH_3$, $SO_2CF_3$, $SO_2CH(CH_3)_2$, $SO_2tBu$,

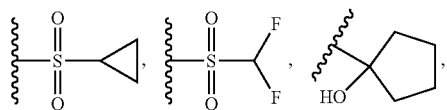

$SO_2NHCH(CH_3)_2$, tBu, $OCHF_2$, $CH_2CH_3$, $OCH_2CH_3$,

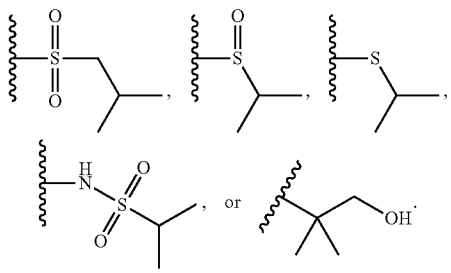

In another embodiment,

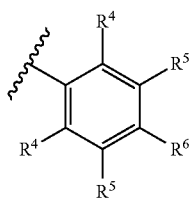

is selected from:

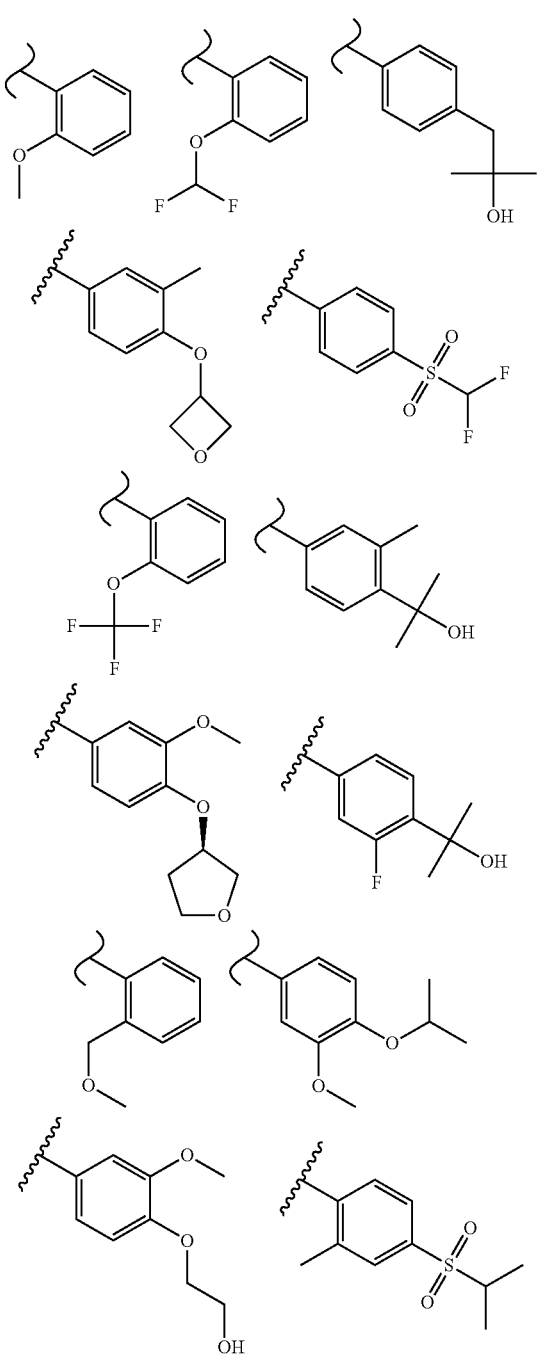

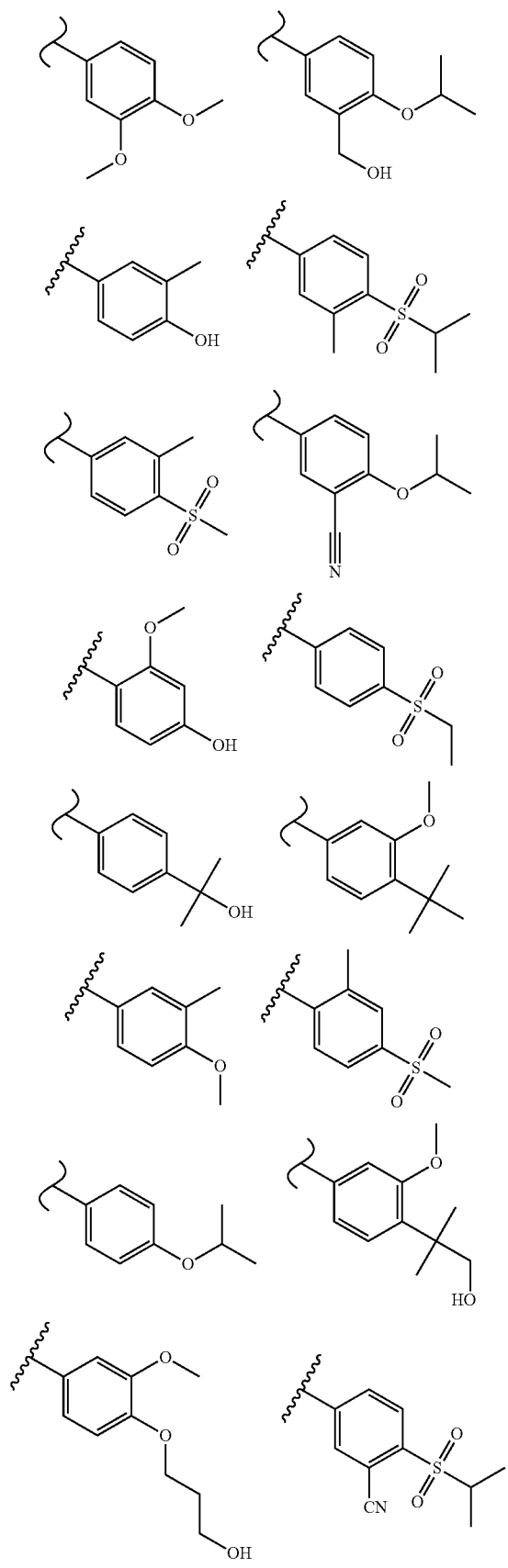
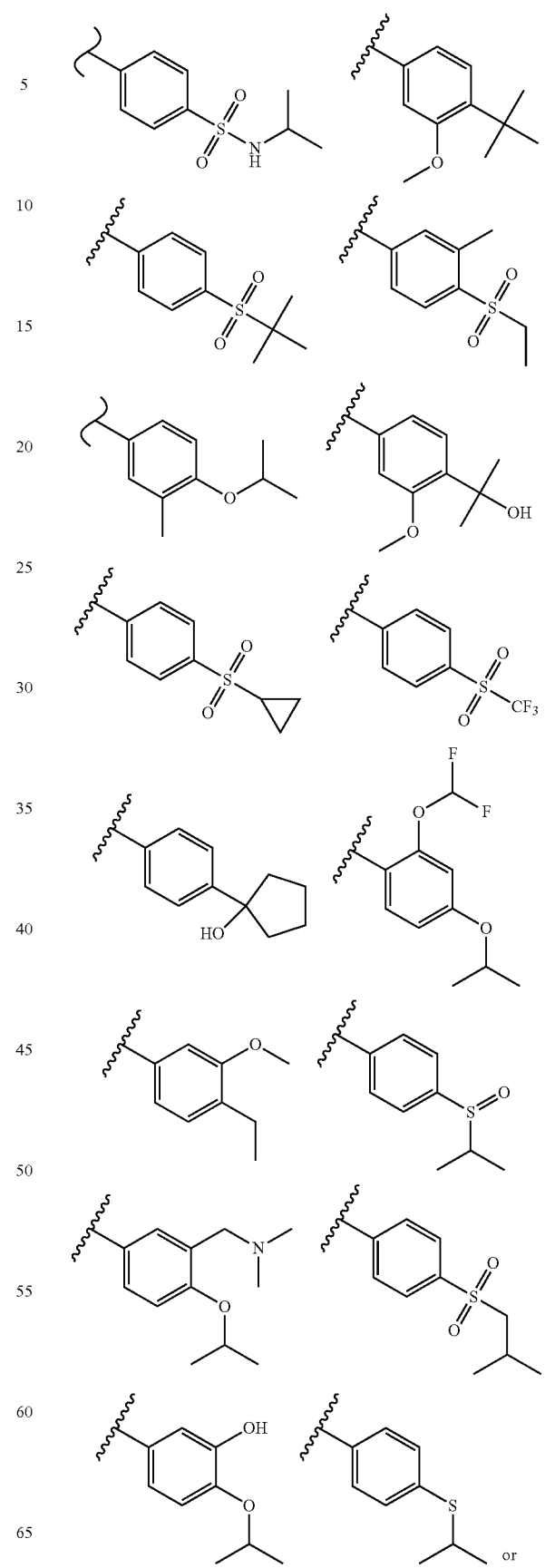

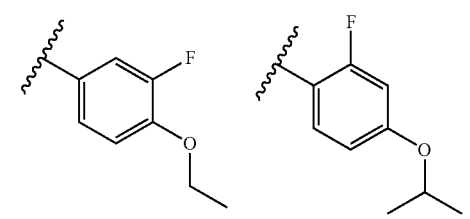
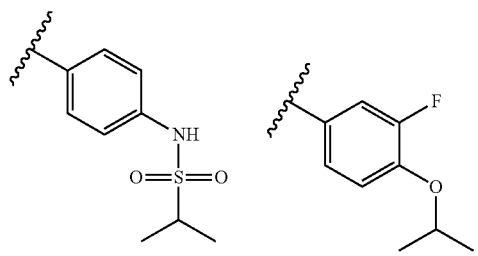
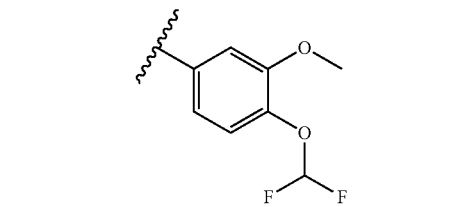
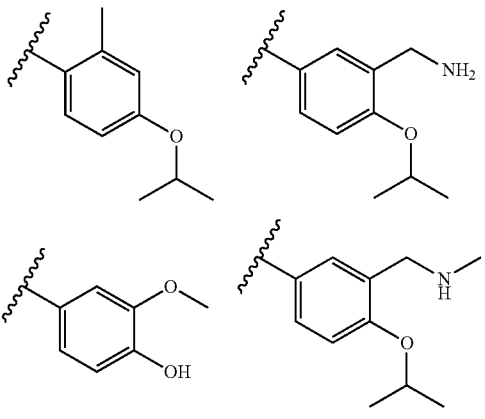
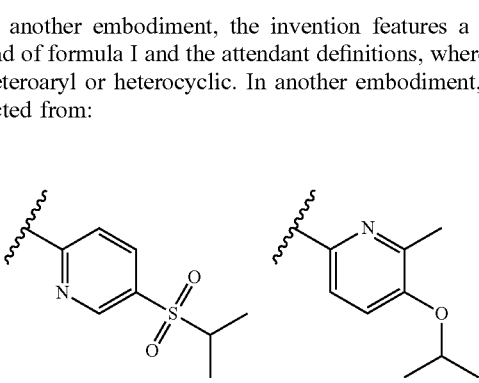
In another embodiment, the invention features a compound of formula I and the attendant definitions, wherein A is heteroaryl or heterocyclic. In another embodiment, A is selected from:
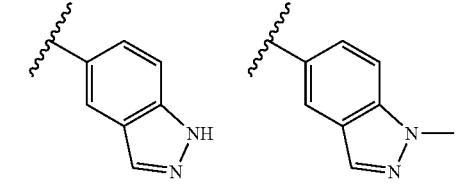
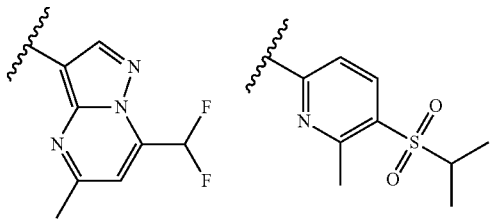
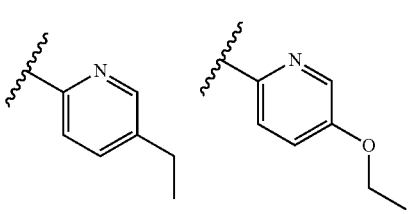
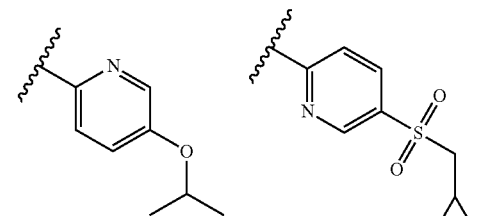
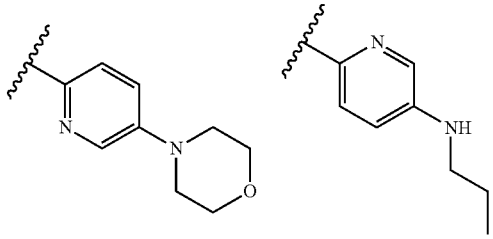
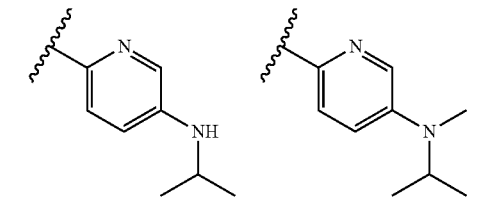
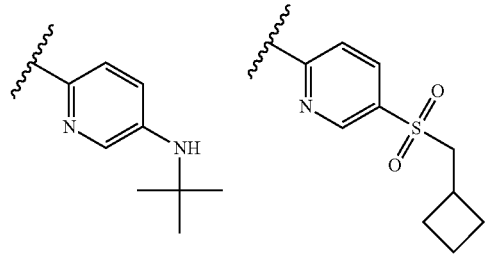
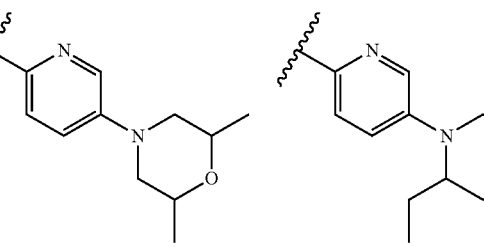

-continued

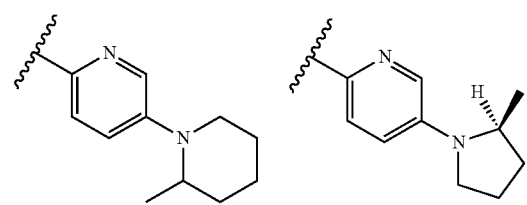

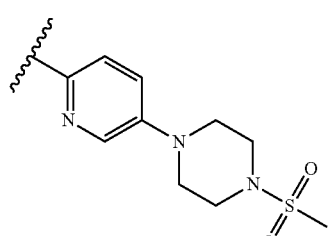

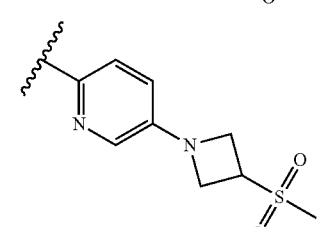

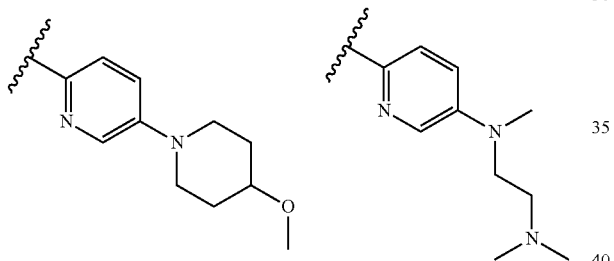

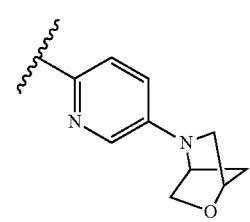

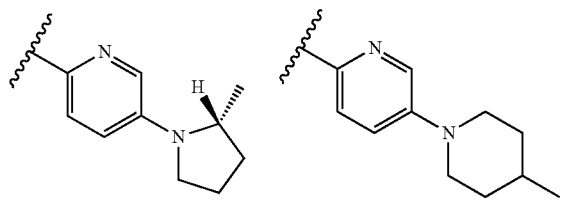

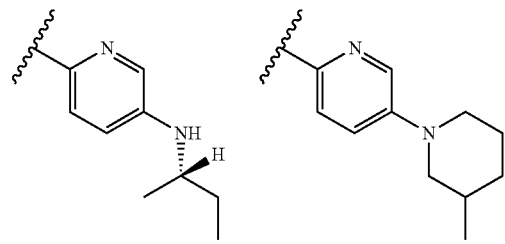

-continued

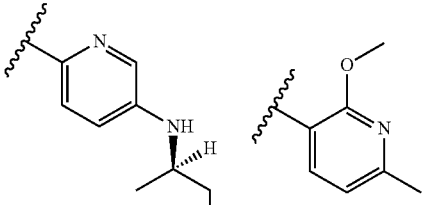

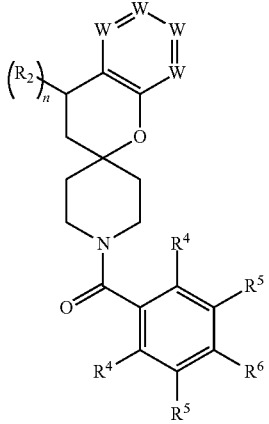

or

In another embodiment, the invention features a compound of formula I and the attendant definitions, wherein the compound has formula IA:

IA or a pharmaceutically acceptable salt thereof,
wherein, independently for each occurrence:
$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $R^8$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$;
$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, $SO_2$, or $NR^7$;
$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$; or two occurrences of $R^4$ and $R^5$, or $R^5$ and $R^6$ together with the carbons to which they are attached form an optionally substituted ring comprising up to 2 heteroatoms; and n is 1 or 2.

In another embodiment, one W is $CR^1$. In another embodiment, one W is N.

In another embodiment, $R^1$ is C1-C6 alkyl, C1-C6 alkoxy, halo, CN, $CON(R^7)_2$, $OR^7$, $R^8$, or a straight chain, branched, or cyclic (C1-C8)-$R^8$ wherein up to two $CH_2$ units may be replaced with O, S, SO, $SO_2$, or $NR^7$. In another embodiment, $R^1$ is F or CN.

In another embodiment, $R^2$ is C1-C6 alkyl, C1-C6 alkoxy, OH, $N(R^7)_2$, aryl, or a straight chain, branched, or cyclic (C1-C8)-$R^8$ wherein up to two $CH_2$ units may be replaced with O, S, SO, $SO_2$ or $NR^7$. In another embodiment, $R^2$ is $OCH_3$, $CH_2OCH_3$, $OCH_2CH_3$, OH, $OCH_2CH=CH_2$, $CH_3$, $CH(CH_3)_2$, $OCH(CH_3)_2$, $CH_2OCH(CH_3)_2$, $CH_2OCHF_2$, $CH_2OCH_2CH_3$, $CH(CH_3)OCH_3$,

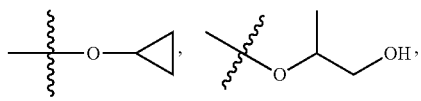

$CH_2SCH_3$, $OCH_2CH_2SO_2CH_3$, $NHCH(CH_3)_2$, OtBu,

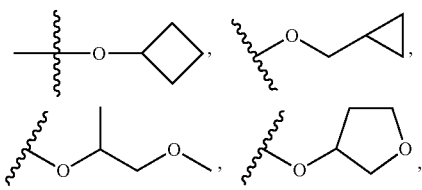

$OCH_2CH_2N(C_2H_5)_2$, $OCH_2Ph$,

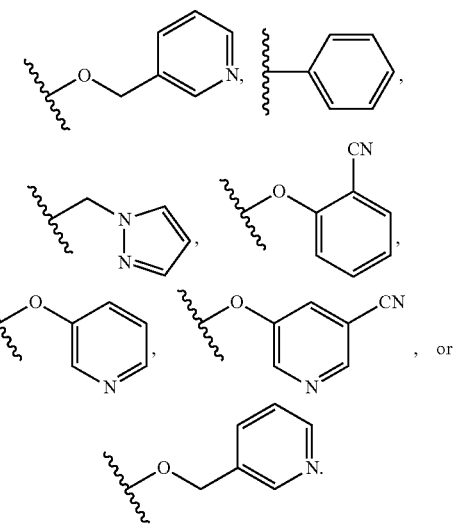, or

In another embodiment, $R^4$ is H, C1-C6 alkyl, C1-C6 alkoxy, halo, CN, OH, $OR^7$, $CHF_2$, $CF_3$, $OCHF_2$, $OCF_3$, $R^8$, or a straight chain, branched, or cyclic (C1-C8)-$R^8$ wherein up to three $CH_2$ units may be replaced with O, S, SO, $SO_2$, or $NR^7$. In another embodiment, $R^4$ is H, $OCH_3$, $OCHF_2$, $OCF_3$, F, $CH_3$, or $CH_3$.

In another embodiment, $R^5$ is H, C1-C6 alkyl, C1-C6 alkoxy, CN, or a straight chain, branched, or cyclic (C1-C8)-$R^8$ wherein up to three $CH_2$ units may be replaced with O, S, SO, $SO_2$, or $NR^7$. In another embodiment, $R^5$ is H, $CH_3$, $OCH_3$, $CH_2OH$, F, OH, $CH_2NH_2$, $CH_2NHCH_3$, $CH_2N(CH_3)_2$, or CN.

In another embodiment, $R^6$ is H, C1-C6 alkyl, C1-C6 alkoxy, $SO_2R^7$, $SO_2N(R^7)_2$, or a straight chain, branched, or cyclic (C1-C8)-$R^8$, wherein up to three $CH_2$ units may be replaced with O, S, SO, $SO_2$, or $NR^7$. In another embodiment, $R^6$ is H, OH, $OCH_3$, $OCH(CH_3)_2$, $OCH_2CH_2OH$, $OCH_2CH_2CH_2OH$,

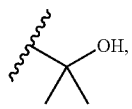

$SO_2CH_3$, $SO_2CH_2CH_3$, $SO_2CF_3$, $SO_2CH(CH_3)_2$, $SO_2tBu$, $SO_2CHF_2$, tBu,

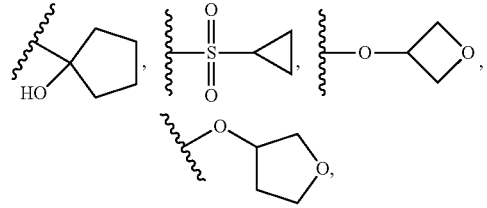

$OCHF_2$, $CH_2CH_3$, $OCH_2CH_3$,

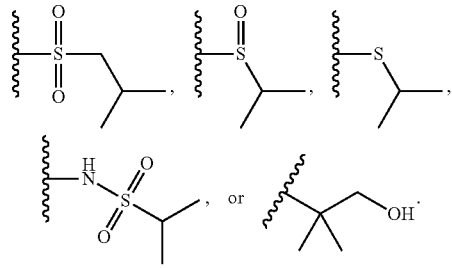

In another embodiment, n is 1.

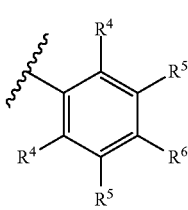

In another embodiment, is selected from:
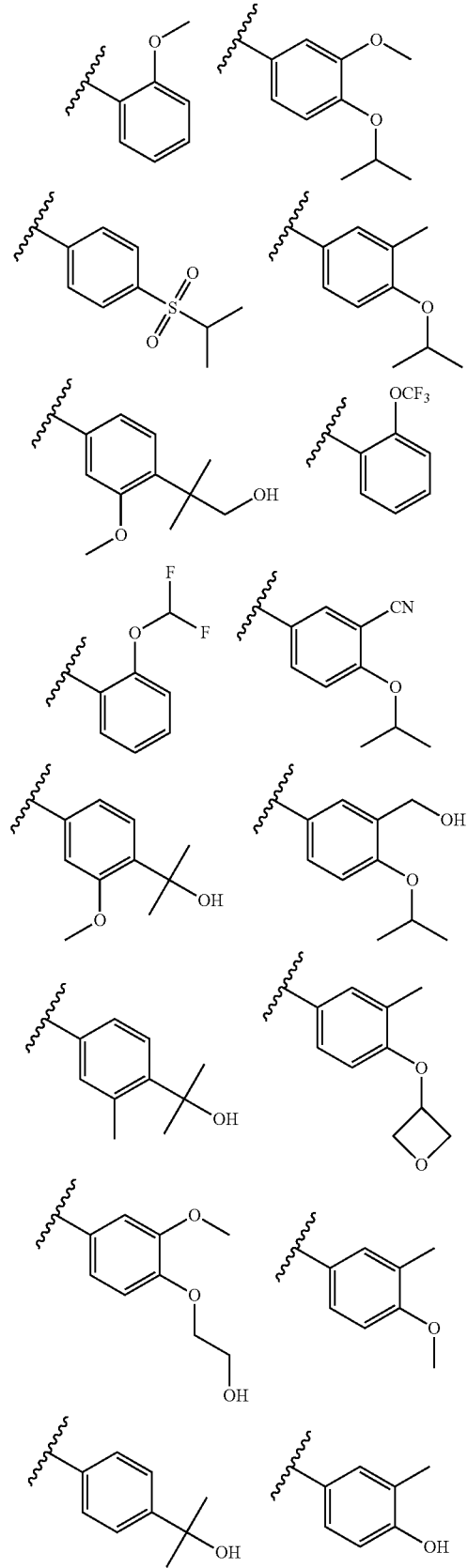
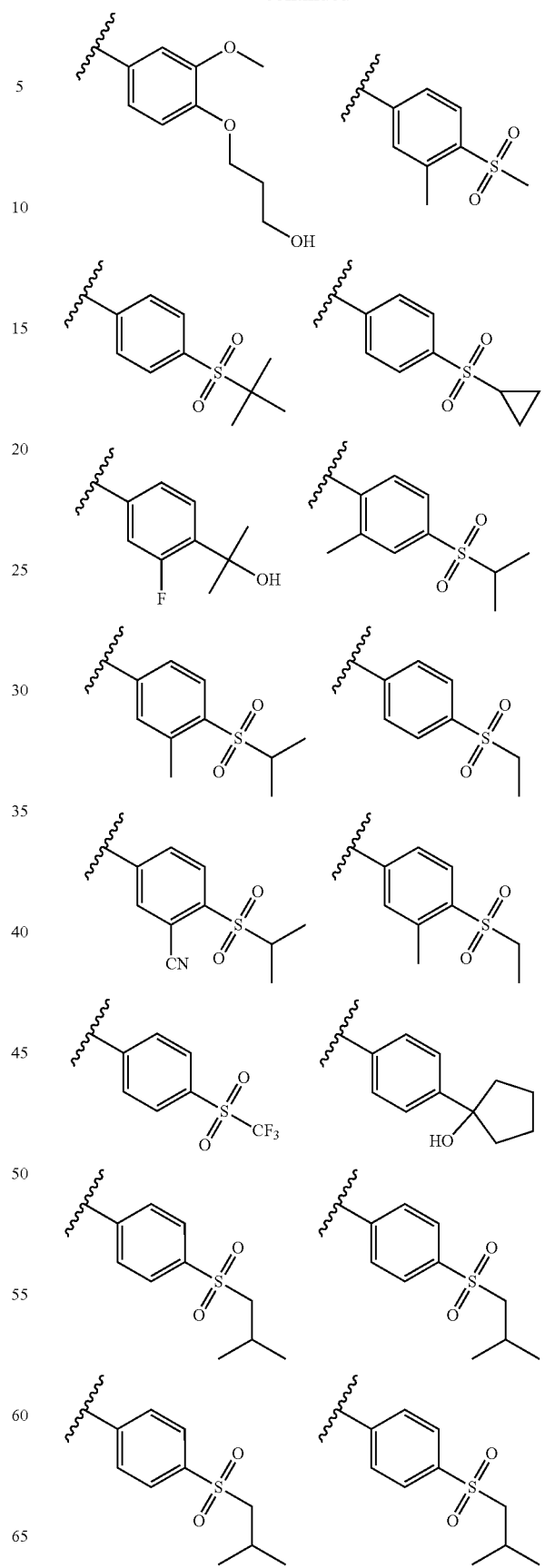

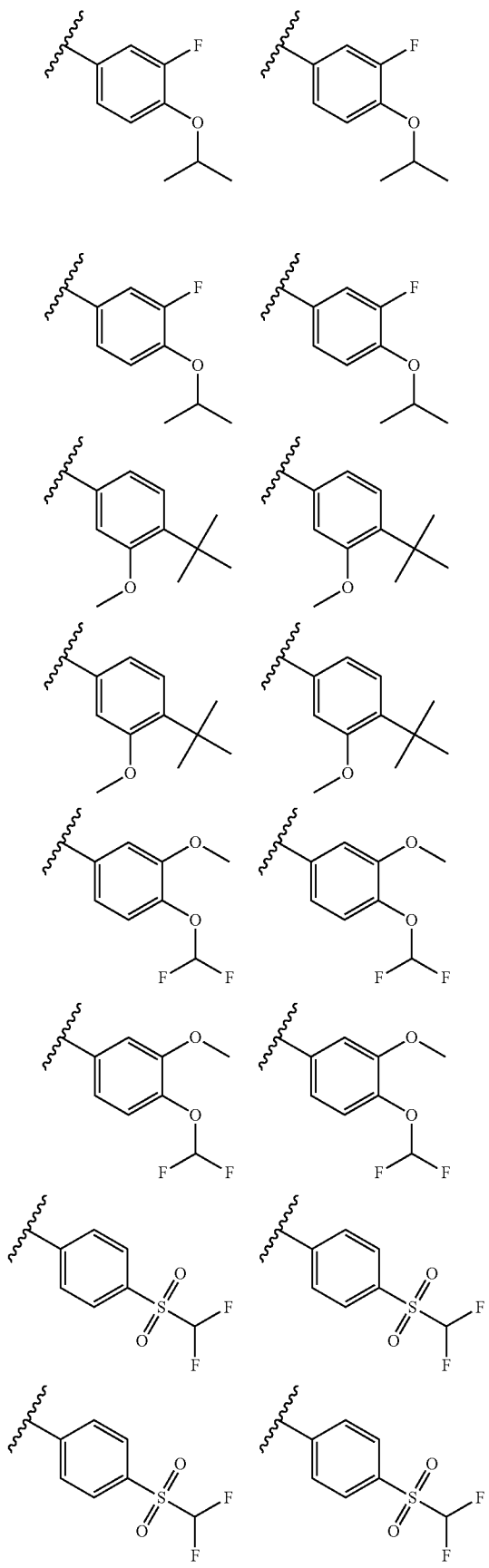

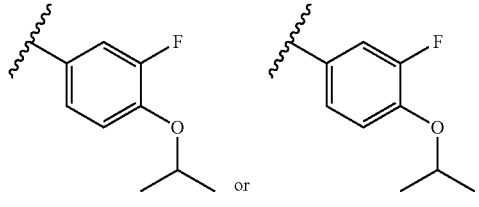

or

In another embodiment, the invention features a compound of formula I and the attendant definitions, wherein the compound has formula IB:

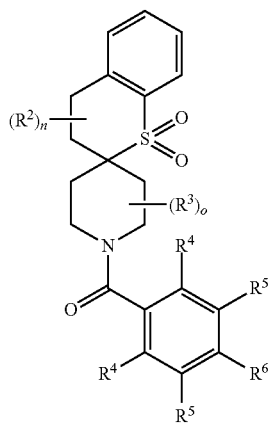

IB or a pharmaceutically acceptable salt thereof, wherein, independently for each occurrence:

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$; or two occurrences of $R^4$ and $R^5$, or $R^5$ and $R^6$ together with the carbons to which they are attached form an optionally substituted ring comprising up to 2 heteroatoms.

In another embodiment, $R^2$ is H, C1-C6 alkyl, C1-C6 alkoxy. In another embodiment, $R^2$ is $OCH_3$, $OC_2H_5$, or $OCH(CH_3)_2$.

In another embodiment, $R^4$ is H, C1-C6 alkyl, C1-C6 alkoxy. In another embodiment, $R^4$ is H or $OCHF_2$.

In another embodiment, $R^5$ is H, C1-C6 alkyl, C3-C8 cycloalkyl, C1-C6 alkoxy or a straight chain, branched, or cyclic (C1-C8)-$R^8$ wherein up to three $CH_2$ units may be replaced with O, S, SO, $SO_2$, or $NR^7$. In another embodiment, $R^5$ is H, $CH_3$ or $OCH_3$.

In another embodiment, $R^6$ is H, C1-C6 alkyl, C3-C8 cycloalkyl, C1-C6 alkoxy or a straight chain, branched, or cyclic (C1-C8)-$R^8$ wherein up to three $CH_2$ units may be replaced with O, S, SO, $SO_2$, or $NR^7$. In another embodiment, $R^6$ is $OCH(CH_3)_2$.

In another embodiment, n is 0 or 1. In another embodiment, n is 1. In another embodiment, o is 0.

In another embodiment,

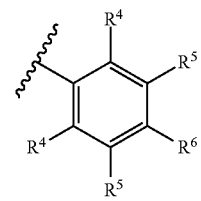

is selected from:

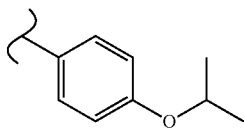

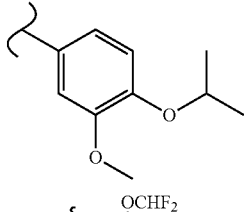

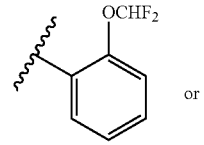

or

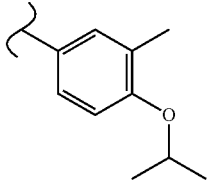

In another embodiment, the invention features a compound of formula I and the attendant definitions, wherein the compound has formula IC:

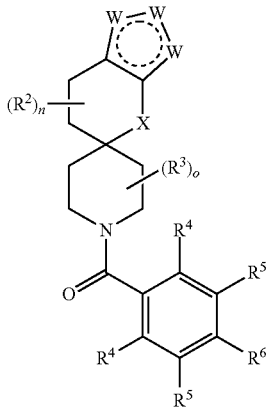

or a pharmaceutically acceptable salt thereof, wherein, independently for each occurrence:

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl or a straight chain, branched, or cyclic (C1-C8)-$R^8$ wherein up to three $CH_2$ units may be replaced with O, S, SO, $SO_2$, or $NR^7$; or two occurrences of $R^4$ and $R^5$, or $R^5$ and $R^6$ together with the carbons to which they are attached form an optionally substituted ring comprising up to 2 heteroatoms.

In another embodiment, W is N or NR'. In another embodiment, R' is a C1-C6 alkyl. In another embodiment, R' is $CH_3$ or tBu.

In another embodiment, $R^2$ is H or C1-C6 alkoxy. In another embodiment, $R^2$ is $OCH(CH_3)_2$.

In another embodiment, $R^4$ is H.

In another embodiment, $R^5$ is H, C1-C6 alkyl, or C1-C6 alkoxy. In another embodiment, $R^5$ is $CH_3$ or $OCH_3$.

In another embodiment, $R^6$ is H or C1-C6 alkoxy. In another embodiment, $R^6$ is $OCH(CH_3)_2$.

In another embodiment, n is 0 or 1. In another embodiment, n is 1. In another embodiment, o is 0.

In another embodiment,
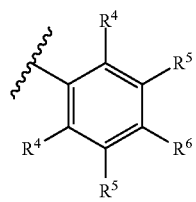
is
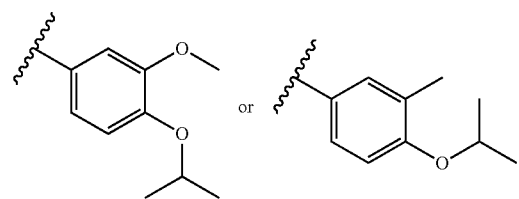
In another embodiment, the invention features a compound of formula I and the attendant definitions, wherein the compound is selected from the following table:
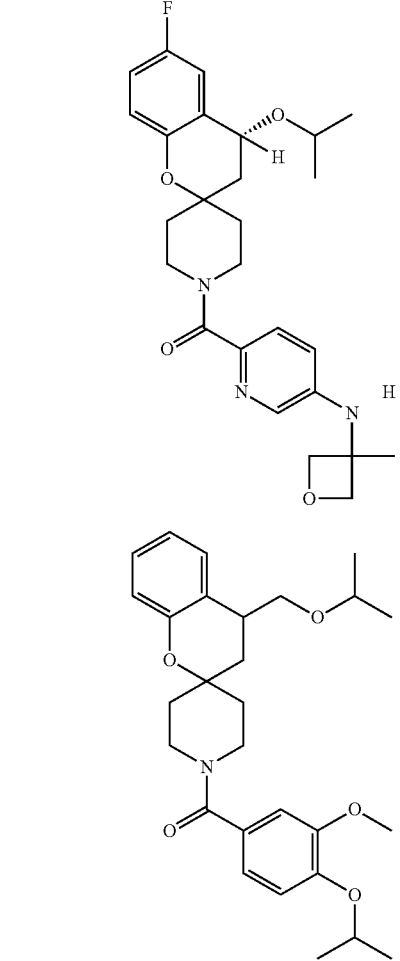
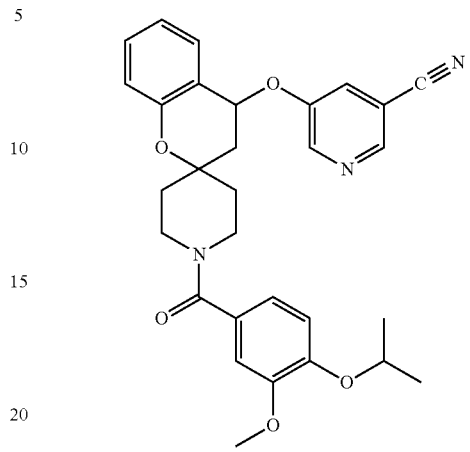
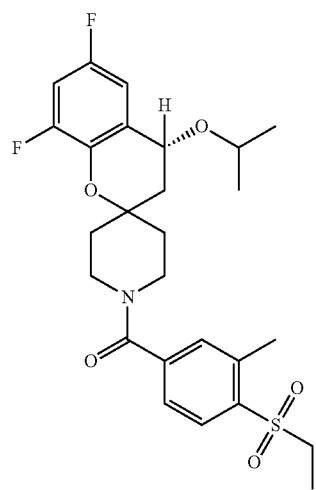 [SMILES: CCS(=O)(=O)c1ccc(C(=O)N2CCC3(CC2)C[C@@H](OC(C)C)c2cc(F)cc(F)c2O3)cc1C]
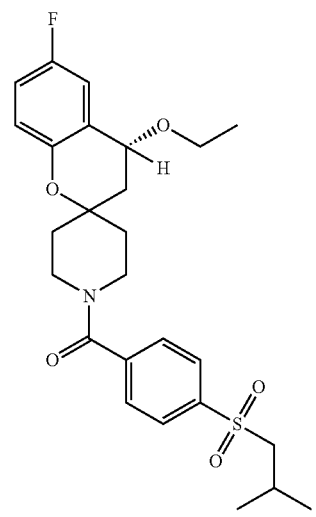 [SMILES: CCO[C@@H]1CC2(CCN(C(=O)c3ccc(S(=O)(=O)CC(C)C)cc3)CC2)Oc2ccc(F)cc21]

6
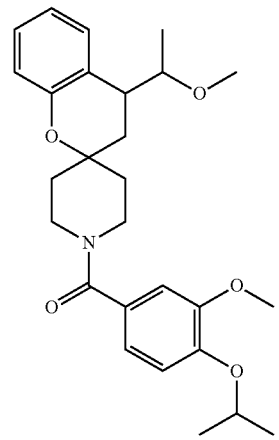 [SMILES: COc1cc(C(=O)N2CCC3(CC2)CC(C(C)OC)c2ccccc2O3)ccc1OC(C)C]
7
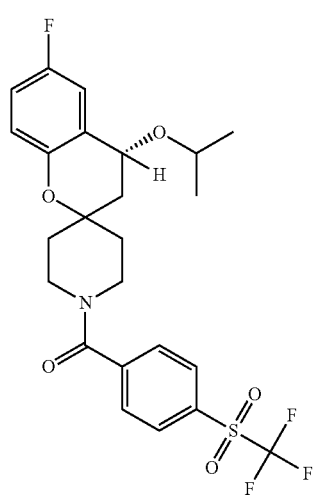 [SMILES: CC(C)O[C@@H]1CC2(CCN(C(=O)c3ccc(S(=O)(=O)C(F)(F)F)cc3)CC2)Oc2ccc(F)cc21]
8
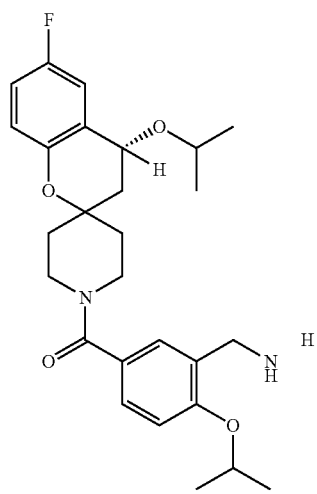
9
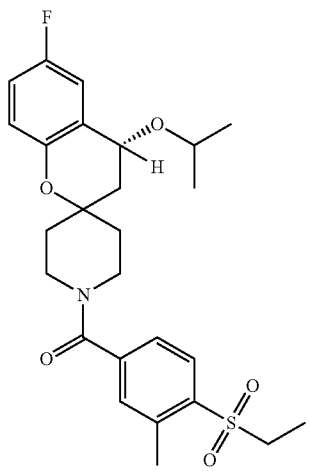 [SMILES: CCS(=O)(=O)c1ccc(C(=O)N2CCC3(CC2)C[C@@H](OC(C)C)c2cc(F)ccc2O3)cc1C]
10
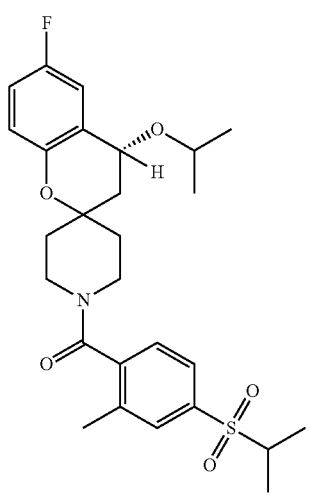 [SMILES: Cc1cc(S(=O)(=O)C(C)C)ccc1C(=O)N1CCC2(CC1)C[C@@H](OC(C)C)c1cc(F)ccc1O2]

| 33 -continued | 34 -continued |
|---|---|
| 12 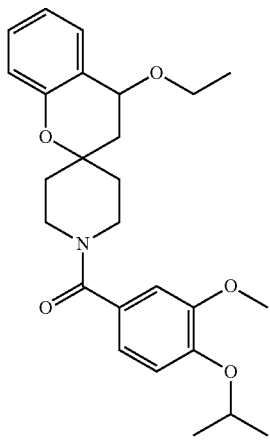 | 15 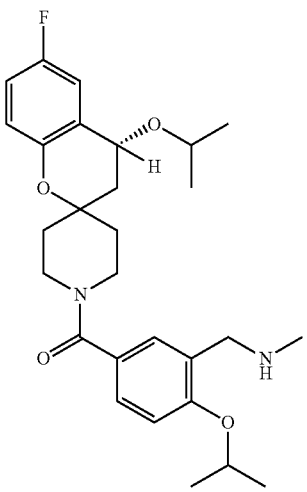 |
| 13 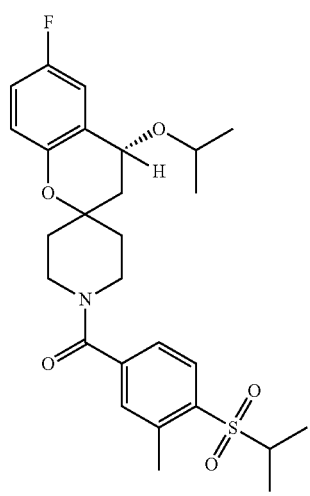 [SMILES: Cc1cc(C(=O)N2CCC3(CC2)C[C@@H](OC(C)C)c2cc(F)ccc2O3)ccc1S(=O)(=O)C(C)C] | 16 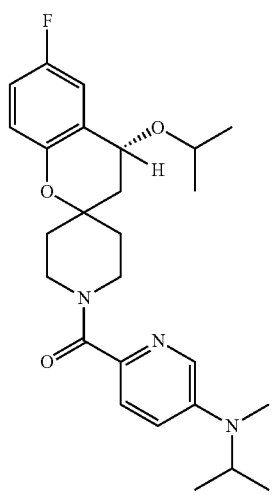 |
| 14 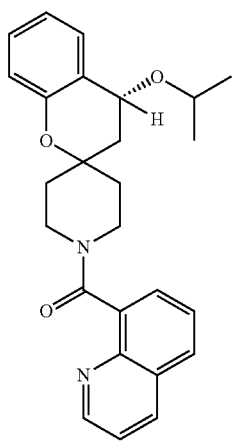 [SMILES: CC(C)O[C@@H]1CC2(CCN(C(=O)c3cccc4cccnc34)CC2)Oc2ccccc21] | 17 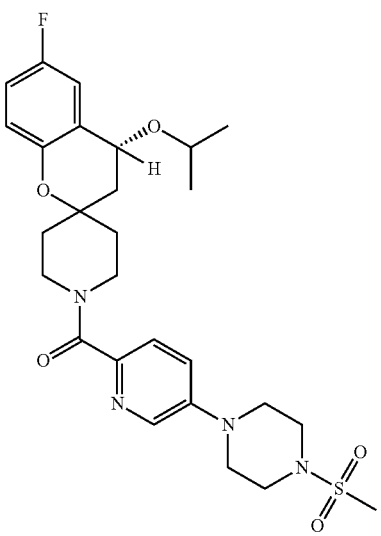 [SMILES: CC(C)O[C@@H]1CC2(CCN(C(=O)c3ccc(N4CCN(S(C)(=O)=O)CC4)cn3)CC2)Oc2ccc(F)cc21] |

| 35 -continued | 36 -continued |
|---|---|
| 18 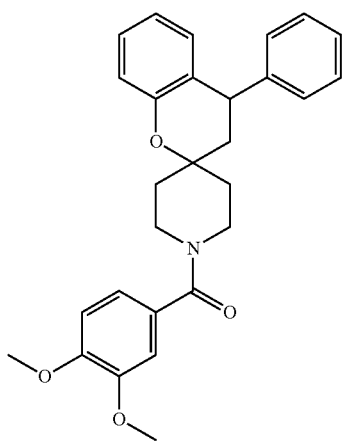 [SMILES: COc1ccc(C(=O)N2CCC3(CC2)CC(c2ccccc2)c2ccccc2O3)cc1OC] | 21 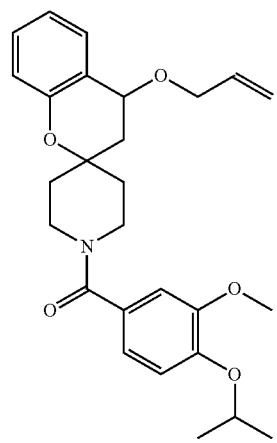 [SMILES: C=CCOC1CC2(CCN(C(=O)c3ccc(OC(C)C)c(OC)c3)CC2)Oc2ccccc21] |
| 19 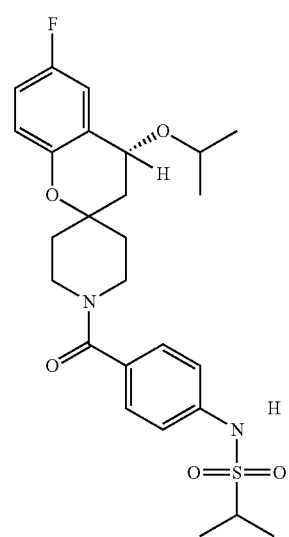 | 22 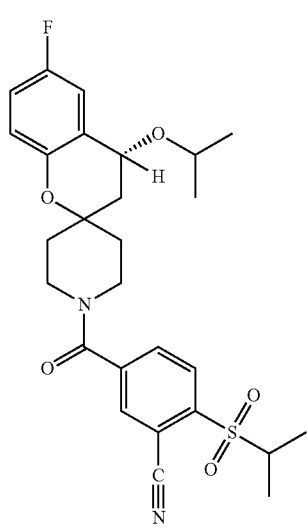 |
| 20 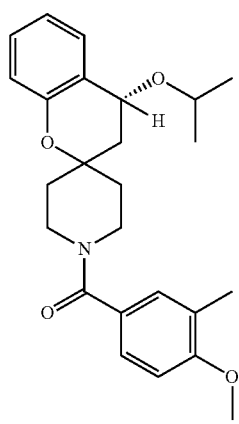 | 23 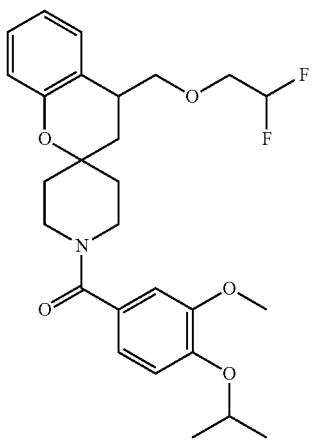 [SMILES: COc1cc(C(=O)N2CCC3(CC2)CC(COCC(F)F)c2ccccc2O3)ccc1OC(C)C] |

-continued
24
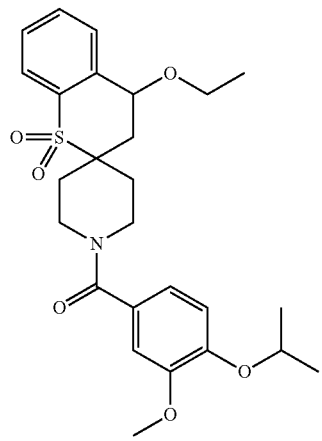 [SMILES: CCOC1CC2(CCN(C(=O)c3ccc(OC(C)C)c(OC)c3)CC2)S(=O)(=O)c2ccccc21]
25
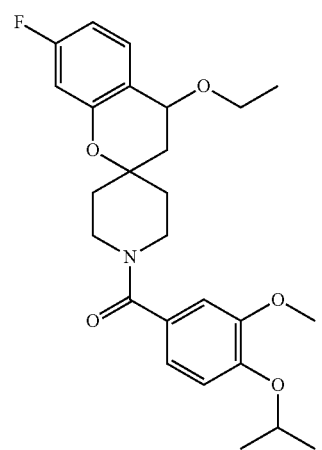 [SMILES: CCOC1CC2(CCN(C(=O)c3ccc(OC(C)C)c(OC)c3)CC2)Oc2cc(F)ccc21]
26
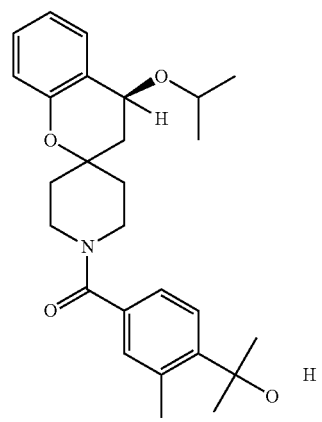
-continued
27
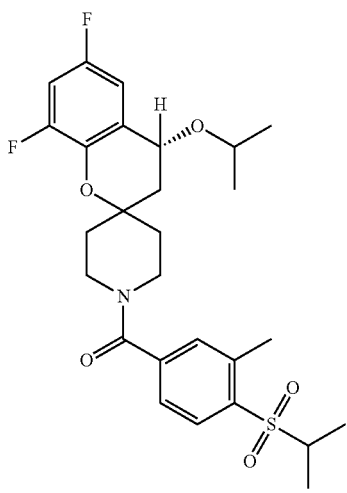 [SMILES: Cc1cc(C(=O)N2CCC3(CC2)C[C@@H](OC(C)C)c2cc(F)cc(F)c2O3)ccc1S(=O)(=O)C(C)C]
28
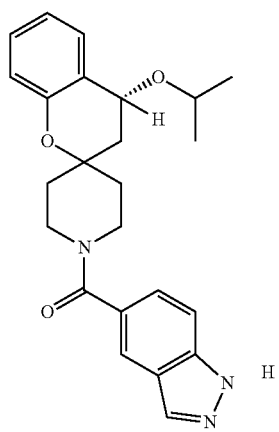
29
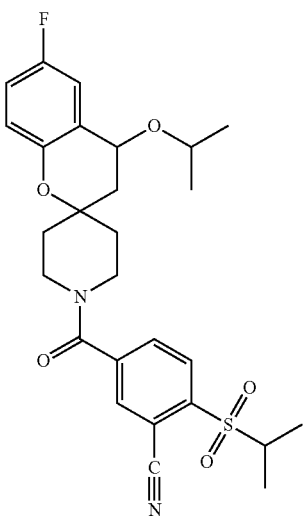

| 30 | 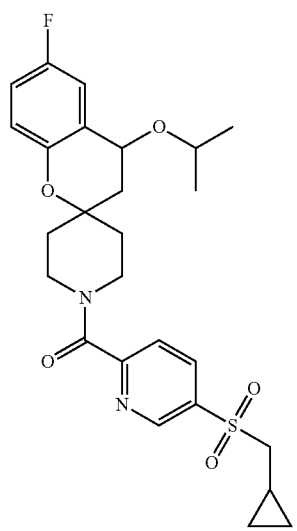 [SMILES: CC(C)OC1CC2(CCN(C(=O)c3ccc(S(=O)(=O)CC4CC4)cn3)CC2)Oc2ccc(F)cc21] |
|---|---|
| 31 | 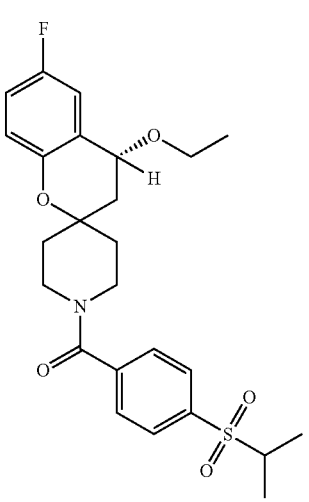 [SMILES: CCO[C@@H]1CC2(CCN(C(=O)c3ccc(S(=O)(=O)C(C)C)cc3)CC2)Oc2ccc(F)cc21] |
| 33 | 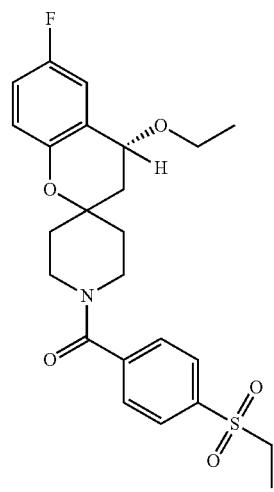 [SMILES: CCO[C@@H]1CC2(CCN(C(=O)c3ccc(S(=O)(=O)CC)cc3)CC2)Oc2ccc(F)cc21] |
|---|---|
| 34 | 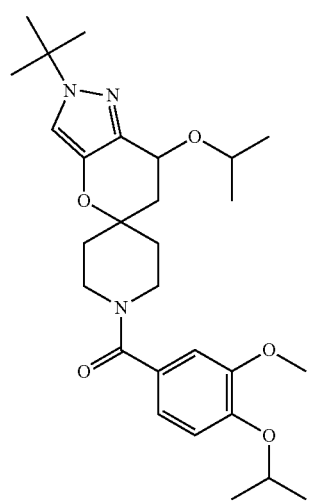 [SMILES: COc1cc(C(=O)N2CCC3(CC2)CC(OC(C)C)c2nn(C(C)(C)C)cc2O3)ccc1OC(C)C] |

36
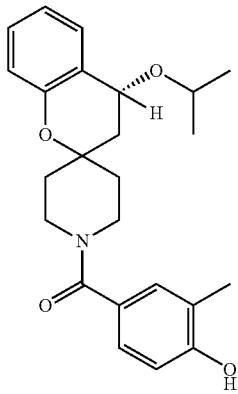 [SMILES: Cc1cc(C(=O)N2CCC3(CC2)C[C@@H](OC(C)C)c2ccccc2O3)ccc1O]
37
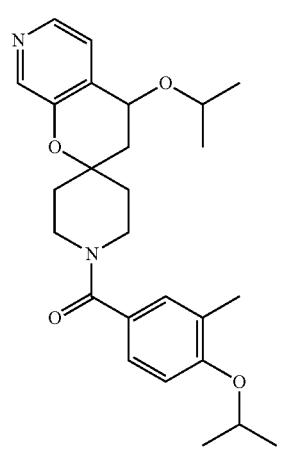
38
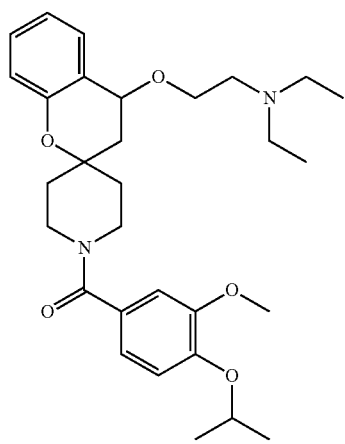 [SMILES: CCN(CC)CCOC1CC2(CCN(C(=O)c3ccc(OC(C)C)c(OC)c3)CC2)Oc2ccccc21]
39
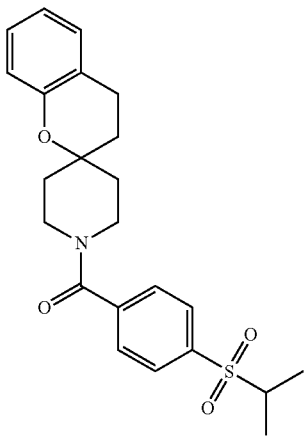 [SMILES: CC(C)S(=O)(=O)c1ccc(C(=O)N2CCC3(CCc4ccccc4O3)CC2)cc1]
40
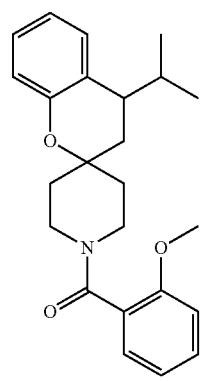 [SMILES: COc1ccccc1C(=O)N1CCC2(CC1)CC(C(C)C)c1ccccc1O2]
41
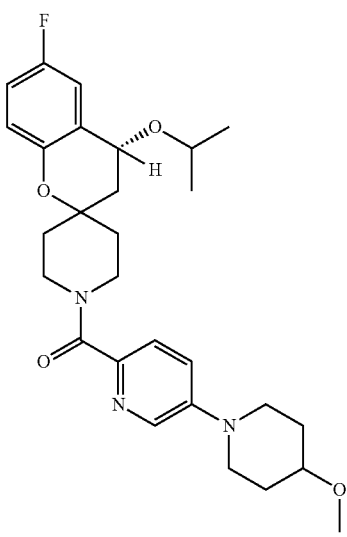 [SMILES: COC1CCN(c2ccc(C(=O)N3CCC4(CC3)C[C@@H](OC(C)C)c3cc(F)ccc3O4)nc2)CC1]

42
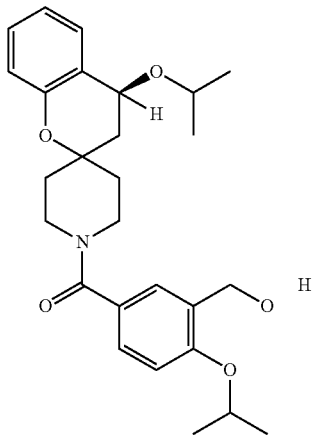
43
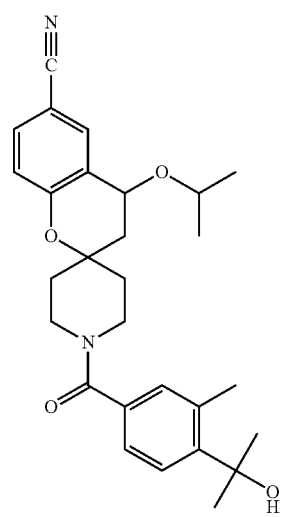 [SMILES: Cc1cc(C(=O)N2CCC3(CC2)CC(OC(C)C)c2cc(C#N)ccc2O3)ccc1C(C)(C)O]
44
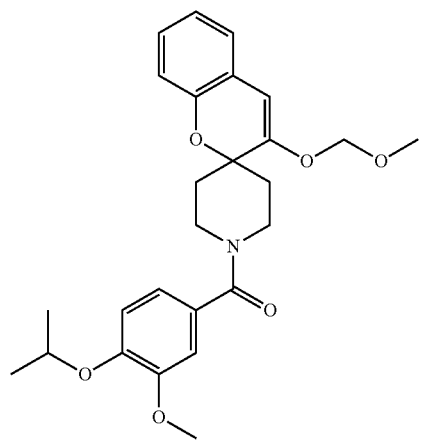 [SMILES: COCOC1=Cc2ccccc2OC12CCN(C(=O)c1ccc(OC(C)C)c(OC)c1)CC2]
45
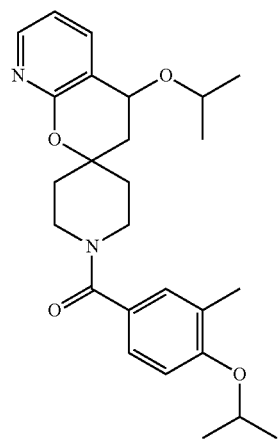
46
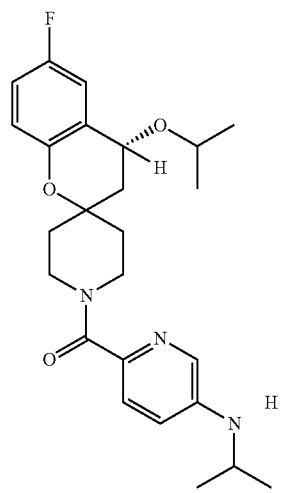
47
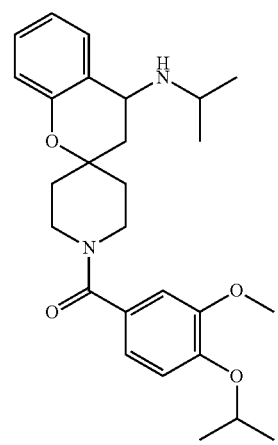 [SMILES: COc1cc(C(=O)N2CCC3(CC2)CC(NC(C)C)c2ccccc2O3)ccc1OC(C)C]

48
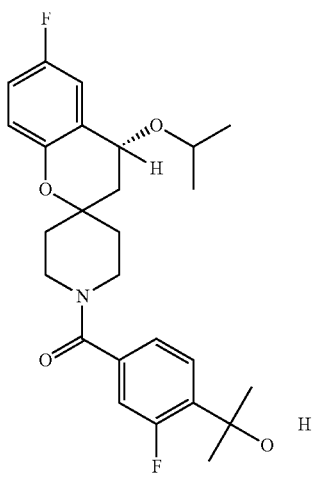
49
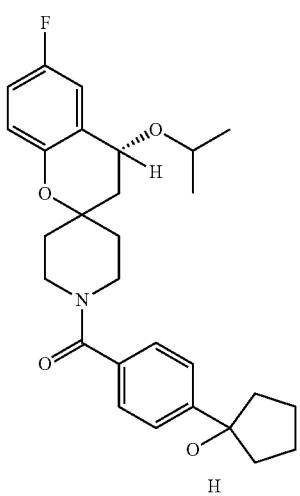
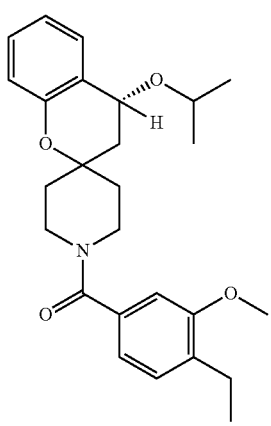 [SMILES: CCc1ccc(C(=O)N2CCC3(CC2)C[C@@H](OC(C)C)c2ccccc2O3)cc1OC]
51
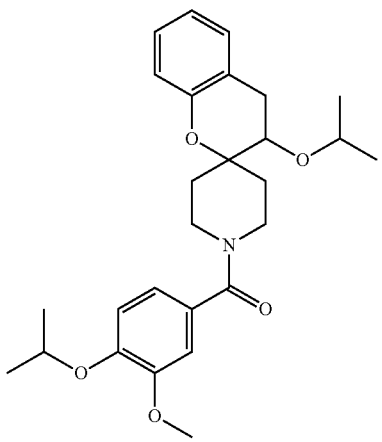 [SMILES: COc1cc(C(=O)N2CCC3(CC2)Oc2ccccc2CC3OC(C)C)ccc1OC(C)C]
52
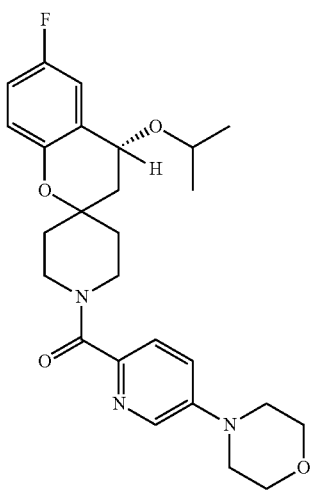 [SMILES: CC(C)O[C@@H]1CC2(CCN(C(=O)c3ccc(N4CCOCC4)cn3)CC2)Oc2ccc(F)cc21]
53
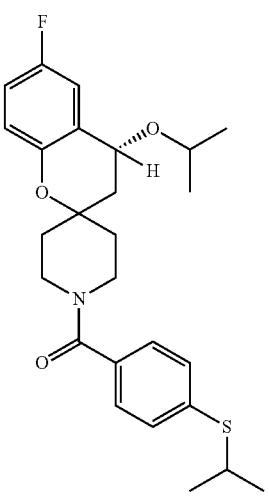 [SMILES: CC(C)O[C@@H]1CC2(CCN(C(=O)c3ccc(SC(C)C)cc3)CC2)Oc2ccc(F)cc21]

54
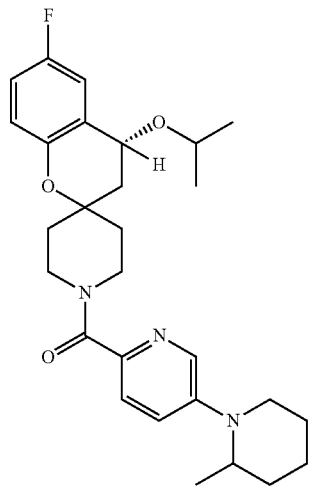 [SMILES: CC(C)O[C@@H]1CC2(CCN(C(=O)c3ccc(N4CCCCC4C)cn3)CC2)Oc2ccc(F)cc21]
55
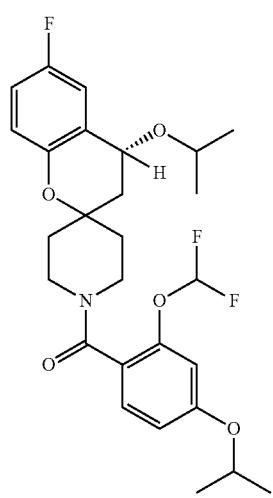 [SMILES: CC(C)Oc1ccc(C(=O)N2CCC3(CC2)C[C@@H](OC(C)C)c2cc(F)ccc2O3)c(OC(F)F)c1]
56
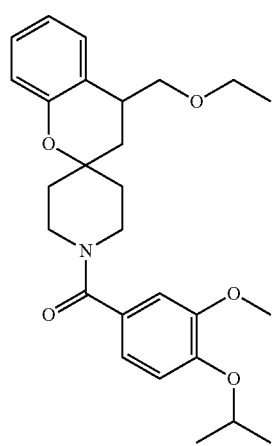
57
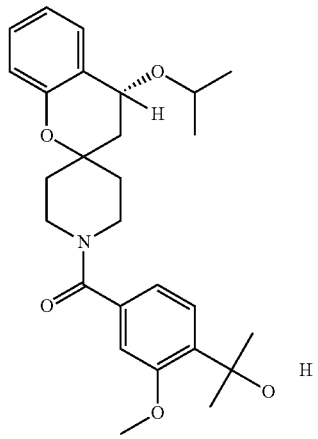
58
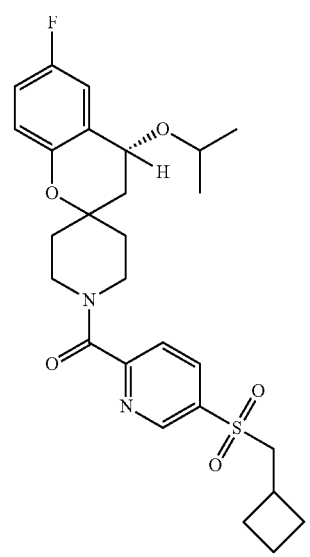 [SMILES: CC(C)O[C@@H]1CC2(CCN(C(=O)c3ccc(S(=O)(=O)CC4CCC4)cn3)CC2)Oc2ccc(F)cc21]
59
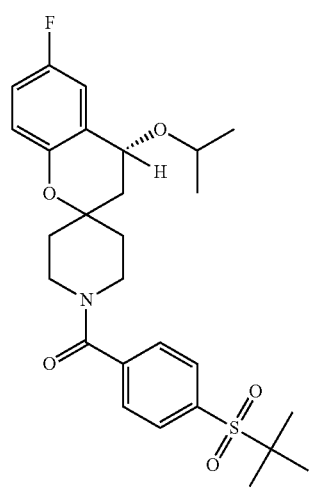 [SMILES: CC(C)O[C@@H]1CC2(CCN(C(=O)c3ccc(S(=O)(=O)C(C)(C)C)cc3)CC2)Oc2ccc(F)cc21]

| 49 -continued | 50 -continued |
|---|---|
| 60 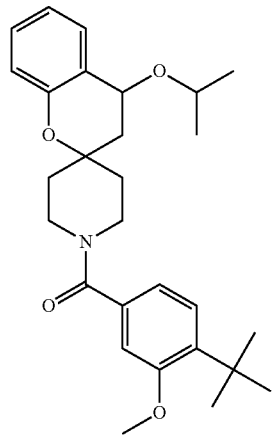 [SMILES: COc1cc(C(=O)N2CCC3(CC2)CC(OC(C)C)c2ccccc2O3)ccc1C(C)(C)C] | 63 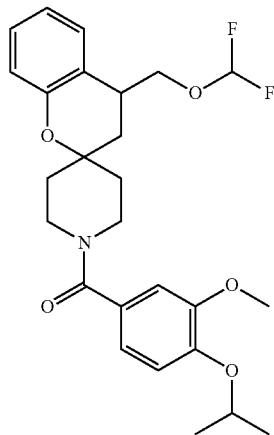 |
| 61 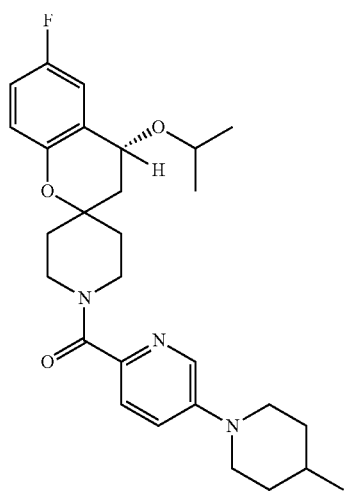 [SMILES: CC1CCN(c2ccc(C(=O)N3CCC4(CC3)C[C@@H](OC(C)C)c3cc(F)ccc3O4)nc2)CC1] | 64 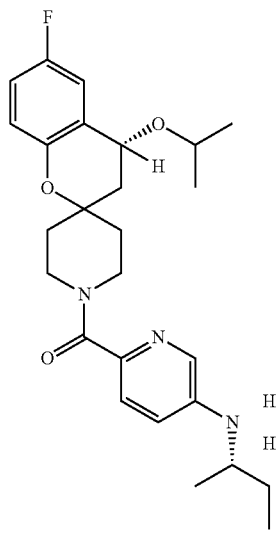 |
| 62 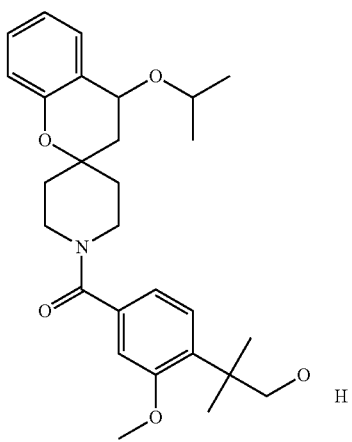 | 65 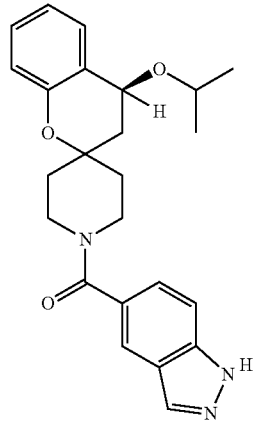 |

| 66 | 69 |
|---|---|
| 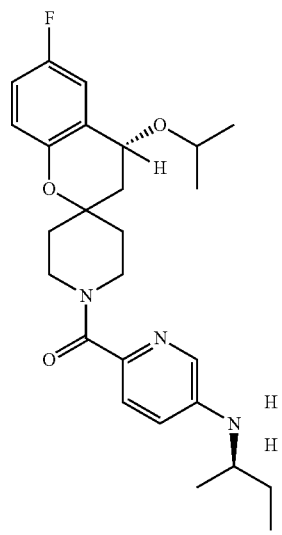 | 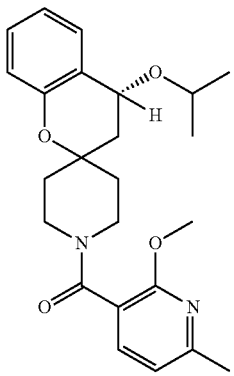 |
| 67 | 70 |
| 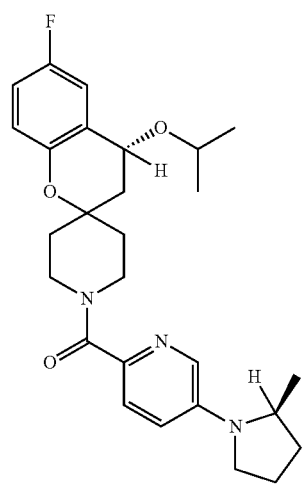 [SMILES: CC(C)O[C@@H]1CC2(CCN(C(=O)c3ccc(N4CCC[C@@H]4C)cn3)CC2)Oc2ccc(F)cc21] | 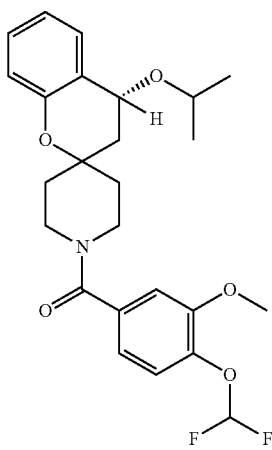 [SMILES: COc1cc(C(=O)N2CCC3(CC2)C[C@@H](OC(C)C)c2ccccc2O3)ccc1OC(F)F] |
| 68 | 71 |
| 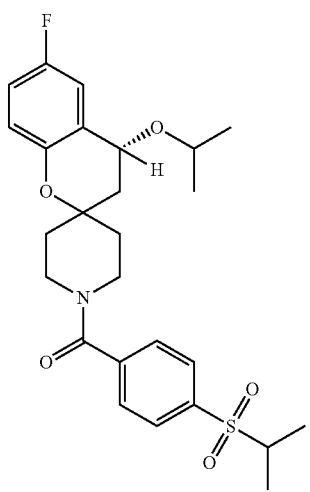 | 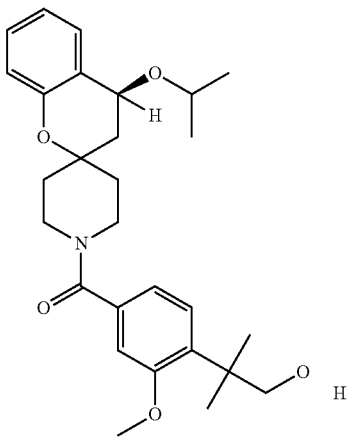 |

| | |
|---|---|
| 72 | 75 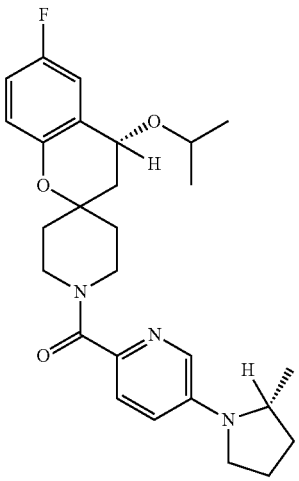 |
| 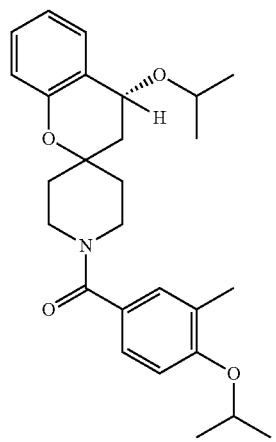 | |
| 73 | 76 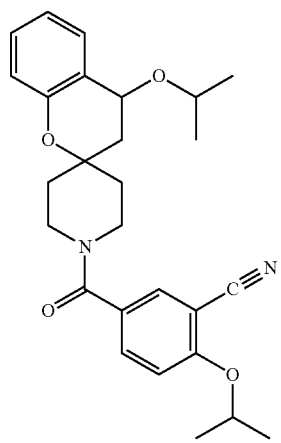 |
| 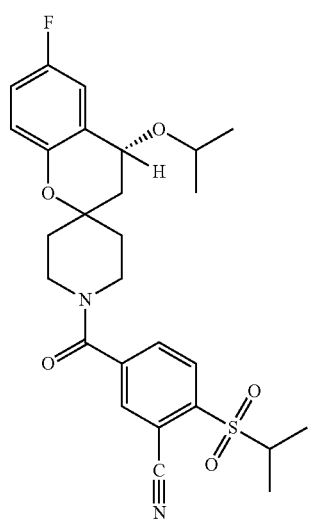 | |
| 74 | 77 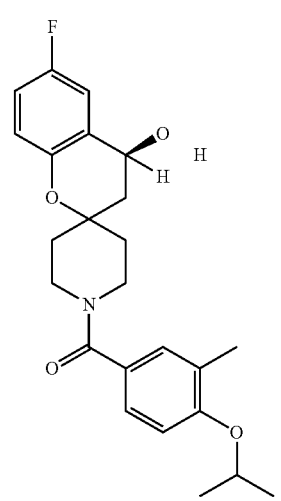 |
| 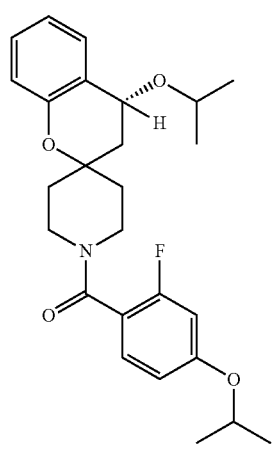 | |

| 78 | 81 |
|---|---|
| 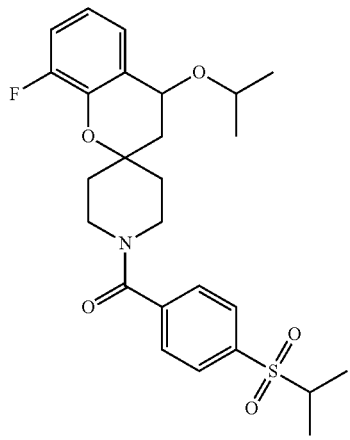 [SMILES: CC(C)OC1CC2(CCN(C(=O)c3ccc(S(=O)(=O)C(C)C)cc3)CC2)Oc2c(F)cccc21] | 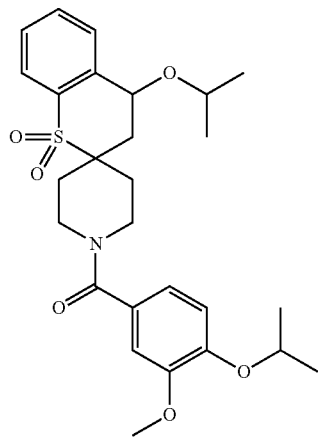 |
| 79 | 82 |
| 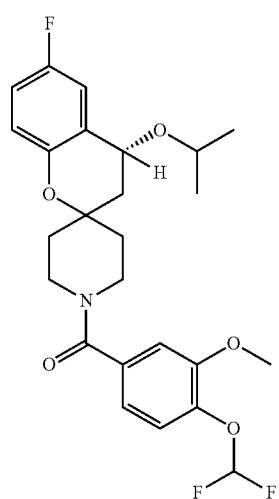 [SMILES: COc1cc(C(=O)N2CCC3(CC2)C[C@@H](OC(C)C)c2cc(F)ccc2O3)ccc1OC(F)F] | 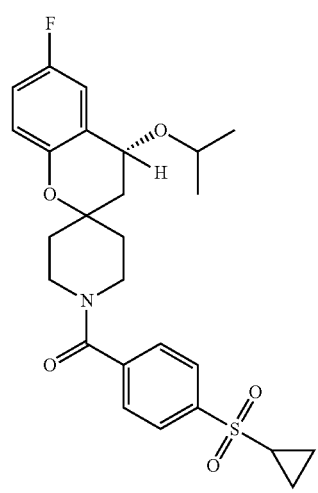 |
| 80 | 83 |
| 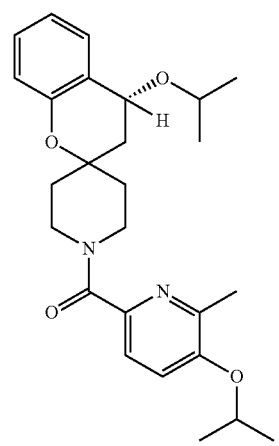 [SMILES: Cc1nc(C(=O)N2CCC3(CC2)C[C@@H](OC(C)C)c2ccccc2O3)ccc1OC(C)C] | 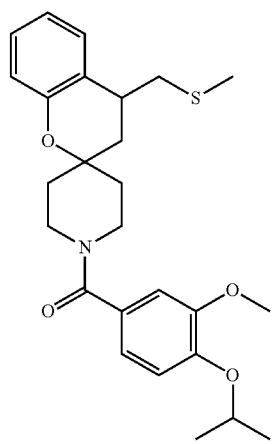 [SMILES: COc1cc(C(=O)N2CCC3(CC2)CC(CSC)c2ccccc2O3)ccc1OC(C)C] |

84
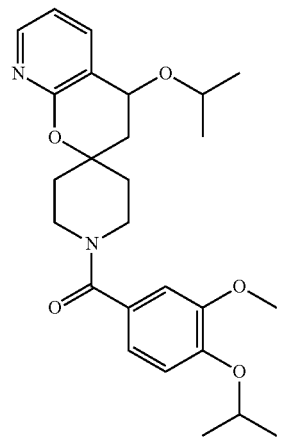
85
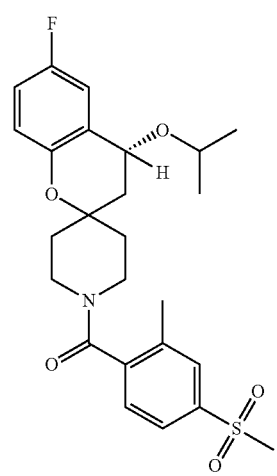 [SMILES: Cc1cc(S(C)(=O)=O)ccc1C(=O)N1CCC2(CC1)C[C@@H](OC(C)C)c1cc(F)ccc1O2]
86
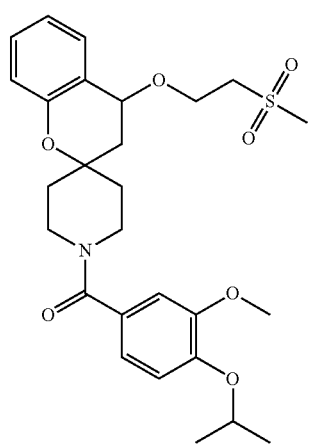 [SMILES: COc1cc(C(=O)N2CCC3(CC2)CC(OCCS(C)(=O)=O)c2ccccc2O3)ccc1OC(C)C]
87
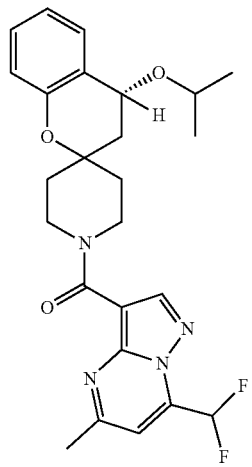 [SMILES: Cc1cc(C(F)F)n2ncc(C(=O)N3CCC4(CC3)C[C@@H](OC(C)C)c3ccccc3O4)c2n1]
88
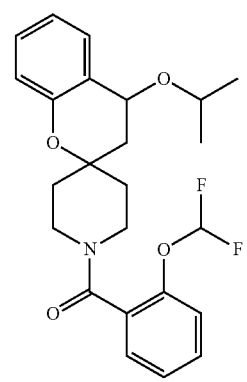 [SMILES: CC(C)OC1CC2(CCN(C(=O)c3ccccc3OC(F)F)CC2)Oc2ccccc21]
89
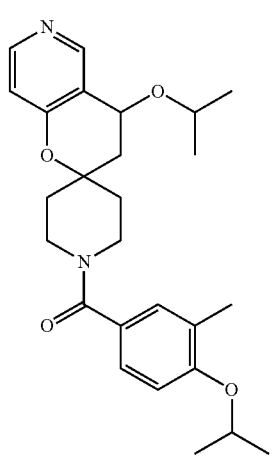 [SMILES: Cc1cc(C(=O)N2CCC3(CC2)CC(OC(C)C)c2cnccc2O3)ccc1OC(C)C]

| 90 | 93 |
|---|---|
| 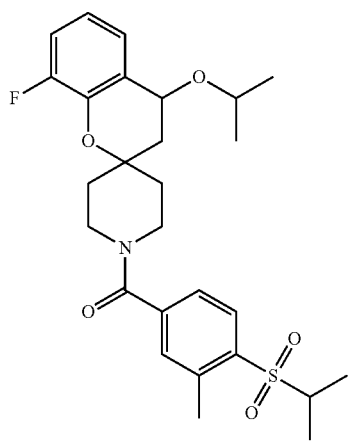 [SMILES: Cc1cc(C(=O)N2CCC3(CC2)CC(OC(C)C)c2cccc(F)c2O3)ccc1S(=O)(=O)C(C)C] | 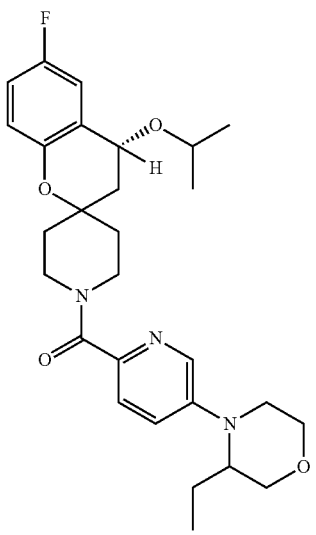 |
| 91 | 94 |
| 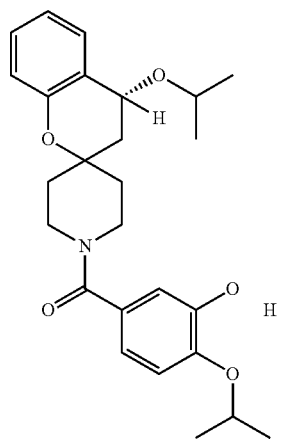 | 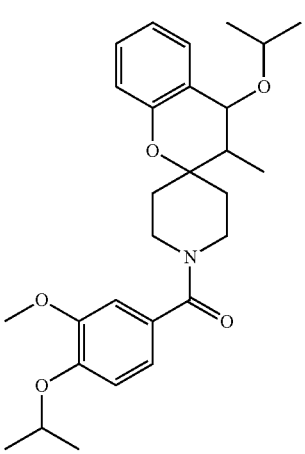 |
| 92 | 95 |
| 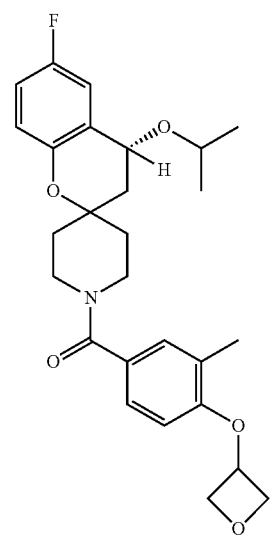 [SMILES: Cc1cc(C(=O)N2CCC3(CC2)C[C@@H](OC(C)C)c2cc(F)ccc2O3)ccc1OC1COC1] | 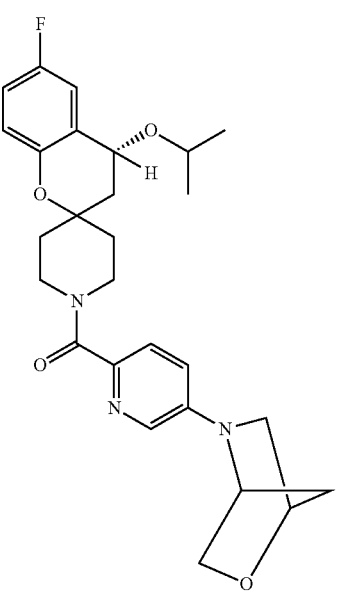 [SMILES: CC(C)O[C@@H]1CC2(CCN(C(=O)c3ccc(N4CC5CC4CO5)cn3)CC2)Oc2ccc(F)cc21] |

| 96 | 99 |
|---|---|
| 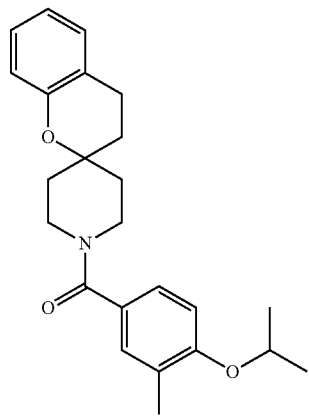 [SMILES: Cc1cc(C(=O)N2CCC3(CCc4ccccc4O3)CC2)ccc1OC(C)C] | 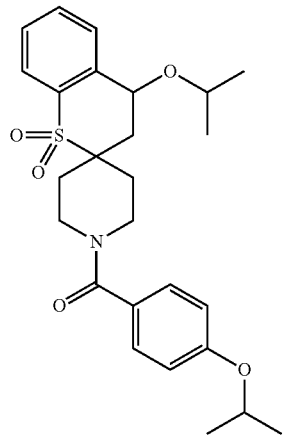 |
| 97 | 100 |
| 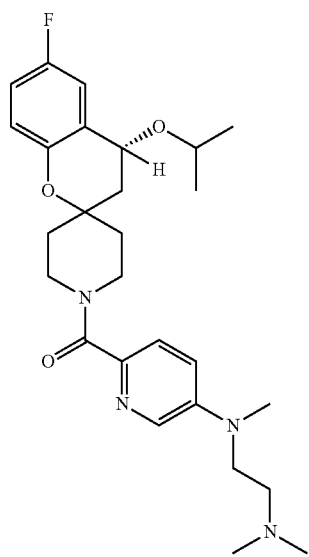 [SMILES: CC(C)O[C@@H]1CC2(CCN(C(=O)c3ccc(N(C)CCN(C)C)cn3)CC2)Oc2ccc(F)cc21] | 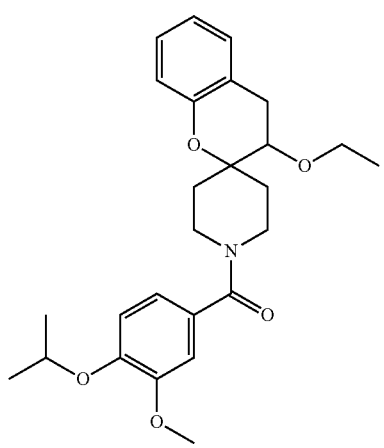 |
| 98 | 101 |
| 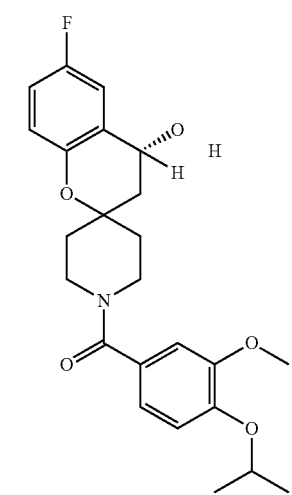 | 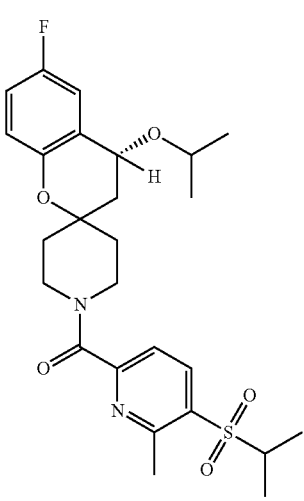 [SMILES: Cc1nc(C(=O)N2CCC3(CC2)C[C@@H](OC(C)C)c2cc(F)ccc2O3)ccc1S(=O)(=O)C(C)C] |

| 102 | 105 |
|---|---|
| 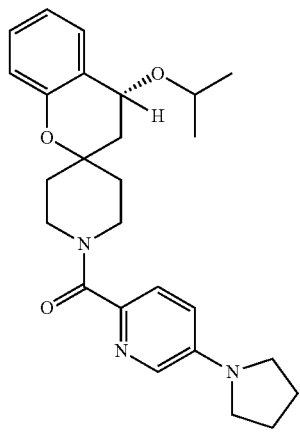 [SMILES: CC(C)O[C@@H]1CC2(CCN(C(=O)c3ccc(N4CCCC4)cn3)CC2)Oc2ccccc21] | 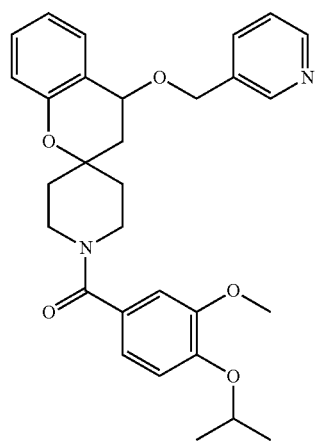 |
| 103 | 106 |
| 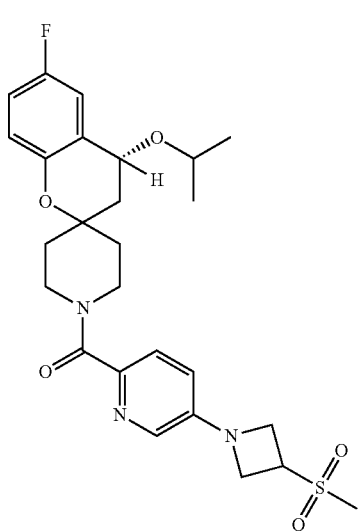 [SMILES: CC(C)O[C@@H]1CC2(CCN(C(=O)c3ccc(N4CC(S(C)(=O)=O)C4)cn3)CC2)Oc2ccc(F)cc21] | 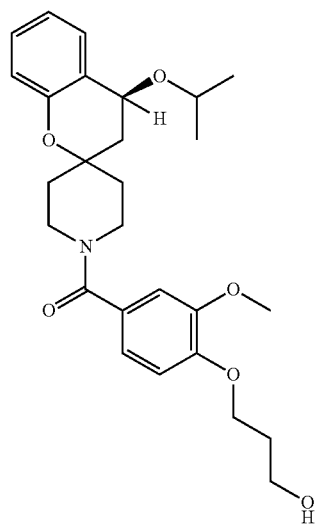 |
| 104 | 107 |
| 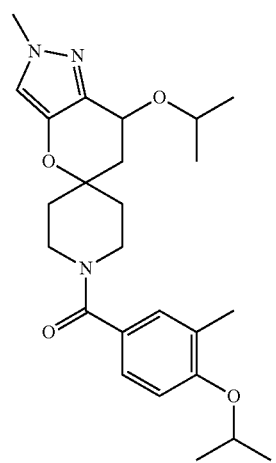 [SMILES: Cc1cc(C(=O)N2CCC3(CC2)CC(OC(C)C)c2nn(C)cc2O3)ccc1OC(C)C] | 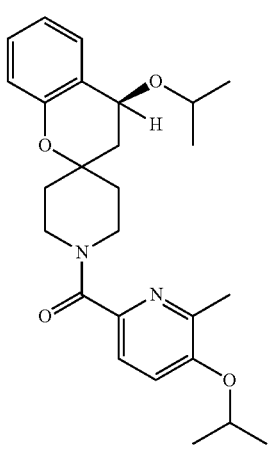 [SMILES: Cc1nc(C(=O)N2CCC3(CC2)C[C@H](OC(C)C)c2ccccc2O3)ccc1OC(C)C] |

108
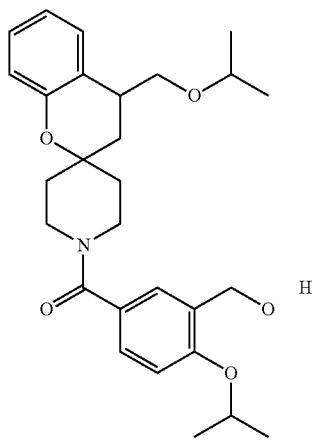
109
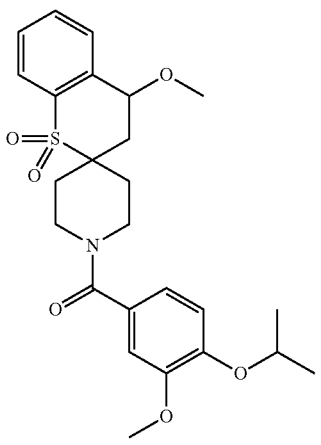 [SMILES: COc1cc(C(=O)N2CCC3(CC2)CC(OC)c2ccccc2S3(=O)=O)ccc1OC(C)C]
110
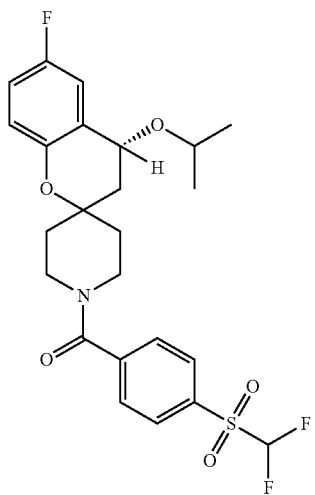 [SMILES: CC(C)O[C@@H]1CC2(CCN(C(=O)c3ccc(S(=O)(=O)C(F)F)cc3)CC2)Oc2ccc(F)cc21]
111
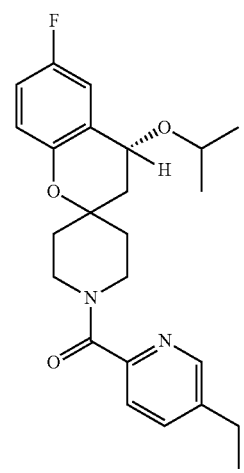 [SMILES: CCc1ccc(C(=O)N2CCC3(CC2)C[C@@H](OC(C)C)c2cc(F)ccc2O3)nc1]
112
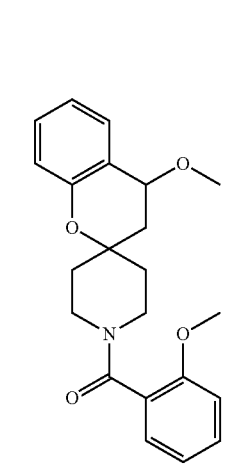 [SMILES: COc1ccccc1C(=O)N1CCC2(CC1)CC(OC)c1ccccc1O2]
113

114
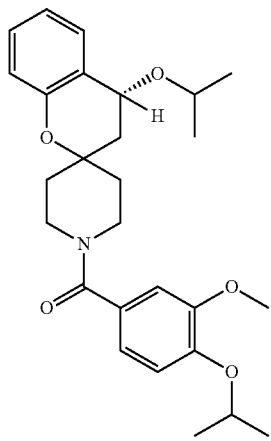
115
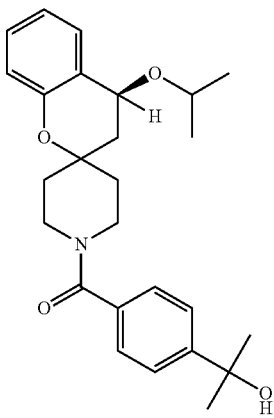 [SMILES: CC(C)O[C@H]1CC2(CCN(C(=O)c3ccc(C(C)(C)O)cc3)CC2)Oc2ccccc21]
116
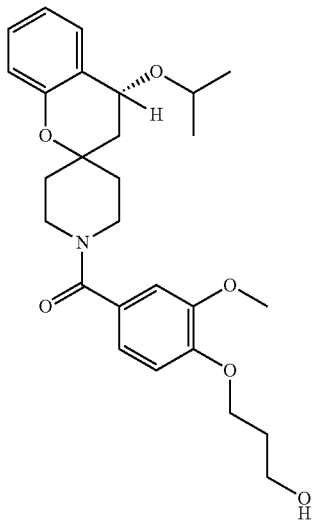 [SMILES: COc1cc(C(=O)N2CCC3(CC2)C[C@@H](OC(C)C)c2ccccc2O3)ccc1OCCCO]
117
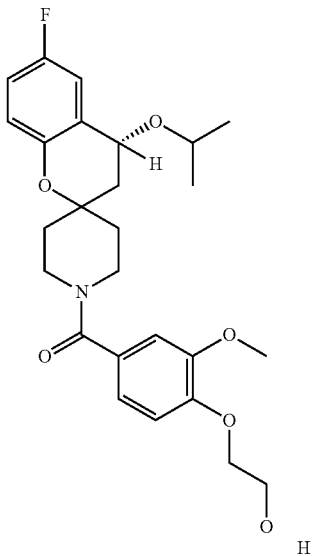
118
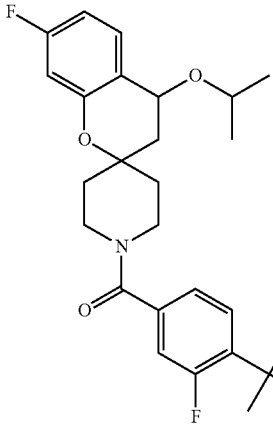
119
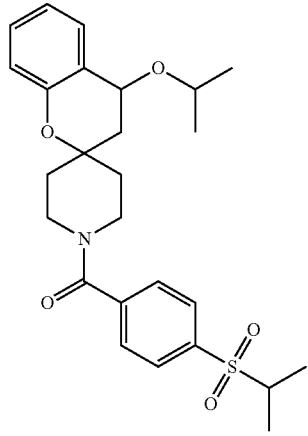 [SMILES: CC(C)OC1CC2(CCN(C(=O)c3ccc(S(=O)(=O)C(C)C)cc3)CC2)Oc2ccccc21]

| | |
|---|---|
| 120 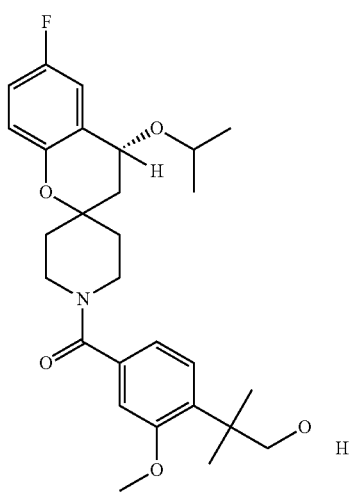 | 123 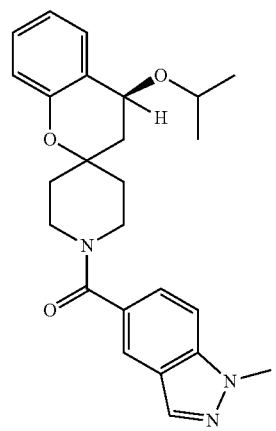 |
| 121 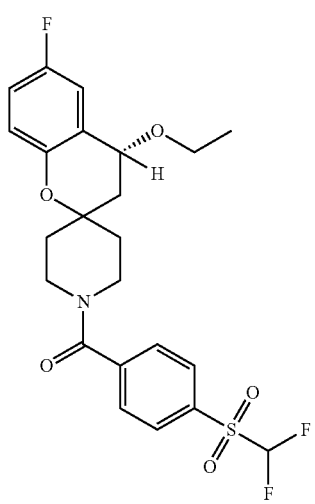 [SMILES: CCO[C@@H]1CC2(CCN(C(=O)c3ccc(S(=O)(=O)C(F)F)cc3)CC2)Oc2ccc(F)cc21] | 124 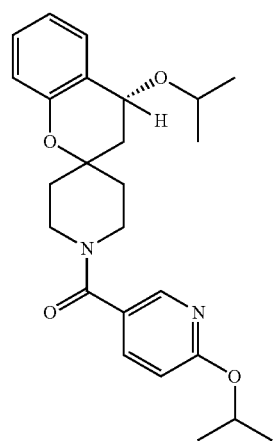 |
| 122 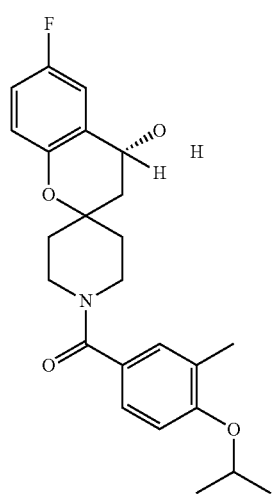 | 125 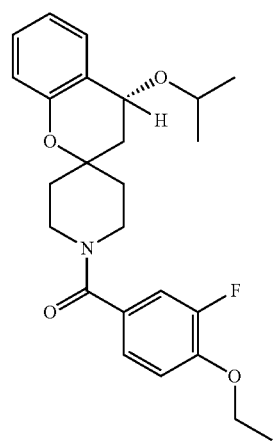 [SMILES: CCOc1ccc(C(=O)N2CCC3(CC2)C[C@@H](OC(C)C)c2ccccc2O3)cc1F] |

126
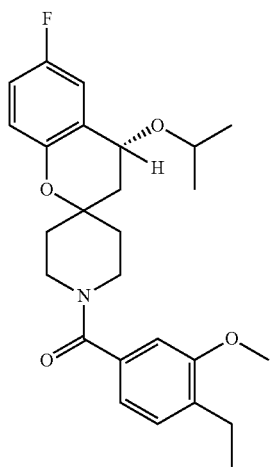 [SMILES: CCc1ccc(C(=O)N2CCC3(CC2)C[C@@H](OC(C)C)c2cc(F)ccc2O3)cc1OC]
127
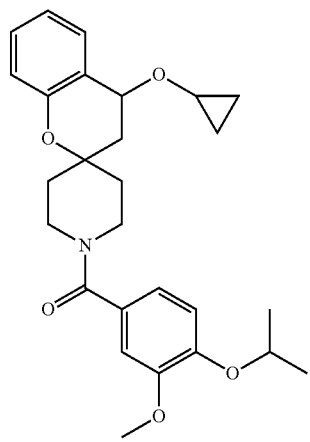 [SMILES: COc1cc(C(=O)N2CCC3(CC2)CC(OC2CC2)c2ccccc2O3)ccc1OC(C)C]
128
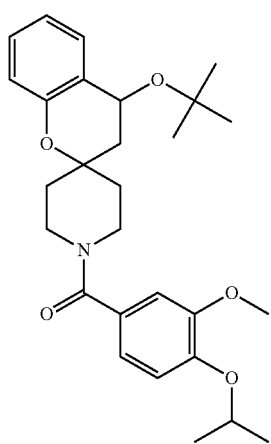 [SMILES: COc1cc(C(=O)N2CCC3(CC2)CC(OC(C)(C)C)c2ccccc2O3)ccc1OC(C)C]
129
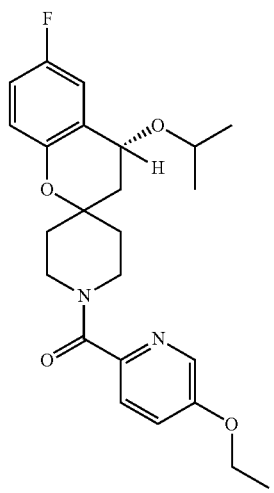 [SMILES: CCOc1ccc(C(=O)N2CCC3(CC2)C[C@@H](OC(C)C)c2cc(F)ccc2O3)nc1]
130
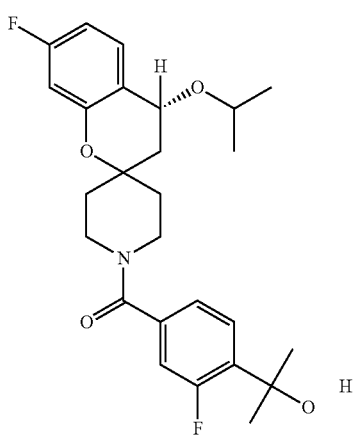
131
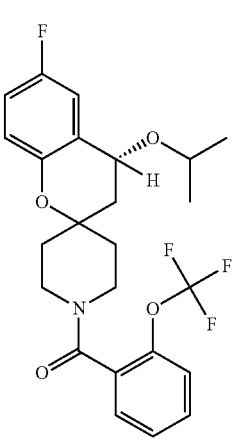 [SMILES: CC(C)O[C@@H]1CC2(CCN(C(=O)c3ccccc3OC(F)(F)F)CC2)Oc2ccc(F)cc21]

-continued
132
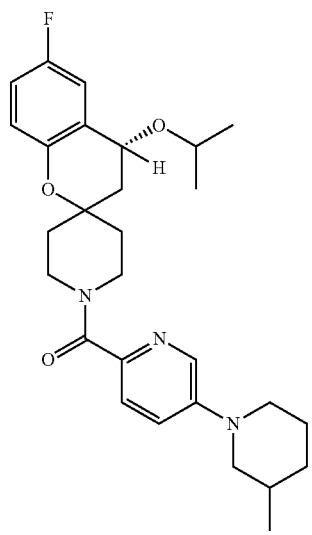 [SMILES: CC1CCCN(c2ccc(C(=O)N3CCC4(CC3)C[C@@H](OC(C)C)c3cc(F)ccc3O4)nc2)C1]
133
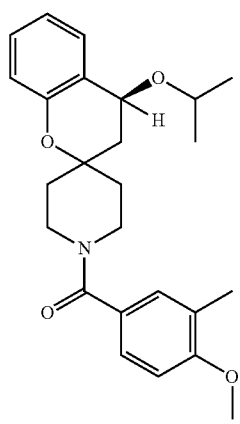 [SMILES: COc1ccc(C(=O)N2CCC3(CC2)C[C@H](OC(C)C)c2ccccc2O3)cc1C]
134
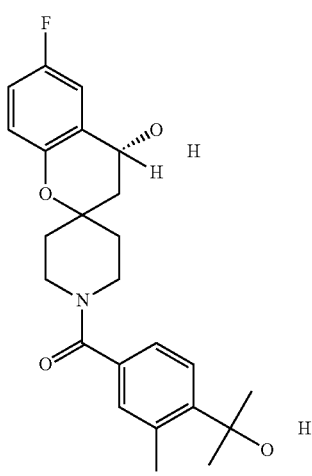
-continued
135
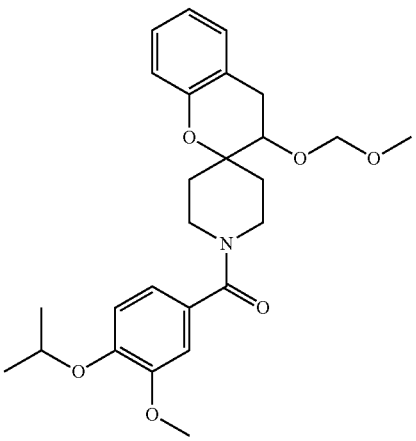 [SMILES: COCOC1Cc2ccccc2OC12CCN(C(=O)c1ccc(OC(C)C)c(OC)c1)CC2]
136
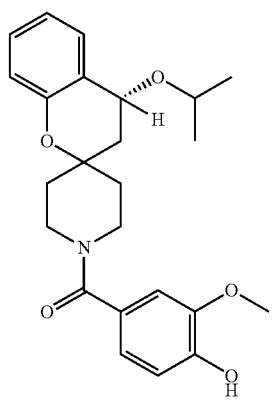 [SMILES: COc1cc(C(=O)N2CCC3(CC2)C[C@@H](OC(C)C)c2ccccc2O3)ccc1O]
137
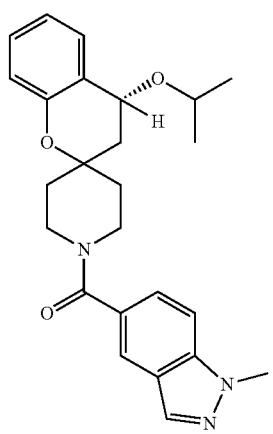 [SMILES: CC(C)O[C@@H]1CC2(CCN(C(=O)c3ccc4c(cnn4C)c3)CC2)Oc2ccccc21]

| 138 | 141 |
|---|---|
| 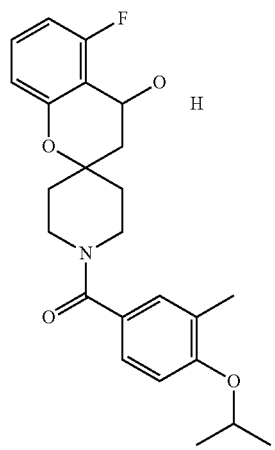 | 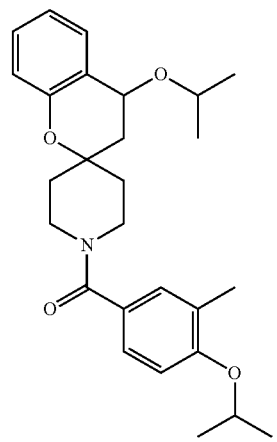 [SMILES: Cc1cc(C(=O)N2CCC3(CC2)CC(OC(C)C)c2ccccc2O3)ccc1OC(C)C] |
| 139 | 142 |
| 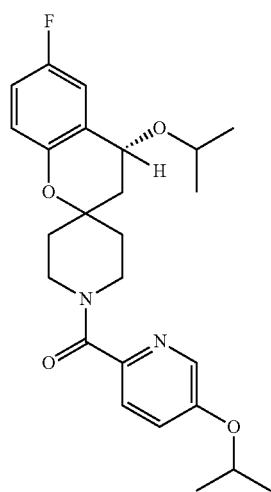 | 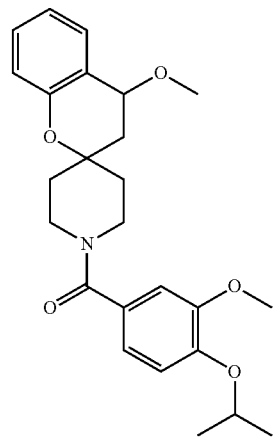 [SMILES: COc1cc(C(=O)N2CCC3(CC2)CC(OC)c2ccccc2O3)ccc1OC(C)C] |
| 140 | 143 |
| 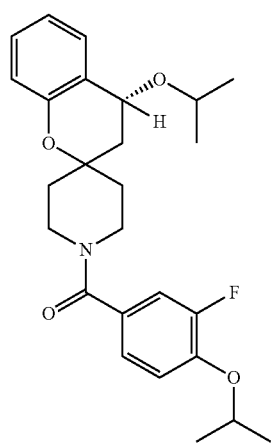 | 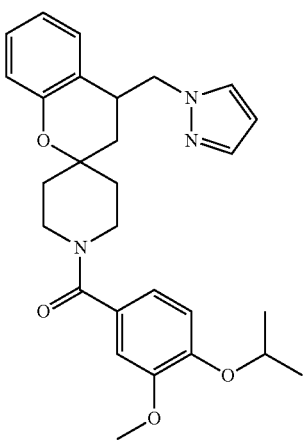 [SMILES: COc1cc(C(=O)N2CCC3(CC2)CC(Cn2cccn2)c2ccccc2O3)ccc1OC(C)C] |

| 77 -continued | 78 -continued |
|---|---|
| 144 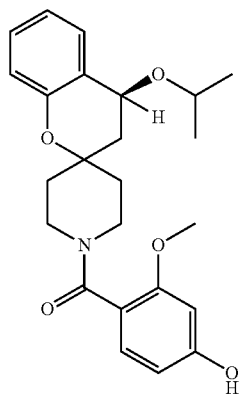 [SMILES: COc1cc(O)ccc1C(=O)N1CCC2(CC1)C[C@H](OC(C)C)c1ccccc1O2] | 147 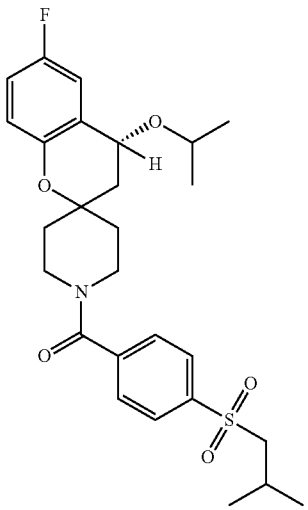 |
| 145 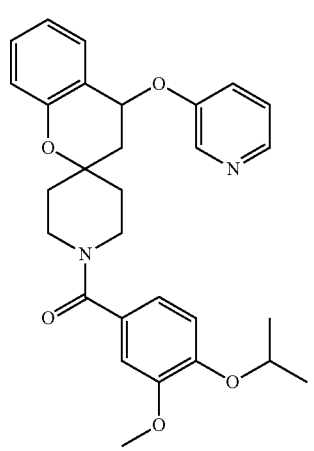 [SMILES: COc1cc(C(=O)N2CCC3(CC2)CC(Oc2cccnc2)c2ccccc2O3)ccc1OC(C)C] | 148 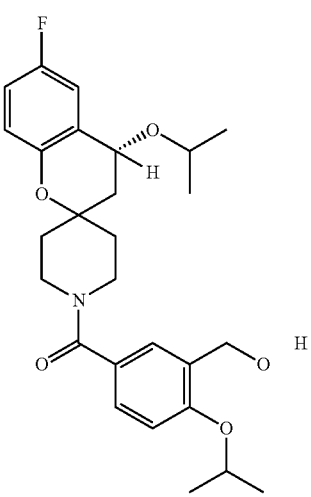 |
| 146 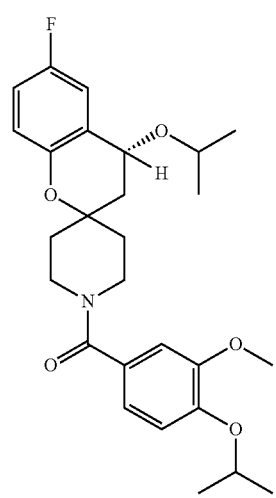 | 149 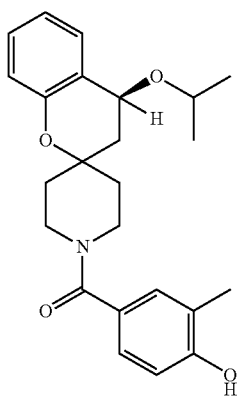 |

150
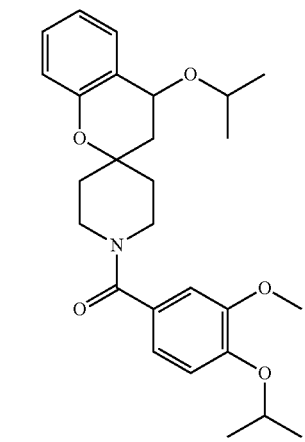
151
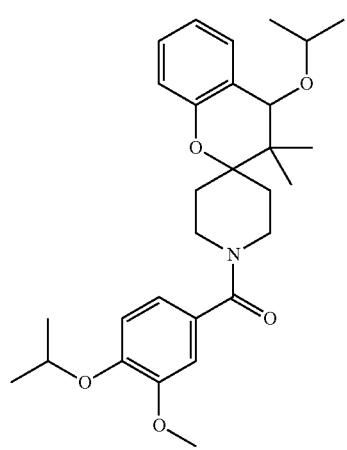 [SMILES: COc1cc(C(=O)N2CCC3(CC2)Oc2ccccc2C(OC(C)C)C3(C)C)ccc1OC(C)C]
152
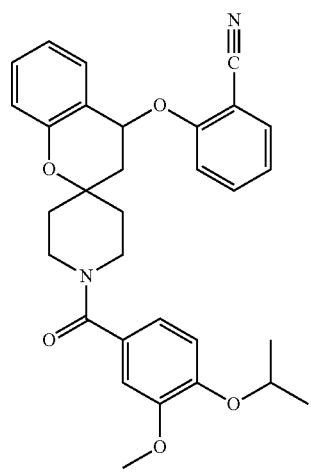 [SMILES: COc1cc(C(=O)N2CCC3(CC2)CC(Oc2ccccc2C#N)c2ccccc2O3)ccc1OC(C)C]
153
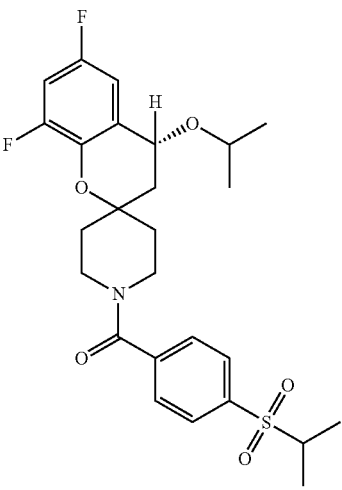 [SMILES: CC(C)O[C@@H]1CC2(CCN(C(=O)c3ccc(S(=O)(=O)C(C)C)cc3)CC2)Oc2c(F)cc(F)cc21]
154
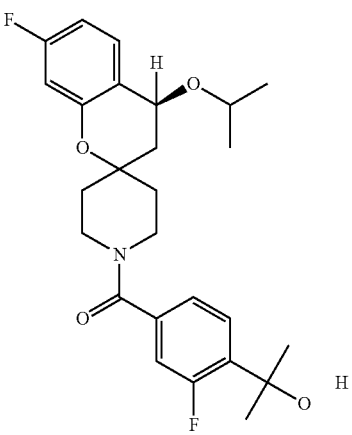
155
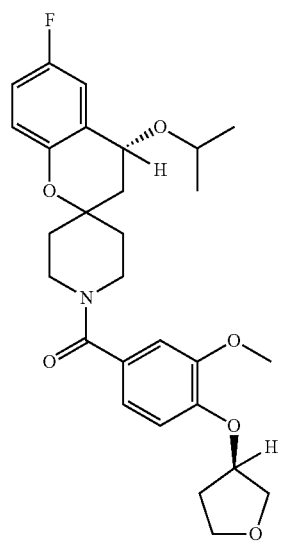 [SMILES: COc1cc(C(=O)N2CCC3(CC2)C[C@@H](OC(C)C)c2cc(F)ccc2O3)ccc1O[C@@H]1CCOC1]

| 156 | 159 |
|---|---|
| 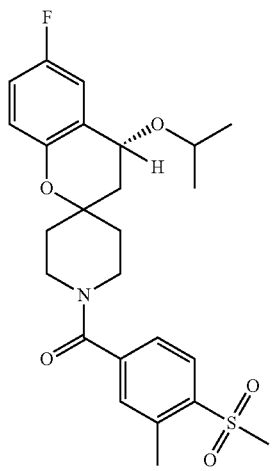 [SMILES: Cc1cc(C(=O)N2CCC3(CC2)C[C@@H](OC(C)C)c2cc(F)ccc2O3)ccc1S(C)(=O)=O] | 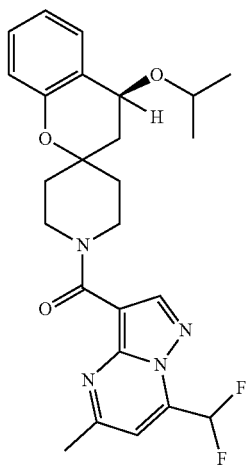 |
| 157 | 160 |
| 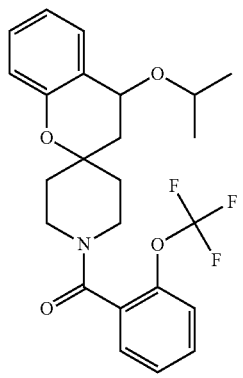 [SMILES: CC(C)OC1CC2(CCN(C(=O)c3ccccc3OC(F)(F)F)CC2)Oc2ccccc21] | 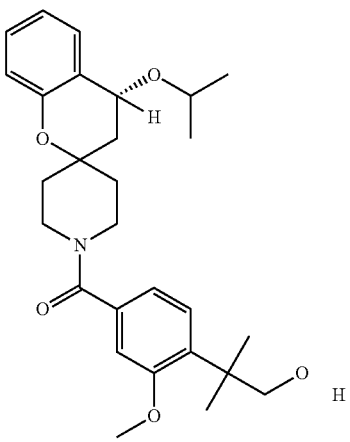 |
| 158 | 161 |
| 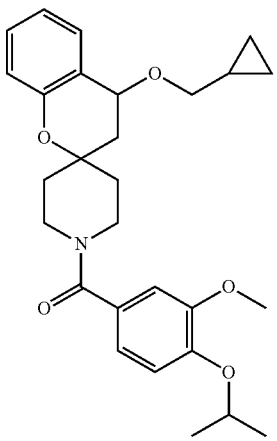 [SMILES: COc1cc(C(=O)N2CCC3(CC2)CC(OCC2CC2)c2ccccc2O3)ccc1OC(C)C] | 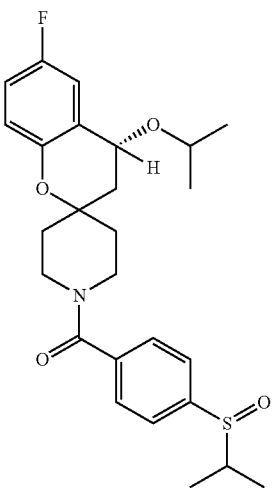 [SMILES: CC(C)O[C@@H]1CC2(CCN(C(=O)c3ccc(S(=O)C(C)C)cc3)CC2)Oc2ccc(F)cc21] |

| 162 | 165 |
|---|---|
| 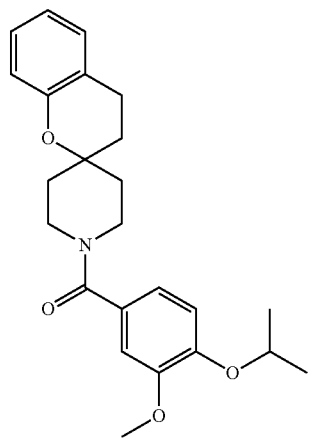 [SMILES: COc1cc(C(=O)N2CCC3(CCc4ccccc4O3)CC2)ccc1OC(C)C] | 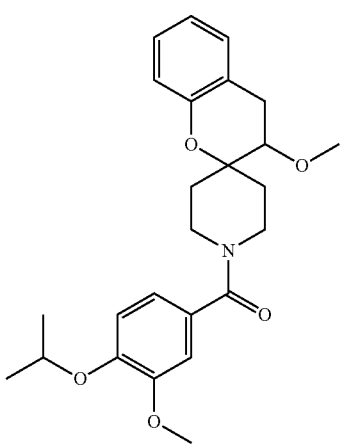 |
| 163 | 166 |
| 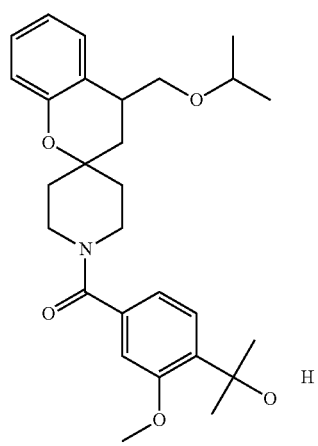 | 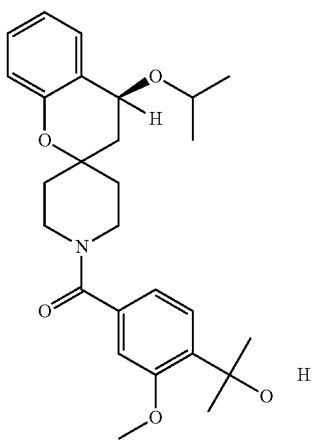 |
| 164 | 167 |
| 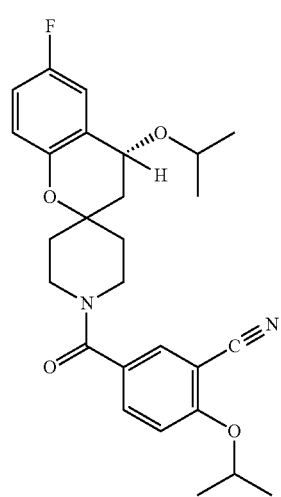 [SMILES: CC(C)Oc1ccc(C(=O)N2CCC3(CC2)C[C@@H](OC(C)C)c2cc(F)ccc2O3)cc1C#N] | 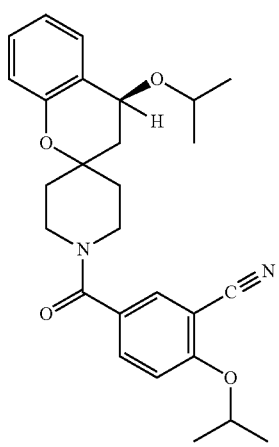 [SMILES: CC(C)Oc1ccc(C(=O)N2CCC3(CC2)C[C@H](OC(C)C)c2ccccc2O3)cc1C#N] |

168
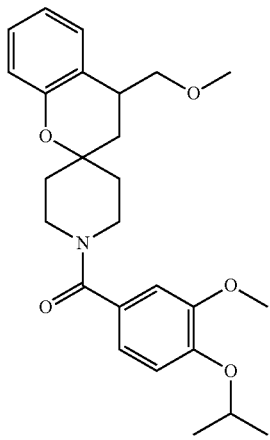
169
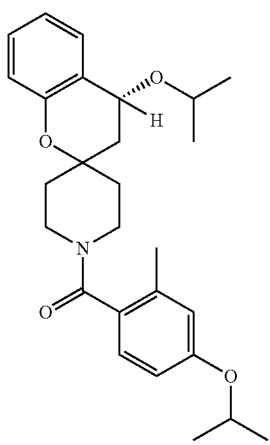
170
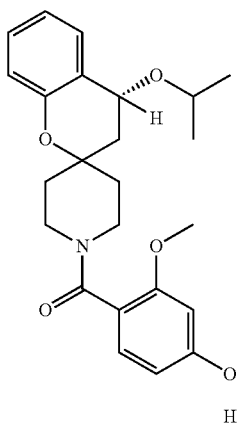
171
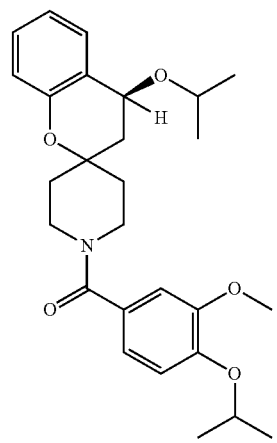 [SMILES: COc1cc(C(=O)N2CCC3(CC2)C[C@H](OC(C)C)c2ccccc2O3)ccc1OC(C)C]
172
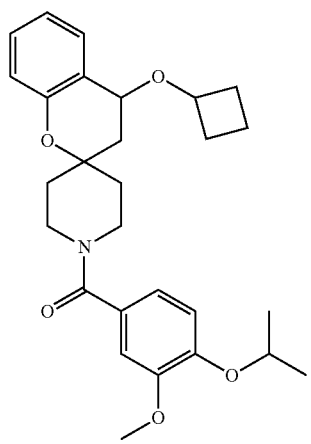 [SMILES: COc1cc(C(=O)N2CCC3(CC2)CC(OC2CCC2)c2ccccc2O3)ccc1OC(C)C]
173
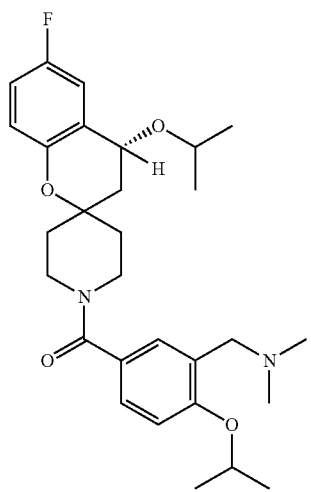 [SMILES: CC(C)Oc1ccc(C(=O)N2CCC3(CC2)C[C@@H](OC(C)C)c2cc(F)ccc2O3)cc1CN(C)C]

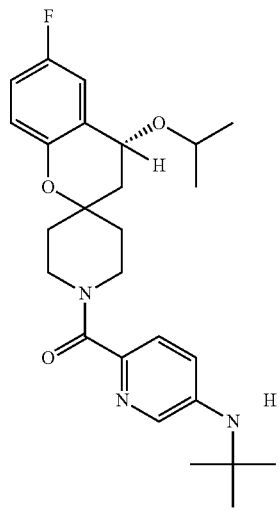

174

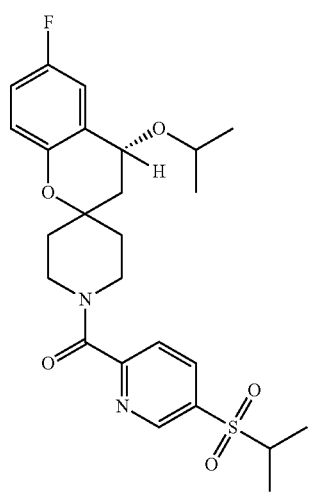

175

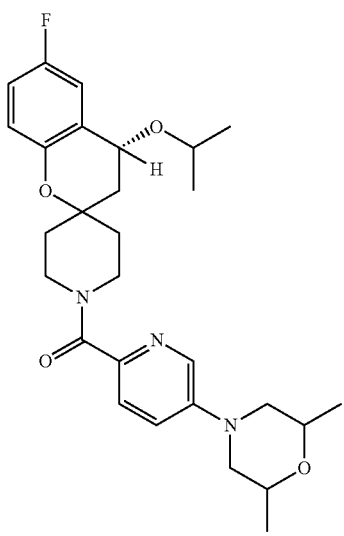 [SMILES: CC(C)O[C@@H]1CC2(CCN(C(=O)c3ccc(N4CC(C)OC(C)C4)cn3)CC2)Oc2ccc(F)cc21]

176

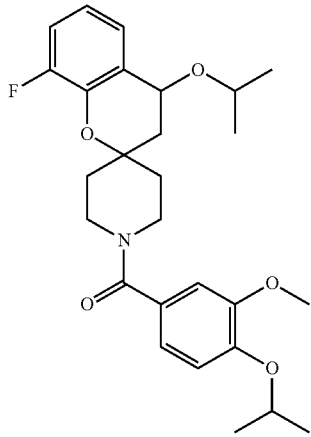 [SMILES: COc1cc(C(=O)N2CCC3(CC2)CC(OC(C)C)c2cccc(F)c2O3)ccc1OC(C)C]

177

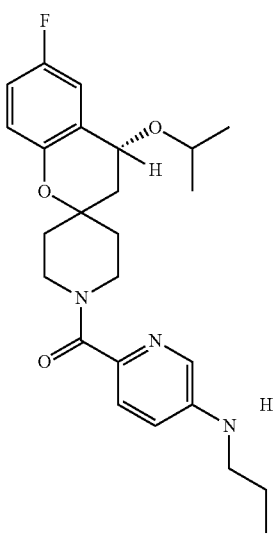

178

In another aspect, the invention features a pharmaceutical composition comprising a compound of the invention and a pharmaceutically acceptable carrier.

In another aspect, the invention features a method of inhibiting a voltage-gated sodium ion channel in:
a patient; or
a biological sample;
comprising administering to the patient, or contacting the biological sample, with a compound or composition of the invention. In another embodiment, the voltage-gated sodium ion channel is NaV 1.7.

In another aspect, the invention features a method of treating or lessening the severity of the pain in a subject afflicted with acute, chronic, neuropathic, or inflammatory pain, arthritis, migraine, cluster headaches, trigeminal neuralgia, herpatic neuralgia, general neuralgias, epilepsy or epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, stroke, cerebral ischemia, traumatic brain injury, amyotrophic lateral sclerosis, stress- or exercise induced angina, palpitations, hypertension, migraine, or abormal gastro-intestinal motility, comprising administering an effective amount of a compound or composition of the invention.

In another embodiment, the method is used for treating or lessening the severity of the pain in a subject afflicted with femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, abdominal pain; pancreatic; IBS pain; chronic and acute headache pain; migraine; tension headache, including, cluster headaches; chronic and acute neuropathic pain, post-herpatic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, abdominal pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn and trauma pain; acute intermittent pain, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); prostatitis; complex regional pain syndrome (CRPS), type I and type II; widespread pain, paroxysmal extreme pain, pruritis, tinnitus, or angina-induced pain.

The compounds of the invention may be prepared readily using the following methods. Illustrated below in Scheme 1 through Scheme 6 are methods for preparing the compounds of the invention.

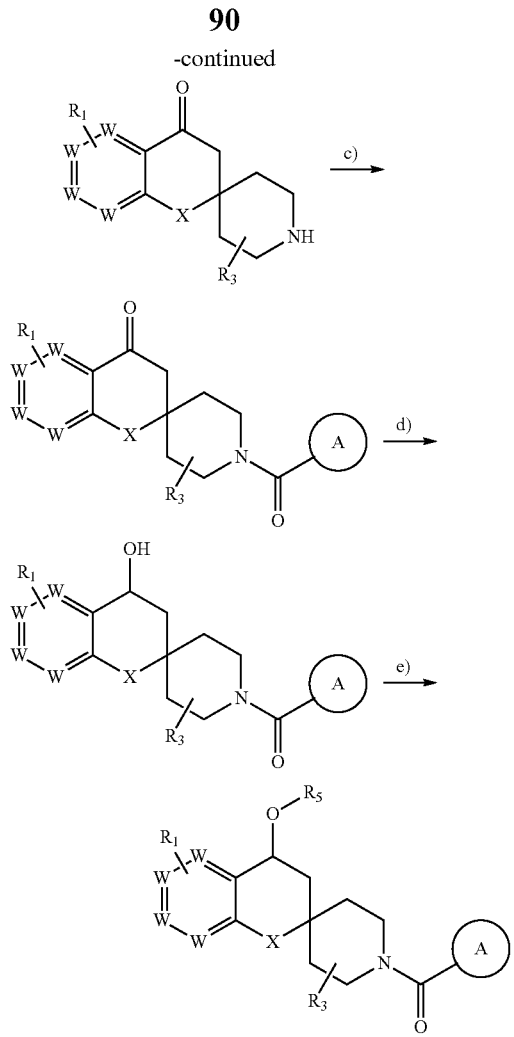

$R_4$ = benzyl, $CO_2Bn$, BOC, COAryl; LG = leaving group (i.e. Cl, Br, I, OMs, OTs).
a) pyrrolidine, MeOH; b) $R_4$ = BOC: acid (i.e. HCl), solvent (i.e. dioxane, iPrOH, EtOH, $CH_3CN$); $R_4$ = $CO_2Bn$: catalyst (i.e. Pd/C), $H_2$, solvent (i.e. iPrOH, EtOH);
c) A—$CO_2H$, coupling agent (i.e. HATU, EDCI, HBTU), base (i.e Et$_3$N, Et$_2$NiPr), solvent (i.e. DMF, $CH_2Cl_2$, $CH_3CN$) or A—C(O)Cl, base (i.e. Et$_3$N, Et$_2$NiPr), solvent (i.e. $CH_2Cl_2$); d) reducing agent (i.e. NaBH$_4$), solvent (i.e. MeOH, EtOH); e)$R_5$—LG, base (i.e. NaH, Et$_3$N), solvent (i.e. DMF, THF) or $R_5$—OH, acid (i.e. HCl) solvent (i.e. dioxane).

Scheme 1

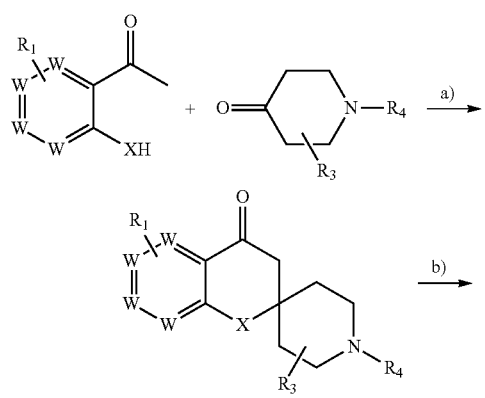

Scheme 2

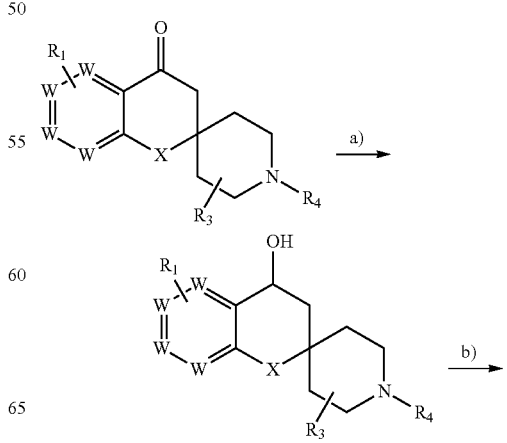

91

-continued

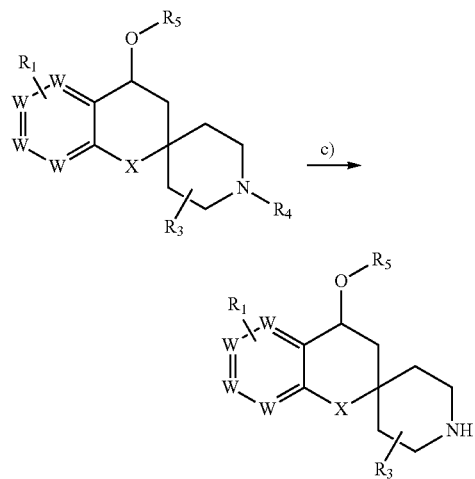

R$_4$ = benzyl, CO$_2$Bn, BOC; LG = leaving group (i.e. Cl, Br, I, OMs, OTs).
a) Reducing agent (i.e. NaBH$_4$), solvent (i.e. MeOH, EtOH); b) R$_2$—LG, base (i.e. NaH, Et$_3$N), solvent (i.e. DMF, THF) or R$_5$—OH, acid (i.e. HCl), solvent (i.e. dioxane) or catalyst (i.e. KAuCl$_4$), R$_5$—OH; c) R$_4$ = BOC: acid (i.e. HCl), solvent (i.e. dioxane, iPrOH, EtOH, CH$_3$CN) or R$_4$ = CO$_2$Bn: catalyst (i.e. Pd/C), H$_2$, solvent (i.e. iPrOH, EtOH).

Scheme 3

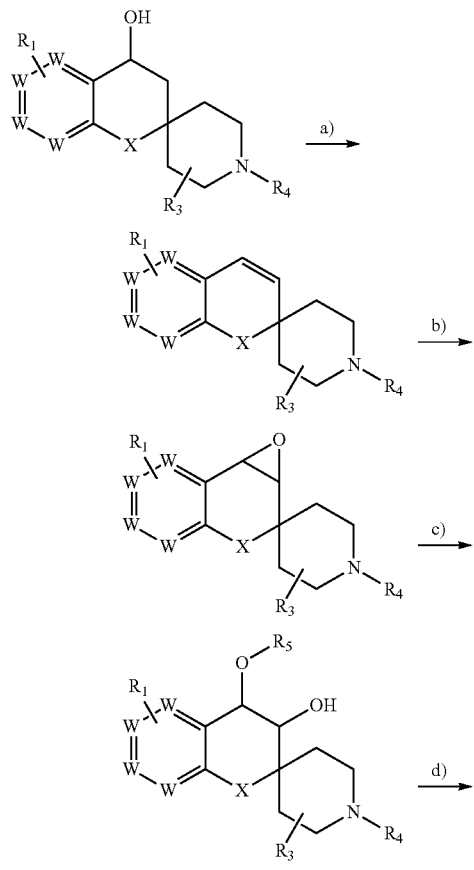

92

-continued

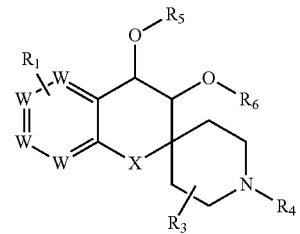

R$_4$ = benzyl, CO$_2$Bn, BOC, COAryl; LG = leaving group (i.e. Cl, Br, I, OMs, OTs).
a) acid (i.e. pTsOH), solvent (i.e. dioxane); b) epoxidizing agent (i.e. mCPBA, MeReO$_3$/H$_2$O$_2$/pyridine), solvent (i.e CH$_2$Cl$_2$); c) acid or Lewis Acid catalyst (i.e. InCl$_3$), R$_5$—OH; d) R$_6$—LG, base (i.e. NaH), solvent (i.e. DMF, THF).

Scheme 4

-continued

R$_4$ = benzyl, CO$_2$Bn, BOC, COAryl; LG = leaving group (i.e. Cl, Br, I, OMs, OTs).
a) catalyst (i.e. ZnI), solvent (i.e. benzene); b) R$_4$ = BOC: acid (i.e. HCl), solvent (i.e. dioxane, EtOH, iPrOH, CH$_3$CN); R$_4$ = CO$_2$Bn: catalyst (i.e. Pd/C), H$_2$, solvent (i.e. iPrOH, EtOH); c) A—CO$_2$H, coupling agent (i.e. HATU, EDCI, HBTU), base (i.e Et$_3$N, Et$_2$NiPr), solvent (i.e. DMF, CH$_2$Cl$_2$, CH$_3$CN) or A—C(O)Cl, base (i.e. Et$_3$N, Et$_2$NiPr), solvent (i.e. CH$_2$Cl$_2$); d) base (i.e. NaH, LiHMDS),R$_2$—LG, solvent (i.e. DMF, THF); e) catalyst (i.e. Pd/C), H$_2$, solvent (i.e. MeOH, EtOH, iPrOH).

Scheme 5

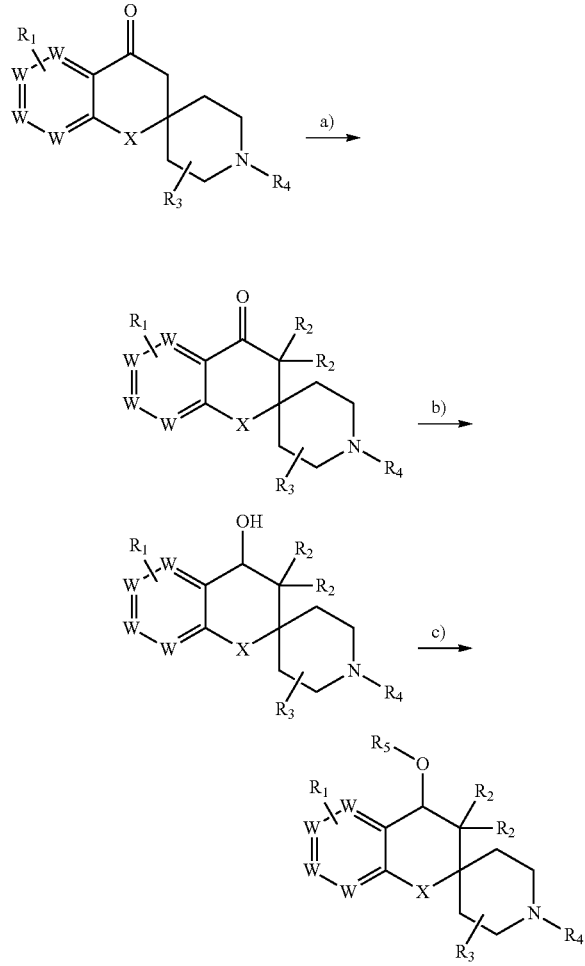

R$_4$ = benzyl, CO$_2$Bn, BOC, COAr; LG = leaving group (i.e. Cl, Br, I, OMs, OTs).
a) base (i.e. LiHMDS), R$_2$—LG, solvent (i.e. THF, DMF); b) Reducing agent (i.e. NaBH$_4$), solvent (i.e. MeOH, EtOH); c) acid (i.e. HCl), R$_5$—OH.

Scheme 6

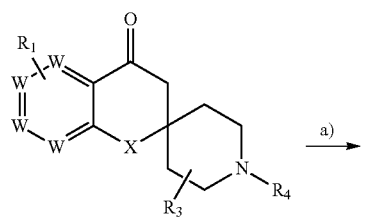

-continued

R$_4$ = benzyl, CO$_2$Bn, BOC, COAr.
a) base (i.e. LiHMDS), solvent (i.e. THF), PhNTf$_2$; b) catalyst (i.e. Pd(OAc)$_2$, Pd(c-hex$_2$PhP)(tBu$_3$P)Cl$_2$), base (i.e. Cs$_2$CO$_3$, K$_2$CO$_3$), solvent (i.e. dioxane, water, DMF), R$_2$—B(OR)$_2$ or R$_2$—BF$_3$K; c) catalyst (i.e. Pd/C), H$_2$, solvent (i.e. AcOH, MeOH, EtOH, iPrOH).

Uses, Formulation and Administration

Pharmaceutically Acceptable Compositions

As discussed above, the invention provides compounds that are inhibitors of voltage-gated sodium ion channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of invention can exist in free form for treatment, or where appropriate, as a pharmaceutically acceptable derivative thereof. According to the invention, a pharmaceutically acceptable derivative includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel.

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, dipolar disorder, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof.

In certain embodiments, a method of treatment or lessening the severity of stroke, cerebral ischemia, traumatic brain injury, amyotrophic lateral sclerosis, stress- or exercise induced angina, palpitations, hypertension, migraine, or abormal gastro-intestinal motility is provided comprising administering an effective amount of a compound, or a pharmaceutically acceptable composition comprising a compound to a subject in need thereof.

In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitus or cancer pain is provided comprising administering an effective amount of a compound or a pharmaceutically acceptable composition to a subject in need thereof.

In certain embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic and acute headache pain; migraine; tension headache, including, cluster headaches; chronic and acute neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; postmastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/ exercise pain; acute visceral pain, including, abdominal pain; pyelonephritis; appendicitis; cholecystitis; intestinal obstruction; hernias; etc; chest pain, including, cardiac Pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain including sinusitis pain, dental pain; multiple sclerosis (MS) pain; pain in depression; leprosy pain; behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis; complex regional pain syndrome (CRPS), type I and type II; angina-induced pain is provided, comprising administering an effective amount of a compound or a pharmaceutically acceptable composition to a subject in need thereof.

In certain embodiments of the invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels. In one embodiment, the compounds and compositions of the invention are inhibitors of one or more of NaV 1.1, NaV 1.2, NaV 1.3, NaV1.4, NaV1.5, NaV1.6, NaV1.7, NaV1.8, or NaV1.9, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease, condition, or disorder. When activation or hyperactivity of NaV1.1, NaV1.2, NaV1.3, NaV1.4, NaV1.5, NaV1.6, NaV1.7, NaV1.8, or NaV1.9 is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder". Accordingly, in another aspect, the invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, or NaV1.9 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, or NaV1.9 may be assayed according to methods described generally in the Examples herein, or according to methods available to one of ordinary skill in the art.

In certain exemplary embodiments, compounds of the invention are useful as inhibitors of NaV1.7 and/or NaV1.8.

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) an Hi antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine, lamotrigine, topiratmate or valproate;

(12) a tachykinin (NK) antagonist, particularly an NK-3, NK-2 or NK-I antagonist, e.g. ([alpha]R,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g. oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin) or antagonist (e.g. capsazepine);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HTi B/I D agonist such as eletriptan, sumatriptan, naratriptan, zolmitriptan or rizatriptan;

(22) a 5-HT2A receptor antagonist such as RH-alpha-(2,3-dimethoxy-phenyl)-1-[2-(4-fluorophenylethyl)]-4-piperidinemethanol (MDL-100907);

(23) a cholinergic (nicotinic) analgesic, such as isproniclidine (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®;

(25) a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7//-pyrazolo[4,3-<i]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-<i]pyrimidm-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide; an alpha-2-delta ligand such as gabapentin, pregabalin, 3-methyl gabapentin, (1[α],3[α],5[α])(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(26) a cannabinoid;

(27) metabotropic glutamate subtype 1 receptor (mGluRl) antagonist;

(28) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(29) a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

(30) a dual serotonin-noradrenaline reuptake inhibitor, such as venlafaxine, venlafaxine metabolite O-desmethyl-venlafaxine, clomipramine, clomipramine metabolite desmethylclomipramine, duloxetine, milnacipran and imipramine;

(31) an inducible nitric oxide synthase (iNOS) inhibitor such as S-[2-[(1-iminoethyl)amino]ethyl]-L-homocysteine, 5-[2-[(1-iminoethyl)-amino]ethyl]-4,4-dioxo-L-cysteine, 5-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-4-chloro-5-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl] phenyl]thiophene-2-carboxamidine, or guanidinoethyldisulfide;

(32) an acetylcholinesterase inhibitor such as donepezil;

(33) a prostaglandin E2 subtype 4 (EP4) antagonist such as 7V-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl]benzoic acid;

(34) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870,

(35) a 5-lipoxygenase inhibitor, such as zileuton, 6-[(3-fluoro-5-[4-methoxy-3,4,5,6-tetrahydro-2H-pyran-4-yl]) phenoxy-methyl]-1-methyl-2-quinolone (ZD-2138), or 2,3,5-trimethyl-6-(3-pyridylmethyl),1,4-benzoquinone (CV-6504); (36) a sodium channel blocker, such as lidocaine;

(36) a 5-HT3 antagonist, such as ondansetron; and the pharmaceutically acceptable salts and solvates thereof.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, or NaV1.9, activity in a biological sample or a subject, which method comprises administering to the subject, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, or NaV1.9, activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

General Methods.

$^1$H NMR (400 MHz) and $^{13}$C NMR (100 MHz) spectra were obtained as solutions in deuterioacetonitrile (CD$_3$CN), chloroform-d (CDCl$_3$) or dimethyl sulfoxide-D$_6$ (DMSO). Mass spectra (MS) were obtained using an Applied Biosystems API EX LC/MS system equipped with a Phenomenex 50×4.60 mm luna-5µ C18 column. The LC/MS eluting system was 10-99% acetonitrile in H$_2$O with 0.035% v/v trifluoroacetic acid or 5 mM HCl using a 3, 4, 5, 6 or 15 minute linear gradient and a flow rate of 4.0 mL/minute. Silica gel chromatography was performed using silica gel-60 with a particle size of 230-400 mesh. Pyridine, dichloromethane (CH$_2$Cl$_2$), tetrahydrofuran (THF), dimethylformamide (DMF), acetonitrile (ACN), methanol (MeOH), and 1,4-dioxane were from Aldrich Sure-Seal bottles kept under dry nitrogen. All reactions were stirred magnetically unless otherwise noted.

Spiro[chromane-2,4'-piperidine]-4-one hydrogen chloride

Step 1: tert-Butyl 4-oxospiro[chromane-2,4'-piperidine]-1'-carboxylate

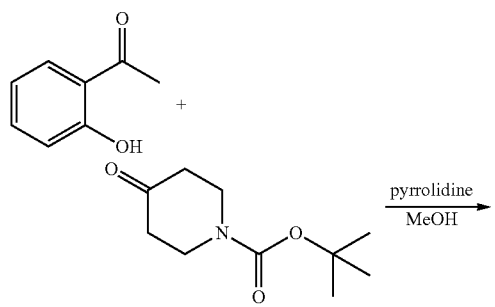

-continued

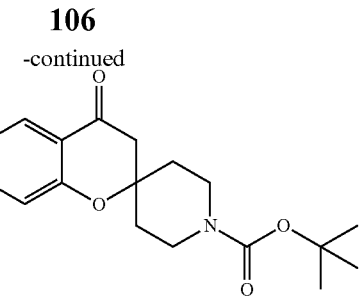

To a solution of tert-butyl 4-oxopiperidine-1-carboxylate (93.67 g, 470.1 mmol) in pyrrolidine (56.2 mL, 673.3 mmol) and anhydrous MeOH (112 mL) was added 1-(2-hydroxyphenyl)ethanone (56.36 mL, 468.2 mmol). The reaction mixture was stirred at 80° C. for 2.5 hours. Methanol was removed under reduced pressure. The resulting residue was dissolved in EtOAc (150 mL), washed with 1N HCl (150 mL) and brine (2×100 mL). The organic layer was dried over sodium sulfate, filtered and concentrated under reduced pressure to give a yellow oil. The oil was diluted with hexanes (400 mL) and the mixture was heated at 60° C. until in solution. Once dissolved, the solution was allowed to cool to ambient temperature. The crystals were collected via vacuum filtration and were rinsed with hexanes to obtain tert-butyl 4-oxospiro[chromane-2,4'-piperidine]-1'-carboxylate (105 g, 70%) as light yellow solid. ESI-MS m/z calc. 317.2, found 318.2 (M+1)$^+$; Retention time: 2.54 minutes (4 min run). $^1$H NMR (400 MHz, CDCl$_3$) δ 7.87 (dd, J=7.8, 1.6 Hz, 1H), 7.53-7.46 (m, 1H), 7.05-6.96 (m, 2H), 3.88 (d, J=13.2 Hz, 2H), 3.27-3.16 (m, 2H), 2.72 (s, 2H), 2.03 (d, J=13.6 Hz, 2H), 1.66-1.56 (m, 2H), 1.46 (s, 9H).

The following compounds were prepared using the procedure reported above:

| Ketone | Product |
|---|---|
| 1-(2-fluoro-6-hydroxyphenyl)ethanone | tert-butyl 5-fluoro-4-oxospiro[chroman-2,4'-piperidine]-1'-carboxylate |
| 1-(5-bromo-2-hydroxyphenyl)ethanone | tert-butyl 6-bromo-4-oxospiro[chroman-2,4'-piperidine]-1'-carboxylate |

Step 2: Spiro[chromane-2,4'-piperidine]-4-one hydrogen chloride

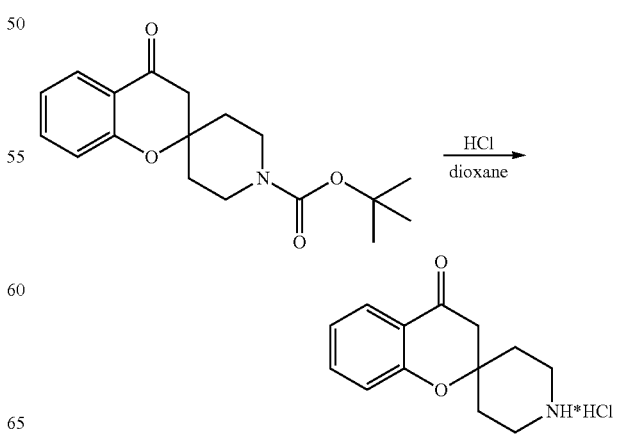

To a 1 L flask was added tert-butyl 4-oxospiro[chromane-2,4'-piperidine]-1'-carboxylate (30.0 g, 94.5 mmol) and 1,4-dioxane (200 mL). HCl (118 mL of 4.0 M, 472 mmol) in dioxane was added and the mixture was allowed to stir overnight at ambient temperature. The mixture was concentrated to give spiro[chromane-2,4'-piperidine]-4-one hydrogen chloride (23.9 g, 99%). ESI-MS m/z calc. 217.1, found 218.2 (M+1)$^+$; Retention time: 0.42 minutes (3 min run).

The following compound was prepared using the procedure reported above:
6-bromospiro[chroman-2,4'-piperidin]-4-one.

Spiro[chromane-2,4'-piperidine]-4-one

Step 1: Benzyl 4-oxospiro[chromane-2,4'-piperidine]-1'-carboxylate

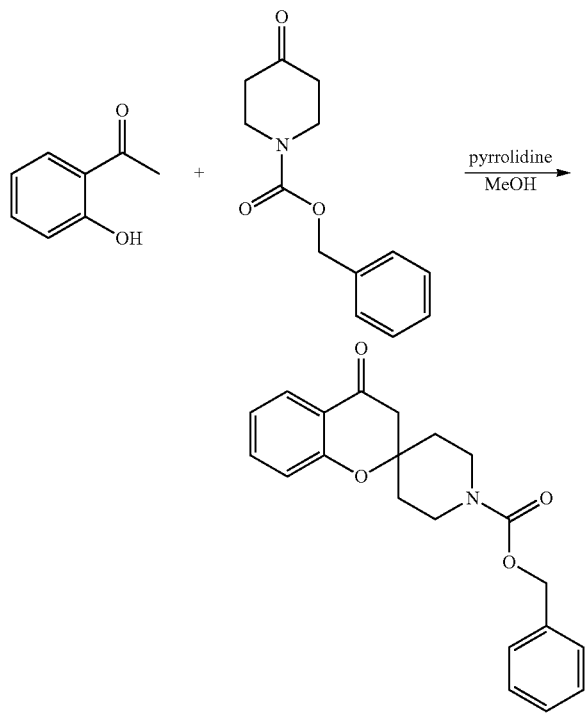

A flask was charged with 1-(2-hydroxyphenyl)ethanone (100 g, 735 mmol), benzyl 4-oxopiperidine-1-carboxylate (145 mL, 735 mmol), pyrrolidine (123 mL, 1.47 mol) and methanol (24 mL) which provided a clear amber solution. The mixture was heated at 80° C. for 20 h. The dark solution was cooled to 25° C., diluted with ethyl acetate (1000 mL) and partitioned with 1M HCl (800 mL). The aqueous layer was drained and the residual organic layer was washed with 1M HCl (2×800 mL), water (800 mL), saturated sodium chloride solution (800 mL), dried over magnesium sulfate and filtered. The filtrate was concentrated under reduced pressure to provide an amber oil. The residue was purified by silica gel chromatography eluting with a gradient of 0% to 30% ethyl acetate in hexane. The desired product fractions were combined and evaporated under reduced pressure to provide benzyl 4-oxospiro[chromane-2,4'-piperidine]-1'-carboxylate (207 g, 80%). ESI-MS m/z calc. 351.2, found 352.3 (M+1)$^+$; Retention time: 2.41 minutes (3 min run). $^1$H NMR (400 MHz, CDCl$_3$) δ 7.86 (d, J=7.8 Hz, 1H), 7.49 (dd, J=11.3, 4.2 Hz, 1H), 7.40-7.27 (m, 5H), 7.00 (dd, J=15.4, 7.8 Hz, 2H), 5.14 (s, 2H), 3.98 (s, 2H), 3.29 (s, 2H), 2.71 (s, 2H), 2.12-1.96 (m, 2H), 1.68-1.54 (m, 2H).

The following compounds were prepared using the procedure reported above:

| Ketone | Product |
| --- | --- |
| 1-(5-fluoro-2-hydroxyphenyl)ethanone | benzyl 6-fluoro-4-oxospiro[chroman-2,4'-piperidine]-1'-carboxylate |
| 1-(3,5-difluoro-2-hydroxyphenyl)ethanone | benzyl 6,8-difluoro-4-oxospiro[chroman-2,4'-piperidine]-1'-carboxylate |
| 1-(3-fluoro-2-hydroxyphenyl)ethanone | benzyl 8-fluoro-4-oxospiro[chroman-2,4'-piperidine]-1'-carboxylate |
| 1-(4-fluoro-2-hydroxyphenyl)ethanone | benzyl 7-fluoro-4-oxospiro[chroman-2,4'-piperidine]-1'-carboxylate |

Step 2: Spiro[chromane-2,4'-piperidine]-4-one

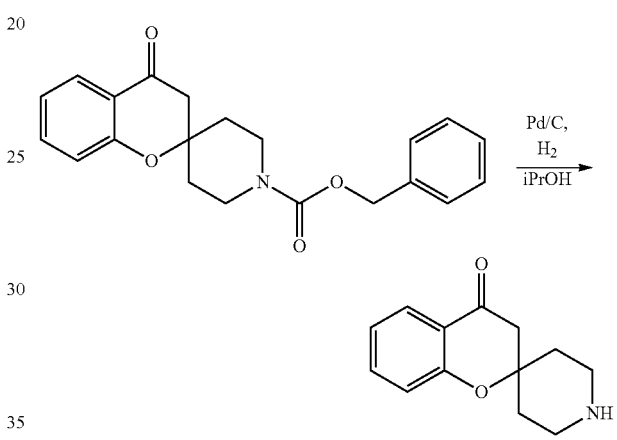

To benzyl 4-oxospiro[chromane-2,4'-piperidine]-1'-carboxylate (3.50 g, 9.96 mmol) was added i-PrOH (39 mL) and 10% Pd/C (530 mg, 0.498 mmol). A hydrogen balloon was attached and the reaction was allowed to stir overnight at 25° C. The mixture was filtered and the filtrate was evaporated to give spiro[chromane-2,4'-piperidine]-4-one (2.11 g, 98%). ESI-MS m/z calc. 217.1, found 218.2 (M+1)$^+$; Retention time: 0.41 minutes (3 min run).

The following compounds were prepared using the procedure reported above:
6-fluorospiro[chroman-2,4'-piperidin]-4-one;
6,8-difluorospiro[chroman-2,4'-piperidin]-4-one;
8-fluorospiro[chroman-2,4'-piperidin]-4-one;
7-fluorospiro[chroman-2,4'-piperidin]-4-one.

4-Isopropoxyspiro[chroman-2,4'-piperidine]

Step 1: Benzyl 4-hydroxyspiro[chroman-2,4'-piperidine]-1'-carboxylate

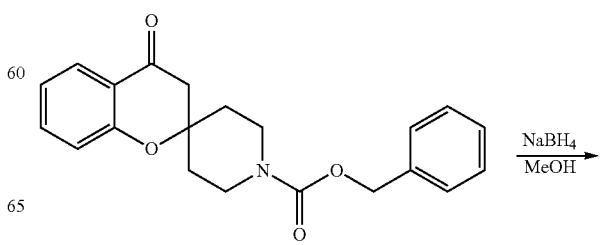

110

Step 3: 4-Isopropoxyspiro[chroman-2,4'-piperidine

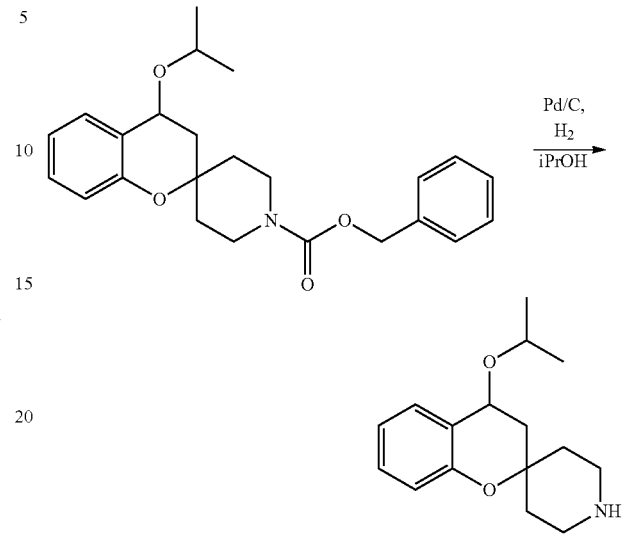

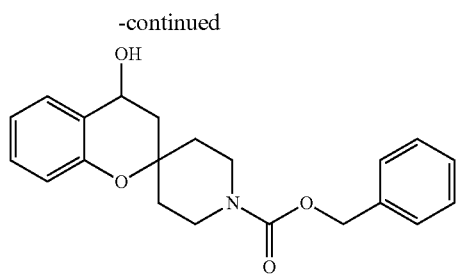

A mixture of benzyl 4-oxospiro[chromane-2,4'-piperidine]-1'-carboxylate (2.00 g, 5.69 mmol) and MeOH (25 mL) was cooled to 0° C. before NaBH$_4$ (646 mg, 17.1 mmol) was added portion-wise. The reaction mixture was allowed to stir for 30 minutes before it was quenched with 1M HCl. The mixture was extracted with CH$_2$Cl$_2$ (3×). The organic layers were dried over sodium sulfate and evaporated to give benzyl 4-hydroxyspiro-[chroman-2,4'-piperidine]-1'-carboxylate (1.97 g, 98%). ESI-MS m/z calc. 353.2, found 354.2 (M+1)$^+$; Retention time: 2.94 minutes (5 min run).

Step 2: 4-Isopropoxyspiro[chromane-2,4'-piperidine]-1'-carboxylate

To benzyl 4-isopropoxyspiro[chromane-2,4'-piperidine]-1'-carboxylate (247 mg, 0.6245 mmol) was added Pd/C (66 mg, 0.062 mmol) and isopropanol (3 mL). The reaction flask was equipped with a septa and a hydrogen balloon was attached. The reaction was allowed to stir overnight at 25° C. before it was filtered. The solvent was removed to give 4-isopropoxyspiro[chroman-2,4'-piperidine] (134 mg, 82%). ESI-MS m/z calc. 261.2, found 262.3 (M+1)$^+$; Retention time: 1.18 minutes (3 min run).

The following compound was prepared using the procedures reported above:
4(R) 4-Ethoxy-6-fluoro-spiro[chromane-2,4'-piperidine.

(R)-Benzyl 4-hydroxyspiro[chroman-2,4'-piperidine]-1'-carboxylate

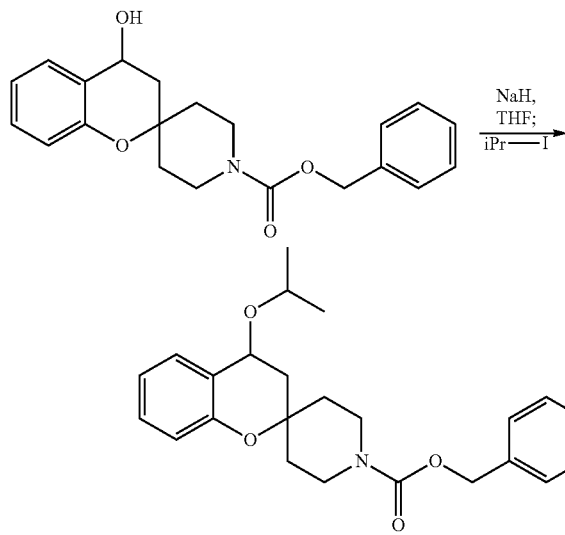

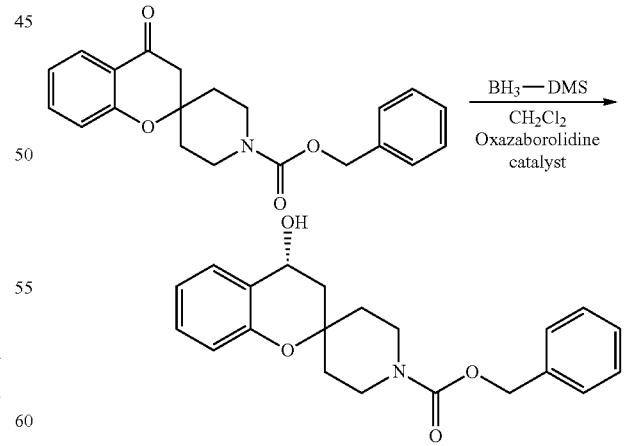

A mixture of benzyl 4-hydroxyspiro-[chroman-2,4'-piperidine]-1'-carboxylate (160 mg, 0.453 mmol) and THF (1.5 mL) was chilled to 0° C. NaH (22 mg, 0.54 mmol) was added portion-wise and the mixture was allowed to stir for 20 minutes. 2-Iodopropane (90 µL, 0.91 mmol) was added and the reaction mixture was allowed to stir overnight at 25° C. The reaction mixture was concentrated and the residue was purified by silica gel chromatography (3%-70% ethyl acetate in hexanes) to give 4-isopropoxyspiro[chromane-2,4'-piperidine]-1'-carboxylate (135 mg, 75%). ESI-MS m/z calc. 395.2, found 396. (M+1)$^+$; Retention time: 2.13 minutes (3 min run).

To a dry 250 mL round bottomed flask was added benzyl 4-oxospiro[chromane-2,4'-piperidine]-1'-carboxylate (6.0 g, 17.1 mmol) and dichloromethane (24 mL). The flasked was purged with nitrogen and chilled to −20° C. Isopropanol (1.03 g, 1.31 mL, 17.1 mmol) was added followed by borane-DMS complex (3.2 g, 3.8 mL, 42.7 mmol) and the reaction was stirred at −30° C. for 30 minutes. By LCMS, no reduction of the ketone was observed. (3aS)-1-methyl-3,3-diphenyl-3a,4,5,6-tetrahydropyrrolo[1,2-c][1,3,2]oxazaborole (3.4 mL of a 1 M solution in THF, 3.4 mmol) was added and the reaction held at −30° C. for 30 minutes and then allowed to warm slowly to 15° C. over 45 minutes. Complete conversion to the alcohol was determined by LCMS. The reaction was quenched with methanol at 15° C. The reaction flask was then evaporated to remove the solvent and the volatiles. The crude reaction was purified by column chromatography DCM:EtOAc 0-20% EtOAc in dichloromethane and was isolated as a white foam. The product was determined to have an ee of 96.3 by chiral HPLC (Column: ChiralPak AD-H (250×4.6 mm), 5 μm; Mobile phase: 40% MeOH w 0.1% DEA, 60% $CO_2$; Flow rate: 3.0 mL/min). ESI-MS m/z calc. 353.2, found 354.2 (M+1)+; Retention time: 2.94 minutes (5 min run).

The following compounds were prepared using the procedure reported above using the appropriate enantiomer of the catalyst:

| Ketone | Product |
| --- | --- |
| Benzyl 4-oxospiro[chromane-2,4'-piperidine]-1'-carboxylate | (S)-Benzyl 4-hydroxyspiro[chroman-2,4'-piperidine]-1'-carboxylate |
| Benzyl 6-fluoro-4-oxospiro[chroman-2,4'-piperidine]-1'-carboxylate | (R)-Benzyl 4-hydroxyspiro[6-fluoro-chroman-2,4'-piperidine]-1'-carboxylate |
| Benzyl 6,8-difluoro-4-oxospiro[chroman-2,4'-piperidine]-1'-carboxylate | (R)-Benzyl 4-hydroxyspiro[6,8-difluoro-chroman-2,4'-piperidine]-1'-carboxylate |
| 6-fluoro-1'-(4-isopropoxy-3-methoxybenzoyl)spiro[chroman-2,4'-piperidin]-4-one | (R)-(6-fluoro-4-hydroxyspiro[chroman-2,4'-piperidine]-1'-yl)(4-isopropoxy-3-methoxyphenyl)methanone |
| 6-fluoro-1'-(4-isopropoxy-3-methylbenzoyl)spiro[chroman-2,4'-piperidin]-4-one | (R)-(6-fluoro-4-hydroxyspiro[chroman-2,4'-piperidine]-1'-yl)(4-isopropoxy-3-methylphenyl)methanone |
| 6-fluoro-1'-(4-(2-hydroxypropan-2-yl)-3-methylbenzoyl)spiro[chroman-2,4'-piperidin]-4-one | (R)-(6-fluoro-4-hydroxyspiro[chroman-2,4'-piperidine]-1'-yl)(4-(2-hydroxypropan-2-yl)-3-methylphenyl)methanone |
| 6-fluoro-1'-(4-isopropoxy-3-methylbenzoyl)spiro[chroman-2,4'-piperidin]-4-one | (S)-(6-fluoro-4-hydroxyspiro[chroman-2,4'-piperidine]-1'-yl)(4-isopropoxy-3-methylphenyl)methanone |

Spiro[3H-pyrano[2,3-b]pyridine-2,4'-piperidine]-4-one hydrogen chloride

Step 1: 1-(1-Oxidopyridin-1-ium-3-yl)ethanone

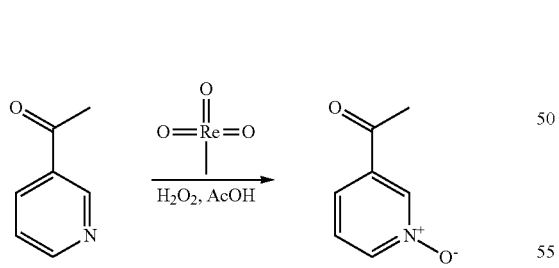

To a solution 1-(3-pyridyl)ethanone (9.54 g, 78.8 mmol) in glacial acetic acid (97 mL) was added methyl(trioxo)rhenium (982 mg, 3.94 mmol). Hydrogen peroxide (16.4 mL of 30% w/w, 161 mmol) was added slowly and the mixture was stirred at room temperature for 16 hours. The mixture was concentrated, the acetic acid was neutralized with a saturated aqueous solution of sodium bicarbonate, and the mixture was extracted with dichloromethane (3×150 mL). The combined organics were dried over sodium sulfate, filtered and the solvent was evaporated under reduced pressure to yield 1-(1-oxidopyridin-1-ium-3-yl)ethanone (6.00 g, 56%). ESI-MS m/z calc. 137.1, found 138.1 (M+1)+; Retention time: 0.23 minutes (3 min run). $^1$H NMR (400 MHz, DMSO) δ 8.65 (s, 1H), 8.43 (d, J=6.4 Hz, 1H), 7.79 (d, J=8.0 Hz, 1H), 7.65-7.48 (m, 1H), 2.61 (s, 3H).

Step 2: 3-Acetyl-1H-pyridin-2-one and 5-acetyl-1H-pyridin-2-one

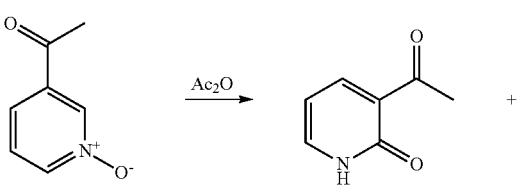

-continued

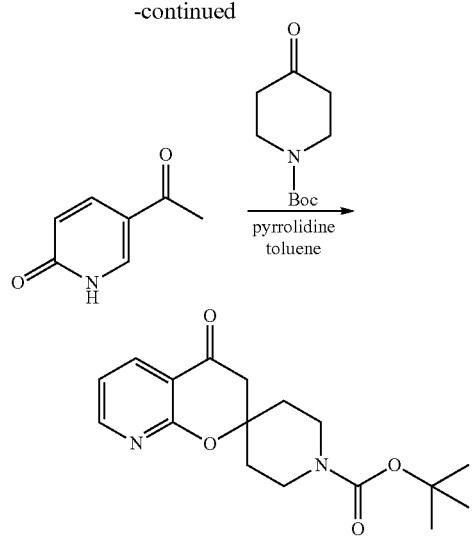

A suspension of 1-(1-oxidopyridin-1-ium-3-yl)ethanone (1.93 g, 14.0 mmol) in acetic anhydride (21.6 mL, 229 mmol) was heated at reflux for 64 hours. The solvent was evaporated under reduced pressure and the crude residue was dissolved in ethyl acetate. Silica gel was added and the slurry was stirred. The slurry was filtered using ethyl acetate and the filtrate was evaporated under reduced pressure to give a mixture of 3-acetylpyridin-2(1H)-one and 5-acetylpyridin-2(1H)-one. To the mixture was added tert-butyl 4-oxopiperidine-1-carboxylate (2.78 g, 14.0 mmol), pyrrolidine (2.57 mL, 30.7 mmol) and toluene (19 mL). Molecular sieves (1 g) were added and the mixture was heated at 110° C. for 17 hours. The mixture was cooled to room temperature and was filtered using ethyl acetate. The filtrate was washed with water (2×50 mL). The combined organics were dried over sodium sulfate, filtered and the solvent was evaporated under reduced pressure. The crude residue was purified on silica gel utilizing a gradient of 0-100% ethyl acetate in hexane to yield tert-butyl 4-oxospiro[3H-pyrano[2,3-b]pyridine-2,4'-piperidine]-1'-carboxylate (614 mg, 14%). ESI-MS m/z calc. 318.2, found 319.5 (M+1)$^+$; Retention time: 1.32 minutes (3 min run).

Step 3: Spiro[3H-pyrano[2,3-b]pyridine-2,4'-piperidine]-4-one dihydrochloride tert-Butyl 4-oxospiro[3H-pyrano[2,3-b]pyridine-2,4'-piperidine]-1'-carboxylate (614 mg, 1.93 mmol) was dissolved in toluene (4.6 mL). HCl in dioxane (2.4 mL of 4.0 M, 9.6 mmol) was added and the reaction mixture was stirred at room temperature for 40 minutes. The solvent was evaporated under reduced pressure to yield spiro[3H-pyrano[2,3-b]pyridine-2,4'-piperidine]-4-one dihydrochloride. ESI-MS m/z calc. 218.1, found 219.5 (M+1)$^+$; Retention time: 0.20 minutes (3 min run).

Spiro[piperidine-4,2'-thiochromane]-4'-one

Step 1: 1-(2-Sulfanylphenyl)ethanone

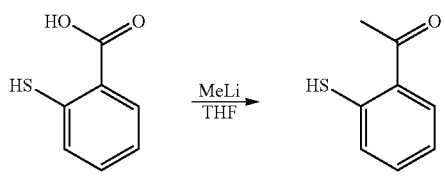

To a solution of 2-sulfanylbenzoic acid (25.0 g, 162 mmol) in THF (810 mL) was added methyllithium (334 mL of 1.6 M, 535 mmol) at 0° C. over 1 h. The mixture was stirred overnight at ambient temperature before it was quenched with water and sat. aq. NH$_4$Cl. The mixture was made acidic (pH~2) with the addition of 1N HCl. The phases were separated and the aqueous phase was extracted with ethyl acetate (3×). The combined organics were dried over sodium sulfate, filtered, and concentrated. The residue was purified by column chromatography (0-100% ethyl acetate/hexanes) to give 1-(2-sulfanylphenyl)ethanone (23.6 g, 91%) as an orange oil. ESI-MS m/z calc. 152.0, found 153.1 (M+1)$^+$; Retention time: 1.10 minutes (3 min run). $^1$H NMR (400 MHz, CDCl$_3$) δ 7.88 (d, J=8.0 Hz, 1H), 7.31 (d, J=3.8 Hz, 2H), 7.25-7.12 (m, 1H), 4.48 (s, 1H), 2.63 (s, 3H).

Step 2: tert-Butyl 4'-oxospiro[piperidine-4,2'-thiochromane]-1-carboxylate

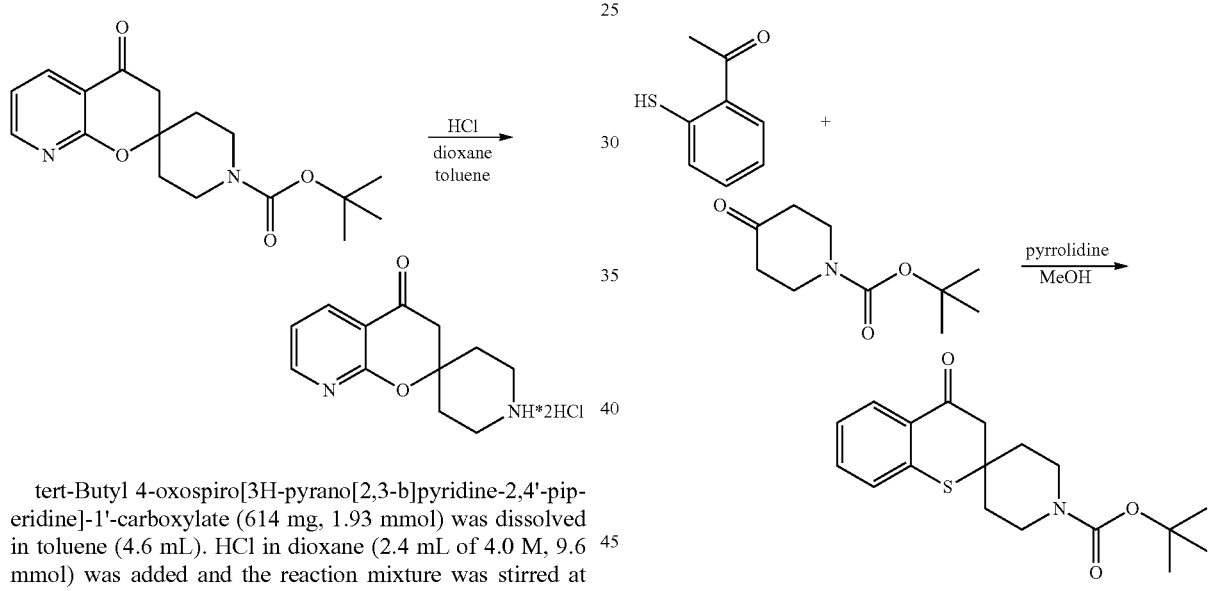

To a solution of tert-butyl 4-oxopiperidine-1-carboxylate (342 mg, 1.72 mmol) in pyrrolidine (285 μL, 3.42 mmol) and anhydrous MeOH (460 μL) was added 1-(2-sulfanylphenyl)ethanone (260 mg, 1.71 mmol). The reaction mixture was stirred at 80° C. for 2.5 hours. Methanol was removed under reduced pressure. The resulting residue was dissolved in ethyl acetate (25 mL), washed with 1 N HCl (25 mL) and brine (25 mL). The organic layer was dried over sodium sulfate, filtered and concentrated under reduced pressure to give a yellow oil. The oil was diluted with hexanes (25 mL) and was heated at 60° C. until in solution. Once dissolved, the solution was filtered and was allowed to cool to ambient temperature. Crystals were collected via vacuum filtration and were rinsed with hexanes to obtain tert-butyl 4'-oxospiro[piperidine-4,2'-thiochromane]-1-carboxylate (350 mg, 61%) as a tan solid. ESI-MS m/z calc. 333.1, found 334.2

(M+1)⁺; Retention time: 1.87 minutes (3 min run). ¹H NMR (400 MHz, CDCl₃) δ 8.08 (dd, J=7.9, 1.1 Hz, 1H), 7.46-7.36 (m, 1H), 7.30-7.23 (m, 1H), 7.23-7.14 (m, 1H), 3.85 (s, 2H), 3.23 (t, J=12.0 Hz, 2H), 2.93 (s, 2H), 1.92 (d, J=13.6 Hz, 2H), 1.74-1.57 (m, 2H), 1.45 (s, 9H).

Step 3: Spiro[piperidine-4,2'-thiochromane]-4'-one hydrochloride (2-Methoxyphenyl)-(4-methoxyspiro[chromane-2,4'-piperidine]-1'-yl)methanone Step 1: 1'-(2-Methoxybenzoyl)spiro[chromane-2,4'-piperidine]-4-one

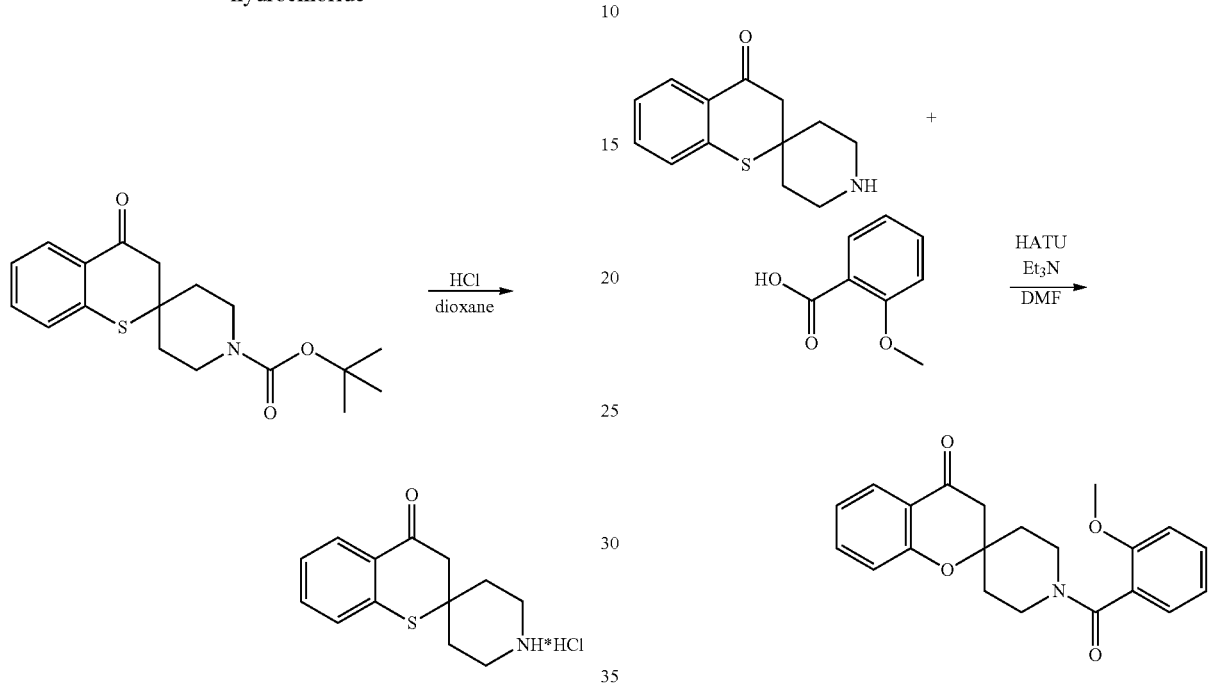

A mixture of tert-butyl 4'-oxospiro[piperidine-4,2'-thiochromane]-1-carboxylate (7.98 g, 23.9 mmol) and HCl in dioxane (18 mL of 4.0 M, 72 mmol) in iPrOH (120 mL) was allowed to stir for 30 min at 50° C. The mixture was concentrated in vacuo to give spiro[piperidine-4,2'-thiochromane]-4'-one hydrochloride (6.4 g, 99%) as a light brown solid. ESI-MS m/z calc. 233.1, found 234.2 (M+1)⁺; Retention time: 0.74 minutes (3 min run). ¹H NMR (400 MHz, DMSO) δ 8.98 (s, 1H), 8.84 (s, 1H), 7.97 (d, J=7.9 Hz, 1H), 7.56 (t, J=7.5 Hz, 1H), 7.40 (d, J=7.9 Hz, 1H), 7.30 (t, J=7.5 Hz, 1H), 3.24-3.14 (m, 2H), 3.14-2.94 (m, 4H), 2.00 (dd, J=9.0, 4.2 Hz, 4H).

A mixture of 2-methoxybenzoic acid (609 mg, 4.00 mmol), HATU (1.67 g, 4.40 mmol), DMF (4 mL), and Et₃N (1.67 mL, 12.0 mmol) was allowed to stir for 10 minutes at room temperature. Spiro[chroman-2,4'-piperidin]-4-one (869 mg, 4.00 mmol) was added and the mixture was allowed to stir for 3 hours. The reaction was quenched with brine and was extracted with ethyl acetate (3×). The combined organics were dried over sodium sulfate and the solvent was evaporated. The residue was purified by silica gel chromatography (3%-70% ethyl acetate/hexanes) to give 1'-(2-methoxybenzoyl)spiro[chromane-2,4'-piperidine]-4-one as a white solid. ESI-MS m/z calc. 351.2, found 352.5 (M+1)⁺; Retention time: 1.49 minutes (3 min run).

The following compounds were prepared using procedures reported above:

| Product | Amine | Carboxylic Acid |
| --- | --- | --- |
| 1'-(2-(trifluoromethoxy)benzoyl)spiro[chroman-2,4'-piperidin]-4-one | spiro[chroman-2,4'-piperidin]-4-one | 2-(trifluoromethoxy)benzoic acid |
| 1'-(2-(difluoromethoxy)benzoyl)spiro[chroman-2,4'-piperidin]-4-one | spiro[chroman-2,4'-piperidin]-4-one | 2-(difluoromethoxy)benzoic acid |
| 2-isopropoxy-5-(4-oxospiro[chroman-2,4'-piperidine]-1'-ylcarbonyl)benzonitrile | spiro[chroman-2,4'-piperidin]-4-one | 3-cyano-4-isopropoxybenzoic acid |

-continued

| Product | Amine | Carboxylic Acid |
| --- | --- | --- |
| 1'-(4-tert-butyl-3-methoxybenzoyl)spiro[chroman-2,4'-piperidin]-4-one | spiro[chroman-2,4'-piperidin]-4-one | 4-tert-butyl-3-methoxybenzoic acid |
| 1'-(4-bromo-3-methoxy-benzoyl)spiro[chromane-2,4'-piperidine]-4-one | spiro[chromane-2,4'-piperidine]-4-one | 4-bromo-3-methoxy-benzoic acid |
| 6-bromo-1'-(4-(2-hydroxypropan-2-yl)-3-methylbenzoyl)spiro[chroman-2,4'-piperidin]-4-one | 6-bromospiro[chroman-2,4'-piperidin]-4-one | 4-(2-hydroxypropan-2-yl)-3-methylbenzoic acid |

Step 2: (4-hydroxyspiro[chromane-2,4'-piperidine]-1'-yl)-(2-methoxyphenyl)methanone Step 3: (2-Methoxyphenyl)-(4-methoxyspiro[chromane-2,4'-piperidine]-1'-yl)methanone

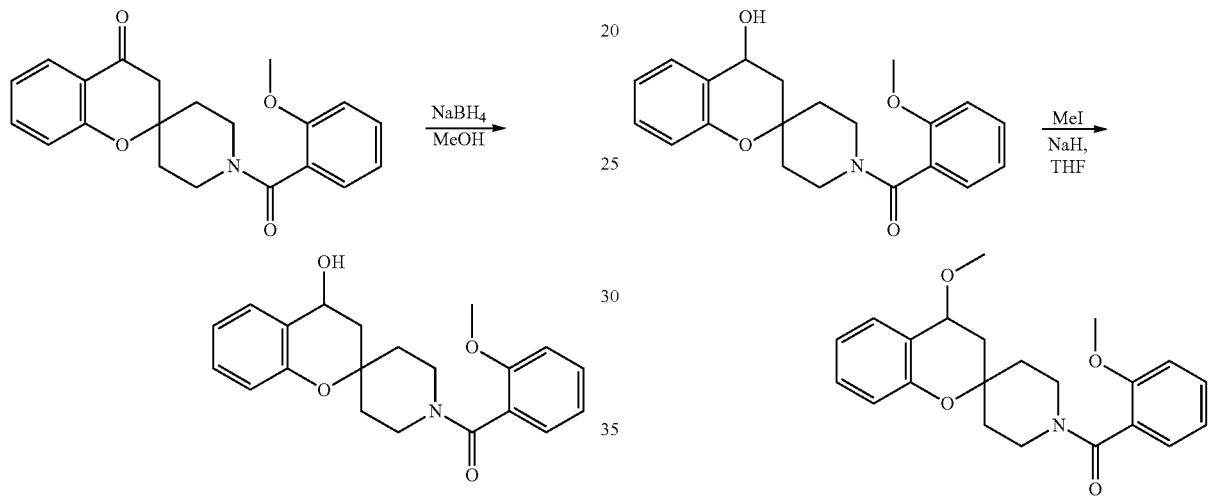

A mixture of 1'-(2-methoxybenzoyl)spiro[chromane-2,4'-piperidine]-4-one (351 mg, 1.00 mmol) in MeOH (4 mL) was cooled to 0° C. Sodium borohydride (75 mg, 2.0 mmol) was added portion-wise and the mixture was allowed to warm to room temperature. The reaction was concentrated, quenched with sat. aq. NH$_4$Cl and extracted with ethyl acetate (3×). The combined organics were dried over sodium sulfate and the solvent was evaporated. The residue was dissolved in DMF and was purified by preparative HPLC (1-99% MeOH:H$_2$O) to give (4-hydroxyspiro[chromane-2,4'-piperidine]-1'-yl)-(2-methoxyphenyl)methanone. ESI-MS m/z calc. 353.2, found 354.3 (M+1)$^+$; Retention time: 1.37 minutes (3 min run).

The following compounds were prepared using procedures reported above:

| Ketone | Alcohol |
| --- | --- |
| 1'-(4-tert-butyl-3-methoxybenzoyl)spiro[chroman-2,4'-piperidin]-4-one | (4-tert-butyl-3-methoxyphenyl)(4-hydroxyspiro[chroman-2,4'-piperidine]-1'-yl)methanone |
| 1'-(4-bromo-3-methoxy-benzoyl)spiro[chromane-2,4'-piperidine]-4-one | (4-bromo-3-methoxyphenyl)(4-hydroxyspiro[chroman-2,4'-piperidine]-1'-yl)methanone |
| 5-fluoro-1'-(4-isopropoxy-3-methylbenzoyl)spiro[chroman-2,4'-piperidin]-4-one | (5-fluoro-4-hydroxyspiro[chroman-2,4'-piperidine]-1'-yl)(4-isopropoxy-3-methylphenyl)methanone |

To a solution of (4-hydroxyspiro[chromane-2,4'-piperidine]-1'-yl)-(2-methoxyphenyl)-methanone (35 mg, 0.10 mmol) in THF (1 mL) was added NaH (6 mg, 0.15 mmol, 60%). MeI (7.5 µL, 0.12 mmol) was added and the mixture was stirred at room temperature overnight before it was filtered and purified by preparative HPLC (1-99% MeOH:H$_2$O) to give (2-methoxyphenyl)-(4-methoxyspiro[chromane-2,4'-piperidine]-1'-yl)methanone. ESI-MS m/z calc. 367.2, found 368.3 (M+1)$^+$; Retention time: 1.65 minutes (3 min run).

(4-Isopropoxy-3-methoxyphenyl)(4-isopropoxyspiro[chroman-2,4'-piperidine]-1'-yl)methanone

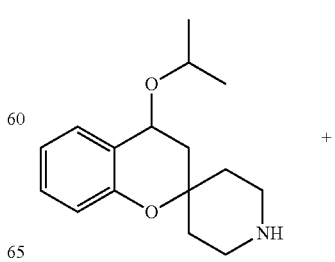

+

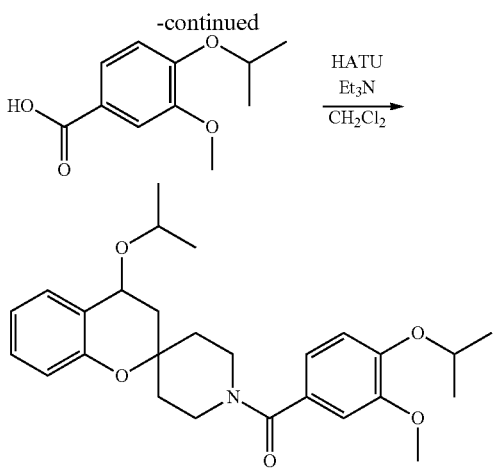

A mixture of 4-isopropoxy-3-methoxybenzoic acid (21 mg, 0.10 mmol), HATU (42 mg, 0.11 mmol), DMF (0.7 mL), and Et$_3$N (42 µL, 0.30 mmol) was allowed to stir for 10 minutes at room temperature. 4-Isopropoxyspiro[chroman-2,4'-piperidine] (26 mg, 0.10 mmol) was added and the mixture was allowed to stir for 3 hours. The reaction was quenched with brine and was extracted with ethyl acetate (3×). The combined organics were dried over sodium sulfate and the solvent was evaporated. The residue was purified by silica gel chromatography (3%-70% ethyl acetate/hexanes) to give (4-isopropoxy-3-methoxyphenyl)(4-isopropoxyspiro[chroman-2,4'-piperidine]-1'-yl)methanone as a white solid. ESI-MS m/z calc. 453.3, found 454.7 (M+1)$^+$; Retention time: 2.00 minutes (3 min run).

The following compounds were prepared using the procedure reported above:

| Product | Amine | Carboxylic Acid |
| --- | --- | --- |
| (4-isopropoxyspiro[chromane-2,4'-piperidine]-1'-yl)-(4-isopropylsulfonylphenyl)methanone | 4-isopropoxyspiro[chroman-2,4'-piperidine] | 4-isopropylsulfonyl benzoic acid |
| (S)-(4-isopropoxy-3-methoxyphenyl)(4-isopropoxyspiro[chroman-2,4'-piperidine]-1'-yl)methanone | (S)-4-isopropoxyspiro[chroman-2,4'-piperidine] | 4-isopropoxy-3-methoxybenzoic acid |
| (R)-(4-isopropoxy-3-methoxyphenyl)(4-isopropoxyspiro[chroman-2,4'-piperidine]-1'-yl)methanone | (R)-4-isopropoxyspiro[chroman-2,4'-piperidine] | 4-isopropoxy-3-methoxybenzoic acid |
| (4-isopropoxy-3-methylphenyl)(4-isopropoxyspiro[chroman-2,4'-piperidine]-1'-yl)methanone | (4-isopropoxyspiro[chroman-2,4'-piperidine] | 4-isopropoxy-3-methylbenzoic acid |
| (R)-(4-(2-hydroxypropan-2-yl)phenyl)(4-isopropoxyspiro[chroman-2,4'-piperidine]-1'-yl)methanone | (R)-4-isopropoxyspiro[chroman-2,4'-piperidine] | 4-(2-hydroxypropan-2-yl)benzoic acid |
| (R)-(3-(hydroxymethyl)-4-isopropoxyphenyl)(4-isopropoxyspiro[chroman-2,4'-piperidine]-1'-yl)methanone | (R)-4-isopropoxyspiro[chroman-2,4'-piperidine] | 3-(hydroxymethyl)-4-isopropoxybenzoic acid |
| (R)-4-(4-isopropoxyspiro[chroman-2,4'-piperidine]-1'-ylcarbonyl)-N-isopropylbenzenesulfonamide | (R)-4-isopropoxyspiro[chroman-2,4'-piperidine] | 4-(N-isopropylsulfamoyl)benzoic acid |
| (R)-(4-isopropoxyphenyl)(4-isopropoxyspiro[chroman-2,4'-piperidine]-1'-yl)methanone | (R)-4-isopropoxyspiro[chroman-2,4'-piperidine] | 4-isopropoxybenzoic acid |
| (R)-(4-(2-hydroxy-2-methylpropyl)phenyl)(4-isopropoxyspiro[chroman-2,4'-piperidine]-1'-yl)methanone | (R)-4-isopropoxyspiro[chroman-2,4'-piperidine] | 4-(2-hydroxy-2-methylpropyl)benzoic acid |
| (R)-(4-isopropoxyspiro[chroman-2,4'-piperidine]-1'-yl)(2-(methoxymethyl)phenyl)methanone | (R)-4-isopropoxyspiro[chroman-2,4'-piperidine] | 2-(methoxymethyl)benzoic acid |
| (R)-2-isopropoxy-5-(4-isopropoxyspiro[chroman-2,4'-piperidine]-1'-ylcarbonyl)benzonitrile | (R)-4-isopropoxyspiro[chroman-2,4'-piperidine] | 3-cyano-4-isopropoxybenzoic acid |
| (R)-(4-isopropoxyspiro[chroman-2,4'-piperidine]-1'-yl)(3-methyl-4-(methylsulfonyl)phenyl)methanone | (R)-4-isopropoxyspiro[chroman-2,4'-piperidine] | 3-methyl-4-(methylsulfonyl)benzoic acid |
| (R)-(4-(2-hydroxypropan-2-yl)-3-methylphenyl)(4-isopropoxyspiro[chroman-2,4'-piperidine]-1'-yl)methanone | (R)-4-isopropoxyspiro[chroman-2,4'-piperidine] | 4-(2-hydroxypropan-2-yl)-3-methylbenzoic acid |
| [(4R)-6-fluoro-4-isopropoxy-spiro[chromane-2,4'-piperidine]-1'-yl]-(5-isopropylsulfonyl-2-pyridyl)methanone | (4R)-6-fluoro-4-isopropoxy-spiro[chromane-2,4'-piperidine] | 5-isopropyl sulfonylpyridine-2-carboxylic acid |
| [4-(1-hydroxy-1-methyl-ethyl)-3-methoxy-phenyl]-[(4R)-4-isopropoxyspiro[chromane-2,4'-piperidine]-1'-yl]methanone | (4R)-4-isopropoxyspiro[chromane-2,4'-piperidine] | 4-(1-hydroxy-1-methyl-ethyl)-3-methoxy-benzoic acid |

| Product | Amine | Carboxylic Acid |
| --- | --- | --- |
| [3-(hydroxymethyl)-4-isopropoxy-phenyl]-[(4S)-4-isopropoxyspiro[chromane-2,4'-piperidine]-1'-yl]methanone | (4S)-4-isopropoxyspiro[chromane-2,4'-piperidine] | 3-(hydroxymethyl)-4-isopropoxy-benzoic acid |
| [4-(1-hydroxy-1-methyl-ethyl)-3-methyl-phenyl]-[(4S)-4-isopropoxyspiro[chromane-2,4'-piperidine]-1'-yl]methanone | (4S)-4-isopropoxyspiro[chromane-2,4'-piperidine] | 4-(1-hydroxy-1-methyl-ethyl)-3-methyl-benzoic acid |
| [4-(1-hydroxy-1-methyl-ethyl)-3-methoxy-phenyl]-[(4S)-4-isopropoxyspiro[chromane-2,4'-piperidine]-1'-yl]methanone | (4S)-4-isopropoxyspiro[chromane-2,4'-piperidine] | 4-(1-hydroxy-1-methyl-ethyl)-3-methoxy-benzoic acid |
| 2-isopropoxy-5-[(4S)-4-isopropoxyspiro[chromane-2,4'-piperidine]-1'-carbonyl]benzonitrile | (4S)-4-isopropoxyspiro[chromane-2,4'-piperidine] | 3-cyano-4-isopropoxy-benzoic acid |
| [(4R)-6-fluoro-4-isopropoxy-spiro[chromane-2,4'-piperidine]-1'-yl]-[3-(hydroxymethyl)-4-isopropoxy-phenyl]methanone | (4R)-6-fluoro-4-isopropoxy-spiro[chromane-2,4'-piperidine] | 3-(hydroxymethyl)-4-isopropoxy-benzoic acid |
| [(4R)-6-fluoro-4-isopropoxy-spiro[chromane-2,4'-piperidine]-1'-yl]-[3-methyl-4-(oxetan-3-yloxy)phenyl]methanone | (4R)-6-fluoro-4-isopropoxy-spiro[chromane-2,4'-piperidine] | 3-methyl-4-(oxetan-3-yloxy)benzoic acid |
| [(4R)-6-fluoro-4-isopropoxy-spiro[chromane-2,4'-piperidine]-1'-yl]-[4-(1-hydroxy-1-methyl-ethyl)-3-methoxy-phenyl]methanone | (4R)-6-fluoro-4-isopropoxy-spiro[chromane-2,4'-piperidine] | 4-(1-hydroxy-1-methyl-ethyl)-3-methoxy-benzoic acid |
| [(4R)-6-fluoro-4-isopropoxy-spiro[chromane-2,4'-piperidine]-1'-yl]-[3-methoxy-4-[(3R)-tetrahydrofuran-3-yl]oxy-phenyl]methanone | (4R)-6-fluoro-4-isopropoxy-spiro[chromane-2,4'-piperidine] | 3-methoxy-4-[(3R)-tetrahydrofuran-3-yl]oxy-benzoic acid |
| [(4R)-6-fluoro-4-isopropoxy-spiro[chromane-2,4'-piperidine]-1'-yl]-[4-(2-hydroxyethoxy)-3-methoxy-phenyl]methanone | (4R)-6-fluoro-4-isopropoxy-spiro[chromane-2,4'-piperidine] | 4-(2-hydroxyethoxy)-3-methoxy-benzoic acid |
| (4-hydroxy-3-methyl-phenyl)-[(4S)-4-isopropoxyspiro[chromane-2,4'-piperidine]-1'-yl]methanone | (4S)-4-isopropoxyspiro[chromane-2,4'-piperidine] | 4-hydroxy-3-methyl-benzoic acid |
| [7-(difluoromethyl)-5-methyl-pyrazolo[1,5-a]pyrimidin-3-yl]-[(4S)-4-isopropoxyspiro[chromane-2,4'-piperidine]-1'-yl]methanone | (4S)-4-isopropoxyspiro[chromane-2,4'-piperidine] | 7-(difluoromethyl)-5-methyl-pyrazolo[1,5-a]pyrimidine-3-carboxylic acid |
| (4-hydroxy-2-methoxy-phenyl)-[(4S)-4-isopropoxyspiro[chromane-2,4'-piperidine]-1'-yl]methanone | (4S)-4-isopropoxyspiro[chromane-2,4'-piperidine] | 4-hydroxy-2-methoxy-benzoic acid |
| [(4S)-4-isopropoxyspiro[chromane-2,4'-piperidine]-1'-yl]-(4-methoxy-3-methyl-phenyl)methanone | (4S)-4-isopropoxyspiro[chromane-2,4'-piperidine] | 4-methoxy-3-methyl-benzoic acid |
| [4-(1-hydroxy-1-methyl-ethyl)phenyl]-[(4S)-4-isopropoxyspiro[chromane-2,4'-piperidine]-1'-yl]methanone | (4S)-4-isopropoxyspiro[chromane-2,4'-piperidine] | 4-(1-hydroxy-1-methyl-ethyl)benzoic acid |
| (4-hydroxy-3-methyl-phenyl)-[(4R)-4-isopropoxyspiro[chromane-2,4'-piperidine]-1'-yl]methanone | (4R)-4-isopropoxyspiro[chromane-2,4'-piperidine] | 4-hydroxy-3-methyl-benzoic acid |
| [7-(difluoromethyl)-5-methyl-pyrazolo[1,5-a]pyrimidin-3-yl]-[(4R)-4-isopropoxyspiro[chromane-2,4'-piperidine]-1'-yl]methanone | (4R)-4-isopropoxyspiro[chromane-2,4'-piperidine] | 7-(difluoromethyl)-5-methyl-pyrazolo[1,5-a]pyrimidine-3-carboxylic acid |
| (4-hydroxy-2-methoxy-phenyl)-[(4R)-4-isopropoxyspiro[chromane-2,4'-piperidine]-1'-yl]methanone | (4R)-4-isopropoxyspiro[chromane-2,4'-piperidine] | 4-hydroxy-2-methoxy-benzoic acid |
| [(4R)-4-isopropoxyspiro[chromane-2,4'-piperidine]-1'-yl]-(4-methoxy-3-methyl-phenyl)methanone | (4R)-4-isopropoxyspiro[chromane-2,4'-piperidine] | 4-methoxy-3-methyl-benzoic acid |
| [4-(3-hydroxypropoxy)-3-methoxy-phenyl]-[(4R)-4-isopropoxyspiro[chromane-2,4'-piperidine]-1'-yl]methanone | (4R)-4-isopropoxyspiro[chromane-2,4'-piperidine] | 4-(3-hydroxypropoxy)-3-methoxy-benzoic acid |
| [4-(3-hydroxypropoxy)-3-methoxy-phenyl]-[(4S)-4-isopropoxyspiro[chromane-2,4'-piperidine]-1'-yl]methanone | (4S)-4-isopropoxyspiro[chromane-2,4'-piperidine] | 4-(3-hydroxypropoxy)-3-methoxy-benzoic acid |
| (5-isopropoxy-6-methyl-2-pyridyl)-[(4R)-4-isopropoxyspiro[chromane-2,4'-piperidine]-1'-yl]methanone | (4R)-4-isopropoxyspiro[chromane-2,4'-piperidine] | 5-isopropoxy-6-methyl-pyridine-2-carboxylic acid |

| Product | Amine | Carboxylic Acid |
| --- | --- | --- |
| (5-isopropoxy-6-methyl-2-pyridyl)-[(4S)-4-isopropoxyspiro[chromane-2,4'-piperidine]-1'-yl]methanone | (4S)-4-isopropoxyspiro[chromane-2,4'-piperidine] | 5-isopropoxy-6-methyl-pyridine-2-carboxylic acid |
| [(4R)-6-fluoro-4-isopropoxy-spiro[chromane-2,4'-piperidine]-1'-yl]-(3-methyl-4-methylsulfonyl-phenyl)methanone | (4R)-6-fluoro-4-isopropoxy-spiro[chromane-2,4'-piperidine] | 3-methyl-4-methylsulfonyl-benzoic acid |
| [(4R)-6-fluoro-4-isopropoxy-spiro[chromane-2,4'-piperidine]-1'-yl]-(4-isopropylsulfonylphenyl)methanone | (4R)-6-fluoro-4-isopropoxy-spiro[chromane-2,4'-piperidine] | 4-isopropylsulfonyl benzoic acid |
| 1H-indazol-5-yl-[(4S)-4-isopropoxyspiro[chromane-2,4'-piperidine]-1'-yl]methanone | (4S)-4-isopropoxyspiro[chromane-2,4'-piperidine] | 1H-indazole-5-carboxylic acid |
| [(4S)-4-isopropoxyspiro[chromane-2,4'-piperidine]-1'-yl]-(1-methylindazol-5-yl)methanone | (4S)-4-isopropoxyspiro[chromane-2,4'-piperidine] | 1-methylindazole-5-carboxylic acid |
| [(4R)-4-isopropoxyspiro[chromane-2,4'-piperidine]-1'-yl]-(1-methylindazol-5-yl)methanone | (4R)-4-isopropoxyspiro[chromane-2,4'-piperidine] | 1-methylindazole-5-carboxylic acid |
| 1H-indazol-5-yl-[(4R)-4-isopropoxyspiro[chromane-2,4'-piperidine]-1'-yl]methanone | (4R)-4-isopropoxyspiro[chromane-2,4'-piperidine] | 1H-indazole-5-carboxylic acid |
| (4-isopropoxy-3-methyl-phenyl)-(4-isopropoxyspiro[1,4,5,7-tetrahydroindazole-6,4'-piperidine]-1'-yl)methanone | 4-isopropoxyspiro[1,4,5,7-tetrahydroindazole-6,4'-piperidine] | 4-isopropoxy-3-methyl-benzoic acid |
| (4-isopropoxy-3-methyl-phenyl)-(5-isopropoxyspiro[6,8-dihydro-5H-quinazoline-7,4'-piperidine]-1'-yl)methanone | 5-isopropoxyspiro[6,8-dihydro-5H-quinazoline-7,4'-piperidine] | 4-isopropoxy-3-methyl-benzoic acid |
| (4-isopropoxy-3-methyl-phenyl)-(4-isopropoxy-1-methyl-spiro[5,7-dihydro-4H-indazole-6,4'-piperidine]-1'-yl)methanone | 4-isopropoxy-1-methyl-spiro[5,7-dihydro-4H-indazole-6,4'-piperidine] | 4-isopropoxy-3-methyl-benzoic acid |
| (4-tert-butylsulfonylphenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-tert-butylsulfonylbenzoic acid |
| (4-cyclopropylsulfonylphenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-cyclopropylsulfonyl benzoic acid |
| [4-(difluoromethylsulfonyl)phenyl]-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-(difluoromethyl-sulfonyl)benzoic acid |
| (7-fluoro-4-isopropoxy-spiro[chromane-2,4'-piperidine]-1'-yl)-(4-isopropoxy-3-methoxy-phenyl)methanone | 7-fluoro-4-isopropoxy-spiro[chromane-2,4'-piperidine] | 4-isopropoxy-3-methoxy-benzoic acid |
| [3-fluoro-4-(1-hydroxy-1-methyl-ethyl)phenyl]-(7-fluoro-4-isopropoxy-spiro[chromane-2,4'-piperidine]-1'-yl)methanone | 7-fluoro-4-isopropoxy-spiro[chromane-2,4'-piperidine] | 3-fluoro-4-(1-hydroxy-1-methyl-ethyl)benzoic acid |
| [(4R)-6-fluoro-4-isopropoxy-spiro[chromane-2,4'-piperidine]-1'-yl]-(4-isopropylsulfonyl-2-methyl-phenyl)methanone | (4R)-6-fluoro-4-isopropoxy-spiro[chromane-2,4'-piperidine] | 4-isopropylsulfonyl-2-methyl-benzoic acid |
| [(4R)-6-fluoro-4-isopropoxy-spiro[chromane-2,4'-piperidine]-1'-yl]-(4-isopropylsulfonyl-3-methyl-phenyl)methanone | (4R)-6-fluoro-4-isopropoxy-spiro[chromane-2,4'-piperidine] | 4-isopropylsulfonyl-3-methyl-benzoic acid |
| (4-ethylsulfonylphenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-ethylsulfonylbenzoic acid |
| [(4R)-6-fluoro-4-isopropoxy-spiro[chromane-2,4'-piperidine]-1'-yl]-(2-methyl-4-methylsulfonyl-phenyl)methanone | (4R)-6-fluoro-4-isopropoxy-spiro[chromane-2,4'-piperidine] | 2-methyl-4-methylsulfonyl-benzoic acid |
| 5-(6-fluoro-4-isopropoxy-spiro[chromane-2,4'-piperidine]-1'-carbonyl)-2-isopropylsulfonyl-benzonitrile | 6-fluoro-4-isopropoxy-spiro[chromane-2,4'-piperidine] | 3-cyano-4-isopropylsulfonyl-benzoic acid |

| Product | Amine | Carboxylic Acid |
|---|---|---|
| (4-ethylsulfonyl-3-methyl-phenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-ethylsulfonyl-3-methyl-benzoic acid |
| 5-[(4R)-6-fluoro-4-isopropoxy-spiro[chromane-2,4'-piperidine]-1'-carbonyl]-2-isopropylsulfonyl-benzonitrile | (4R)-6-fluoro-4-isopropoxy-spiro[chromane-2,4'-piperidine] | 3-cyano-4-isopropylsulfonyl-benzoic acid |
| [(4R)-6,8-difluoro-4-isopropoxy-spiro[chromane-2,4'-piperidine]-1'-yl]-(4-isopropylsulfonylphenyl)methanone | (4R)-6,8-difluoro-4-isopropoxy-spiro[chromane-2,4'-piperidine] | 4-isopropylsulfonyl benzoic acid |
| [(4R)-6,8-difluoro-4-isopropoxy-spiro[chromane-2,4'-piperidine]-1'-yl]-(4-ethylsulfonyl-3-methyl-phenyl)methanone | (4R)-6,8-difluoro-4-isopropoxy-spiro[chromane-2,4'-piperidine] | 4-ethylsulfonyl-3-methyl-benzoic acid |
| [(4R)-6,8-difluoro-4-isopropoxy-spiro[chromane-2,4'-piperidine]-1'-yl]-(4-isopropylsulfonyl-3-methyl-phenyl)methanone | (4R)-6,8-difluoro-4-isopropoxy-spiro[chromane-2,4'-piperidine] | 4-isopropylsulfonyl-3-methyl-benzoic acid |
| [(4R)-6-fluoro-4-isopropoxy-spiro[chromane-2,4'-piperidine]-1'-yl]-[4-(trifluoromethylsulfonyl)phenyl]methanone | (4R)-6-fluoro-4-isopropoxy-spiro[chromane-2,4'-piperidine] | 4-(trifluoromethyl-sulfonyl)benzoic acid |
| [(4R)-6-fluoro-4-isopropoxy-spiro[chromane-2,4'-piperidine]-1'-yl]-[4-(1-hydroxycyclopentyl)phenyl]methanone | (4R)-6-fluoro-4-isopropoxy-spiro[chromane-2,4'-piperidine] | 4-(1-hydroxycyclopentyl)benzoic acid |
| [2-(difluoromethoxy)-4-isopropoxy-phenyl]-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 2-(difluoromethoxy)-4-isopropoxy-benzoic acid |
| [(4R)-6-fluoro-4-isopropoxy-spiro[chromane-2,4'-piperidine]-1'-yl]-(5-isopropylsulfonyl-2-pyridyl)methanone | (4R)-6-fluoro-4-isopropoxy-spiro[chromane-2,4'-piperidine] | 5-isopropylsulfonyl-pyridine-2-carboxylic acid |
| [4-(1-hydroxy-1-methyl-ethyl)-3-methoxy-phenyl]-[(4R)-4-isopropoxyspiro[chromane-2,4'-piperidine]-1'-yl]methanone | (4R)-4-isopropoxyspiro[chromane-2,4'-piperidine] | 4-(1-hydroxy-1-methyl-ethyl)-3-methoxy-benzoic acid |
| [3-(hydroxymethyl)-4-isopropoxy-phenyl]-[(4S)-4-isopropoxyspiro[chromane-2,4'-piperidine]-1'-yl]methanone | (4S)-4-isopropoxyspiro[chromane-2,4'-piperidine] | 3-(hydroxymethyl)-4-isopropoxy-benzoic acid |
| [4-(1-hydroxy-1-methyl-ethyl)-3-methyl-phenyl]-[(4S)-4-isopropoxyspiro[chromane-2,4'-piperidine]-1'-yl]methanone | (4S)-4-isopropoxyspiro[chromane-2,4'-piperidine] | 4-(1-hydroxy-1-methyl-ethyl)-3-methyl-benzoic acid |
| [4-(1-hydroxy-1-methyl-ethyl)-3-methoxy-phenyl]-[(4S)-4-isopropoxyspiro[chromane-2,4'-piperidine]-1'-yl]methanone | (4S)-4-isopropoxyspiro[chromane-2,4'-piperidine] | 4-(1-hydroxy-1-methyl-ethyl)-3-methoxy-benzoic acid |
| 2-isopropoxy-5-[(4S)-4-isopropoxyspiro[chromane-2,4'-piperidine]-1'-carbonyl]benzonitrile | (4S)-4-isopropoxyspiro[chromane-2,4'-piperidine] | 3-cyano-4-isopropoxy-benzoic acid |
| [(4R)-6-fluoro-4-isopropoxy-spiro[chromane-2,4'-piperidine]-1'-yl]-[3-(hydroxymethyl)-4-isopropoxy-phenyl]methanone | (4R)-6-fluoro-4-isopropoxy-spiro[chromane-2,4'-piperidine] | 3-(hydroxymethyl)-4-isopropoxy-benzoic acid |
| (R)-2-(4-(4-isopropoxyspiro[chroman-2,4'-piperidine]-1'-ylcarbonyl)-2-methoxyphenyl)-2-methylpropanal | (4R)-4-isopropoxyspiro[chromane-2,4'-piperidine] | 3-methoxy-4-(2-methyl-1-oxopropan-2-yl)benzoic acid |
| (S)-2-(4-(4-isopropoxyspiro[chroman-2,4'-piperidine]-1'-ylcarbonyl)-2-methoxyphenyl)-2-methylpropanal | (4S)-4-isopropoxyspiro[chromane-2,4'-piperidine] | 3-methoxy-4-(2-methyl-1-oxopropan-2-yl)benzoic acid |
| (R)-(6-fluoro-4-isopropoxyspiro[chroman-2,4'-piperidine]-1'-yl)(4-(1-hydroxy-2-methylpropan-2-yl)-3-methoxyphenyl)methanone | (4R)-6-fluoro-4-isopropoxy-spiro[chromane-2,4'-piperidine] | 3-methoxy-4-(2-methyl-1-oxopropan-2-yl)benzoic acid |
| (4-isopropoxy-3-methoxyphenyl)(4-(isopropoxymethyl)spiro[chroman-2,4'-piperidine]-1'-yl)methanone | 4-(isopropoxymethyl)spiro[chroman-2,4'-piperidine] | 4-isopropoxy-3-methoxybenzoic acid |
| (4-(2-hydroxypropan-2-yl)phenyl)(4- | 4-(isopropoxymethyl)spiro[chroman- | 4-(2-hydroxypropan-2-yl)benzoic acid |

| Product | Amine | Carboxylic Acid |
|---|---|---|
| (isopropoxymethyl)spiro[chroman-2,4'-piperidine]-1'-yl)methanone | 2,4'-piperidine] | |
| (4-(2-hydroxypropan-2-yl)-3-methoxyphenyl)(4-(isopropoxymethyl)spiro[chroman-2,4'-piperidine]-1'-yl)methanone | 4-(isopropoxymethyl)spiro[chroman-2,4'-piperidine] | 4-(2-hydroxypropan-2-yl)-3-methoxybenzoic acid |
| (3-(hydroxymethyl)-4-isopropoxyphenyl)(4-(isopropoxymethyl)spiro[chroman-2,4'-piperidine]-1'-yl)methanone | 4-(isopropoxymethyl)spiro[chroman-2,4'-piperidine] | 3-(hydroxymethyl)-4-isopropoxybenzoic acid |
| (8-fluoro-4-(trideuteriomethoxymethyl)spiro[chroman-2,4'-piperidine]-1'-yl)(4-(2-hydroxypropan-2-yl)-3-methylphenyl)methanone | 8-fluoro-4-(trideuteriomethoxymethyl)spiro[chroman-2,4'-piperidine] | 4-(2-hydroxypropan-2-yl)-3-methylbenzoic acid |
| (8-fluoro-4-(trideuteriomethoxymethyl)spiro[chroman-2,4'-piperidine]-1'-yl)(4-(2-hydroxypropan-2-yl)phenyl)methanone | 8-fluoro-4-(trideuteriomethoxymethyl)spiro[chroman-2,4'-piperidine] | 4-(2-hydroxypropan-2-yl)benzoic acid |
| (8-fluoro-4-(methoxymethyl)spiro[chroman-2,4'-piperidine]-1'-yl)(4-isopropoxy-3-methoxyphenyl)methanone | 8-fluoro-4-(trideuteriomethoxymethyl)spiro[chroman-2,4'-piperidine] | 4-isopropoxy-3-methoxybenzoic acid |
| [3-fluoro-4-(1-hydroxy-1-methyl-ethyl)phenyl]-[(4R)-7-fluoro-4-isopropoxy-spiro[chromane-2,4'-piperidine]-1'-yl]methanone | (4R)-7-fluoro-4-isopropoxy-spiro[chromane-2,4'-piperidine] | 3-fluoro-4-(1-hydroxy-1-methyl-ethyl)benzoic acid |
| [3-fluoro-4-(1-hydroxy-1-methyl-ethyl)phenyl]-[(4S)-7-fluoro-4-isopropoxy-spiro[chromane-2,4'-piperidine]-1'-yl]methanone | (4S)-7-fluoro-4-isopropoxy-spiro[chromane-2,4'-piperidine] | 3-fluoro-4-(1-hydroxy-1-methyl-ethyl)benzoic acid |
| [(4R)-6-fluoro-4-isopropoxy-spiro[chromane-2,4'-piperidine]-1'-yl]-(5-isopropylsulfonyl-6-methyl-2-pyridyl)methanone | (4R)-6-fluoro-4-isopropoxy-spiro[chromane-2,4'-piperidine] | 5-isopropylsulfonyl-6-methyl-pyridine-2-carboxylic acid |
| [(4R)-6-fluoro-4-isopropoxy-spiro[chromane-2,4'-piperidine]-1'-yl]-(4-isobutylsulfonylphenyl)methanone | (4R)-6-fluoro-4-isopropoxy-spiro[chromane-2,4'-piperidine] | 4-isobutylsulfonyl benzoic acid |
| [(4R)-4-ethoxy-6-fluoro-spiro[chromane-2,4'-piperidine]-1'-yl]-(4-isopropylsulfonylphenyl)methanone | (4R)-4-ethoxy-6-fluoro-spiro[chromane-2,4'-piperidine] | 4-isopropylsulfonyl benzoic acid |
| 5-[(4R)-4-ethoxy-6-fluoro-spiro[chromane-2,4'-piperidine]-1'-carbonyl]-2-isopropylsulfonyl-benzonitrile | (4R)-4-ethoxy-6-fluoro-spiro[chromane-2,4'-piperidine] | 3-cyano-4-isopropylsulfonyl-benzoic acid |
| [(4R)-4-ethoxy-6-fluoro-spiro[chromane-2,4'-piperidine]-1'-yl]-(4-isobutylsulfonylphenyl)methanone | (4R)-4-ethoxy-6-fluoro-spiro[chromane-2,4'-piperidine] | 4-isobutylsulfonyl benzoic acid |
| [4-(difluoromethylsulfonyl)phenyl]-[(4R)-4-ethoxy-6-fluoro-spiro[chromane-2,4'-piperidine]-1'-yl]methanone | (4R)-4-ethoxy-6-fluoro-spiro[chromane-2,4'-piperidine] | 4-(difluoromethyl-sulfonyl)benzoic acid |
| [(4R)-6-fluoro-4-isopropoxy-spiro[chromane-2,4'-piperidine]-1'-yl]-[2-(trifluoromethoxy)phenyl]methanone | (4R)-6-fluoro-4-isopropoxy-spiro[chromane-2,4'-piperidine] | 2-(trifluoromethoxy)benzoic acid |
| (3-fluoro-4-isopropoxy-phenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 3-fluoro-4-isopropoxy-benzoic acid |
| [3-fluoro-4-(1-hydroxy-1-methyl-ethyl)phenyl]-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 3-fluoro-4-(1-hydroxy-1-methyl-ethyl)benzoic acid |
| (5-ethyl-2-pyridyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 5-ethylpyridine-2-carboxylic acid |
| (5-ethoxy-2-pyridyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 5-ethoxypyridine-2-carboxylic acid |

| Product | Amine | Carboxylic Acid |
|---|---|---|
| [5-(cyclopropylmethylsulfonyl)-2-pyridyl]-(6-fluoro-4-isopropoxy-spiro[chromane-2,4'-piperidine]-1'-yl)methanone | 6-fluoro-4-isopropoxy-spiro[chromane-2,4'-piperidine] | 5-(cyclopropylmethyl-sulfonyl)pyridine-2-carboxylic acid |
| [4-(difluoromethoxy)-3-methoxy-phenyl]-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-(difluoromethoxy)-3-methoxy-benzoic acid |
| (4-ethyl-3-methoxy-phenyl)-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 4-ethyl-3-methoxy-benzoic acid |
| [5-(cyclobutylmethylsulfonyl)-2-pyridyl]-[(4R)-6-fluoro-4-isopropoxy-spiro[chromane-2,4'-piperidine]-1'-yl]methanone | (4R)-6-fluoro-4-isopropoxy-spiro[chromane-2,4'-piperidine] | 5-(cyclobutylmethyl-sulfonyl)pyridine-2-carboxylic acid |
| (3-hydroxy-4-isopropoxy-phenyl)-[(4R)-4-isopropoxyspiro[chromane-2,4'-piperidine]-1'-yl]methanone | (4R)-4-isopropoxyspiro[chromane-2,4'-piperidine] | 3-hydroxy-4-isopropoxy-benzoic acid |
| [(4R)-4-isopropoxyspiro[chromane-2,4'-piperidine]-1'-yl]-(2-methoxy-6-methyl-3-pyridyl)methanone | (4R)-4-isopropoxyspiro[chromane-2,4'-piperidine] | 2-methoxy-6-methyl-pyridine-3-carboxylic acid |
| [(4R)-4-isopropoxyspiro[chromane-2,4'-piperidine]-1'-yl]-(8-quinolyl)methanone | (4R)-4-isopropoxyspiro[chromane-2,4'-piperidine] | quinoline-8-carboxylic acid |
| (6-isopropoxy-3-pyridyl)-[(4R)-4-isopropoxyspiro[chromane-2,4'-piperidine]-1'-yl]methanone | (4R)-4-isopropoxyspiro[chromane-2,4'-piperidine] | 6-isopropoxypyridine-3-carboxylic acid |
| [4-(difluoromethoxy)-3-methoxy-phenyl]-[(4R)-4-isopropoxyspiro[chromane-2,4'-piperidine]-1'-yl]methanone | (4R)-4-isopropoxyspiro[chromane-2,4'-piperidine] | 4-(difluoromethoxy)-3-methoxy-benzoic acid |
| [3-fluoro-4-(1-hydroxy-1-methyl-ethyl)phenyl]-[(4R)-4-isopropoxyspiro[chromane-2,4'-piperidine]-1'-yl]methanone | (4R)-4-isopropoxyspiro[chromane-2,4'-piperidine] | 3-fluoro-4-(1-hydroxy-1-methyl-ethyl)benzoic acid |
| (3-fluoro-4-isopropoxy-phenyl)-[(4R)-4-isopropoxyspiro[chromane-2,4'-piperidine]-1'-yl]methanone | (4R)-4-isopropoxyspiro[chromane-2,4'-piperidine] | 3-fluoro-4-isopropoxy-benzoic acid |
| (2-fluoro-4-isopropoxy-phenyl)-[(4R)-4-isopropoxyspiro[chromane-2,4'-piperidine]-1'-yl]methanone | (4R)-4-isopropoxyspiro[chromane-2,4'-piperidine] | 2-fluoro-4-isopropoxy-benzoic acid |
| (4-ethyl-3-methoxy-phenyl)-[(4R)-4-isopropoxyspiro[chromane-2,4'-piperidine]-1'-yl]methanone | (4R)-4-isopropoxyspiro[chromane-2,4'-piperidine] | 4-ethyl-3-methoxy-benzoic acid |
| (4-isopropoxy-2-methyl-phenyl)-[(4R)-4-isopropoxyspiro[chromane-2,4'-piperidine]-1'-yl]methanone | (4R)-4-isopropoxyspiro[chromane-2,4'-piperidine] | 4-isopropoxy-2-methyl-benzoic acid |
| (4-ethoxy-3-fluoro-phenyl)-[(4R)-4-isopropoxyspiro[chromane-2,4'-piperidine]-1'-yl]methanone | (4R)-4-isopropoxyspiro[chromane-2,4'-piperidine] | 4-ethoxy-3-fluoro-benzoic acid |
| (4-isopropoxy-3-methyl-phenyl)-[(4R)-4-isopropoxyspiro[chromane-2,4'-piperidine]-1'-yl]methanone | (4R)-4-isopropoxyspiro[chromane-2,4'-piperidine] | 4-isopropoxy-3-methyl-benzoic acid |
| (4-hydroxy-3-methoxy-phenyl)-[(4R)-4-isopropoxyspiro[chromane-2,4'-piperidine]-1'-yl]methanone | (4R)-4-isopropoxyspiro[chromane-2,4'-piperidine] | 4-hydroxy-3-methoxy-benzoic acid |
| [(4R)-6-fluoro-4-isopropoxy-spiro[chromane-2,4'-piperidine]-1'-yl]-(4-isopropylsulfinylphenyl)methanone | (4R)-6-fluoro-4-isopropoxy-spiro[chromane-2,4'-piperidine] | 4-isopropylsulfinyl benzoic acid |
| [(4R)-6-fluoro-4-isopropoxy-spiro[chromane-2,4'-piperidine]-1'-yl]-(4-isopropylsulfanylphenyl)methanone | (4R)-6-fluoro-4-isopropoxy-spiro[chromane-2,4'-piperidine] | 4-isopropylsulfanyl benzoic acid |
| N-[4-[(4R)-6-fluoro-4-isopropoxy-spiro[chromane-2,4'-piperidine]-1'-carbonyl]phenyl]propane-2-sulfonamide | (4R)-6-fluoro-4-isopropoxy-spiro[chromane-2,4'-piperidine] | 4-(isopropylsulfonyl-amino)benzoic acid |
| 5-[(4R)-6-fluoro-4-isopropoxy-spiro[chromane-2,4'-piperidine]-1'-carbonyl]-2-isopropoxy-benzonitrile | (4R)-6-fluoro-4-isopropoxy-spiro[chromane-2,4'-piperidine] | 3-cyano-4-isopropoxy-benzoic acid |

| Product | Amine | Carboxylic Acid |
| --- | --- | --- |
| [(4R)-6-fluoro-4-isopropoxy-spiro[chromane-2,4'-piperidine]-1'-yl]-(5-hydroxy-2-pyridyl)methanone | (4R)-6-fluoro-4-isopropoxy-spiro[chromane-2,4'-piperidine] | 5-hydroxypyridine-2-carboxylic acid |

(4-Isopropoxy-3-methoxy-phenyl)-(4-methoxyspiro[chromane-2,4'-piperidine]-1'-yl)methanone Step 1: 1'-(4-Isopropoxy-3-methoxy-benzoyl)spiro[chromane-2,4'-piperidine]-4-one

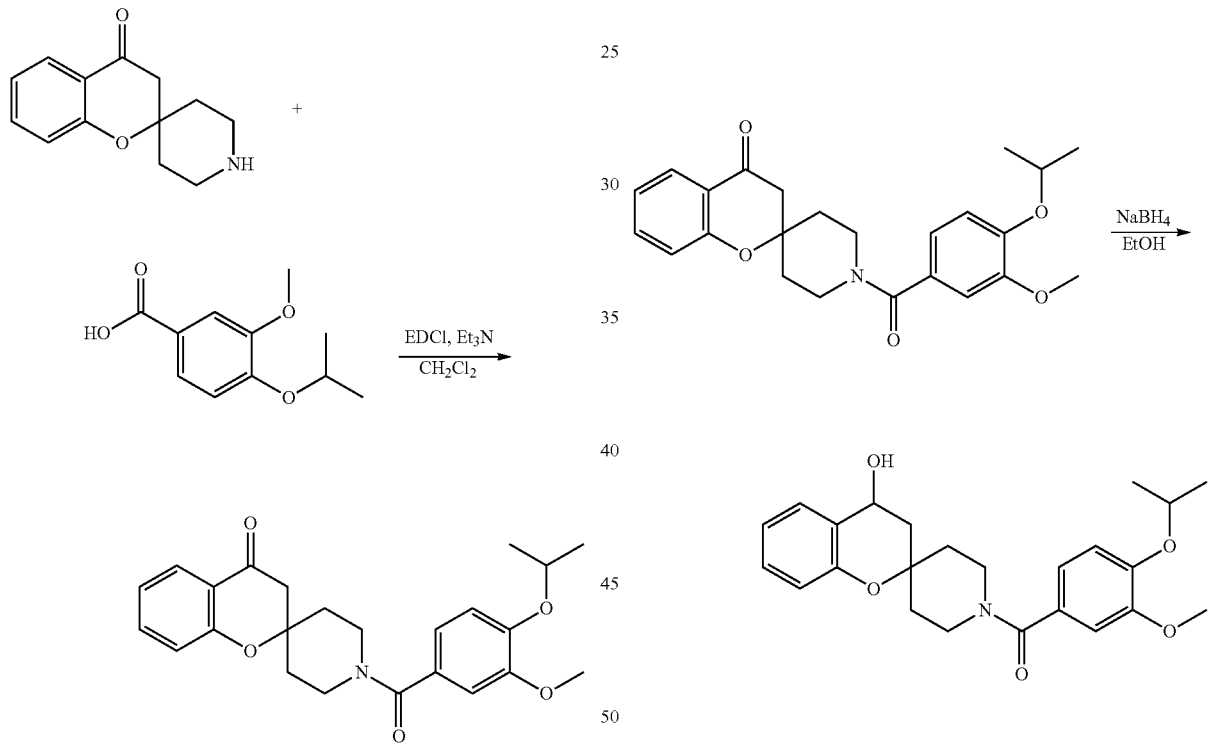

Spiro[chroman-2,4'-piperidine]-4-one (3.26 g, 12.9 mmol), 4-isopropoxy-3-methoxy-benzoic acid (2.97 g, 14.1 mmol), Et$_3$N (6.50 mL, 46.6 mmol), and EDCI (2.71 g, 14.1 mmol) were combined in CH$_2$Cl$_2$ (35 mL). The reaction mixture was stirred at room temperature for 16 hours. The reaction mixture was washed three times with a 1M solution of hydrochloric acid, followed by three washes with a saturated aqueous solution of sodium bicarbonate, followed by three washes of a saturated aqueous solution of sodium chloride. The organic layer was dried over sodium sulfate, filtered, and evaporated to dryness to yield 1'-(4-isopropoxy-3-methoxy-benzoyl)spiro[chromane-2,4'-piperidine]-4-one (5.14 g, 97%) as a pale yellow solid. ESI-MS m/z calc. 409.2, found 410.5 (M+1)$^+$; Retention time: 1.61 minutes (3 min run). $^1$H NMR (400 MHz, DMSO) δ 7.73 (dd, J=7.8, 1.6 Hz, 1H), 7.66-7.51 (m, 1H), 7.14-6.88 (m, 5H), 4.59 (hept, J=6.0 Hz, 1H), 4.38-3.82 (m, 1H), 3.76 (s, 3H), 3.32 (s, 3H), 2.87 (s, 2H), 2.06-1.62 (m, 4H), 1.26 (d, J=6.0 Hz, 6H).

Step 2: (4-Hydroxyspiro[chromane-2,4'-piperidine]-1'-yl)-(4-isopropoxy-3-methoxy-phenyl)methanone 1'-(4-Isopropoxy-3-methoxy-benzoyl)spiro[chromane-2,4'-piperidine]-4-one (1.74 g, 4.24 mmol) was dissolved in EtOH (10 mL). NaBH$_4$ (80 mg, 2.1 mmol) was added and the reaction mixture was allowed to stir for 6 hours at room temperature. The reaction mixture was then partitioned between a saturated aqueous solution of sodium bicarbonate and ethyl acetate. The layers were separated and the organic layer was washed with a saturated aqueous solution of sodium chloride. The organic layer was dried over sodium sulfate, filtered, and evaporated to dryness to yield (4-hydroxyspiro[chromane-2,4'-piperidine]-1'-yl)-(4-isopropoxy-3-methoxy-phenyl)methanone (1.45 g, 83%) as a white solid. ESI-MS m/z calc. 411.2, found 412.5 (M+1)$^+$; Retention time: 1.47 minutes (3 min run).

The following compounds were prepared using procedures reported above:

| Ketone | Alcohol |
|---|---|
| 1'-(2-(trifluoromethoxy)-benzoyl)spiro[chroman-2,4'-piperidin]-4-one | (4-hydroxyspiro[chroman-2,4'-piperidine]-1'-yl)(2-(trifluoromethoxy)phenyl)methanone |
| 1'-(2-(difluoromethoxy)-benzoyl)spiro[chroman-2,4'-piperidin]-4-one | (2-(difluoromethoxy)phenyl)(4-hydroxyspiro[chroman-2,4'-piperidine]-1'-yl)methanone |
| 2-isopropoxy-5-(4-oxospiro[chroman-2,4'-piperidine]-1'-ylcarbonyl)benzonitrile | 5-(4-hydroxyspiro[chroman-2,4'-piperidine]-1'-ylcarbonyl)-2-isopropoxybenzonitrile |

Step 3: (4-Isopropoxy-3-methoxy-phenyl)-(4-methoxyspiro[chromane-2,4'-piperidine]-1'-yl)methanone

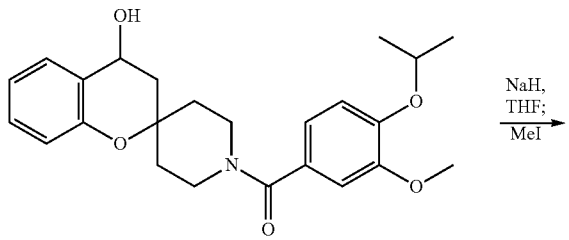

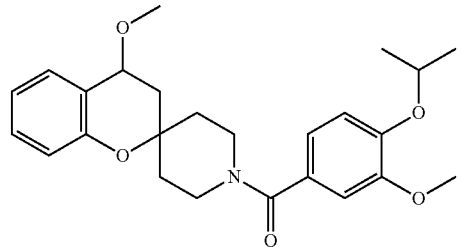

To a vial was added (4-hydroxyspiro[chromane-2,4'-piperidine]-1'-yl)-(4-isopropoxy-3-methoxy-phenyl)methanone (50 mg, 0.12 mmol) and THF (1 mL). The vial was cooled to 0° C. before NaH (7.3 mg, 0.18 mmol, 60%) was added. The mixture was allowed to stir for 10 minutes before MeI (51 mg, 0.36 mmol) was added. The mixture was allowed to stir overnight before it was filtered and concentrated. The residue was dissolved in DMF and was purified by preparative HPLC (20%-99% MeOH:$H_2O$) to give (4-isopropoxy-3-methoxy-phenyl)-(4-methoxyspiro[chromane-2,4'-piperidine]-1'-yl)methanone. ESI-MS m/z calc. 425.2, found 426.3 $(M+1)^+$; Retention time: 1.81 minutes (3 min run).

The following compounds were prepared using the procedure reported above:

| Product | Alkyl halide |
|---|---|
| (4-ethoxyspiro[chroman-2,4'-piperidine]-1'-yl)(4-isopropoxy-3-methoxyphenyl)methanone | iodoethane |
| (4-(cyclopropylmethoxy)spiro[chroman-2,4'-piperidine]-1'-yl)(4-isopropoxy-3-methoxyphenyl)methanone | (iodomethyl)cyclopropane |
| (4-isopropoxy-3-methoxyphenyl)(4-(pyridin-3-ylmethoxy)spiro[chroman-2,4'-piperidine]-1'-yl)methanone | 3-(bromomethyl)pyridine hydrobromide |
| (4-(2-(diethylamino)ethoxy)spiro[chroman-2,4'-piperidine]-1'-yl)(4-isopropoxy-3-methoxyphenyl)methanone | 2-bromo-N,N-diethylethanamine hydrobromide |
| (4-cyclopropoxyspiro[chroman-2,4'-piperidine]-1'-yl)(4-isopropoxy-3-methoxyphenyl)methanone | bromocyclopropane |
| (R)-(6-fluoro-4-isopropoxyspiro[chroman-2,4'-piperidine]-1'-yl)(4-isopropoxy-3-methoxyphenyl)methanone | 2-bromopropane |
| (4-(allyloxy)spiro[chroman-2,4'-piperidine]-1'-yl)(4-isopropoxy-3-methoxyphenyl)methanone | allyl bromide |
| (4'-isopropoxy-3',4'-dihydrospiro[piperidine-4,2'-pyrano[3,2-c]pyridine]-1-yl)(4-isopropoxy-3-methylphenyl)methanone | 2-bromopropane |
| (4'-isopropoxy-3',4'-dihydrospiro[piperidine-4,2'-pyrano[2,3-c]pyridine]-1-yl)(4-isopropoxy-3-methylphenyl)methanone | 2-bromopropane |
| 2-(1'-(4-isopropoxy-3-methoxybenzoyl)spiro[chroman-2,4'-piperidine]-4-yloxy)benzonitrile | 2-fluorobenzonitrile |
| (4-isopropoxy-3-methoxyphenyl)(4-(pyridin-3-yloxy)spiro[chroman-2,4'-piperidine]-1'-yl)methanone | 3-fluoropyridine |
| 5-(1'-(4-isopropoxy-3-methoxybenzoyl)spiro[chroman-2,4'-piperidine]-4-yloxy)nicotinonitrile | 5-fluoronicotinonitrile |

135

(4-Isopropoxy-3-methoxy-phenyl)-[4-(2-methylsulfonylethoxy)spiro[chromane-2,4'-piperidine]-1'-yl]methanone

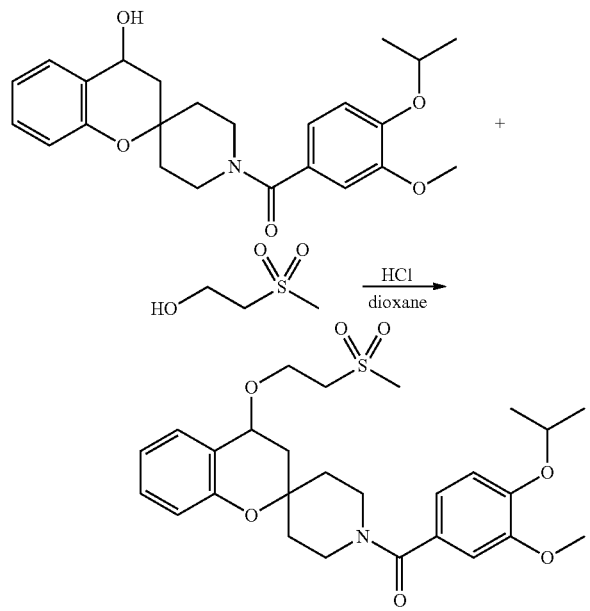

To a vial was added (4-hydroxyspiro[chromane-2,4'-piperidine]-1'-yl)-(4-isopropoxy-3-methoxy-phenyl)methanone (21 mg, 0.050 mmol), 2-(methylsulfonyl)ethanol (19 mg, 0.15 mmol), dioxane (0.5 mL), and HCl (38 μL, 0.15 mmol, 4.0 M in dioxane). The mixture was heated at 65° C. for 6 hours before it was filtered and purified by preparative HPLC (20%-99% MeOH:H$_2$O) to give (4-isopropoxy-3-methoxy-phenyl)-[4-(2-methylsulfonylethoxy)spiro[chromane-2,4'-piperidine]-1'-yl]methanone. ESI-MS m/z calc. 517.2, found 518.1 (M+1)$^+$; Retention time: 1.63 minutes (3 min run).

The following compounds were prepared using procedures reported above:

| Product | Alcohol |
|---|---|
| (4-isopropoxy-3-methoxyphenyl)(4-((S)-1-methoxypropan-2-yloxy)spiro[chroman-2,4'-piperidine]-1'-yl)methanone | (S)-1-methoxypropan-2-ol |
| (4-isopropoxy-3-methoxyphenyl)(4-((R)-tetrahydrofuran-3-yloxy)spiro[chroman-2,4'-piperidine]-1'-yl)methanone | (R)-tetrahydrofuran-3-ol |
| (4-isopropoxy-3-methoxyphenyl)(4-((R)-1-methoxypropan-2-yloxy)spiro[chroman-2,4'-piperidine]-1'-yl)methanone | (R)-1-methoxypropan-2-ol |
| (4-isopropoxy-3-methoxyphenyl)(4-((S)-tetrahydrofuran-3-yloxy)spiro[chroman-2,4'-piperidine]-1'-yl)methanone | (S)-tetrahydrofuran-3-ol |
| (4-isopropoxyspiro[chroman-2,4'-piperidine]-1'-yl)(2-(trifluoromethoxy)phenyl)methanone | propan-2-ol |
| (2-(difluoromethoxy)phenyl)(4-isopropoxyspiro[chroman-2,4'-piperidine]-1'-yl)methanone | propan-2-ol |
| 2-isopropoxy-5-(4-isopropoxyspiro[chroman-2,4'-piperidine]-1'-ylcarbonyl)benzonitrile | propan-2-ol |
| (4-cyclobutoxyspiro[chroman-2,4'-piperidine]-1'-yl)(4-isopropoxy-3-methoxyphenyl)methanone | cyclobutanol |
| (4-tert-butyl-3-methoxyphenyl)(4-isopropoxyspiro[chroman-2,4'-piperidine]-1'-yl)methanone | propan-2-ol |
| (4-bromo-3-methoxyphenyl)(4-isopropoxyspiro[chroman-2,4'-piperidine]-1'-yl)methanone | propan-2-ol |
| (2S)-methyl 2-(1'-(4-isopropoxy-3-methoxybenzoyl)spiro[chroman-2,4'-piperidine]-4-yloxy)propanoate | (S)-methyl 2-hydroxypropanoate |

(8-fluoro-4-isopropoxy-spiro[chromane-2,4'-piperidine]-1'-yl)-(4-isopropylsulfonyl-3-methyl-phenyl)methanone To a solution of (8-fluoro-4-hydroxy-spiro[chromane-2,4'-piperidine]-1'-yl)-(4-isopropylsulfonyl-3-methyl-phenyl)methanone (134 mg, 0.29 mmol) in iPrOH (0.5 mL) was added trifluoromethylsulfonyl trifluoromethanesulfonate (8.2 mg, 4.9 μL, 0.029 mmol). The solution was heated under microwave irradiation at 110° C. for 30 minutes. After allowing to stand for 1 hour, the reaction mixture was filtered to collect crystalline white solids. They were dissolved in DMF and purified by UV-triggered HPLC to provide (8-fluoro-4-isopropoxy-spiro[chromane-2,4'-piperidine]-1'-yl)-(4-isopropylsulfonyl-3-methyl-phenyl)methanone as a colorless solid. $^1$H NMR (400 MHz, CDCl$_3$) δ 8.02 (d, J=8.6 Hz, 1H), 7.38 (d, J=7.4 Hz, 2H), 7.10 (d, J=7.8 Hz, 1H), 7.03-6.95 (m, 1H), 6.86 (td, J=7.9, 4.9 Hz, 1H), 4.53 (t, J=14.2 Hz, 2H), 3.91-3.80 (m, 1H), 3.67-3.20 (m, 4H), 2.71 (s, 3H), 2.32 (d, J=13.4 Hz, 1H), 2.18-1.94 (m, 3H), 1.79 (dd, J=25.7, 10.1 Hz, 2H), 1.57 (d, J=10.4 Hz, 2H), 1.31 (d, J=6.8 Hz, 6H), 1.28 (d, J=5.9 Hz, 3H), 1.22 (s, 3H). ESI-MS m/z calc. 503.21417, found 504.4 (M+1); Retention time: 1.88 minutes.

The following compounds were prepared using the procedure reported above:

(8-fluoro-4-isopropoxyspiro[chroman-2,4'-piperidine]-1'-yl)(4-isopropoxy-3-methoxyphenyl)methanone;

(8-fluoro-4-isopropoxyspiro[chroman-2,4'-piperidine]-1'-yl)(4-(isopropylsulfonyl)phenyl)methanone.

137

((R)-4-((S)-1-Hydroxypropan-2-yloxy)spiro[chroman-2,4'-piperidine]-1'-yl)(4-isopropoxy-3-methoxyphenyl)methanone and ((S)-4-((S)-1-hydroxypropan-2-yloxy)spiro[chroman-2,4'-piperidine]-1'-yl)(4-isopropoxy-3-methoxyphenyl)methanone

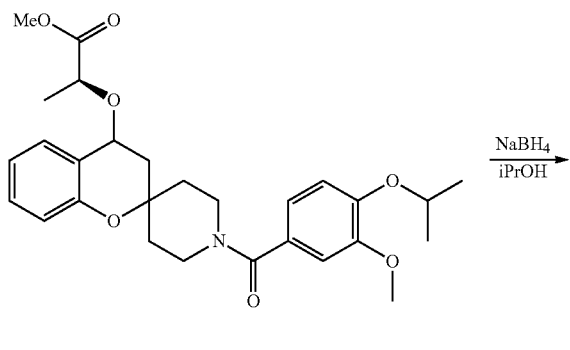

To a vial containing methyl (2S)-2-[1'-(4-isopropoxy-3-methoxy-benzoyl)spiro-[chromane-2,4'-piperidine]-4-yl]oxypropanoate (20 mg, 0.040 mmol) was added iPrOH (2 mL) and NaBH$_4$ (4.6 mg, 0.12 mmol). The mixture was allowed to stir for 3 h at ambient temperature. The mixture was filtered and purified by preparative HPLC (20%-99% MeOH:H$_2$O) to give ((R)-4-((S)-1-hydroxypropan-2-yloxy)spiro[chroman-2,4'-piperidine]-1'-yl)(4-isopropoxy-3-methoxyphenyl)methanone [ESI-MS m/z calc. 469.3, found 470.5 (M+1)$^+$; Retention time: 1.64 minutes (3 min run)] and ((S)-4-((S)-1-hydroxypropan-2-yloxy)spiro[chroman-2,4'-piperidine]-1'-yl)(4-isopropoxy-3-methoxyphenyl)methanone [ESI-MS m/z calc. 469.3, found 470.5 (M+1)$^+$; Retention time: 1.58 minutes (3 min run)].

138

(R)-(4-(1-hydroxy-2-methylpropan-2-yl)-3-methoxyphenyl)(4-isopropoxyspiro[chroman-2,4'-piperidine]-1'-yl)methanone

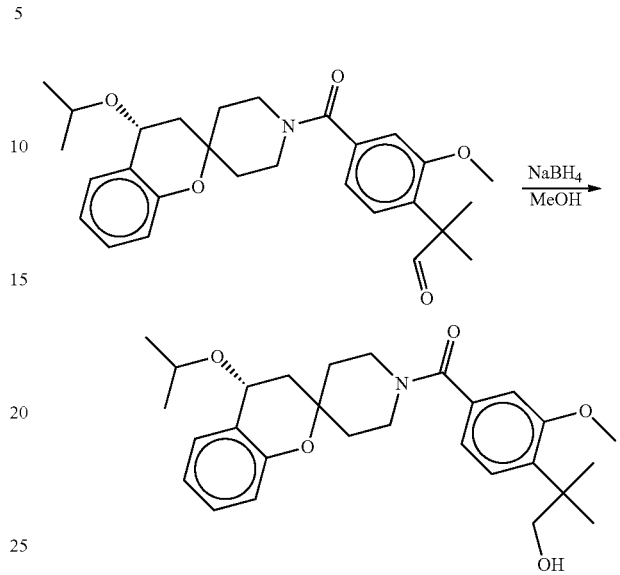

Sodium borohydride (26.8 mg, 0.7 mmol) was added to a solution of (R)-2-(4-(4-isopropoxyspiro[chroman-2,4'-piperidine]-1'-ylcarbonyl)-2-methoxyphenyl)-2-methylpropanal (110 mg, 0.24 mmol) in methanol at room temperature. After 30 minutes, the mixture was filtered and concentrated and purified by mass triggered HPLC (10%-99%) ACN:H$_2$O with no modifier. ESI-MS m/z calc. 467.4, found 468.6 (M+1)$^+$; Retention time: 5.85 minutes (15 min run).

The following compounds were prepared using the procedure reported above:

(S)-(4-(1-hydroxy-2-methylpropan-2-yl)-3-methoxyphenyl)(4-isopropoxyspiro[chroman-2,4'-piperidine]-1'-yl)methanone;

(R)-(6-fluoro-4-isopropoxyspiro[chroman-2,4'-piperidine]-1'-yl)(4-(1-hydroxy-2-methylpropan-2-yl)-3-methoxyphenyl)methanone.

(4-Isopropoxy-3-methoxyphenyl)(4-isopropoxy-3-methoxyspiro[chroman-2,4'-piperidine]-1-yl)methanone Step 1: (4-Isopropoxy-3-methoxy-phenyl)-spiro[chromene-2,4'-piperidine]-1-ylmethanone

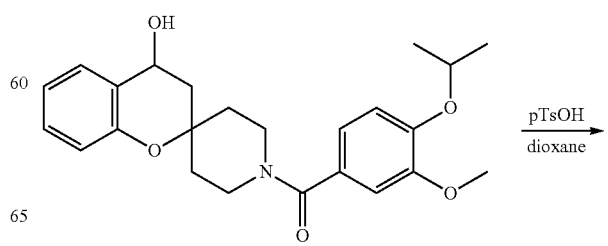

139

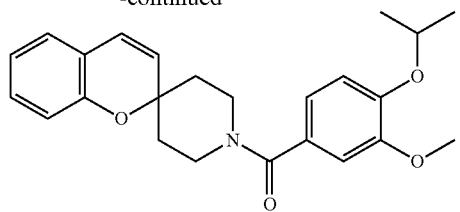

(4-Hydroxyspiro[chromane-2,4'-piperidine]-1'-yl)-(4-isopropoxy-3-methoxy-phenyl)methanone (1.45 g, 3.52 mmol) was dissolved in dioxane (10 mL). 4-methylbenzenesulfonic acid hydrate (771 mg, 4.05 mmol) was added and the reaction mixture was heated at 90° C. for 2 h. The reaction mixture was then partitioned between a saturated aqueous solution of sodium bicarbonate and ethyl acetate. The ethyl acetate layer was washed two times with a saturated aqueous solution of sodium bicarbonate, once with a saturated aqueous solution of sodium chloride, dried over sodium sulfate, filtered, and evaporated to dryness to yield (4-isopropoxy-3-methoxy-phenyl)-spiro[chromene-2,4'-piperidine]-1'-yl-methanone (1.40 g, 99%) as a pale yellow oil. ESI-MS m/z calc. 393.2, found 394.5 (M+1)+; Retention time: 1.85 minutes (3 min run).

Step 2: (1a,7b-Dihydrospiro[oxireno[2,3-c]chromene-2,4'-piperidine]-1'-yl)(4-isopropoxy-3-methoxyphenyl)methanone To (4-isopropoxy-3-methoxy-phenyl)-spiro[chromene-2,4'-piperidine]-1'-yl-methanone (180 mg, 0.458 mmol) and CH$_2$Cl$_2$ (4 mL) was added mCPBA (154 mg, 0.686 mmol) and the mixture was allowed to stir at 25° C. for 2 h. The reaction mixture was quenched with aqueous sodium sulfite and was allowed to stir for 30 minutes. The mixture was extracted with CH$_2$Cl$_2$ (2×). The combined organics were dried over sodium sulfate and evaporated. The residue was purified by silica gel chromatography (10-70% ethyl acetate/hexanes) to give (1a,7b-dihydrospiro[oxireno[2,3-c]chromene-2,4'-piperidine]-1'-yl)(4-isopropoxy-3-methoxyphenyl)methanone as a colorless oil.

140

Step 3: (3-Hydroxy-4-isopropoxyspiro[chroman-2,4'-piperidine]-1-yl)(4-isopropoxy-3-methoxyphenyl)methanone

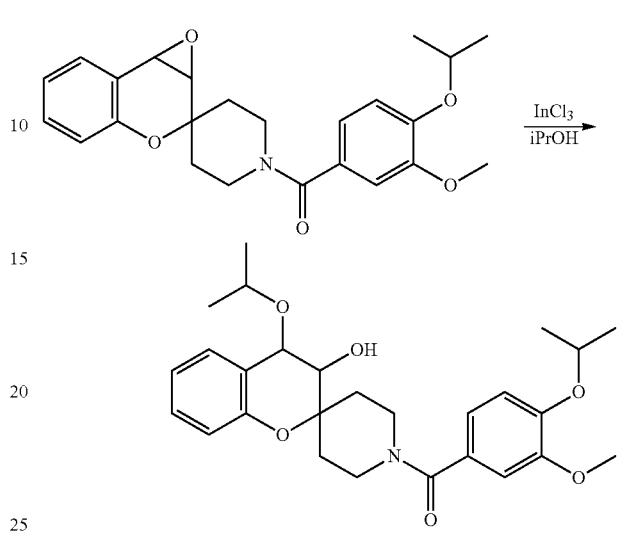

To (1a,7b-dihydrospiro[oxireno[2,3-c]chromene-2,4'-piperidine]-1'-yl)(4-isopropoxy-3-methoxyphenyl)methanone (27 mg, 0.066 mmol) was added iPrOH (720 µL, 9.40 mmol) followed by InCl$_3$ (10.1 mg, 0.0459 mmol). The mixture was allowed to stir for 2 hours before it was filtered and purified by preparative HPLC (20%-99% MeOH:H$_2$O) to yield (4-isopropoxy-3-methoxy-phenyl)-[(3S,4R)-4-isopropoxy-3-methoxy-spiro[chromane-2,4'-piperidine]-1'-yl]methanone (33 mg, 14%) as a white solid. ESI-MS m/z calc. 469.3, found 470.5 (M+1)+; Retention time: 1.71 minutes (3 min run).

Step 4: (4-Isopropoxy-3-methoxyphenyl)(4-isopropoxy-3-methoxyspiro[chroman-2,4'-piperidine]-1'-yl)methanone

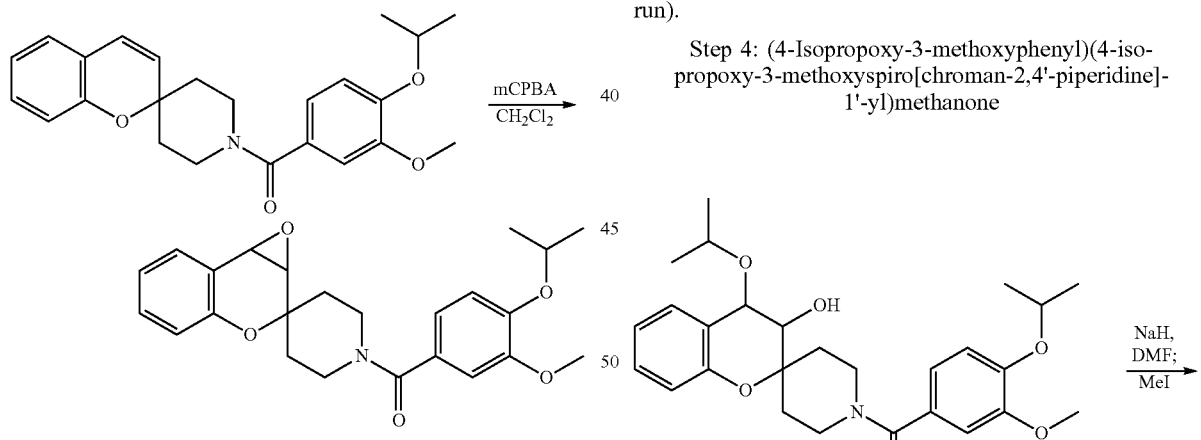

To (4-isopropoxy-3-methoxy-phenyl)-[(3S,4R)-4-isopropoxy-3-methoxy-spiro-[chromane-2,4'-piperidine]-1'-yl]methanone (33 mg, 0.07 mmol) was added DMF (1 mL), NaH (20 mg, 0.50 mmol), and MeI (31 µL, 0.50 mmol). The mixture was allowed to stir for 30 min at ambient temperature before it was filtered and purified by preparative HPLC (20%-99% MeOH:H₂O) to give (4-isopropoxy-3-methoxyphenyl)(4-isopropoxy-3-methoxyspiro[chroman-2,4'-piperidine]-1'-yl)methanone. ESI-MS m/z calc. 483.3, found 484.5 (M+1)⁺; Retention time: 1.92 minutes (3 min run).

(4-Hydroxy-3-methylspiro[chroman-2,4'-piperidine]-1'-yl)(4-isopropoxy-3-methoxyphenyl)methanone and (4-hydroxy-3,3-dimethylspiro[chroman-2,4'-piperidine]-1'-yl)(4-isopropoxy-3-methoxyphenyl)methanone Step 1: 1'-(4-Isopropoxy-3-methoxybenzoyl)-3-methylspiro[chroman-2,4'-piperidin]-4-one and r-(4-isopropoxy-3-methoxybenzoyl)-3,3-dimethylspiro[chroman-2,4'-piperidin]-4-one

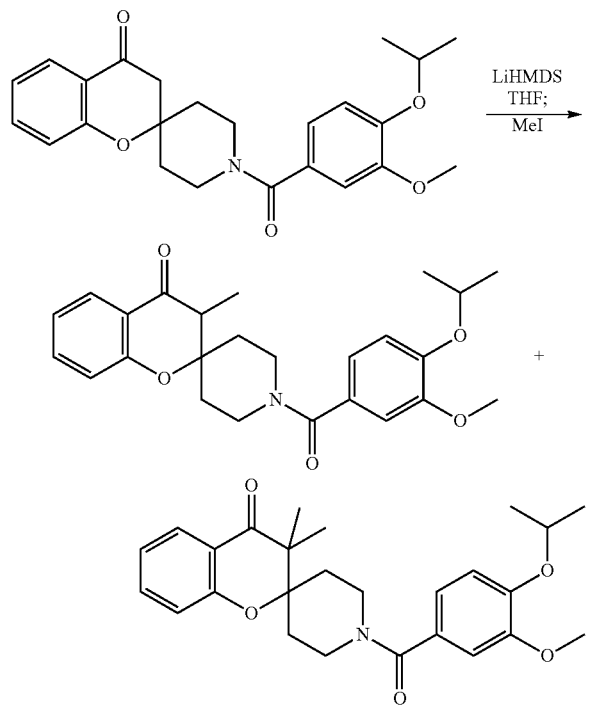

A mixture of 1'-(4-isopropoxy-3-methoxy-benzoyl)spiro[chromane-2,4'-piperidine]-4-one (265 mg, 0.647 mmol) and THF (3.0 mL) was cooled to −78° C. and allowed to stir for 10 minutes. LiHMDS (650 µL, 1.0 M in THF, 0.65 mmol) was added dropwise and the mixture was allowed to stir for 30 minutes at −78° C. MeI (41 µL, 0.65 mmol) dissolved in 0.5 mL of THF was added at −78° C. and the reaction mixture was allowed to warm to room temperature overnight. The reaction mixture was quenched with sat. NH₄Cl and was extracted with EtOAc (3×). The combined organic layers were dried over sodium sulfate and evaporated to give a mixture of 1'-(4-isopropoxy-3-methoxybenzoyl)-3-methylspiro[chroman-2,4'-piperidine]-4-one and 1'-(4-isopropoxy-3-methoxybenzoyl)-3,3-dimethylspiro[chroman-2,4'-piperidin]-4-one.

Step 2: (4-Hydroxy-3-methylspiro[chroman-2,4'-piperidine]-1'-yl)(4-isopropoxy-3-methoxyphenyl)methanone and (4-hydroxy-3,3-dimethylspiro[chroman-2,4'-piperidine]-1'-yl)(4-isopropoxy-3-methoxyphenyl)methanone

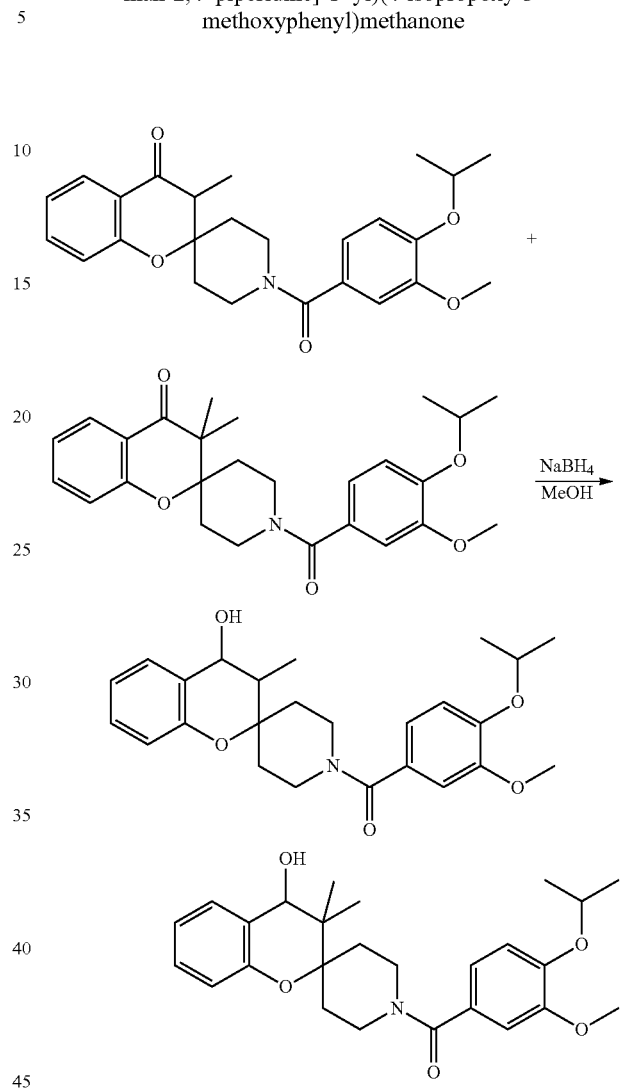

To a mixture of 1'-(4-isopropoxy-3-methoxybenzoyl)-3-methylspiro[chroman-2,4'-piperidin]-4-one and 1'-(4-isopropoxy-3-methoxybenzoyl)-3,3-dimethylspiro[chroman-2,4'-piperidin]-4-one in MeOH (5 mL) cooled to 0° C. was added NaBH₄ (50 mg, 1.3 mmol). The reaction mixture was allowed to warm to room temperature over 30 min. The solvent was evaporated and the residue was quenched with sat. NH₄Cl. The mixture was extracted with ethyl acetate (3×). The combined organic layers were dried over sodium sulfate and evaporated. The residue was purified by preparative HPLC (20%-99% MeOH:H₂O) to give (4-hydroxy-3-methylspiro[chroman-2,4'-piperidine]-1'-yl)(4-isopropoxy-3-methoxyphenyl)methanone, ESI-MS m/z calc. 425.2, found 426.3 (M+1)⁺; Retention time: 1.56 minutes (3 min run), and (4-hydroxy-3,3-dimethylspiro[chroman-2,4'-piperidine]-1'-yl)(4-isopropoxy-3-methoxyphenyl)methanone, ESI-MS m/z calc. 439.2, found 440.3 (M+1)⁺; Retention time: 1.63 minutes (3 min run).

(4-Isopropoxy-3-methoxyphenyl)(4-isopropoxy-3-methylspiro[chroman-2,4'-piperidine]-1'-yl)methanone

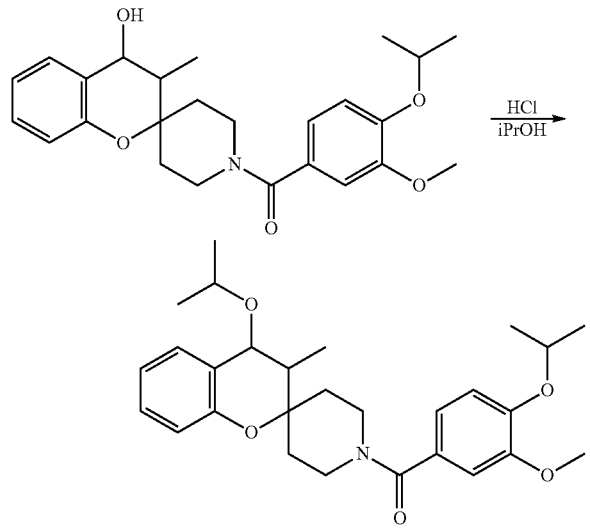

To (4-hydroxy-3-methylspiro[chroman-2,4'-piperidine]-1'-yl)(4-isopropoxy-3-methoxy-phenyl)methanone (265 mg, 0.647 mmol) and iPrOH (495 µL, 6.47 mmol) was added HCl (16 µL, 4.0 M in dioxane, 0.064 mmol). The reaction mixture was heated at 65° C. for 5 h. The mixture was filtered and purified by preparative HPLC (20%-99% MeOH:H₂O) to give (4-isopropoxy-3-methoxyphenyl)(4-isopropoxy-3-methylspiro[chroman-2,4'-piperidine]-1'-yl) methanone as a white solid. ESI-MS m/z calc. 467.3, found 468.5 (M+1)⁺; Retention time: 2.06 minutes (3 min run).

(4-Isopropoxy-3,3-dimethylspiro[chroman-2,4'-piperidine]-1'-yl)(4-isopropoxy-3-methoxyphenyl) methanone

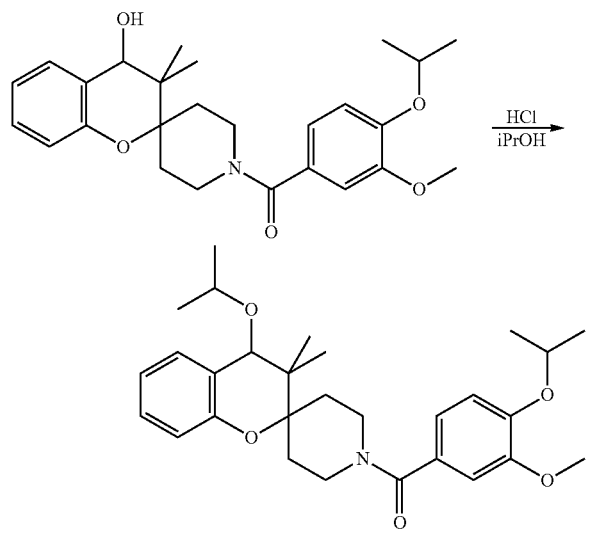

To (4-hydroxy-3,3-dimethylspiro[chroman-2,4'-piperidine]-1'-yl)(4-isopropoxy-3-methoxyphenyl)methanone (265 mg, 0.647 mmol) and iPrOH (495 µL, 6.47 mmol) was added HCl (16 µL, 4.0 M in dioxane, 0.064 mmol). The reaction mixture was heated at 65° C. for 5 h. The mixture was filtered and purified by preparative HPLC (20%-99% MeOH:H₂O) to give (4-isopropoxy-3,3-dimethylspiro[chroman-2,4'-piperidine]-1'-yl)(4-isopropoxy-3-methoxyphenyl)methanone as a white solid. ESI-MS m/z calc. 481.3, found 482.5 (M+1)⁺; Retention time: 2.13 minutes (3 min run).

(4-tert-Butoxyspiro[chromane-2,4'-piperidine]-1'-yl)-(4-isopropoxy-3-methoxy-phenyl)methanone

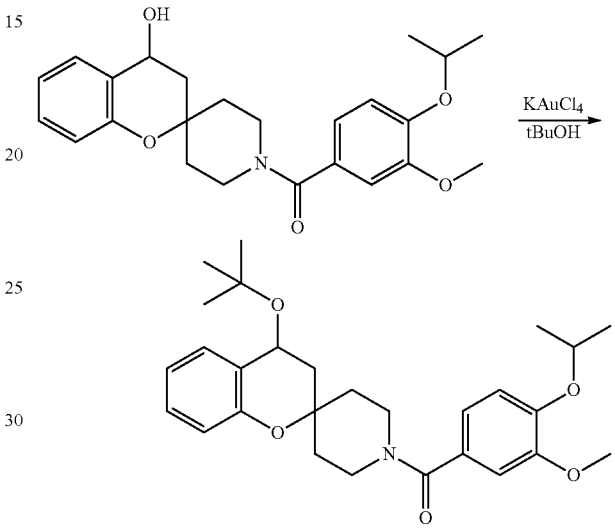

To (4-hydroxyspiro[chromane-2,4'-piperidine]-1'-yl)-(4-isopropoxy-3-methoxy-phenyl)-methanone (65 mg, 0.16 mmol) in tBuOH (630 µL) was added KAuCl₄ (1.6 mg, 0.0079 mmol). The mixture was sealed and heated at 70° C. for 48 h. The mixture filtered and subjected to preparative HPLC (20%-99% MeOH:H₂O) to give (4-tert-butoxyspiro [chromane-2,4'-piperidine]-1'-yl)-(4-isopropoxy-3-methoxyphenyl)-methanone. ESI-MS m/z calc. 467.3, found 468.3 (M+1)⁺; Retention time: 2.13 minutes (3 min run).

(4'-Isopropoxy-3',4'-dihydrospiro[piperidine-4,2'-pyrano[2,3-b]pyridine]-1-yl)(4-isopropoxy-3-methylphenyl)methanone Step 1: 1-(4-Isopropoxy-3-methylbenzoyl)spiro[piperidine-4,2'-pyrano[2,3-b]pyridin]-4'(3'H)-one

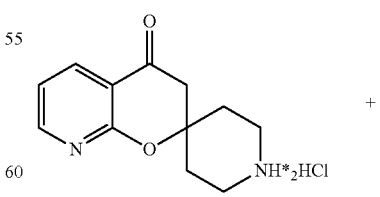

-continued

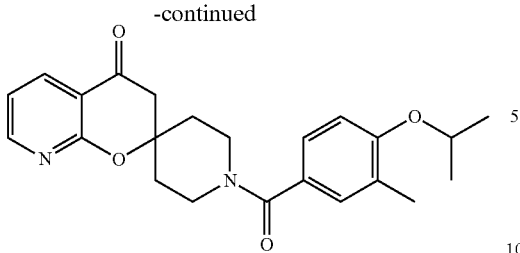

A mixture of spiro[3H-pyrano[2,3-b]pyridine-2,4'-piperidine]-4-one dihydrochloride (264 mg, 0.900 mmol), CH$_2$Cl$_2$ (7 mL) and Et$_3$N (505 μL, 3.62 mmol) was stirred at room temperature for 10 minutes. 4-Isopropoxy-3-methylbenzoic acid (176 mg, 0.900 mmol) was added and the mixture was stirred for 5 minutes. EDCI (191 mg, 1.00 mmol) was added and the reaction mixture was stirred at room temperature for 14 hours. The reaction mixture was washed three times with a 1M solution of hydrochloric acid (3×3 mL), followed by three washes with a saturated aqueous solution of sodium bicarbonate (3×3 mL), followed by three washes of a saturated aqueous solution of sodium chloride (3×3 mL). The organic layer was dried over sodium sulfate, filtered, and evaporated to dryness. The crude product was purified on silica gel utilizing a gradient of 0-100% ethyl acetate in hexane to yield 1-(4-isopropoxy-3-methylbenzoyl)spiro[piperidine-4,2'-pyrano[2,3-b]pyridin]-4'(3'H)-one as a yellow viscous solid. ESI-MS m/z calc. 394.2, found 395.3 (M+1)$^+$; Retention time: 1.51 minutes (3 min run).

Step 2: (4'-Hydroxy-3',4'-dihydrospiro[piperidine-4,2'-pyrano[2,3-b]pyridine]-1-yl)(4-isopropoxy-3-methylphenyl)methanone

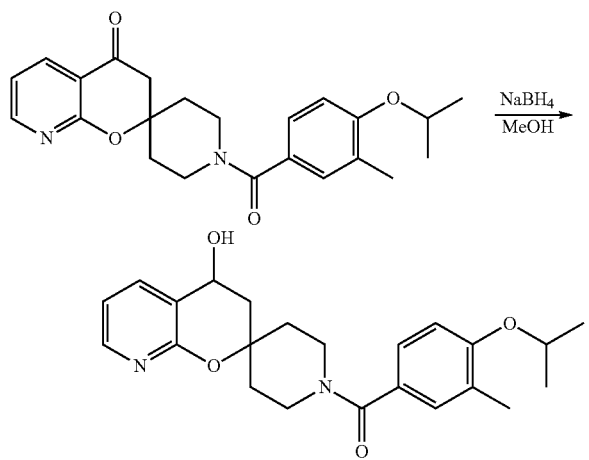

To 1-(4-isopropoxy-3-methylbenzoyl)spiro[piperidine-4,2'-pyrano[2,3-b]pyridin]-4'(3'H)-one (302 mg, 0.760 mmol) in MeOH (5.8 mL) was added NaBH$_4$ (51.4 mg, 1.36 mmol) and the mixture was allowed to stir at room temperature for 35 minutes. The reaction mixture was quenched with a saturated aqueous solution of NH$_4$Cl (3 mL). Water (3 mL) was added to the mixture and it was extracted with ethyl acetate (3×10 mL). The combined organic layers was dried over sodium sulfate, filtered and the solvent was evaporated under reduced pressure to yield (4'-hydroxy-3',4'-dihydrospiro[piperidine-4,2'-pyrano[2,3-b]pyridine]-1-yl)(4-isopropoxy-3-methylphenyl)methanone. ESI-MS m/z calc. 396.2, found 397.3 (M+1)$^+$; Retention time: 1.17 minutes (3 min run).

Step 3: (4'-Isopropoxy-3',4'-dihydrospiro[piperidine-4,2'-pyrano[2,3-b]pyridine]-1-yl)(4-isopropoxy-3-methylphenyl)methanone

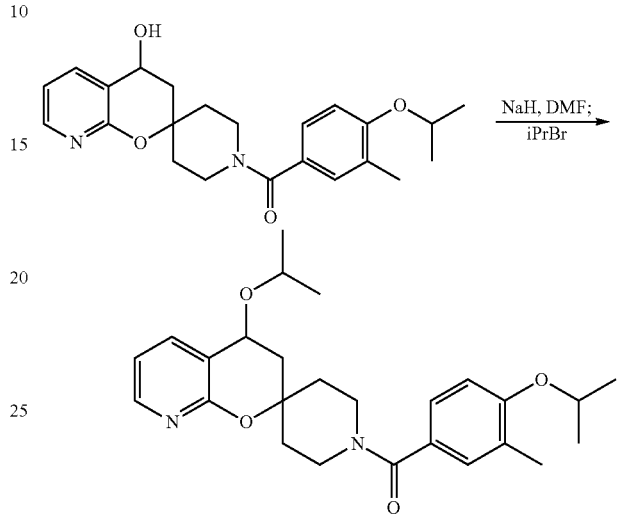

To a mixture of (4'-hydroxy-3',4'-dihydrospiro[piperidine-4,2'-pyrano[2,3-b]pyridine]-1-yl)(4-isopropoxy-3-methylphenyl)methanone (280 mg, 0.71 mmol) and DMF (2 mL) under N$_2$ atmosphere was added NaH (85 mg, 2.13 mmol) and the mixture was stirred at room temperature for 10 minutes. 2-Bromopropane (638 μl, 6.79 mmol) and 4-dimethylaminopyridine (0.14 mmol) were added and the mixture was stirred at 35° C. The reaction was recharged 6 additional times with NaH and 2-bromopropane. MeOH was added to the reaction and the mixture was filtered. The solvent was evaporated under reduced pressure and the residue was dissolved in ethyl acetate (10 mL) before it was washed with water (5 mL), a saturated aqueous solution of sodium bicarbonate (5 mL), and a saturated aqueous solution of sodium chloride (5 mL). The organic layer was dried over sodium sulfate, filtered and the solvent was evaporated under reduced pressure to yield a mixture that was purified on silica gel utilizing a gradient of 0-100% ethyl acetate in hexane to give (4'-isopropoxy-3',4'-dihydrospiro[piperidine-4,2'-pyrano[2,3-b]pyridine]-1-yl)(4-isopropoxy-3-methylphenyl)methanone (75 mg, 23%) as a yellow solid. ESI-MS m/z calc. 438.3, found 439.5 (M+1)$^+$; Retention time: 4.01 minutes (15 min run). $^1$H NMR (400 MHz, DMSO) δ 8.14-8.03 (m, 1H), 7.70 (d, J=6.8 Hz, 1H), 7.27-7.18 (m, 2H), 7.07-6.90 (m, 2H), 4.71-4.56 (m, 2H), 4.35-3.18 (m, 5H), 2.26-2.15 (m, 1H), 2.14 (s, 3H), 1.99-1.65 (m, 5H), 1.29 (d, J=6.0 Hz, 6H), 1.22 (d, J=6.0 Hz, 3H), 1.15 (d, J=6.1 Hz, 3H).

(4'-Isopropoxy-3',4'-dihydrospiro[piperidine-4,2'-pyrano[2,3-b]pyridine]-1-yl)(4-isopropoxy-3-methoxyphenyl)methanone was prepared following a procedure similar as described above. The crude product was purified on silica gel utilizing a gradient of 0-100% ethyl acetate in hexane to yield a yellow solid (67 mg, 7%). ESI-MS m/z calc. 454.3, found 455.7 (M+1)$^+$; Retention time: 3.05 minutes (15 min run). $^1$H NMR (400 MHz, DMSO) δ 8.15-8.04 (m, 1H), 7.70 (d, J=7.4 Hz, 1H), 7.06-6.89 (m, 4H), 4.67-4.50 (m, 2H), 4.34-3.81 (m, 2H), 3.77 (s, 3H), 3.67-3.21 (m, 3H), 2.25-2.12 (m, 1H), 2.04-1.67 (m, 5H), 1.26 (d, J=6.0 Hz, 6H), 1.22 (d, J=6.0 Hz, 3H), 1.15 (d, J=6.1 Hz, 3H).

(R)-(5-Bromopyridin-2-yl)(4-isopropoxyspiro[chroman-2,4'-piperidine]-1'-yl)methanone

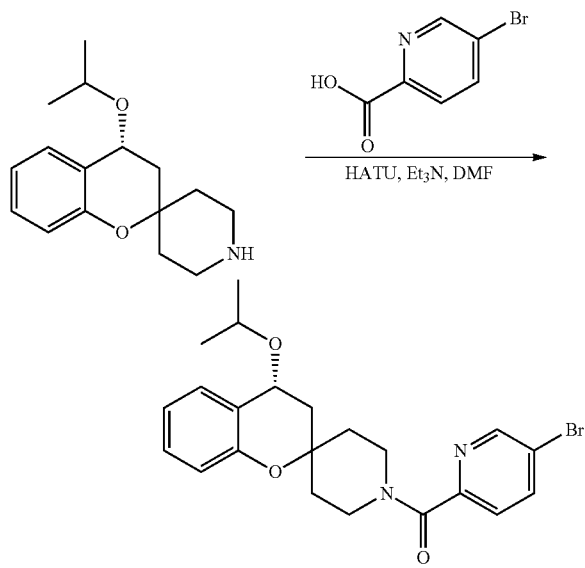

To a 250 mL rbf was added 5-bromopyridine-2-carboxylic acid (2.1 g, 10.2 mmol), HATU (3.9 g, 10.2 mmol), DMF (30 mL), and triethylamine (4.1 mL, 29.1 mmol). The reaction was allowed to stir for 10 minutes. (4R)-4-isopropoxyspiro[chromane-2,4'-piperidine] (2.5 g, 9.7 mmol) (dissolved in 10 mL DMF) was added and the reaction was allowed to stir at rt for 1 h. The reaction was found to be complete by lcms and the reaction was quenched with brine. The mixture was extracted 3 times with EtOAc and the organic layers were dried over sodium sulfate and evaporated. The crude reaction mixture was purified via column chromatography (0-30%) EtOAc in dichloromethane. (5-Bromo-2-pyridyl)-[(4R)-4-isopropoxyspiro[chromane-2,4'-piperidine]-1'-yl]methanone (3.3 g, 77%) was isolated as a thick yellow oil which eluted off the column at 12% EtOAc in dichloromethane. ESI-MS m/z calc. 444.1, found 445.1 (M+1)⁺; Retention time: 1.92 minutes (3 min run).

(R)-(5-bromopyridin-2-yl)(6-fluoro-4-isopropoxyspiro[chroman-2,4'-piperidine]-1'-yl)methanone

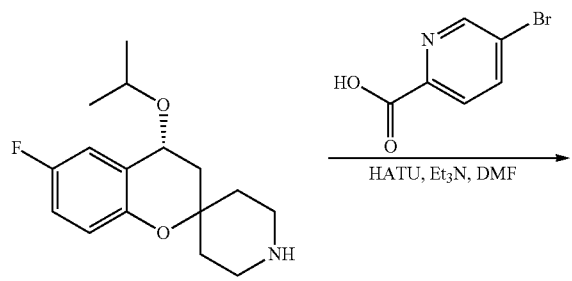

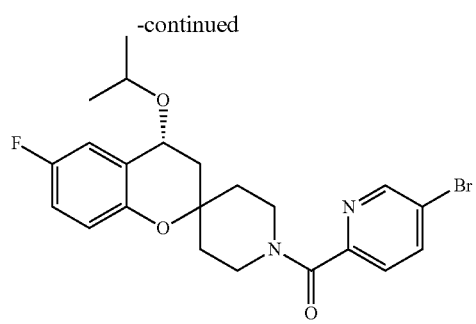

To a 100 mL rbf was added 5-bromopyridine-2-carboxylic acid (721 mg, 3.6 mmol), HATU (1.4 g, 3.6 mmol), DMF (10 mL), and triethylamine (1.0 g, 1.4 mL, 10.2 mmol). The reaction was allowed to stir for 10 minutes and then a solution of (4R)-6-fluoro-4-isopropoxy-spiro[chromane-2,4'-piperidine] (949 mg, 3.4 mmol) in DMF (10 mL) was added and the reaction was allowed to stir at rt for 3 h. The reaction was found to be complete by lcms and the reaction was quenched with brine. The reaction was extracted 3 times with EtOAc and the organic layers were dried over sodium sulfate and evaporated. The crude reaction mixture was purified via silica gel chromatography (0%-60%) EtOAc in dichloromethane. The product elutes at 25% EtOAc in dichloromethane. (5-bromo-2-pyridyl)-[(4R)-6-fluoro-4-isopropoxy-spiro[chromane-2,4'-piperidine]-1'-yl]methanone (920 mg, 58%) was isolated as a pink oil. ESI-MS m/z calc. 462.1, found 465.0 (M+1)⁺; Retention time: 1.95 minutes (3 min run).

Buchwald Coupling Procedure

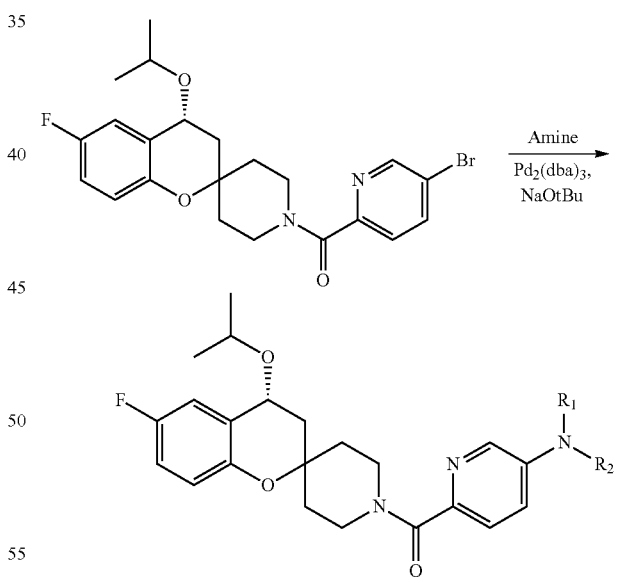

To a 2 mL microwave vial equipped with a stir bar was added Pd₂(dba)₃ (3.6 mg, 0.004 mmol), Xantphos (6.9 mg, 0.12 mmol), and sodium tert-butoxide (19.2 mg, 0.2 mmol). The reaction vial was capped and purged with nitrogen. A solution of (R)-(5-bromopyridin-2-yl)(6-fluoro-4-isopropoxyspiro[chroman-2,4'-piperidine]-1'-yl)methanone (46.3 mg, 0.1 mmol) in THF (0.5 mL) was added followed by the amine (0.2 mmol). The reaction was placed in a preheated 80° C. oil bath and was allowed to stir overnight. The reaction was removed from the oil bath and allowed to cool to rt. The reactions were diluted with DMF (0.5 mL) and filtered through a fit. The crude reaction mixtures were purified via HPLC (10%-99%) ACN:H₂O with a 0.1% HCl modifier.

The following compounds were prepared by the general procedure above using the appropriate bromide and amine.

[(4R)-6-fluoro-4-isopropoxy-spiro[chromane-2,4'-piperidine]-1'-yl]-(5-morpholino-2-pyridyl)methanone;
[(4R)-6-fluoro-4-isopropoxy-spiro[chromane-2,4'-piperidine]-1'-yl]-[5-(propylamino)-2-pyridyl]methanone;
[(4R)-6-fluoro-4-isopropoxy-spiro[chromane-2,4'-piperidine]-1'-yl]-[5-(isopropylamino)-2-pyridyl]methanone;
[(4R)-6-fluoro-4-isopropoxy-spiro[chromane-2,4'-piperidine]-1'-yl]-[5-[isopropyl(methyl)amino]-2-pyridyl]methanone;
[5-(tert-butylamino)-2-pyridyl]-[(4R)-6-fluoro-4-isopropoxy-spiro[chromane-2,4'-piperidine]-1'-yl]methanone;
[(4R)-6-fluoro-4-isopropoxy-spiro[chromane-2,4'-piperidine]-1'-yl]-[5-[(2S)-2-methylpyrrolidin-1-yl]-2-pyridyl]methanone;
[(4R)-6-fluoro-4-isopropoxy-spiro[chromane-2,4'-piperidine]-1'-yl]-[5-(4-methylsulfonylpiperazin-1-yl)-2-pyridyl]methanone;
[(4R)-6-fluoro-4-isopropoxy-spiro[chromane-2,4'-piperidine]-1'-yl]-[5-(3-methylsulfonylazetidin-1-yl)-2-pyridyl]methanone;
[(4R)-6-fluoro-4-isopropoxy-spiro[chromane-2,4'-piperidine]-1'-yl]-[5-(4-methoxy-1-piperidyl)-2-pyridyl]methanone;
[5-[2-dimethylaminoethyl(methyl)amino]-2-pyridyl]-[(4R)-6-fluoro-4-isopropoxy-Spiro[chromane-2,4'-piperidine]-1'-yl]methanone;
[(4R)-6-fluoro-4-isopropoxy-spiro[chromane-2,4'-piperidine]-1'-yl]-[5-[(3-methyloxetan-3-yl)amino]-2-pyridyl]methanone;
[(4R)-6-fluoro-4-isopropoxy-spiro[chromane-2,4'-piperidine]-1'-yl]-[5-[(2R)-2-methylpyrrolidin-1-yl]-2-pyridyl]methanone;
[(4R)-6-fluoro-4-isopropoxy-spiro[chromane-2,4'-piperidine]-1'-yl]-[5-(4-methyl-1-piperidyl)-2-pyridyl]methanone;
[(4R)-6-fluoro-4-isopropoxy-spiro[chromane-2,4'-piperidine]-1'-yl]-[5-[[(1S)-1-methylpropyl]amino]-2-pyridyl]methanone;
[(4R)-6-fluoro-4-isopropoxy-spiro[chromane-2,4'-piperidine]-1'-yl]-[5-[[(1R)-1-methylpropyl]amino]-2-pyridyl]methanone;
[(4R)-4-isopropoxyspiro[chromane-2,4'-piperidine]-1'-yl]-(5-pyrrolidin-1-yl-2-pyridyl)methanone;
(5-(2,6-dimethylmorpholino)pyridin-2-yl)((4R)-6-fluoro-4-isopropoxyspiro[chroman-2,4'-piperidine]-1'-yl)methanone;
(5-(3-ethylmorpholino)pyridin-2-yl)((4R)-6-fluoro-4-isopropoxyspiro[chroman-2,4'-piperidine]-1'-yl)methanone;
((4R)-6-fluoro-4-isopropoxyspiro[chroman-2,4'-piperidine]-1'-yl)(5-(2-methylpiperidin-1-yl)pyridin-2-yl)methanone;
(5-(2-oxa-5-azabicyclo[2.2.1]heptan-5-yl)pyridin-2-yl)((4R)-6-fluoro-4-isopropoxyspiro[chroman-2,4'-piperidine]-1'-yl)methanone;
((4R)-6-fluoro-4-isopropoxyspiro[chroman-2,4'-piperidine]-1'-yl)(5-(3-methylpiperidin-1-yl)pyridin-2-yl)methanone.

(4R)-(3-(Aminomethyl)-4-isopropoxyphenyl)(6-fluoro-4-isopropoxyspiro[chroman-2,4'-piperidine]-1'-yl)methanone

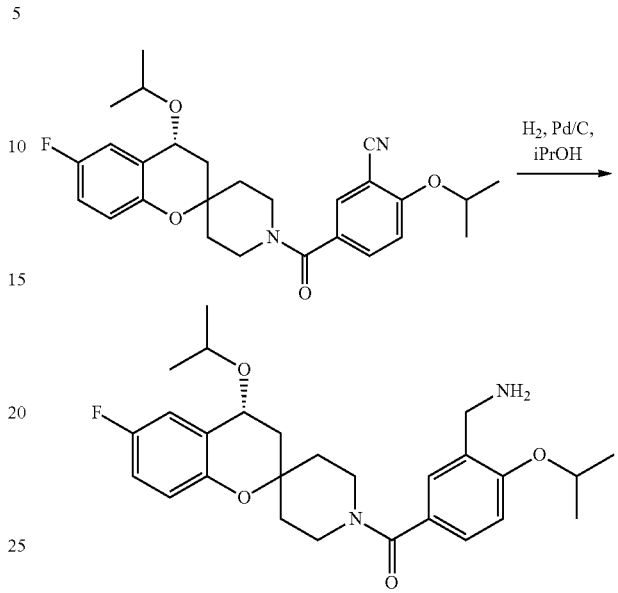

To a 100 mL flask was added 5-[(4R)-6-fluoro-4-isopropoxy-spiro[chromane-2,4'-piperidine]-1'-carbonyl]-2-isopropoxy-benzonitrile (450 mg, 0.97 mmol) Pd on C, wet, Degussa (127 mg) and isopropanol (10 mL). The reaction was purged with nitrogen and a balloon of hydrogen was attached. The reaction was heated overnight at 40° C. and showed product by lcms. The reaction was filtered and the solvent was evaporated. The crude reaction mixture was purified via hplc (10%-99%) ACN:H₂O with no modifier. ESI-MS m/z calc. 470.2, found 471.2 (M+1)⁺; Retention time: 1.6 minutes (3 min run).

(R)-(6-Fluoro-4-isopropoxyspiro[chroman-2,4'-piperidine]-1'-yl)(4-isopropoxy-3-((methylamino)methyl)phenyl)methanone

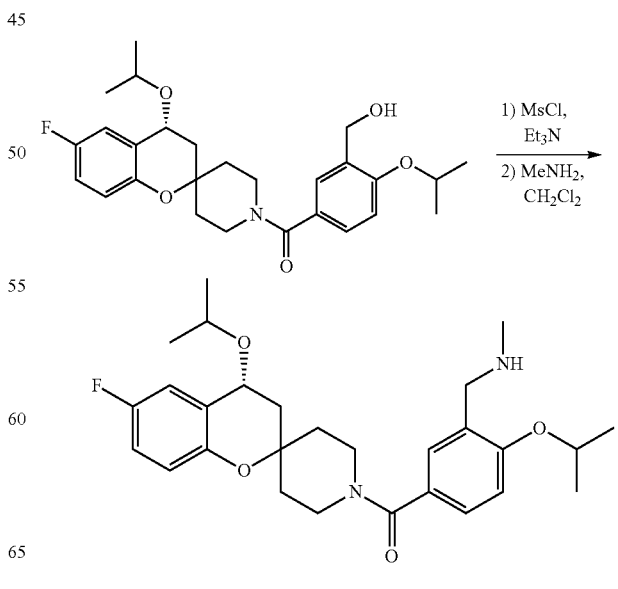

151

To a 25 mL rbf was added [(4R)-6-fluoro-4-isopropoxy-spiro[chromane-2,4'-piperidine]-1'-yl]-[3-(hydroxymethyl)-4-isopropoxy-phenyl]methanone (200 mg, 0.42 mmol) and dichloromethane (2 mL) and the reaction was chilled to 0° C. Triethylamine (177 µL, 1.3 mmol) was added followed by methane sulfonyl chloride (36 µL, 0.47 mmol) and the reaction was allowed to stir for 1 h while warming to 25° C.

To a 10 mL rbf was added 1 mL of the above reaction mixture and methylamine was added. The reaction was allowed to stir at rt for 1 h and was complete by lcms. The reaction was filtered and purified via HPLC (10%-99%) (ACN:H$_2$O). ESI-MS m/z calc. 484.27374, found 485.6 (M+1)$^+$; Retention time: 1.64 minutes (3 min run).

(R)-(3-((Dimethylamino)methyl)-4-isopropoxyphenyl)(6-fluoro-4-isopropoxyspiro[chroman-2,4'-piperidine]-1'-yl)methanone

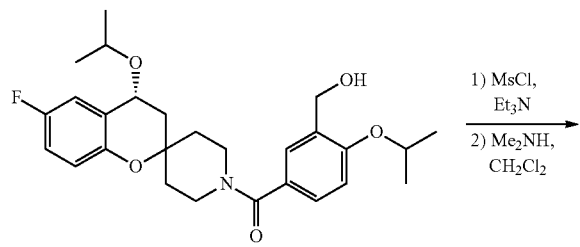

To a 25 mL rbf was added [(4R)-6-fluoro-4-isopropoxy-spiro[chromane-2,4'-piperidine]-1'-yl]-[3-(hydroxymethyl)-4-isopropoxy-phenyl]methanone (200 mg, 0.42 mmol) and dichloromethane (2 mL) and the reaction was chilled to 0° C. Triethylamine (177 µL, 1.27 mmol) was added followed by methanesulfonyl chloride (36 µL, 0.47 mmol) and the reaction was allowed to stir for 1 h while warming to 25° C.

To a 10 mL rbf was added 1 mL of the above reaction mixture and dimethylamine (318 µL of 2 M solution in THF, 0.64 mmol) was added. The reaction was allowed to stir at rt for 1. The reaction was filtered and purified via HPLC (10%-99%) (ACN:H$_2$O). ESI-MS m/z calc. 498.3, found 499.5 (M+1)$^+$; Retention time: 1.63 minutes (3 min run).

152

(R)-(6-Fluoro-4-isopropoxyspiro[chroman-2,4'-piperidine]-1'-yl)(5-(isopropylsulfonyl)-6-methylpyridin-2-yl)methanone

Step 1: Methyl 5-isopropylsulfonylpyridine-2-carboxylate

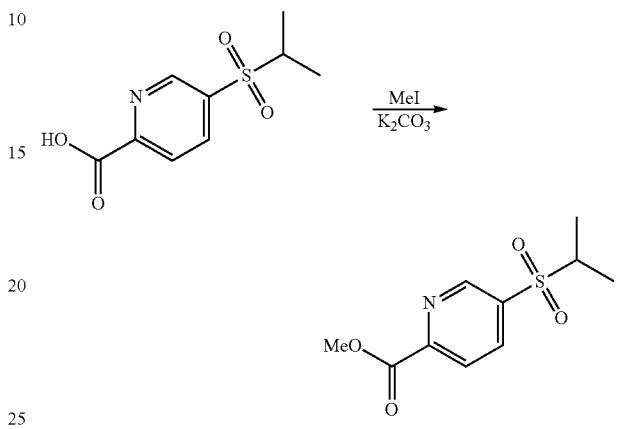

To a 100 mL rbf was added 5-isopropylsulfonylpyridine-2-carboxylic acid (300 mg, 1.3 mmol), potassium carbonate (360 mg, 2.6 mmol) and DMF (6 mL) and the reaction was allowed to stir for 10 minutes. Iodomethane (89 µL, 1.4 mmol) was added and the reaction was allowed to stir at rt for 1 h. The reaction was quenched with brine. The reaction was extracted 3 times with EtOAc and the organic layers were dried over sodium sulfate and evaporated. Methyl 5-isopropylsulfonylpyridine-2-carboxylate (310 mg) was isolated and used in the next step without purification.

Step 2: Methyl 6-bromo-5-isopropylsulfonyl-pyridine-2-carboxylate

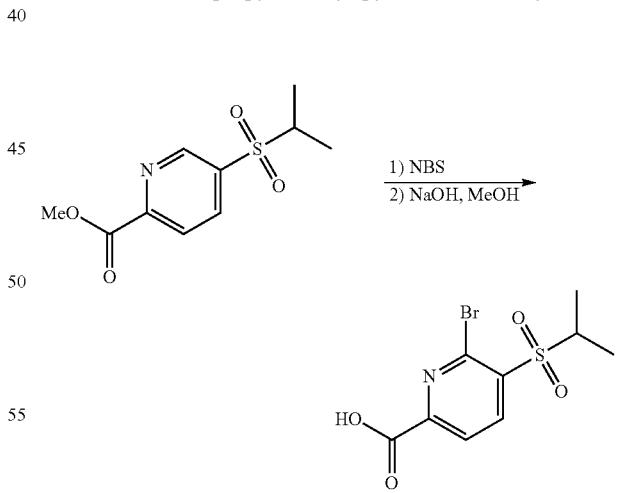

To a 20 mL microwave vial was added methyl 5-isopropylsulfonylpyridine-2-carboxylate (310 mg), N-bromosuccinimide (2.3 g, 13 mmol), chloroform (6 mL), and methanol (1.5 mL) and the reaction vessel was sealed. The reaction was heated at 80° C. for 24 h and the reaction showed only partial conversion and starting material. The reaction was stopped and allowed to warm to 25° C. The reaction was filtered and purified by HPLC (1%-99%) ACN:H$_2$O with 0.1% TFA. Methyl 6-bromo-5-isopropylsulfonyl-pyridine-2-carboxylate (131 mg, 31%) was isolated as an off-white solid.

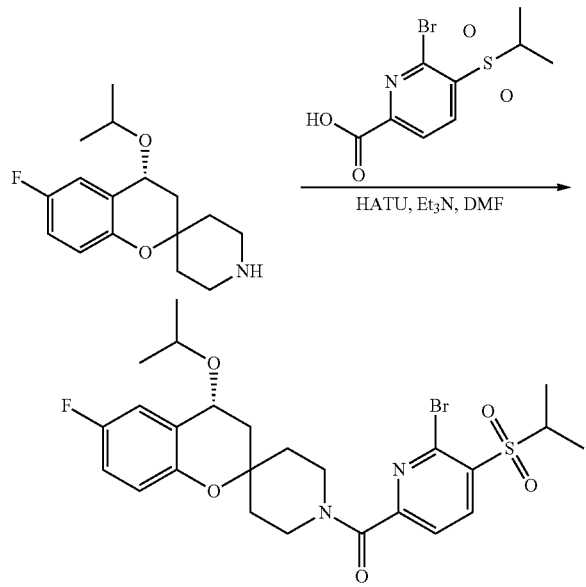

Step 3: (R)-(6-Bromo-5-(isopropylsulfonyl)pyridin-2-yl)(6-fluoro-4-isopropoxyspiro[chroman-2,4'-piperidine]-1'-yl)methanone To a rbf was added 6-bromo-5-(isopropylsulfonyl)picolinic acid (48 mg, 0.16 mmol), HATU (60 mg, 0.16 mmol), DMF (1 mL), and triethylamine (62 µL, 0.45 mmol) and the reaction was allowed to stir at rt for 10 minutes. (R)-6-Fluoro-4-isopropoxyspiro[chroman-2,4'-piperidine] (42 mg, 0.15 mmol) was added and the reaction was allowed to stir at rt for 1 h. The reaction was filtered and the crude reaction mixture was purified by HPLC (10%-99%) ACN:H$_2$O with no modifier. ESI-MS m/z calc. 569.4, found 571.2 (M+1)$^+$; Retention time: 1.96 minutes (3 min run).

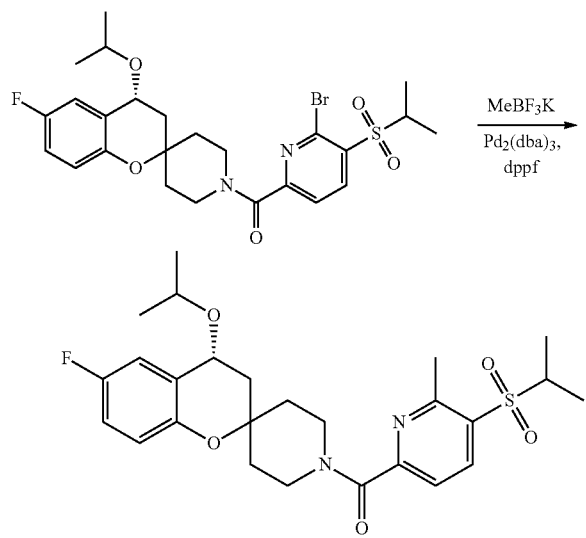

Step 4: [(4R)-6-Fluoro-4-isopropoxy-spiro[chromane-2,4'-piperidine]-1'-yl]-(5-isopropylsulfonyl-6-methyl-2-pyridyl)methanone To a microwave vial was added Pd$_2$(dba)$_3$ (6.4 mg, 0.007 mmol), dppf (7.7 mg, 0.014 mmol), potassium trifluoro(methyl)boranuide (25 mg, 0.21 mmol), and THF (3 mL) and the reaction was purged with nitrogen. (6-Bromo-5-isopropylsulfonyl-2-pyridyl)-[(4R)-6-fluoro-4-isopropoxy-spiro[chromane-2,4'-piperidine]-1'-yl]methanone (40 mg, 0.07024 mmol) dissolved in THF (0.3 mL) was added followed by potassium carbonate (210 µL of 3 M, 0.63 mmol). The reaction was heated at 80° C. overnight. The reaction showed product by LCMS. The reaction was filtered and evaporated. The crude reaction mixture was purified by HPLC (10%-99%) ACN:H$_2$O with no modifier. ESI-MS m/z calc. 504.2, found 505.2 (M+1)$^+$; Retention time: 1.84 minutes (3 min run).

[(4R)-6-Fluoro-4-isopropoxy-spiro[chromane-2,4'-piperidine]-1'-yl]-(5-isopropoxy-2-pyridyl)methanone

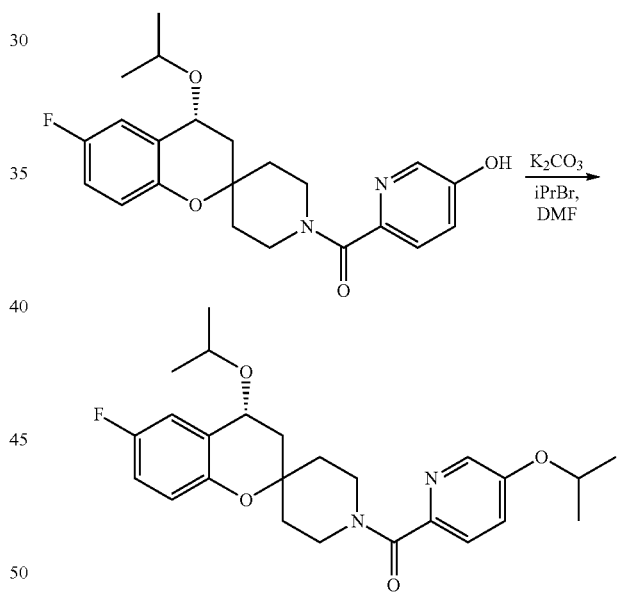

To a vial containing [(4R)-6-fluoro-4-isopropoxy-spiro[chromane-2,4'-piperidine]-1'-yl]-(5-hydroxy-2-pyridyl)methanone (41 mg, 0.10 mmol) was added DMF (1 mL) followed by potassium carbonate (42 mg, 0.30 mmol). The reaction was allowed to stir for 10 minutes and then 2-bromopropane (28 µL, 0.31 mmol) was added. The reaction was allowed to stir overnight. The reaction was filtered and purified via hplc (10%-99%) ACN:H$_2$O with no modifier. [(4R)-6-Fluoro-4-isopropoxy-spiro[chromane-2,4'-piperidine]-1'-yl]-(5-isopropoxy-2-pyridyl)methanone (24 mg, 52%) was isolated as a yellow oil. ESI-MS m/z calc. 442.2, found 443.4 (M+1)+; Retention time: 1.96 minutes (3 min run).

1'-(4-Isopropoxy-3-methoxybenzoyl)spiro[chroman-2,4'-piperidin]-3-one

Step 1: tert-Butyl 4-hydroxyspiro[chroman-2,4'-piperidine]-1'-carboxylate

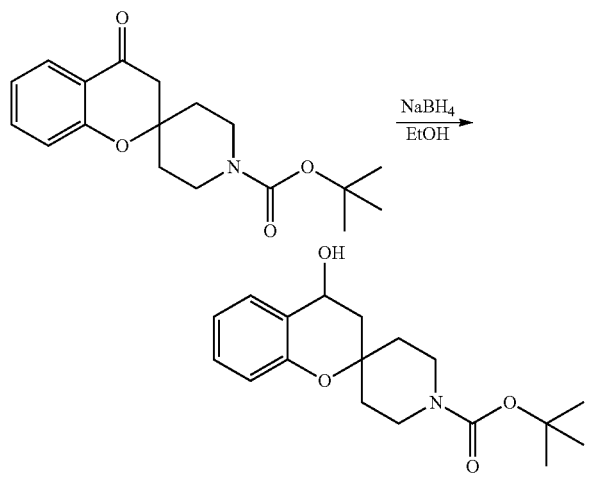

A solution of tert-butyl 4-oxospiro[chromane-2,4'-piperidine]-1'-carboxylate (5.00 g, 15.8 mmol) in EtOH (25 mL) was slowly added to a suspension of NaBH$_4$ (435 mg, 11.5 mmol) in EtOH (7.4 mL) over a period of 45 minutes. The reaction mixture was then heated at 75° C. for 2 hours. The reaction mixture was evaporated to dryness and the residue was partitioned between ethyl acetate and a saturated aqueous solution of sodium bicarbonate. The layers were separated and the organic layer was washed with a saturated aqueous solution of sodium chloride. The organic layer was dried over sodium sulfate, filtered, and evaporated to dryness to yield tert-butyl 4-hydroxyspiro[chromane-2,4'-piperidine]-1'-carboxylate as a white solid. ESI-MS m/z calc. 319.2, found 320.5 (M+1)$^+$; Retention time: 1.63 minutes (3 min run).

Step 2: tert-Butyl spiro[chromene-2,4'-piperidine]-1'-carboxylate

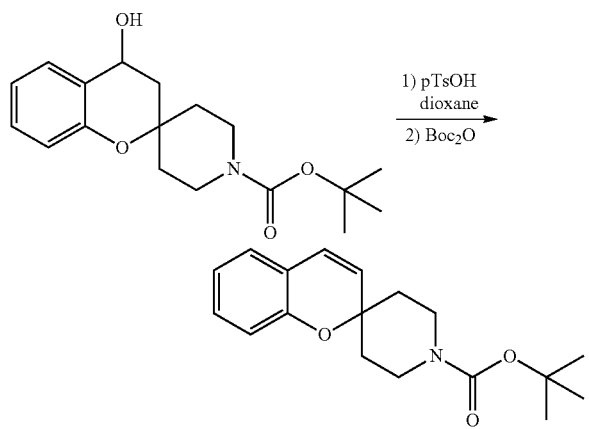

tert-Butyl 4-hydroxyspiro[chromane-2,4'-piperidine]-1'-carboxylate (5.00 g, 15.8 mmol) was dissolved in dioxane (30 mL). 4-Methylbenzenesulfonic acid hydrate (3.34 g, 17.6 mmol) was added and the reaction mixture was heated at 60° C. for 1 hour. An additional aliquot of 4-methylbenzenesulfonic acid hydrate (3.34 g, 17.6 mmol) was added and the reaction mixture was heated at 90° C. for 1 hour. The reaction mixture was evaporated to dryness and the residue was partitioned between ethyl acetate and a 1M aqueous hydrochloric acid solution. The layers were separated and the organic layer was washed with a 1M aqueous hydrochloric acid solution three times. The combined aqueous layers were made basic with a 6M aqueous solution of sodium hydroxide. This solution was then extracted twice with ethyl acetate. The combined ethyl acetate layers were dried over sodium sulfate, filtered, and evaporated to dryness to give a red oil. The oil was then dissolved in dichloromethane (30 mL) containing triethylamine (4.40 mL, 31.5 mmol) and BoC$_2$O (3.80 mL, 16.5 mmol) and the reaction mixture was allowed to stir at room temperature for 10 minutes. The reaction mixture was washed three times with a 1M solution of hydrochloric acid, followed by three washes with a saturated aqueous solution of sodium bicarbonate, followed by three washes of a saturated aqueous solution of sodium chloride. The organic layer was dried over sodium sulfate, filtered, and evaporated to dryness. The crude material was purified on silica gel utilizing a gradient of 0-25% ethyl acetate in hexanes to yield tert-butyl spiro[chromene-2,4'-piperidine]-1'-carboxylate (3.73 g, 78%) as a colorless oil. ESI-MS m/z calc. 301.2, found 302.5 (M+1)$^+$; Retention time: 2.14 minutes (3 min run). $^1$H NMR (400 MHz, DMSO) δ 7.12 (td, J=7.9, 1.4 Hz, 1H), 7.07 (dd, J=7.5, 1.5 Hz, 1H), 6.91-6.79 (m, 2H), 6.48 (d, J=9.8 Hz, 1H), 5.76 (d, J=9.8 Hz, 1H), 3.75-3.63 (m, 2H), 3.30-3.11 (m, 2H), 1.86-1.76 (m, 2H), 1.68-1.53 (m, 2H), 1.41 (s, 9H).

Step 3: tert-Butyl 1a,7b-dihydrospiro[oxireno[2,3-c]chromene-2,4'-piperidine]-1'-carboxylate

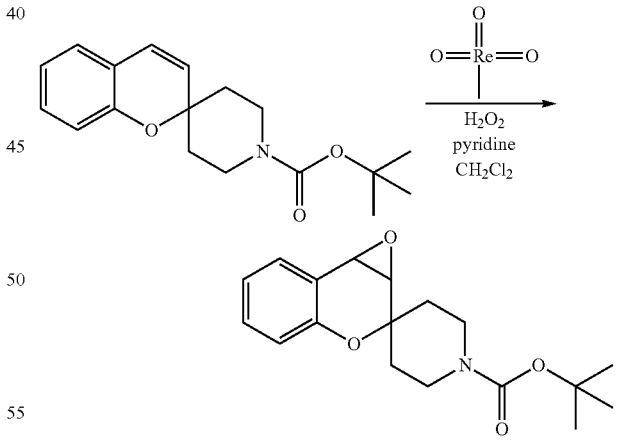

tert-Butyl spiro[chromene-2,4'-piperidine]-1'-carboxylate (3.73 g, 12.4 mmol) and methyl(trioxo)rhenium (61.7 mg, 0.250 mmol) were combined in dichloromethane (34 mL). The reaction mixture was cooled to 0° C. under an atmosphere of nitrogen and pyridine (250 µL, 3.1 mmol) was slowly added to the mixture. Hydrogen peroxide (3.5 mL of 30% w/v, 31 mmol) was then added in a drop-wise manner and the resulting mixture was allowed to stir for 10 minutes at 0° C. The reaction mixture was then allowed to stir for 16 hours at room temperature. Sodium hypochlorite (2.50 mL of 6.15% w/v, 2.07 mmol) (Chlorox brand commercial bleach) was added and the reaction mixture was allowed to stir for 10 minutes. The reaction mixture was then poured into ice and was extracted three times with dichloromethane. The combined organics were washed with a saturated aqueous solution of sodium chloride, dried over sodium sulfate, filtered, and evaporated to dryness to yield tert-butyl spiro[1a,7b-dihydrooxireno[2,3-c]chromene-2,4'-piperidine]-1'-carboxylate (4.07 g, 99%) as a white solid. $^1$H NMR (400 MHz, DMSO) δ 7.46 (dd, J=7.4, 1.3 Hz, 1H), 7.27 (td, J=7.8, 1.5 Hz, 1H), 6.96 (t, J=7.4 Hz, 1H), 6.86 (d, J=8.1 Hz, 1H), 4.04 (d, J=4.4 Hz, 1H), 3.94-3.84 (m, 1H), 3.82-3.69 (m, 1H), 3.72 (d, J=4.5 Hz, 1H), 3.29-3.12 (m, 1H), 3.11-2.88 (m, 1H), 1.87-1.80 (m, 2H), 1.68-1.55 (m, 1H), 1.41 (s, 9H), 1.38-1.28 (m, 1H).

Step 4: Spiro[chroman-2,4'-piperidin]-3-one hydrochloride

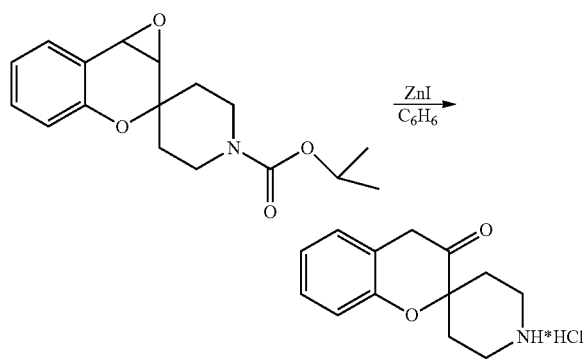

tert-Butyl spiro[1a,7b-dihydrooxireno[2,3-c]chromene-2,4'-piperidine]-1'-carboxylate (650 mg, 2.05 mmol) was dissolved in anhydrous benzene (6.5 mL). Zinc iodide (275 mg, 0.860 mmol) was added and the reaction mixture was shielded from light and was stirred at room temperature 25 hours. The reaction mixture was then filtered, evaporated to dryness, and the residue was treated with HCl in dioxane (3.0 mL of 4.0 M, 12 mmol). The reaction mixture was allowed to stand for 5 minutes before it was concentrated to give spiro[chroman-2,4'-piperidin]-3-one hydrochloride. ESI-MS m/z calc. 217.1, found 218.5 (M+1)$^+$; Retention time: 0.83 minutes (3 min run).

Step 5: 1'-(4-Isopropoxy-3-methoxybenzoyl)spiro[chroman-2,4'-piperidin]-3-one

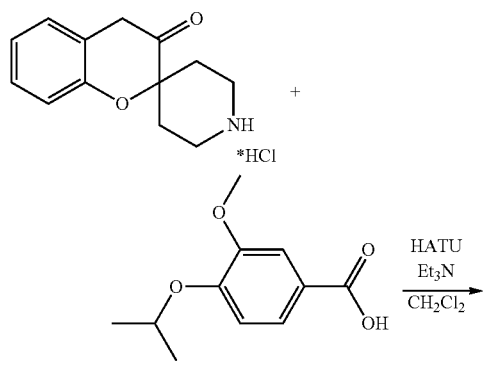

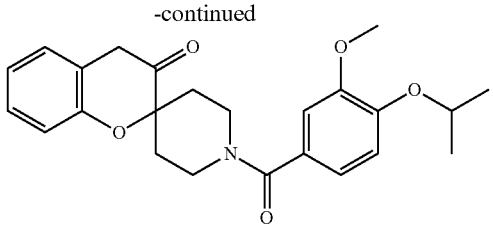

Crude spiro[chromane-2,4'-piperidine]-3-one hydrochloride (520 mg, 2.05 mmol), 4-isopropoxy-3-methoxy-benzoic acid (431 mg, 2.05 mmol), Et$_3$N (856 μL, 6.14 mmol), and HATU (779 mg, 2.05 mmol) were combined in dichloromethane (5 mL). The reaction mixture was stirred at room temperature for 1 hour and then evaporated to dryness. The crude material was purified on silica gel utilizing a gradient of 0-50% ethyl acetate in hexanes. The semi-purified 1'-(4-isopropoxy-3-methoxy-benzoyl)spiro[chromane-2,4'-piperidine]-3-one (462 mg, 55%) was used in the next step without further purification. ESI-MS m/z calc. 409.2, found 410.5 (M+1)+; Retention time: 1.79 minutes (3 min run).

Step 1: (3-Hydroxyspiro[chroman-2,4'-piperidine]-1'-yl)(4-isopropoxy-3-methoxyphenyl)methanone

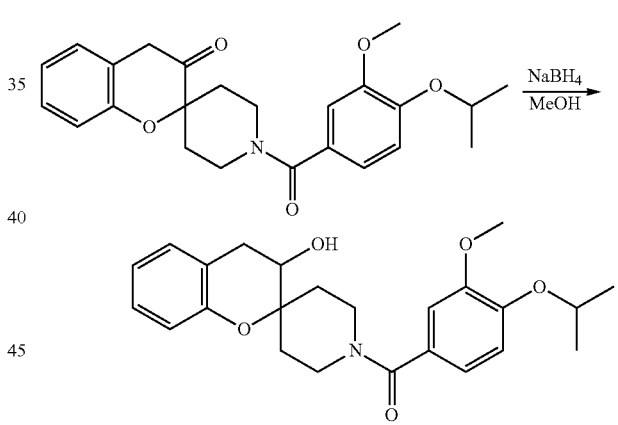

1'-(4-Isopropoxy-3-methoxy-benzoyl)spiro[chromane-2,4'-piperidine]-3-one (224 mg, 0.550 mmol) was dissolved in methanol (5 mL). NaBH$_4$ (10.3 mg, 0.27 mmol) was added and the reaction mixture was allowed to stir for 5 minutes at room temperature. The reaction mixture was evaporated to dryness and the residue was purified by silica gel chromatography utilizing a gradient of 10-100% ethyl acetate in hexanes to yield (3-hydroxyspiro[chromane-2,4'-piperidine]-1'-yl)-(4-isopropoxy-3-methoxy-phenyl)methanone (122 mg, 54%) ESI-MS m/z calc. 411.2, found 412.5 (M+1)$^+$; Retention time: 1.54 minutes (3 min run). $^1$H NMR (400 MHz, DMSO) δ 7.12-7.04 (m, 2H), 7.01-6.91 (m, 3H), 6.87-6.76 (m, 2H), 5.19 (d, J=4.8 Hz, 1H), 4.59 (sept., 1H), 4.51-4.10 (m, 1H), 3.77 (s, 3H), 3.73-3.64 (m, 1H), 3.54-2.98 (m, 3H), 2.92 (dd, J=17.0, 5.0 Hz, 1H), 2.63 (dd, J=16.8, 6.8 Hz, 1H), 1.92-1.42 (m, 4H), 1.26 (d, J=6.0 Hz, 6H).

Step 2: (4-Isopropoxy-3-methoxyphenyl)(3-methoxyspiro[chroman-2,4'-piperidine]-1'-yl)methanone

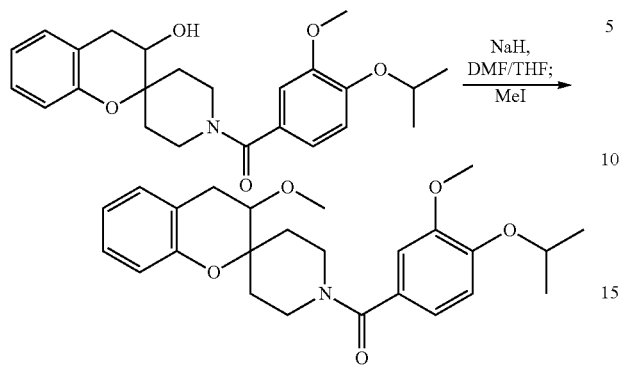

(3-Hydroxyspiro[chromane-2,4'-piperidine]-1'-yl)-(4-isopropoxy-3-methoxy-phenyl)methanone (122 mg, 0.30 mmol) was dissolved in a mixture of THF (0.1 mL) and DMF (0.9 mL). NaH (12 mg, 0.30 mmol) was added and the reaction mixture was allowed to stir for 3 minutes. Iodomethane (18 µL, 0.30 mmol) was added and the reaction mixture was then allowed to stir for 30 minutes. The reaction mixture was evaporated to dryness. The crude material was purified by silica gel chromatography utilizing a gradient of 0-100% ethyl acetate in hexanes to yield (4-isopropoxy-3-methoxy-phenyl)-(3-methoxyspiro[chromane-2,4'-piperidine]-1'-yl)methanone (101 mg, 78%) as a white solid. ESI-MS m/z calc. 425.2, found 426.5 (M+1)$^+$; Retention time: 1.82 minutes (3 min run). $^1$H NMR (400 MHz, DMSO) δ 7.12-7.06 (m, 2H), 7.01-6.91 (m, 3H), 6.87-6.78 (m, 2H), 4.59 (hept, J=6.0 Hz, 1H), 4.47-4.07 (m, 1H), 3.76 (s, 3H), 3.44 (t, J=5.0 Hz, 1H), 3.32 (s, 3H), 3.38-3.05 (m, 3H), 2.98 (dd, J=17.1, 4.4 Hz, 1H), 2.78 (dd, J=17.2, 5.3 Hz, 1H), 1.96-1.48 (m, 4H), 1.26 (d, J=6.0 Hz, 6H).

(3-Ethoxyspiro[chroman-2,4'-piperidine]-1'-yl)(4-isopropoxy-3-methoxyphenyl) and (4-isopropoxy-3-methoxyphenyl)(3-isopropoxyspiro[chroman-2,4'-piperidine]-1'-yl)methanone were prepared using a procedure similar as reported above.

(4-Isopropoxy-3-methoxyphenyl)(4-(methoxymethyl)spiro[chroman-2,4'-piperidine]-1'-yl)methanone Step 1: tert-Butyl 4-(trifluoromethylsulfonyloxy)spiro[chromene-2,4'-piperidine]-1'-carboxylate

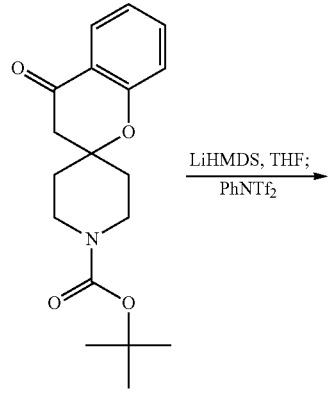

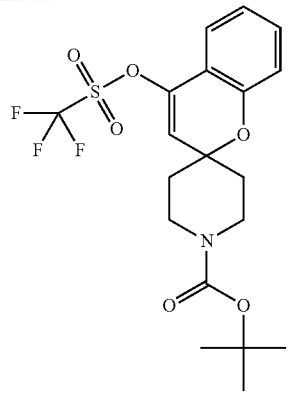

To a solution of tert-butyl 4-oxospiro[chromane-2,4'-piperidine]-1'-carboxylate (4.00 g, 11.5 mmol) in THF (10 mL) at −78° C. was added lithium bis(trimethylsilyl)azanide (14 mL of 1.0 M, 14 mmol) and the reaction mixture was allowed to stir at −78° C. for 1 h. A solution of 1,1,1-trifluoro-N-phenyl-N-(trifluoromethylsulfonyl)methanesulfonamide (4.95 g, 13.9 mmol) dissolved in THF (7 mL) was added dropwise. The reaction mixture was slowly allowed to warm to 25° C. and was stirred overnight. The reaction was quenched with ice water and was extracted with ethyl acetate 3 times. The organic layers were separated, dried over sodium sulfate, and evaporated. The residue was purified by column chromatography using a gradient of 0 to 20% ethyl acetate:hexanes to give tert-butyl 4-(trifluoromethylsulfonyloxy)spiro[chromene-2,4'-piperidine]-1'-carboxylate as a light yellow solid. ESI-MS m/z calc. 449.4, found 450.2 (M+1)$^+$; Retention time: 2.37 minutes (3 min run).

The following compounds were prepared by the procedure described above:
tert-Butyl 4-(trifluoromethylsulfonyloxy)-7-fluoro-spiro[chromene-2,4'-piperidine]-1'-carboxylate;
tert-Butyl 4-(trifluoromethylsulfonyloxy)-8-fluoro-spiro[chromene-2,4'-piperidine]-1'-carboxylate.

Step 2: 4-(Benzyloxymethyl)spiro[chromene-2,4'-piperidine]hydrochloride

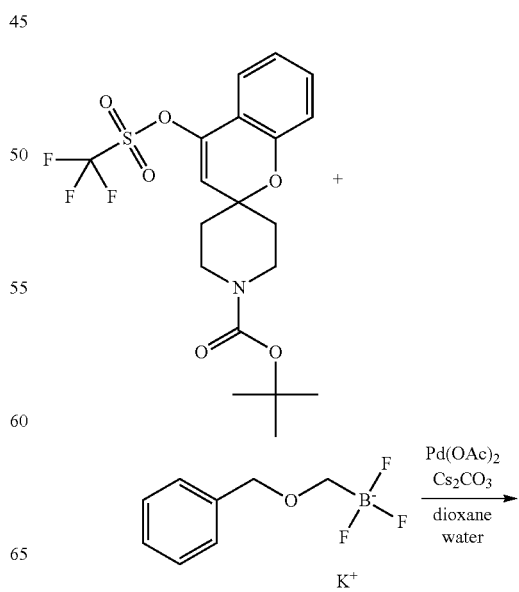

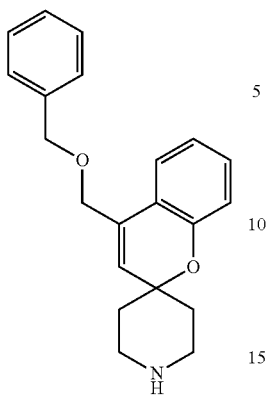

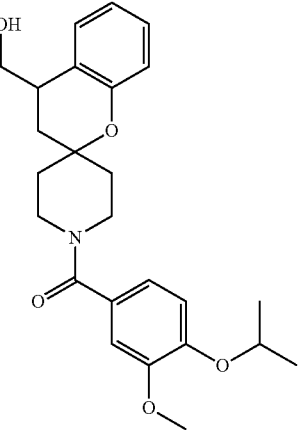

To a microwave vial was added cesium carbonate (3.37 g, 10.4 mmol), potassium (benzyloxymethyl)trifluoroborate (1.18 g, 5.17 mmol), palladium (II) acetate (116 mg, 0.520 mmol), and dicyclohexyl-[2-(2,6-diisopropoxyphenyl)phenyl]-phosphane (483 mg, 1.03 mmol). The vial was capped and purged with nitrogen for 10 minutes. tert-Butyl 4-(trifluoromethylsulfonyloxy)spiro[chromene-2,4'-piperidine]-1'-carboxylate (1.55 g, 3.45 mmol) dissolved in dioxane (12.4 mL) was added followed by water (1.38 mL). The reaction mixture was placed into a preheated 100° C. oil bath overnight. The reaction was quenched with brine and was extracted with ethyl acetate (3×). The organic layers were separated, dried over sodium sulfate and evaporated. The residue was purified via column chromatography (5%-40% ethyl acetate-hexanes) to yield the BOC-protected intermediate as a clear oil. The Boc protected amine was then dissolved in dichloromethane (5 mL) and was treated with HCl (4.3 mL of 4.0 M, 17 mmol). The mixture was allowed to stir for 3 h. The solvent was evaporated to give 4-(benzyloxymethyl)spiro[chromene-2,4'-piperidine]hydrochloride. ESI-MS m/z calc. 321.2, found 322.5 (M+1)$^+$; Retention time: 1.41 minutes (3 min run).

Step 3: (4-(Hydroxymethyl)spiro[chroman-2,4'-piperidine]-1'-yl)(4-isopropoxy-3-methoxyphenyl)methanone To a 250 mL round bottom flask was added 4-isopropoxy-3-methoxy-benzoic acid (517 mg, 2.46 mmol), HATU (935 mg, 2.45 mmol), DMF (5 mL) and Et$_3$N (1.56 mL, 11.2 mmol). The reaction mixture was allowed to stir for 10 minutes. 4-(Benzyloxymethyl)spiro[chromene-2,4'-piperidine] (800 mg, 2.23 mmol) dissolved in DMF (15 mL) was added to the reaction flask and the mixture was allowed to stir for 4 h. The reaction mixture was quenched with brine, extracted 3 times with ethyl acetate and the organic layers were dried over sodium sulfate and evaporated. The residue was purified by silica gel chromatography (3%-70% ethyl acetate in hexanes) to give (4-(benzyloxymethyl)spiro[chromene-2,4'-piperidine]-1'-yl)(4-isopropoxy-3-methoxyphenyl)methanone (1.30 g, 99%) as a pale oil.

To a 250 mL round bottom flask containing [4-(benzyloxymethyl)spiro[chromene-2,4'-piperidine]-1'-yl]-(4-isopropoxy-3-methoxy-phenyl)methanone was added Pd on charcoal (0.13 g, 0.12 mmol) and the reaction flask was purged with nitrogen for 10 minutes. Isopropanol (15 mL) was added and the reaction mixture was stirred for 5 minutes. A balloon filled with hydrogen was placed on top of the flask and the mixture was allowed to stir overnight. The reaction mixture was filtered and the filter cake was washed with isopropanol. The solvent was evaporated to give (4-(hydroxymethyl)spiro-[chroman-2,4'-piperidine]-1'-yl)(4-isopropoxy-3-methoxyphenyl)methanone (547 mg, 99%). ESI-MS m/z calc. 425.5, found 426.2 (M+1)$^+$; Retention time: 1.51 minutes (3 min run).

Step 4: (4-Isopropoxy-3-methoxyphenyl)(4-(methoxymethyl)spiro[chroman-2,4'-piperidine]-1'-yl)methanone

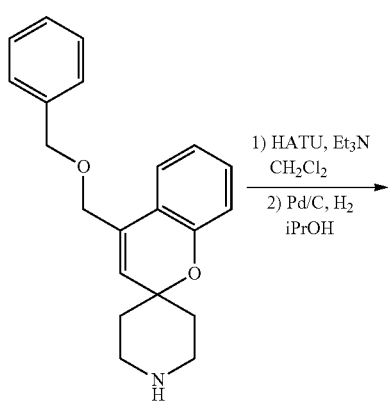

1) HATU, Et$_3$N
CH$_2$Cl$_2$
2) Pd/C, H$_2$
iPrOH

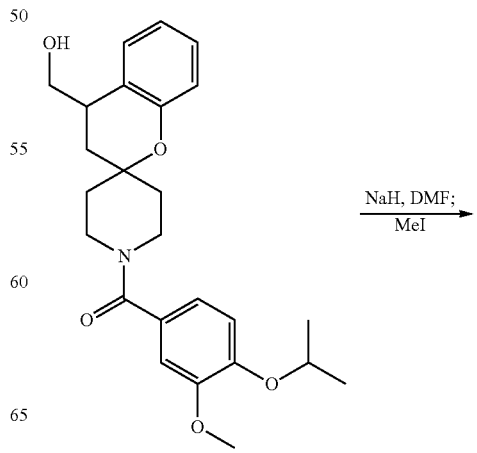

NaH, DMF;
MeI

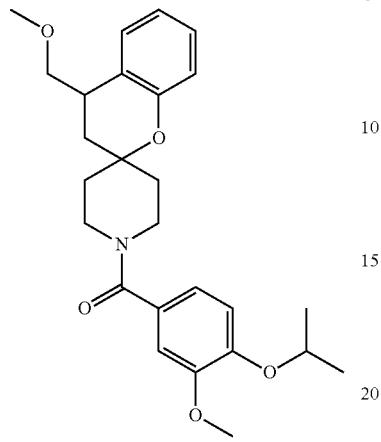

To a vial containing [4-(hydroxymethyl)spiro[chromane-2,4'-piperidine]-1'-yl]-(4-isopropoxy-3-methoxy-phenyl)methanone (13 mg, 0.020 mmol) was added DMF (0.5 mL) and NaH (1.8 mg, 0.040 mmol). The reaction mixture was allowed to stir for 5 minutes. Methyl iodide (2.1 μL, 0.030 mmol) was added and the reaction mixture was allowed to stir for 10 minutes. The reaction mixture was filtered and purified by prep-HPLC (20%-99% MeOH:H$_2$O with no modifier) to yield (4-isopropoxy-3-methoxyphenyl)(4-(methoxymethyl)spiro[chroman-2,4'-piperidine]-1'-yl)methanone as a white solid. ESI-MS m/z calc. 439.5, found 440.5 (M+1)$^+$; Retention time: 1.86 minutes (3 min run).

(4-(Ethoxymethyl)spiro[chroman-2,4'-piperidine]-1'-yl)(4-isopropoxy-3-methoxyphenyl)methanone

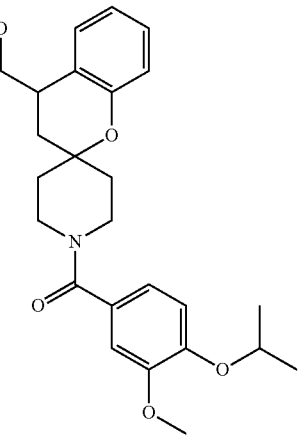

To a vial containing [4-(hydroxymethyl)spiro[chromane-2,4'-piperidine]-1'-yl]-(4-isopropoxy-3-methoxy-phenyl)methanone (13 mg, 0.020 mmol) was added DMF (0.5 mL) and NaH (1.8 mg, 0.040 mmol). The reaction mixture was allowed to stir for 5 minutes. Ethyl iodide (2.6 μL, 0.030 mmol) was added and the reaction mixture was allowed to stir for 10 minutes. The reaction was filtered and purified by prep-HPLC (20%-99% MeOH:H$_2$O with no modifier) to yield (4-(ethoxymethyl)spiro[chroman-2,4'-piperidine]-1'-yl)(4-isopropoxy-3-methoxyphenyl)methanone as a white solid. ESI-MS m/z calc. 453.6, found 454.3 (M+1)$^+$; Retention time: 1.96 minutes (3 min run).

The following compounds were prepared using the procedure reported above:

| Product | Electrophile |
| --- | --- |
| (4-((2,2-difluoroethoxy)methyl)spiro[chroman-2,4'-piperidine]-1'-yl)(4-isopropoxy-3-methoxyphenyl)methanone | 2,2-difluoroethyl methanesulfonate |
| (4-isopropoxy-3-methoxyphenyl)(4-(trideuteriomethoxymethyl)spiro[chroman-2,4'-piperidine]-1'-yl)methanone | trideuteriomethyl iodide |
| (7-fluoro-4-(trideuteriomethoxymethyl)spiro[chroman-2,4'-piperidine]-1'-yl)(4-(2-hydroxypropan-2-yl)phenyl)methanone | trideuteriomethyl iodide |
| (7-fluoro-4-(trideuteriomethoxymethyl)spiro[chroman-2,4'-piperidine]-1'-yl)(4-isopropoxy-3-methoxyphenyl)methanone | trideuteriomethyl iodide | tert-Butyl 4-(isopropoxymethyl)spiro[chromene-2,4'-piperidine]-1'-carboxylate

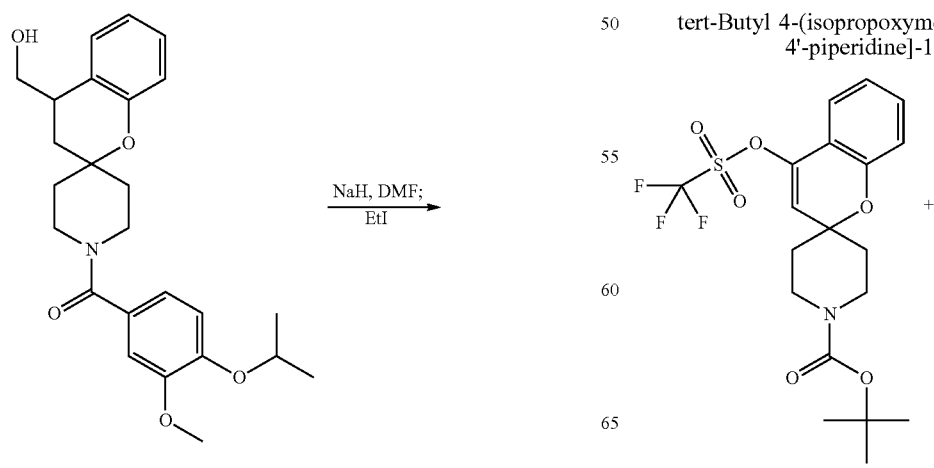

-continued

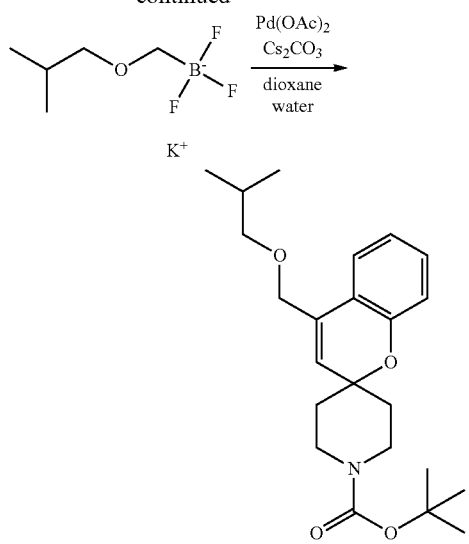

To a 20 mL microwave vial was added cesium carbonate (4.431 g, 13.60 mmol), potassium (isopropoxymethyl)trifluoroborate (1.06 g, 5.9 mmol), palladium (II) acetate (152 mg, 0.68 mmol), and RUPHOS (634 mg, 1.36 mmol) and the reaction vessel was capped and purged with nitrogen for 10 minutes. Dioxane (10 mL) was added and the reaction was stirred for 5 minutes. tert-Butyl 4-(trifluoromethylsulfonyloxy)spiro[chromene-2,4'-piperidine]-1'-carboxylate (2.04 g, 4.53 mmol) (dissolved in 6 mL of dioxane) was added followed by water (1.6 mL). The reaction vessel was placed into a 100° C. preheated oil bath and was allowed to stir overnight. The reaction was quenched with brine and extracted with EtOAc (3 times). The organic layers were separated, dried over sodium sulfate and the solvent was removed. The crude reaction mixture was purified via column chromatography (2%-30%) EtOAc in hexanes. tert-Butyl 4-(isopropoxymethyl)spiro[chromene-2,4'-piperidine]-1'-carboxylate (640 mg, 1.714 mmol, 38%) eluted at 12% EtOAc in hexanes and was isolated as a thick yellow oil. ESI-MS m/z calc. 373.4, found 374.4 (M+1)$^+$; Retention time: 2.3 minutes (3 min run).

4-(Isopropoxymethyl)spiro[chromane-2,4'-piperidine]hydrochloride

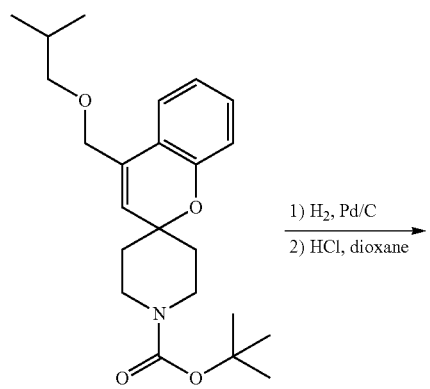

-continued

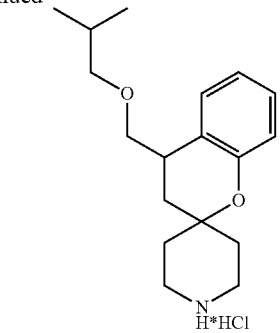

To a 100 mL flask containing tert-butyl 4-(isopropoxymethyl)spiro[chromene-2,4'-piperidine]-1'-carboxylate (640 mg, 1.7 mmol) was added isopropanol (5 mL) and Pd on C, wet, Degussa (547 mg, 0.51 mmol). The reaction was purged with nitrogen. A balloon of hydrogen was added and the reaction was allowed to stir overnight. The reaction was immediately filtered through a frit of celite and washed with isopropanol. The solvent was evaporated providing tert-butyl 4-(isopropoxymethyl)spiro[chromane-2,4'-piperidine]-1'-carboxylate. ESI-MS m/z calc. 375.2, found 376.4 (M+1)$^+$; Retention time: 2.37 minutes (3 min run).

To a 100 mL flask containing tert-butyl 4-(isopropoxymethyl)spiro [chromane-2,4'-piperidine]-1'-carboxylate (640 mg, 1.7 mmol) was added dichloromethane (3 mL) and HCl (1.28 mL of 4 M, 5.14 mmol) in dioxane. The reaction was allowed to stir for 1 h at 25° C. The reaction was evaporated and 4-(isopropoxymethyl)spiro[chromane-2,4'-piperidine] hydrochloride was isolated as a sticky tan solid. ESI-MS m/z calc. 275.2, found 276.2 (M+1)$^+$; Retention time: 1.01 minutes (3 min run).

(3,4-Dimethoxyphenyl)-(4-phenylspiro[chromane-2,4'-piperidine]-1'-yl)methanone

Step 1: tert-Butyl 4-phenylspiro[chromene-2,4'-piperidine]-1'-carboxylate

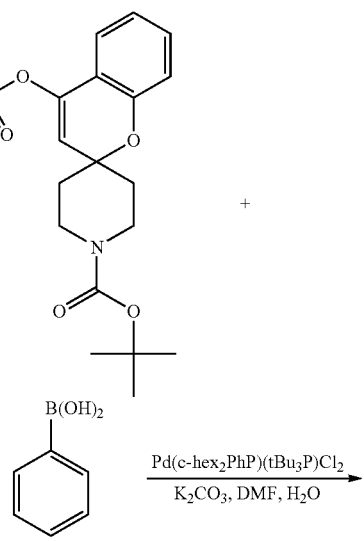

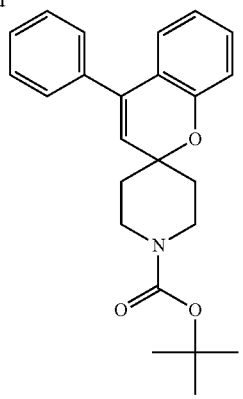

tert-Butyl 4-(trifluoromethylsulfonyloxy)spiro[chromene-2,4'-piperidine]-1'-carboxylate (300 mg, 0.613 mmol), phenylboronic acid (150 mg, 1.24 mmol), dichloro-[dicyclohexyl(phenyl)phosphaniumyl]-tritert-butylphosphaniumyl-palladium (20 mg, 0.031 mmol), aqueous K₂CO₃ (770 µL of 2.0 M, 1.5 mmol), and DMF (3 mL) were combined in a scintillation vial. The mixture was heated at 80° C. overnight before it was cooled to 25° C. The DMF was removed under reduced pressure and the residue was partitioned between ethyl acetate and water. The organic layer was separated, washed with brine, dried over sodium sulfate, and concentrated to provide tert-butyl 4-phenylspiro[chromene-2,4'-piperidine]-1'-carboxylate. ESI-MS m/z calc. 377.2, found 378.2 (M+1)⁺; Retention time: 2.20 minutes (3 min run).

Step 2: 4-Phenylspiro[chromene-2,4'-piperidine] hydrochloride

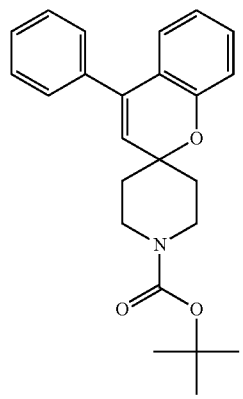

A mixture of tert-butyl 4-phenylspiro[chromene-2,4'-piperidine]-1'-carboxylate (300 mg, 0.795 mmol) and HCl in dioxane (600 µL of 4.0 M, 2.4 mmol) in iPrOH (4.5 mL) was allowed to stir for 30 min at 50° C. The mixture was concentrated in vacuo to give 4-phenylspiro[chromene-2,4'-piperidine]hydrochloride (240 mg, 96%) as a white solid. ESI-MS m/z calc. 277.2, found 278.2 (M+1)⁺; Retention time: 1.11 minutes (3 min run).

Step 3: (3,4-Dimethoxyphenyl)-(4-phenylspiro[chromene-2,4'-piperidine]-1'-yl)methanone

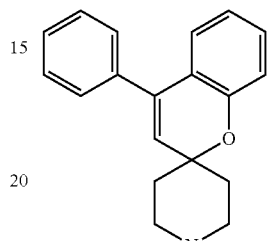

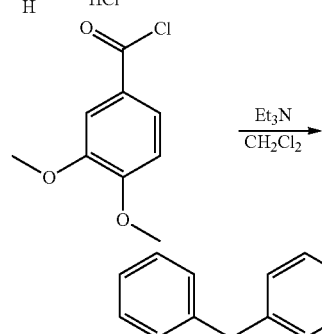

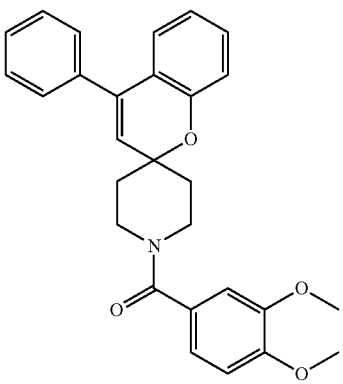

3,4-Dimethoxybenzoyl chloride (307 mg, 1.53 mmol) was added to a mixture of 4-phenylspiro[chromene-2,4'-piperidine]hydrochloride (240 mg, 0.765 mmol), Et₃N (533 µL, 3.82 mmol), and CH₂Cl₂ (5 mL) at rt. The mixture was allowed to stir overnight at rt before it was diluted with CH₂Cl₂ (100 mL) and was washed with 1N HCl, water, then brine. The organic layer was dried over sodium sulfate and was concentrated under reduced pressure. Column chromatography (10-50% ethyl acetate/hexanes) on the residue provided (3,4-dimethoxyphenyl)-(4-phenylspiro[chromene-2,4'-piperidine]-1'-yl)methanone (259 mg, 75%). ESI-MS m/z calc. 441.2, found 442.2 (M+1)⁺; Retention time: 1.11 minutes (3 min run). ¹H NMR (400 MHz, DMSO) δ 7.47-7.39 (m, 3H), 7.35-7.33 (m, 2H), 7.22 (dd, J=1.6, 15.2 Hz, 1H), 7.00-6.87 (m, 6H), 5.82 (s, 1H), 4.15 (br s, 1H), 3.79 (d, J=1.8 Hz, 6H), 3.54-3.40 (m, 3H), 2.02-1.90 (m, 2H), 1.84-1.79 (m, 2H).

Step 4: (3,4-Dimethoxyphenyl)-(4-phenylspiro[chromane-2,4'-piperidine]-1'-yl)methanone

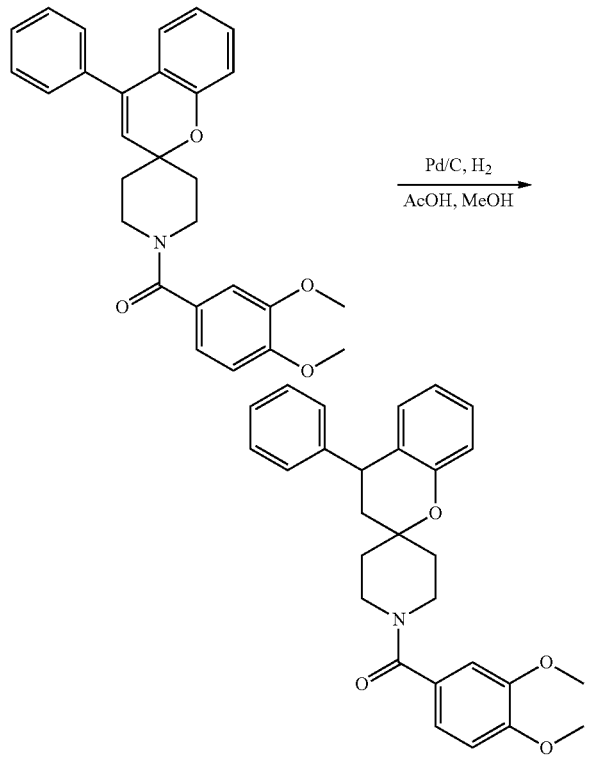

To a suspension of (3,4-dimethoxyphenyl)-(4-phenylspiro[chromene-2,4'-piperidine]-1'-yl)methanone (30 mg, 0.066 mmol) in MeOH (2 mL) and AcOH (0.2 mL) was added Pd/C (10%, 7.1 mg, 0.066 mmol). The mixture was stirred at rt for 1 h under a balloon of hydrogen. The mixture was filtered and the filtrate was concentrated. The residue was taken up in ethyl acetate and the solution was washed with saturated aqueous NaHCO₃, then brine. The organic layer was dried over sodium sulfate and was concentrated in vacuo to give (3,4-dimethoxyphenyl)-(4-phenylspiro[chromane-2,4'-piperidine]-1'-yl)methanone as a white solid. ESI-MS m/z calc. 443.2, found 444.2 (M+1)$^+$; Retention time: 2.83 minutes (3 min run). $^1$H NMR (400 MHz, CDCl₃) δ 7.27-7.16 (m, 2H), 7.12-7.04 (m, 4H), 6.94-6.92 (m, 2H), 6.81 (dd, J=8.3, 19.2 Hz, 2H), 6.70 (dd, J=7.6, 14.3 Hz, 2H), 4.42-4.30 (m, 1H), 4.05 (q, J=7.1 Hz, 1H), 3.83 (s, 3H), 3.65-3.54 (m, 2H), 2.00-1.96 (m, 2H), 1.80 (dd, J=6.8, 13.9 Hz, 1H), 1.70-1.52 (m, 2H) and 1.24-1.14 (m, 2H).

(4-Isopropoxy-3-methoxyphenyl)(4-(1-methoxyethyl)spiro[chroman-2,4'-piperidine]-1'-yl)methanone

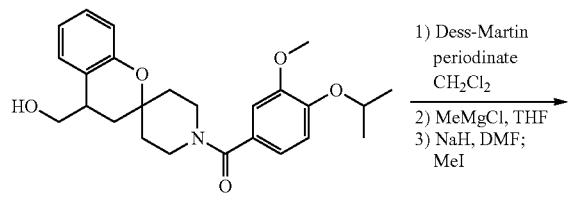

1) Dess-Martin periodinate CH₂Cl₂
2) MeMgCl, THF
3) NaH, DMF; MeI

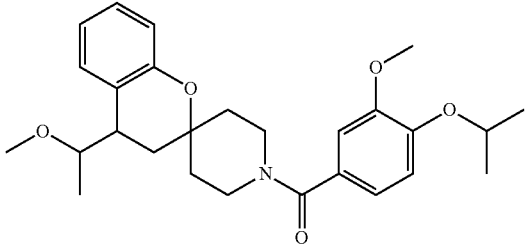

To a 25 mL round bottom flask was added [4-(hydroxymethyl)spiro[chromane-2,4'-piperidine]-1'-yl]-(4-isopropoxy-3-methoxy-phenyl)methanone (160 mg, 0.37 mmol) followed by dichloromethane (1 mL) and Dess-Martin periodinate (2.50 mL of 0.3 M in CH₂Cl₂, 0.75 mmol). The reaction mixture was allowed to stir for 3 h. The reaction was filtered through a plug of celite and the filtrate was concentrated. The crude residue was dissolved in THF (2 mL) and the mixture was cooled to 0° C. Methyl magnesium chloride (150 μL of 3.0 M, 0.45 mmol) was added and the reaction mixture was allowed to warm to 25° C. and was stirred for 1 h. The reaction was filtered and the filtrate was concentrated. The residue was purified by reverse phase prep-HPLC (20%-99% MeOH H₂O) to provide [4-(1-hydroxyethyl)spiro[chromane-2,4'-piperidine]-1'-yl]-(4-isopropoxy-3-methoxy-phenyl)methanone as a white solid (40 mg, 24%). ESI-MS m/z calc. 439.5, found 440.5 (M+1)$^+$; Retention time: 1.57 minutes (3 min run).

[4-(1-Hydroxyethyl)spiro[chromane-2,4'-piperidine]-1'-yl]-(4-isopropoxy-3-methoxy-phenyl)methanone (30 mg, 0.070 mmol) was added to a vial and DMF (1 mL) was added followed by NaH (14 mg, 0.56 mmol). Iodomethane (30 μL, 0.49 mmol) was added and the reaction mixture was allowed to stir for 30 minutes. The reaction was filtered and purified by reverse phase prep-HPLC using a gradient of MeOH:H₂O (20%-99%) to give (4-isopropoxy-3-methoxy-phenyl)(4-(1-methoxyethyl)spiro[chroman-2,4'-piperidine]-1'-yl)methanone. ESI-MS m/z calc. 453.6, found 454.5 (M+1)$^+$; Retention time: 1.88 minutes (3 min run).

(4-Isopropoxy-3-methoxyphenyl)(4-(methylthiomethyl)spiro[chroman-2,4'-piperidine]-1'-yl)methanone

Step 1: 1'-tert-Butyl 4-methyl spiro[chromene-2,4'-piperidine]-1',4-dicarboxylate

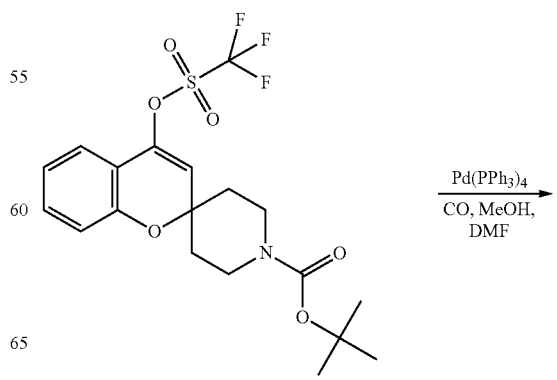

-continued

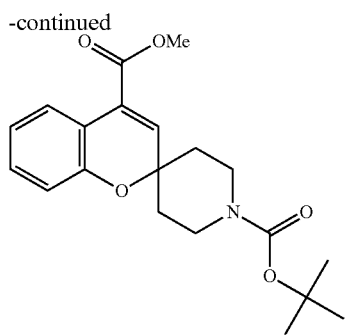

A solution of tert-butyl 4-(trifluoromethylsulfonyloxy) spiro[chromene-2,4'-piperidine]-1'-carboxylate (13 g, 28.92 mmol) in MeOH (58 mL) and DMF (115 mL) was degassed and put under an atmosphere of $N_2$. The mixture was treated with diisopropyl ethyl amine (17.6 mL, 101.2 mmol) and tetrakis(triphenylphosphine)palladium (2.0 g, 1.7 mmol). The mixture was put under a carbon monoxide atmosphere (1 atm, balloon) and was warmed to 50° C. for 20 h. The reaction was cooled, and quenched with saturated aqueous NaCl. The methanol was removed under reduced pressure and the mixture was extracted with DCM (3×50 mL). The combined organics were washed with saturated aqueous NaCl, dried ($Na_2SO_4$), filtered, and concentrated under reduced pressure. The crude product was diluted with EtOAc and the solid product formed was collected by vacuum filtration. After repeating this two more times, the remaining filtrate was purified by flash column chromatography on silica gel (1-30% EtOAc/hexanes) to afford 1'-tert-butyl 4-methyl spiro[chromene-2,4'-piperidine]-1',4-dicarboxylate (9.8 g, 94%) as a yellow solid. ESI-MS m/z calc. 359.4, found 360.5 $(M+1)^+$; Retention time: 2.2 minutes (3 min run).

Step 2: tert-Butyl 4-(hydroxymethyl)spiro[chromane-2,4'-piperidine]-1'-carboxylate

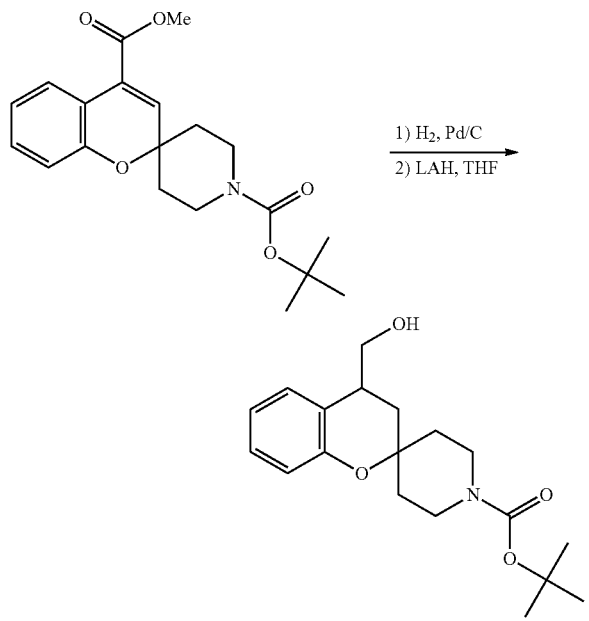

A mixture of 1'-tert-butyl 4-methyl spiro[chromene-2,4'-piperidine]-1',4-dicarboxylate (3.77 g, 10.49 mmol) and iPrOH (260 mL) was purged with nitrogen for 10 minutes. The mixture was treated with Pd (10% on Carbon) (3.5 g, 3.25 mmol) and put under a $H_2$ atmosphere (balloon). The reaction mixture was stirred for 48 h and was filtered through celite. The filtrate was concentrated under reduced pressure and purified by flash column chromatography ($SiO_2$, 1-30% EtOAc/hexanes) to afford 1'-tert-butyl 4-methyl spiro[chroman-2,4'-piperidine]-1',4-dicarboxylate (3.49 g, 92%).

A solution of 1'-tert-butyl 4-methyl spiro[chroman-2,4'-piperidine]-1',4-dicarboxylate (10 g, 27.67 mmol) in THF (265 mL) was cooled to −78° C. and treated with $LiAlH_4$ in THF (15.22 mL of 2 M, 30.44 mmol). The mixture was warmed to 0° C. and stirred for 1 h and was quenched by the addition of $H_2O$ (0.7 mL), 15% aqueous NaOH (0.7 mL) and $H_2O$ (2.1 mL). The mixture was stirred for 1 h, filtered through celite, and diluted with $H_2O$. The mixture was extracted with EtOAc (3×50 mL) and the combined organics were washed with saturated aqueous NaCl, dried ($Na_2SO_4$), filtered, and concentrated under reduced pressure. Purification by flash column chromatography ($SiO_2$, 1-70% EtOAc-hexanes, ELSD detection) afforded tert-butyl 4-(hydroxymethyl)spiro[chromane-2,4'-piperidine]-1'-carboxylate (6.1 g, 66%) as a colorless foam. ESI-MS m/z calc. 333.4, found 334.7 $(M+1)^+$; Retention time: 1.85 minutes (3 min run).

Step 3: Spiro[chromane-2,4'-piperidine]-4-ylmethanol

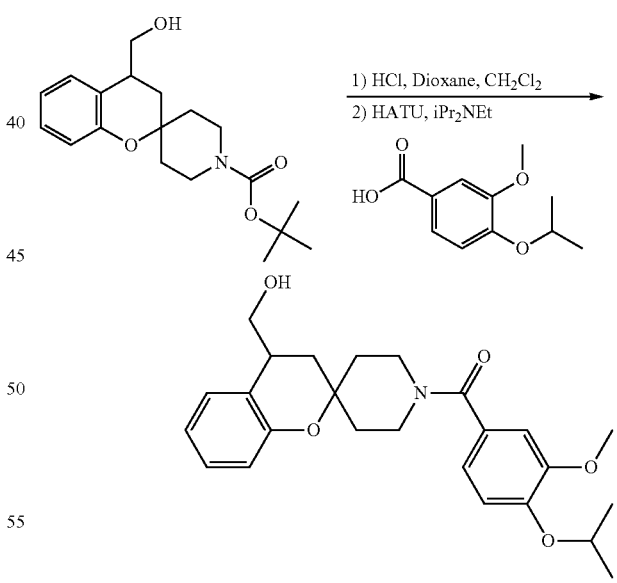

A solution of tert-butyl 4-(hydroxymethyl)spiro[chromane-2,4'-piperidine]-1'-carboxylate (5 g, 15 mmol) in DCM (37 mL) was treated with hydrogen chloride (4M in dioxane) (15 mL of 4 M, 60 mmol). The reaction mixture was stirred for 1 h and was concentrated under reduced pressure to afford spiro[chromane-2,4'-piperidine]-4-yl-methanol hydrogen chloride (3.33 g, 95%) which was used without further purification.

A solution of 4-isopropoxy-3-methoxy-benzoic acid (693 mg, 3.3 mmol) and HATU (1.7 g, 4.5 mmol) in DMF (15 mL) was treated with Et₃N (910 mg, 1.25 mL, 9.0 mmol) and stirred for 10 min. The reaction mixture was treated with spiro[chromane-2,4'-piperidine]-4-ylmethanol hydrogen chloride (0.7 g, 3.0 mmol) and stirred 1 h at 25° C. The reaction was diluted with H₂O (60 mL) and was extracted with EtOAc (3×20 mL). The combined organics were washed with saturated aqueous NaCl, dried (Na₂SO₄), filtered, and concentrated under reduced pressure. Purification by column chromatography (silica, 30-100% EtOAc-hexanes) afforded [4-(hydroxymethyl)spiro[chromane-2,4'-piperidine]-1'-yl]-(4-isopropoxy-3-methoxy-phenyl)methanone (1.25 g, 97%) as a colorless foam. ESI-MS m/z calc. 425.2, found 426.3 (M+1)⁺; Retention time: 1.73 minutes (3 min run).

Step 4: [1'-(4-isopropoxy-3-methoxy-benzoyl)spiro[chromane-2,4'-piperidine]-4-yl]methyl methanesulfonate

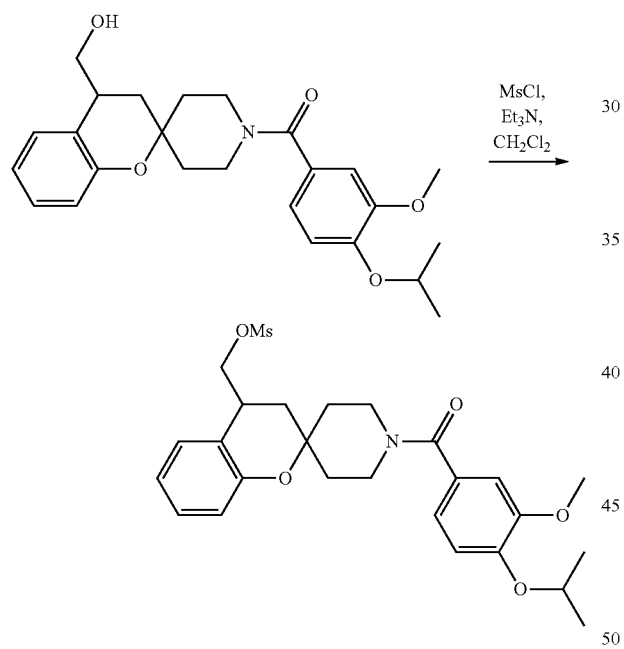

A solution of [4-(hydroxymethyl)spiro[chromane-2,4'-piperidine]-1'-yl]-(4-isopropoxy-3-methoxy-phenyl)methanone (750 mg, 1.76 mmol) and TEA (214 mg, 295 µL. 2.1 mmol) in DCM (35 mL) was cooled to 0° C. and treated dropwise with MsCl (222 mg, 150 µL, 1.9 mmol). The reaction mixture was allowed to warm to 25° C. and stir for 2 h and was poured into H₂O. The mixture was extracted with DCM (3×30 mL). The combined organics were dried (Na₂SO₄), filtered, and concentrated under reduced pressure to afford [1'-(4-isopropoxy-3-methoxy-benzoyl)spiro[chromane-2,4'-piperidine]-4-yl]methyl methanesulfonate (762 mg, mmol, 86%) which was used without further purification. ESI-MS m/z calc. 503, found 504 (M+1)⁺; Retention time: 1.89 minutes (3 min run).

Step 5: (4-Isopropoxy-3-methoxyphenyl)(4-(methylthiomethyl)spiro[chroman-2,4'-piperidine]-1'-yl)methanone

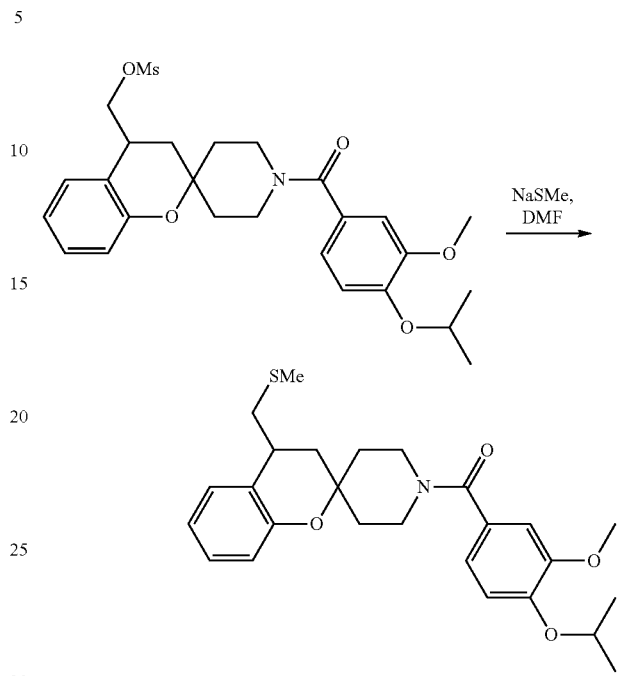

A solution of [1'-(4-isopropoxy-3-methoxy-benzoyl)spiro[chromane-2,4'-piperidine]-4-yl]methyl methanesulfonate (225 mg, 0.45 mmol) in DMF (2 mL) was treated with MeSNa (88.6 mg, 0.54 mmol). The reaction mixture was heated to 50° C. for 12 h, cooled, and poured into cold water. The mixture was extracted with EtOAc (3×20 mL) and the combined organics were washed with saturated aqueous NaCl, dried (Na₂SO₄), filtered, and concentrated under reduced pressure. The crude residue was purified by reverse phase HPLC (1-100% ACN/H₂O, no modifier) to afford (4-isopropoxy-3-methoxyphenyl)(4-(methylthiomethyl)spiro[chroman-2,4'-piperidine]-1'-yl)methanone as a colorless foam. ESI-MS m/z calc. 455.2, found 456.5 (M+1)⁺; Retention time: 0.84 minutes (3 min run).

The following compound was prepared using the procedure reported above:
(4-((1H-pyrazol-1-yl)methyl)spiro[chroman-2,4'-piperidine]-1'-yl)(4-isopropoxy-3-methoxyphenyl)methanone.

(44(Difluoromethoxy)methyl)spiro[chroman-2,4'-piperidine]-1'-yl)(4-isopropoxy-3-methoxyphenyl)methanone

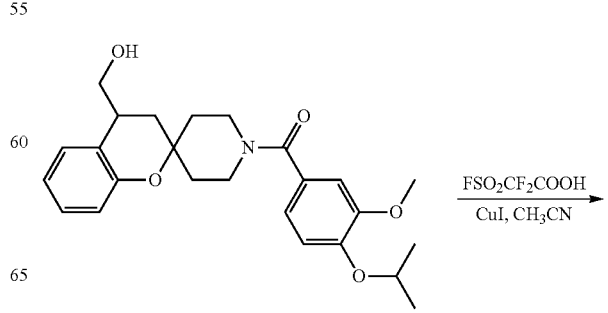

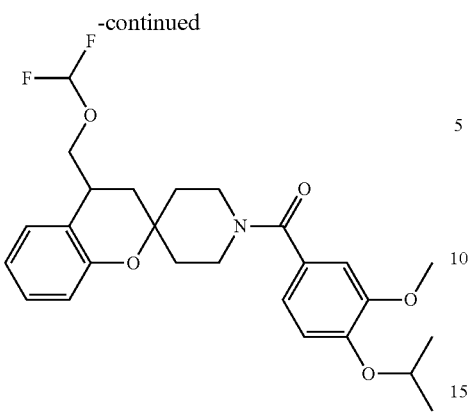

A degassed solution of [4-(hydroxymethyl)spiro[chromane-2,4'-piperidine]-1'-yl]-(4-isopropoxy-3-methoxy-phenyl)methanone (123 mg, 0.29 mmol) in acetonitrile (1.5 mL) was treated with copper (I) iodide (11 mg, 0.058 mmol). To the reaction mixture was added 2,2-difluoro-2-fluorosulfonyl-acetic acid (51.5 mg, 29 μL, 0.29 mmol) dropwise. The reaction was stirred at 45° C. for 4 hours. The solvent was removed in vacuo and ethyl acetate (30 mL) added. The organics were washed with water (30 mL), brine (30 mL), dried (MgSO$_4$), filtered and the solvent removed in vacuo. Purification by reverse phase HPLC (1-100% ACN/H$_2$O; no modifier) afforded the desired product [4-(difluoromethoxymethyl)spiro[chromane-2,4'-piperidine]-1'-yl]-(4-isopropoxy-3-methoxy-phenyl)methanone. ESI-MS m/z calc. 475.2, found 476.3 (M+1)$^+$; Retention time: 2.11 minutes (3 min run).

(4-Isopropoxy-3-methylphenyl)(spiro[chroman-2,4'-piperidine]-1'-yl)methanone

Step 1: Benzyl spiro[chroman-2,4'-piperidine]-1'-carboxylate

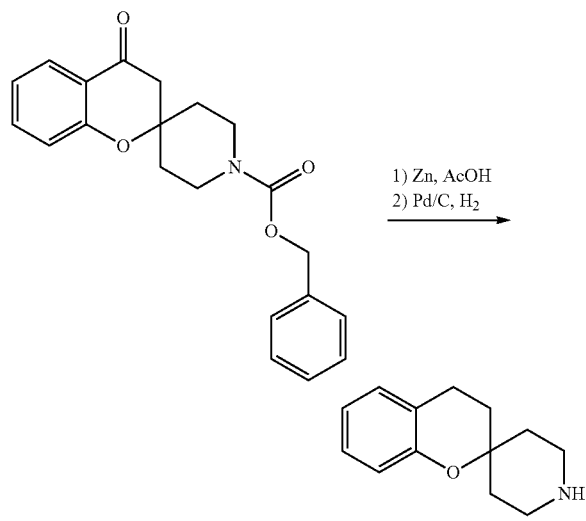

A mixture of benzyl 4-oxospiro[chromane-2,4'-piperidine]-1'-carboxylate (511 mg, 1.45 mmol) and Zn (951 mg, 14.5 mmol) in acetic acid (10 mL) was heated at 100° C. for 3 h. The reaction mixture was evaporated to dryness and the residue was partitioned between dichloromethane and 1N NaOH. The organics were separated and washed with brine, dried over sodium sulfate and evaporated to give benzyl spiro[chroman-2,4'-piperidine]-1'-carboxylate. ESI-MS m/z calc. 337.4, found 338.5 (M+1)$^+$; Retention time: 2.11 minutes (3 min run).

Benzyl spiro[chromane-2,4'-piperidine]-1'-carboxylate (490 mg, 1.45 mmol) and Pd/C (154 mg, 0.145 mmol) were stirred in methanol (5 mL) under a balloon of hydrogen for 16 h. The reaction was filtered and the filtrate was evaporated to give spiro[chromane-2,4'-piperidine] (287 mg, 97%). ESI-MS m/z calc. 203.3, found 204.3 (M+1)$^+$; Retention time: 0.79 minutes (3 min run). $^1$H NMR (400 MHz, MeOD) δ 7.07-6.98 (m, 2H), 6.82-6.72 (m, 2H), 3.08-2.94 (m, 2H), 2.91-2.71 (m, 4H), 1.84-1.73 (m, 4H), 1.65-1.52 (m, 2H).

Step 2: (4-Isopropoxy-3-methylphenyl)(spiro[chroman-2,4'-piperidine]-1'-yl)methanone

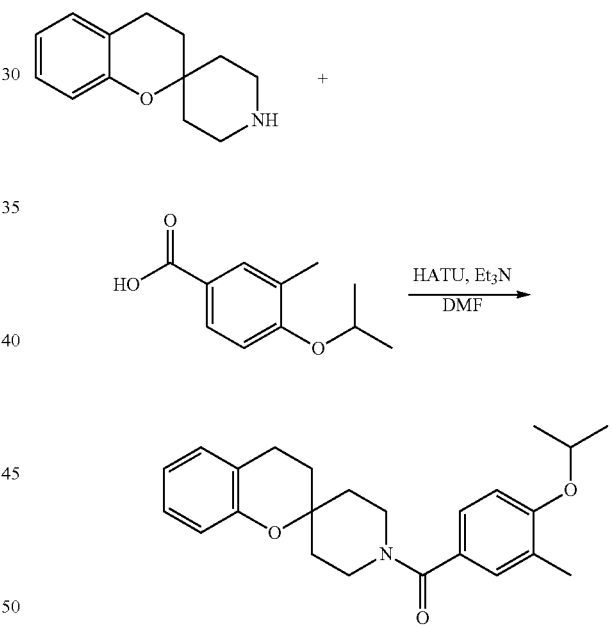

A mixture of spiro[chromane-2,4'-piperidine] (20 mg, 0.1 mmol), 4-isopropoxy-3-methylbenzoic acid (19 mg, 0.1 mmol), HATU (38 mg, 0.1 mmol), and triethylamine (28 μL, 0.2 mmol) in DMF (1 mL) was stirred for 2 h. The reaction mixture was filtered and purified by reverse phase prep-HPLC to give (4-isopropoxy-3-methylphenyl)(spiro[chroman-2,4'-piperidine]-1'-yl)methanone. ESI-MS m/z calc. 379.5, found 380.5 (M+1)$^+$; Retention time: 2.16 minutes (3 min run).

(4-Isopropoxy-3-methoxyphenyl)(spiro[chroman-2,4'-piperidine]-1'-yl)methanone and (4-(isopropylsulfonyl)phenyl)(spiro[chroman-2,4'-piperidine]-1'-yl)methanone were prepared using a procedure similar as reported above.

177

[4-(2-Hydroxy-1,1-dimethyl-ethyl)-3-methoxy-phenyl]-(4-isopropoxyspiro[chromane-2,4'-piperidine]-1'-yl)methanone

178

(4-Isopropoxy-1,1-dioxo-spiro[3,4-dihydrothiochromene-2,4'-piperidine]-1'-yl)-(4-isopropoxy-3-methoxy-phenyl)methanone Step 1: 1-(4-Isopropoxy-3-methoxy-benzoyl)spiro[piperidine-4,2'-thiochromane]-4'-one

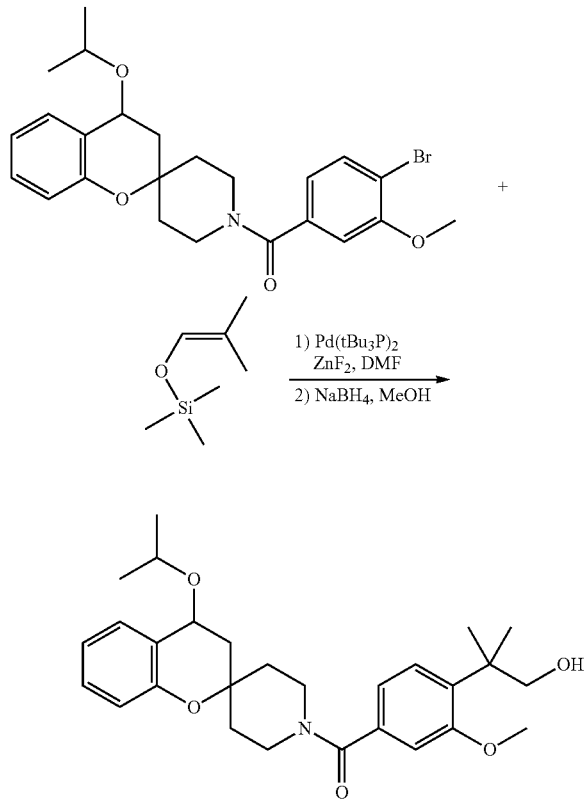

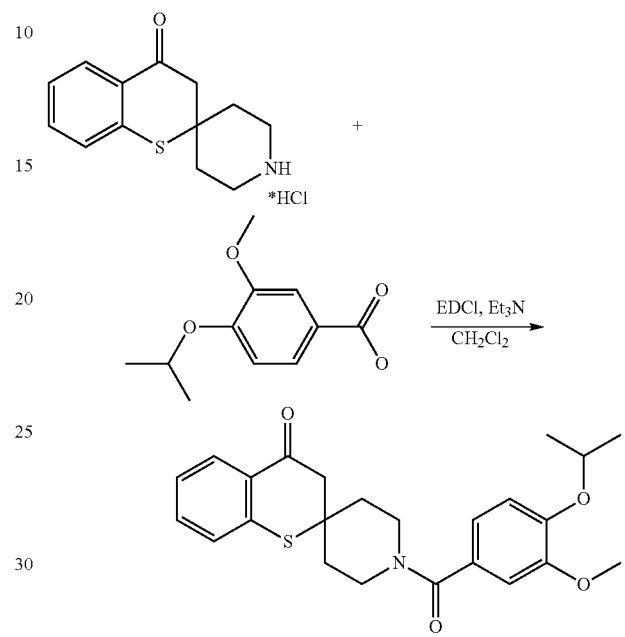

To a 100 mL flask was added Pd(t-Bu$_3$P)$_2$ (103 mg, 0.202 mmol), ZnF$_2$ (174 mg, 1.69 mmol), and DMF (1.5 mL). The mixture was purged with nitrogen and was allowed to stir for 10 minutes. (4-Bromo-3-methoxy-phenyl)-(4-isopropoxyspiro[chromane-2,4'-piperidine]-1'-yl)methanone (320 mg, 0.675 mmol) in DMF (1 mL) was added followed by trimethyl(2-methylprop-1-enoxy)silane (487 mg, 620 µL, 3.37 mmol). The mixture was heated at 80° C. for 3 h. The mixture was quenched with brine and was extracted with ethyl acetate (3×). The combined organics were separated and dried over sodium sulfate. The solvent was evaporated and the crude product was purified by silica gel chromatography (3%-70% ethyl acetate/hexanes) to give 2-(4-(4-isopropoxyspiro[chroman-2,4'-piperidine]-1'-ylcarbonyl)-2-methoxyphenyl)-2-methylpropanal as a white solid. To the solid was added MeOH (1 mL) followed by NaBH$_4$ (51 mg, 1.3 mmol) at 0° C. After 30 minutes, the mixture was concentrated and the residue was purified by prep-HPLC (20-99% MeOH:H$_2$O with no modifier) to give [4-(2-hydroxy-1,1-dimethyl-ethyl)-3-methoxy-phenyl]-(4-isopropoxyspiro[chromane-2,4'-piperidine]-1'-yl)methanone as an off-white solid. ESI-MS m/z calc. 467.3, found 468.7 (M+1)$^+$; Retention time: 1.89 minutes (3 min run).

Et$_3$N (4.13 mL, 29.7 mmol) was added to a mixture of spiro[piperidine-4,2'-thiochromane]-4'-one (2.00 g, 7.41 mmol), 4-isopropoxy-3-methoxy-benzoic acid (1.56 g, 7.41 mmol), EDCI (1.42 g, 7.41 mmol), and CH$_2$Cl$_2$ (50 mL) at room temperature. The mixture was allowed to stir at room temperature overnight before it was washed with 1N HCl, and brine. The organic layer was dried over sodium sulfate, filtered, and concentrated. Column chromatography (0-100% ethyl acetate/hexanes) on the residue gave 1-(4-isopropoxy-3-methoxy-benzoyl)spiro[piperidine-4,2'-thiochromane]-4'-one (2.31 g, 73%). ESI-MS m/z calc. 425.2, found 426.1 (M+1)$^+$; Retention time: 1.72 minutes (3 min run). $^1$H NMR (400 MHz, CDCl$_3$) δ 8.08 (d, J=7.9 Hz, 1H), 7.43 (t, J=7.6 Hz, 1H), 7.28 (d, J=8.1 Hz, 1H), 7.20 (t, J=7.6 Hz, 1H), 6.97 (s, 1H), 6.95-6.90 (m, 1H), 6.86 (d, J=8.2 Hz, 1H), 4.56 (dt, J=12.2, 6.1 Hz, 1H), 3.86 (s, 3H), 3.42 (s, 2H), 2.97 (s, 2H), 2.01 (s, J=26.0 Hz, 2H), 1.75 (s, 2H), 1.61 (s, 2H), 1.37 (d, J=6.1 Hz, 6H).

Step 2: (4-Isopropoxy-3-methoxy-phenyl)-(4'-isopropoxyspiro[piperidine-4,2'-thiochromane]-1-yl)methanone

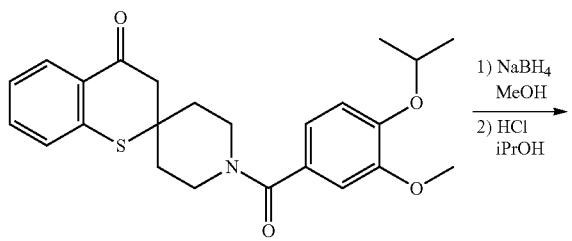

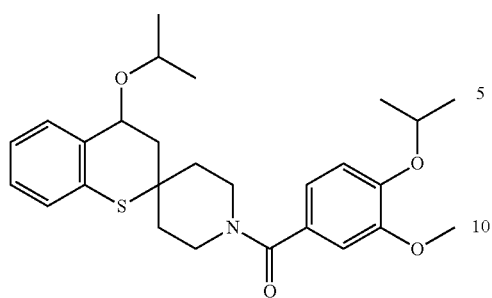

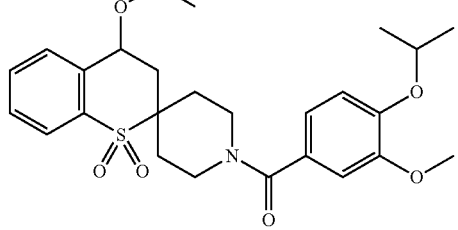

To 1-(4-isopropoxy-3-methoxy-benzoyl)spiro[piperidine-4,2'-thiochromane]-4'-one (750 mg, 1.76 mmol) and MeOH (15 mL) was added NaBH₄ (133 mg, 3.52 mmol). The mixture was allowed to stir for 10 min before it was quenched with sat. NH₄Cl. The pH of the mixture was adjusted to ~7 with 1N HCl and the mixture was extracted with ethyl acetate (3×). The combined organics were dried over sodium sulfate, filtered and concentrated to provide (4'-hydroxyspiro[piperidine-4,2'-thiochroman]-1-yl)(4-isopropoxy-3-methoxyphenyl)methanone. ESI-MS m/z calc. 427.2, found 428.3 (M+1)⁺; Retention time: 1.60 minutes (3 min run).

To (4'-hydroxyspiro[piperidine-4,2'-thiochroman]-1-yl)(4-isopropoxy-3-methoxyphenyl)-methanone was added iPrOH (13.5 mL, 176 mmol) followed by HCl (88 µL of 4.0 M in dioxane, 0.35 mmol) and dioxane (15 mL). The mixture was heated at 60° C. for 5 h. The mixture was cooled to room temperature and was treated with saturated aqueous NaHCO₃. The mixture was extracted with ethyl acetate (3×). The combined organics were dried over sodium sulfate, filtered, and concentrated to give (4-isopropoxy-3-methoxyphenyl)-(4'-isopropoxyspiro[piperidine-4,2'-thiochromane]-1-yl)methanone (170 mg, 20%) [ESI-MS m/z calc. 469.2, found 470.2 (M+1)⁺; Retention time: 2.02 minutes (3 min run)] contaminated with 1-(4-isopropoxy-3-methoxy-benzoyl)spiro[piperidine-4,2'-thiochromane]-4'-one and the elimination product. The mixture was used without further manipulation.

Step 3: (4-Isopropoxy-1,1-dioxo-spiro[3,4-dihydro-thiochromene-2,4'-piperidine]-1'-yl)-(4-isopropoxy-3-methoxy-phenyl)methanone A mixture of (4-isopropoxy-3-methoxy-phenyl)-(4'-isopropoxyspiro[piperidine-4,2'-thiochromane]-1-yl)methanone (150 mg, 0.319 mmol), mCPBA (251 mg, 1.12 mmol), and CH₂Cl₂ (3 mL) was allowed to stir at room temperature for 1 h. The mixture was concentrated and the residue was purified by column chromatography (0-100% ethyl acetate/hexanes), then by prep-HPLC (0-99% ACN/water; no modifier) to give (4-isopropoxy-1,1-dioxo-spiro[3,4-dihydrothiochromene-2,4'-piperidine]-1'-yl)-(4-isopropoxy-3-methoxyphenyl)methanone (45 mg, 28%) as a white solid. ESI-MS m/z calc. 501.2, found 502.2 (M+1)⁺; Retention time: 1.68 minutes (3 min run). ¹H NMR (400 MHz, CDCl₃) δ 7.94 (dd, J=7.1, 4.1 Hz, 1H), 7.69-7.55 (m, 2H), 7.51 (dd, J=10.8, 7.2 Hz, 1H), 7.05-6.93 (m, 2H), 6.87 (dd, J=8.2, 4.1 Hz, 1H), 4.89-4.76 (m, 1H), 4.65-4.50 (m, 1H), 3.92 (dd, J=11.1, 5.1 Hz, 1H), 3.87 (d, J=4.1 Hz, 3H), 3.40 (dd, J=13.7, 9.9 Hz, 2H), 2.67-2.54 (m, 1H), 2.53-2.40 (m, 1H), 2.40-2.16 (m, J=39.2 Hz, 2H), 1.90 (s, 1H), 1.70 (s, 1H), 1.58 (d, J=5.0 Hz, 2H), 1.38 (dd, J=6.0, 4.1 Hz, 6H), 1.35-1.22 (m, 6H).

(4-Isopropoxy-1,1-dioxo-spiro[3,4-dihydrothio-chromene-2,4'-piperidine]-1'-yl)-(4-isopropoxyphenyl)methanone and [(4S)-4-isopropoxy-1,1-dioxo-spiro[3,4-dihydrothiochromene-2,4'-piperidine]-1'-yl]-(4-isopropoxy-3-methyl-phenyl)methanone were prepared using the procedures described above.

(4-Isopropoxy-3-methoxy-phenyl)-(4-methoxy-1,1-dioxo-spiro[3,4-dihydrothiochromene-2,4'-piperidine]-1'-yl)methanone Step 1: (4-Isopropoxy-3-methoxy-phenyl)-(4'-methoxyspiro-[piperidine-4,2'-thiochromane]-1-yl)methanone

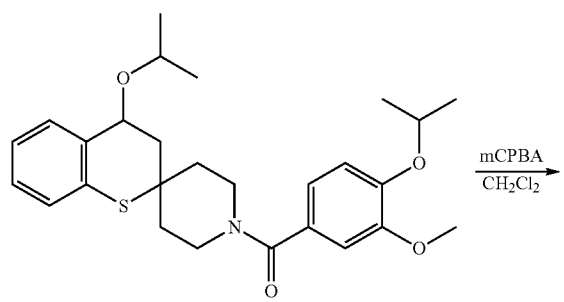

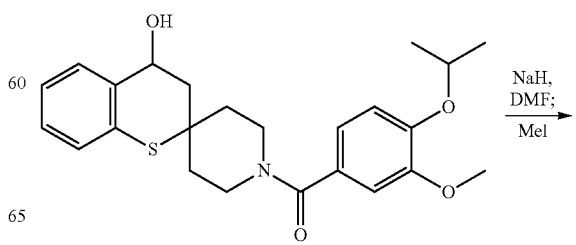

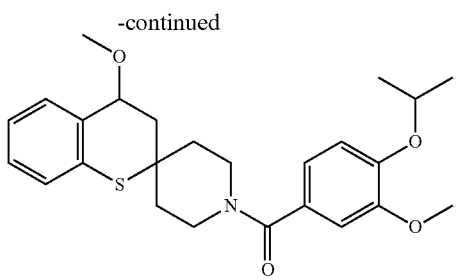

To a mixture of (4'-hydroxyspiro[piperidine-4,2'-thiochromane]-1-yl)-(4-isopropoxy-3-methoxy-phenyl)methanone (190 mg, 0.444 mmol) and DMF (1 mL) was added NaH (53 mg, 1.3 mmol). The mixture was allowed to stir at room temperature for 10 minutes before MeI (111 μL, 1.78 mmol) was added. The reaction mixture was stirred at room temperature for 14 hours. Methanol was added to the reaction and it was filtered. The filtrate was evaporated under reduced pressure and the residue was dissolved in ethyl acetate (5 mL) and was washed with water (3 mL), 1M hydrochloric acid (3 mL), a saturated aqueous solution of sodium bicarbonate (3 mL) and a saturated aqueous solution of sodium chloride (3 mL). The organic layer was dried over sodium sulfate, filtered and the solvent was evaporated under reduced pressure to yield (4-isopropoxy-3-methoxy-phenyl)-(4'-methoxyspiro[piperidine-4,2'-thiochromane]-1-yl)methanone (157 mg, 80%). ESI-MS m/z calc. 441.2, found 442.5 (M+1)$^+$; Retention time: 1.86 minutes (3 min run).

Step 2: (4-Isopropoxy-3-methoxy-phenyl)-(4-methoxy-1,1-dioxo-spiro[3,4-dihydrothiochromene-2,4'-piperidine]-1'-yl)methanone

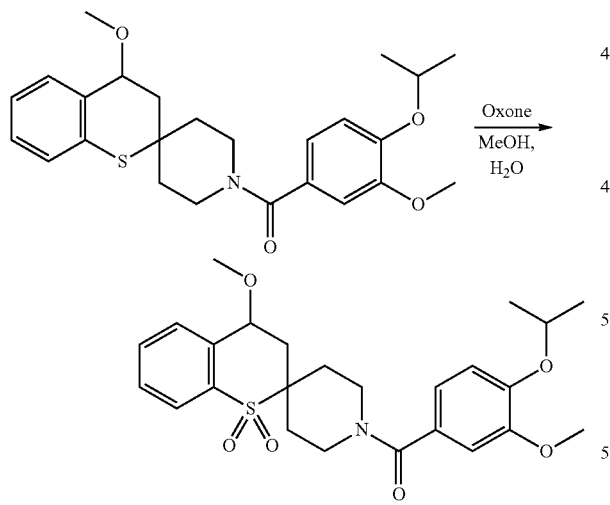

(4-Isopropoxy-3-methoxy-phenyl)-(4'-methoxyspiro[piperidine-4,2'-thiochromane]-1-yl)methanone (157 mg, 0.355 mmol) was dissolved in MeOH (3.9 mL), followed by the addition of water (388 μL) and Oxone (437 mg, 0.711 mmol). The reaction mixture was stirred at room temperature for 4 h. The mixture was filtered and the filtrate was diluted with dichloromethane (5 mL). The solution was washed with water (2×5 mL) and a saturated aqueous solution of sodium chloride (5 mL). The organic layer was dried over sodium sulfate, filtered and the solvent was evaporated under reduced pressure. The residue was purified by column chromatography (0-100% ethyl acetate/hexane) to yield (4-isopropoxy-3-methoxy-phenyl)-(4-methoxy-1,1-dioxo-spiro[3,4-dihydrothiochromene-2,4'-piperidine]-1'-yl)methanone as a white solid. ESI-MS m/z calc. 473.2, found 474.3 (M+1)$^+$; Retention time: 3.90 minutes (15 min run). $^1$H NMR (400 MHz, DMSO) δ 7.84 (d, J=7.9 Hz, 1H), 7.78-7.67 (m, 1H), 7.67-7.57 (m, 2H), 7.07-6.91 (m, 3H), 4.73-4.51 (m, 2H), 4.27-3.64 (m, 5H), 3.56-3.37 (m, 5H), 2.84-2.71 (m, 1H), 2.57-2.52 (m, 1H), 2.13-1.68 (m, 4H), 1.26 (d, J=6.0 Hz, 6H).

(4-Ethoxy-1,1-dioxo-spiro[3,4-dihydrothiochromene-2,4'-piperidine]-1'-yl)-(4-isopropoxy-3-methoxy-phenyl)methanone was also prepared using the procedures described above.

1'-(4-(2-hydroxypropan-2-yl)-3-methylbenzoyl)-4-isopropoxyspiro[chroman-2,4'-piperidine]-6-carbonitrile Step 1: 1'-(4-(2-hydroxypropan-2-yl)-3-methylbenzoyl)-4-oxospiro[chroman-2,4'-piperidine]-6-carbonitrile

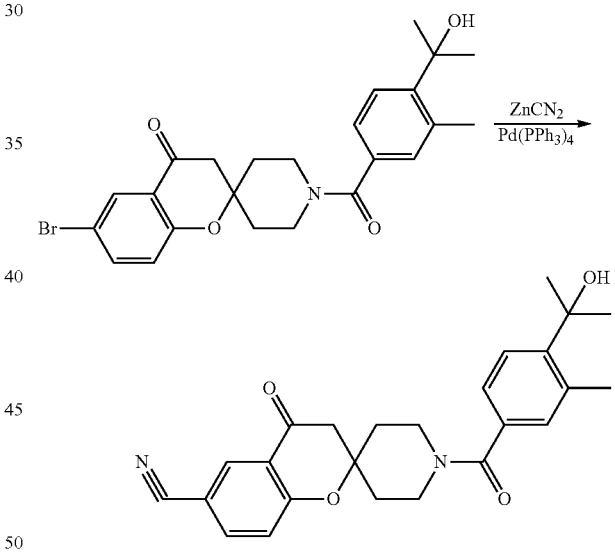

A solution of 6-bromo-1'-[4-(1-hydroxy-1-methyl-ethyl)-3-methyl-benzoyl]spiro[chromane-2,4'-piperidine]-4-one (353 mg, 0.75 mmol) in DMF (1.5 mL) was treated with dicyanozinc (88 mg, 47 μL, 0.75 mmol) and tetrakis(triphenylphosphine)palladium (86 mg, 0.075 mmol). The reaction mixture was warmed to 90° C. for 90 min, cooled, and diluted with DCM and water. The mixture was extracted with DCM (3×15 mL) and the combined organics were dried (Na$_2$SO$_4$), filtered, and concentrated under reduced pressure. Purification by flash column chromatography (silica gel, 1-100% EtOAc/Hexanes) afforded 1'-[4-(1-hydroxy-1-methyl-ethyl)-3-methyl-benzoyl]-4-oxo-spiro[chromane-2,4'-piperidine]-6-carbonitrile (303 mg, 97%) as a colorless oil. ESI-MS m/z calc. 418.2, found 419.5 (M+1)$^+$; Retention time: 1.61 minutes (3 min run).

Step 2: 4-Hydroxy-1'-(4-(2-hydroxypropan-2-yl)-3-methylbenzoyl)spiro[chroman-2,4'-piperidine]-6-carbonitrile

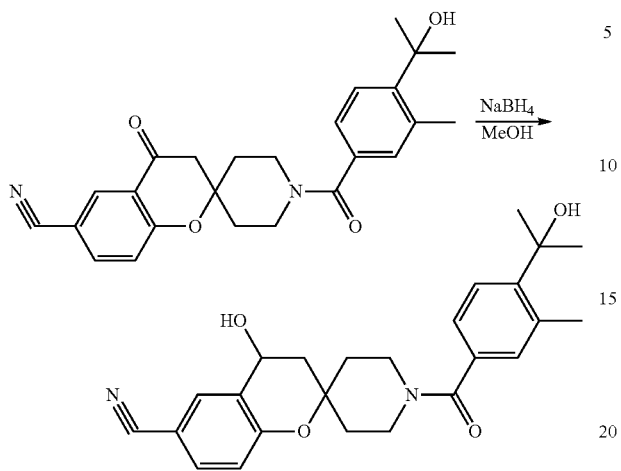

A solution of 1'-[4-(1-hydroxy-1-methyl-ethyl)-3-methyl-benzoyl]-4-oxo-spiro[chromane-2,4'-piperidine]-6-carbonitrile (289 mg, 0.69 mmol) in MeOH (3.5 mL) was treated with NaBH$_4$ (52 mg, 1.38 mmol). The reaction mixture was stirred for 1 h and was quenched by the addition of saturated aqueous NH$_4$Cl. The methanol was removed under reduced pressure and the mixture was extracted with DCM (3×30 mL). The combined organics were dried (Na$_2$SO$_4$), filtered, and concentrated under reduced pressure to afford 4-hydroxy-1'-(4-(2-hydroxypropan-2-yl)-3-methylbenzoyl)spiro[chroman-2,4'-piperidine]-6-carbonitrile (270 mg, 93%) which was used without further purification. ESI-MS m/z calc. 420.2, found 421.5 (M+1)$^+$; Retention time: 1.52 minutes (3 min run).

Step 3: 1'-(4-(2-Hydroxypropan-2-yl)-3-methylbenzoyl)-4-isopropoxyspiro[chroman-2,4'-piperidine]-6-carbonitrile

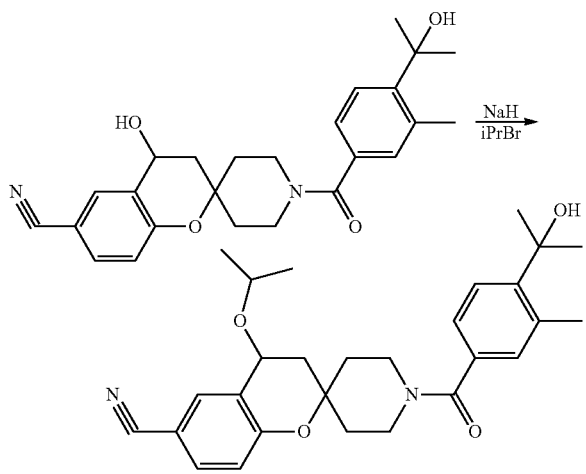

A solution of 4-hydroxy-1'-[4-(1-hydroxy-1-methyl-ethyl)-3-methyl-benzoyl]spiro[chromane-2,4'-piperidine]-6-carbonitrile (313 mg, 0.74 mmol) in DMF (4.5 mL) was cooled to 0° C. and sodium hydride (65 mg, 1.63 mmol) was added. After 5 minutes, 2-bromopropane (109 mg, 84 µL, 0.89 mmol) was added and the reaction was allowed to warm to 25° C. and stirred for 20 minutes. The reaction was filtered and purified by reverse phase hplc (10-99%, no modifier) ACN:H$_2$O to afford 1'-[4-(1-hydroxy-1-methyl-ethyl)-3-methyl-benzoyl]-4-isopropoxy-spiro[chromane-2,4'-piperidine]-6-carbonitrile as a colorless oil. ESI-MS m/z calc. 462.2, found 463.5 (M+1)$^+$; Retention time: 1.92 minutes (3 min run).

(2'-(tert-Butyl)-7'-isopropoxy-6',7'-dihydro-2'H-spiro[piperidine-4,5'-pyrano[3,2-c]pyrazol]-1-yl)(4-isopropoxy-3-methoxyphenyl)methanone

Step 1: tert-Butyl 2-tert-butyl-7-oxo-spiro[6H-pyrano[3,2-c]pyrazole-5,4'-piperidine]-1'-carboxylate

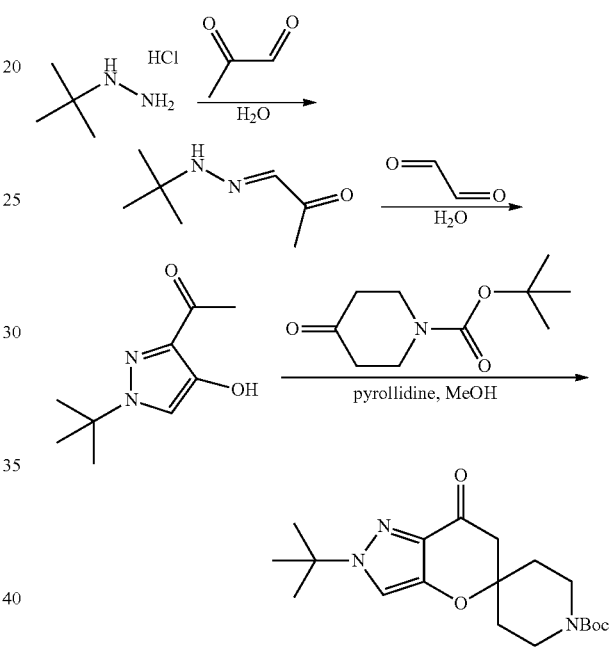

To a 250 mL flask was added tert-butylhydrazine hydrochloride (6.7 g, 54 mmol) in H$_2$O (55 mL) and the solution was stirred for 15 min at 25° C. until all solids dissolved. 2-Oxopropanal (7.5 g, 42 mmol) was added and the mixture was stirred for 4 h during which time it became bright yellow in color (forming two layers). The mixture was extracted with MTBE (2×40 mL) and the combined organics were washed with 1N NaOH (2×50 mL), H$_2$O, and concentrated. The crude material was diluted with H$_2$O (55 mL) and treated with oxaldehyde (13.9 g, 11.0 mL of 40% w/w, 96 mmol). The reaction mixture was warmed to 95° C. for 1 h, cooled to 25° C. and extracted with MTBE (2×50 mL). The combined organics were washed with 1 N NaOH (2×50 mL) and the combined aqueous layers were cooled to 5° C., acidified to pH 3 with HCl 33-40 wt/wt percent in water, then extracted MTBE (3×100 mL). The combined organic layers were washed with H$_2$O and concentrated under reduced pressure. To the concentrate was added MeOH (83 mL), tert-butyl 4-oxopiperidine-1-carboxylate (8.46 g, 42.5 mmol), and pyrrolidine (592 mg, 695 µL, 8.3 mmol). The reaction mixture was heated to 68° C. for 24 h, cooled to 25° C. and neutralized with 1 N HCl. The mixture was concentrated and washed with saturated aqueous NaHCO$_3$. The mixture was extracted with EtOAc (3×150 mL) and the combined organics were washed with saturated aqueous NaCl, dried (Na$_2$SO$_4$), filtered, and concentrated under reduced pressure. Purification by flash column chromatography (SiO$_2$, 1-50% EtOAc-hexanes) afforded tert-butyl 2-tert-butyl-7-oxo-spiro[6H-pyrano[3,2-c]pyrazole-5,4'-piperidine]-1'-carboxylate (9 g, 59%) as a yellow solid. ESI-MS m/z calc. 363.5, found 364.5 (M+1)$^+$; Retention time: 1.83 minutes (3 min run). $^1$H NMR (400 MHz, CDCl$_3$) δ 7.21 (s, 1H), 3.85 (s, 2H), 3.16 (t, J=11.2 Hz, 2H), 2.65 (s, 2H), 2.08-2.00 (m, 2H), 1.69-1.54 (m, 11H), 1.45 (s, 9H).

The following compound was prepared by the procedures described above:
tert-butyl 2'-methyl-7'-oxo-6',7'-dihydro-2'H-spiro[piperidine-4,5'-pyrano[3,2-c]pyrazole]-1-carboxylate.

Step 2: 2-tert-Butylspiro[6H-pyrano[3,2-c]pyrazole-5,4'-piperidine]-7-one

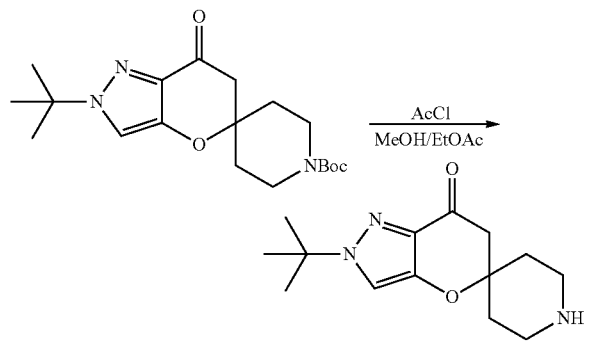

A solution of 2-tert-butyl-7-oxo-spiro[6H-pyrano[3,2-c]pyrazole-5,4'-piperidine]-1'-carboxylate (1.2 g, 3.30 mmol) in MeOH (3.5 mL) and EtOAc (13 mL) was cooled to 0° C. and treated with acetyl chloride (1.8 g, 1.6 mL, 22.5 mmol) dropwise over 30 min. The reaction mixture was allowed to warm to 25° C. and stir for 4 h. The reaction mixture was concentrated under reduced pressure and was diluted with DCM. The mixture was basified with 1 N NaOH and was extracted with DCM (3×100 mL). The combined organics were dried (Na$_2$SO$_4$), filtered, and concentrated under reduced pressure to afford 2-tert-butylspiro[6H-pyrano[3,2-c]pyrazole-5,4'-piperidine]-7-one (508 mg, 58%) as a yellow solid which was used without further purification. ESI-MS m/z calc. 263.3, found 264.3 (M+1)$^+$; Retention time: 0.75 minutes (3 min run).

The following compound was prepared by the procedures described above:
2'-methyl-2'H-spiro[piperidine-4,5'-pyrano[3,2-c]pyrazol]-7'(6'H)-one.

Step 3: 2-tert-Butyl-1'-(4-isopropoxy-3-methoxybenzoyl)spiro[6l'-pyrano[3,2-c]pyrazole-5,4'-piperidine]-7-one

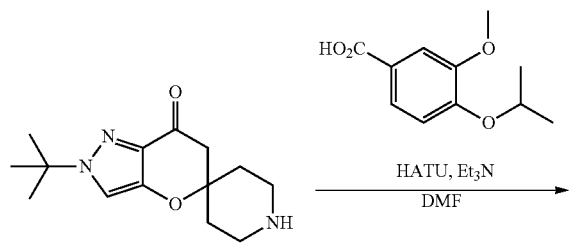

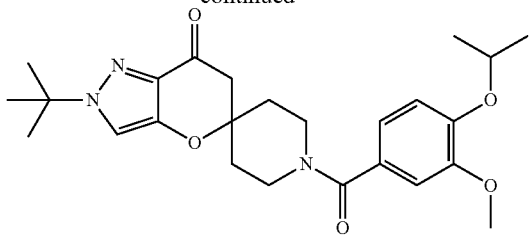

A solution of 4-isopropoxy-3-methoxy-benzoic acid (263 mg, 1.25 mmol) and HATU (650 mg, 1.7 mmol) in DMF (6.4 mL) was treated with Et$_3$N (480 μL, 3.4 mmol) and stirred for 10 min. The reaction mixture was treated with 2-tert-butylspiro[6H-pyrano[3,2-c]pyrazole-5,4'-piperidine]-7-one (300 mg, 1.14 mmol) and stirred for 1 h at 25° C. The reaction mixture was diluted with H$_2$O (60 mL) and was extracted with EtOAc (3×20 mL). The combined organics were washed with saturated aqueous NaCl, dried (Na$_2$SO$_4$), filtered, and concentrated under reduced pressure. Purification by column chromatography (SiO$_2$, 30-100% EtOAc-hexanes) afforded 2-tert-butyl-1'-(4-isopropoxy-3-methoxy-benzoyl)spiro[6H-pyrano[3,2-c]pyrazole-5,4'-piperidine]-7-one (498 mg, 96%) as a colorless foam. ESI-MS m/z calc. 455.2, found 456.1 (M+1)$^+$; Retention time: 1.71 minutes (3 min run).

The following compound was prepared by the procedures described above:
1-(4-isopropoxy-3-methylbenzoyl)-2'-methyl-2'H-spiro[piperidine-4,5'-pyrano[3,2-c]pyrazol]-7'(6'H)-one.

Step 4: (2-tert-Butyl-7-hydroxy-spiro[6,7-dihydropyrano[3,2-c]pyrazole-5,4'-piperidine]-1'-yl)-(4-isopropoxy-3-methoxy-phenyl)methanone

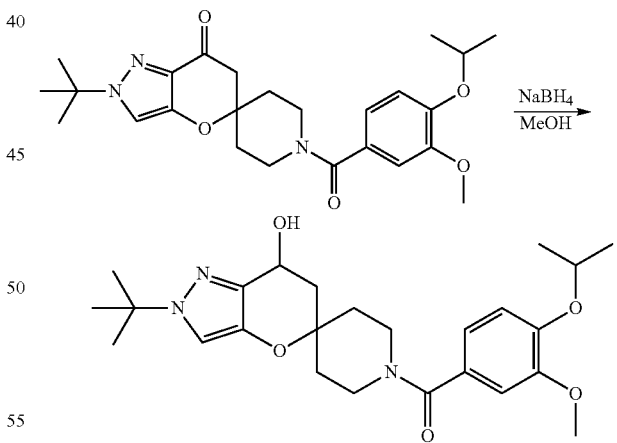

A solution of 2-tert-butyl-1'-(4-isopropoxy-3-methoxy-benzoyl)spiro[6H-pyrano[3,2-c]pyrazole-5,4'-piperidine]-7-one (518 mg, 1.14 mmol) in MeOH (6.2 mL) was treated with NaBH$_4$ (86 mg, 2.27 mmol). The reaction mixture was stirred for 1 h and was quenched by the addition of saturated aqueous NH$_4$Cl. The methanol was removed under reduced pressure and the mixture was extracted with CH$_2$Cl$_2$ (3×30 mL). The combined organics were dried (Na$_2$SO$_4$), filtered, and concentrated under reduced pressure. Purification by column chromatography (SiO$_2$, 24 g, 1-100% EtOAc-hexanes) afforded (2-tert-butyl-7-hydroxy-spiro[6,7-dihydropyrano[3,2-c]pyrazole-5,4'-piperidine]-1'-yl)-(4-isopropoxy-3-methoxy-phenyl)methanone (487 mg, 94%) ESI-MS m/z calc. 457.3, found 458.5 (M+1)+; Retention time: 1.64 minutes (3 min run).

The following compound was prepared by the procedures described above:

(7'-hydroxy-2'-methyl-6',7'-dihydro-2'H-spiro[piperidine-4,5'-pyrano[3,2-c]pyrazole]-1-yl)(4-isopropoxy-3-methylphenyl)methanone.

Step 5: (2'-(tert-Butyl)-7'-isopropoxy-6',7'-dihydro-2'H-spiro[piperidine-4,5'-pyrano[3,2-c]pyrazol]-1-yl)(4-isopropoxy-3-methoxyphenyl)methanone

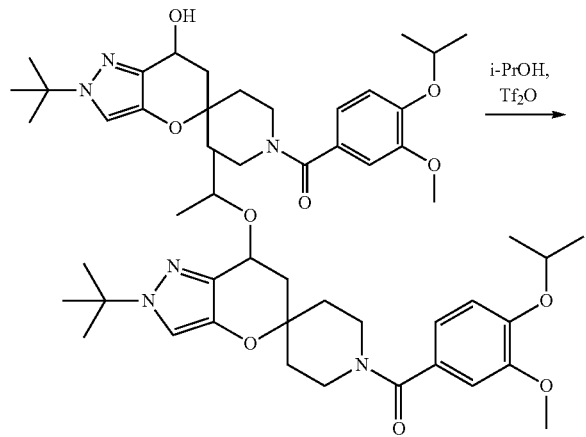

A solution of (2-tert-butyl-7-hydroxy-spiro[6,7-dihydropyrano[3,2-c]pyrazole-5,4'-piperidine]-1'-yl)-(4-isopropoxy-3-methoxy-phenyl)methanone (103 mg, 0.23 mmol) in isopropyl alcohol (0.86 mL, 11.3 mmol) was cooled to 0° C. and treated with trifluoromethanesulfonic anhydride (8 μL, 0.05 mmol). The reaction mixture was allowed to warm to 25° C. and stir for 12 h. The reaction mixture was poured into saturated aqueous NaHCO₃ and was extracted with EtOAc (3×20 mL). The combined organics were dried (Na₂SO₄), filtered, and concentrated under reduced pressure. The crude product was purified by reverse phase HPLC (1-100% ACN/H₂O, no modifier) to afford (2'-(tert-butyl)-7'-isopropoxy-6',7'-dihydro-2'H-spiro[piperidine-4,5'-pyrano[3,2-c]pyrazol]-1-yl)(4-isopropoxy-3-methoxyphenyl)methanone (40 mg, 36%) as a colorless foam. ESI-MS m/z calc. 499.3, found 500.3 (M+1)+; Retention time: 2.07 minutes (3 min run).

(7'-Isopropoxy-2'-methyl-6',7'-dihydro-2'H-spiro[piperidine-4,5'-pyrano[3,2-c]pyrazole]-1-yl)(4-isopropoxy-3-methylphenyl)methanone

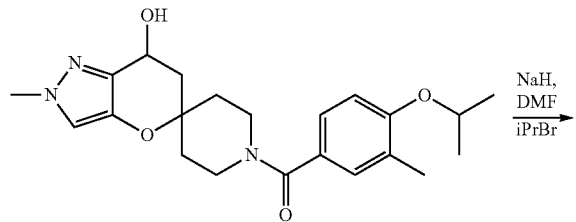

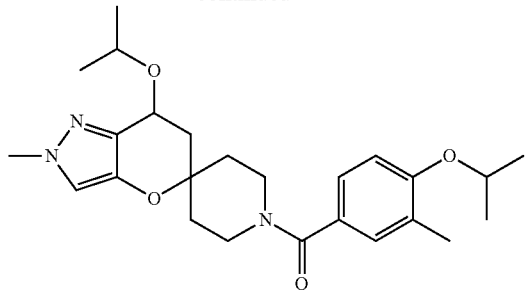

Sodium hydride (54 mg, 1.4 mmol) was added to a mixture of (7-hydroxy-2-methyl-spiro[6,7-dihydropyrano[3,2-c]pyrazole-5,4'-piperidine]-1'-yl)-(4-isopropoxy-3-methyl-phenyl)methanone (380 mg, 0.94 mmol), DMAP (11.5 mg, 0.094 mmol), and DMF (7.5 mL) at ambient temperature before 2-bromopropane (1.16 g, 884 μL, 9.4 mmol) was added. The mixture was allowed to stir for 8 h at 35° C. before the process (NaH addition, then 2-bromopropane addition) was repeated 7× over a 48 h period. The mixture was quenched with MeOH at 0° C. The mixture was partitioned between ethyl acetate and water. The layers were separated and the aqueous layer was extracted with ethyl acetate (2×). The combined organics were dried over sodium sulfate, filtered, and concentrated. The residue was purified by column chromatography (0-100% ethyl acetate/hexanes) to give (4-isopropoxy-3-methyl-phenyl)-(7-isopropoxy-2-methyl-spiro[6,7-dihydropyrano[3,2-c]pyrazole-5,4'-piperidine]-1'-yl)methanone (90 mg, 21%). ESI-MS m/z calc. 441.3, found 442.2 (M+1)+; Retention time: 1.72 minutes (3 min run). ¹H NMR (400 MHz, CDCl₃) δ 7.25-7.17 (m, 2H), 6.94 (s, 1H), 6.81 (d, J=8.3 Hz, 1H), 4.64 (t, J=4.6 Hz, 1H), 4.55 (dt, J=12.1, 6.0 Hz, 1H), 4.38 (s, 1H), 4.04 (dt, J=12.2, 6.1 Hz, 1H), 3.82 (s, 3H), 3.65 (s, 1H), 3.37 (s, 2H), 2.20 (s, 3H), 2.01 (qd, J=14.5, 4.6 Hz, 2H), 1.82 (s, 1H), 1.70 (s, 3H), 1.34 (d, J=6.0 Hz, 6H), 1.21 (t, J=7.0 Hz, 6H).

4-(1-Hydroxy-1-methyl-ethyl)-3-methyl-benzoic Acid

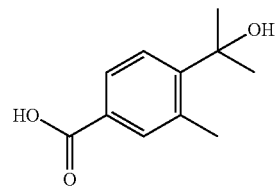

4-Bromo-3-methyl-benzoic acid (3.96 g, 18.4 mmol) was dissolved in tetrahydrofuran (100 mL) and the solution was cooled to −78° C. n-Butyllithium in hexanes (16.2 mL of 2.5 M, 41 mmol) was added dropwise over 20 minutes. The reaction mixture was allowed to stir for 30 minutes at −78° C. and then acetone (1.35 mL, 18.4 mmol) was added in a drop-wise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and then the aqueous layer was made acidic with 4M aqueous hydrochloric acid. The aqueous layer was then extracted 3 times with ethyl acetate. The combined extracts were dried over sodium sulfate and then evaporated to dryness. The crude material was further purified on silica gel utilizing a gradient of 0-10% methanol in dichloromethane to give 4-(1-hydroxy-1-methyl-ethyl)-3-methyl-benzoic acid (1.51 g, 42%). $^1$H NMR (400 MHz, DMSO) δ 12.74 (s, 1H), 7.68 (dd, J=3.9, 2.5 Hz, 2H), 7.55 (d, J=8.7 Hz, 1H), 5.06 (s, 1H), 2.56 (s, 3H), 1.51 (s, 6H).

5-Isopropoxy-6-methylpicolinic Acid

Step 1: 4,6-Dibromo-2-methylpyridin-3-ol

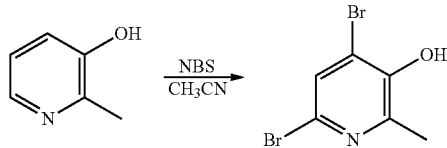

2-Methyl-3-pyridinol (8.3 g, 76.1 mmol) was suspended in acetonitrile (125 mL). A solution of NBS (27.7 g, 155.6 mmol, 2.05 equiv) in acetonitrile (275 mL) was added to the suspension drop-wise over 1 hour. The mixture was heated at reflux for 1.5 h. The mixture was concentrated and the residue was purified by column chromatography (DCM) to give 4,6-dibromo-2-methylpyridin-3-ol (15.8 g, 78%) as a yellow solid. $^1$H NMR (300 MHz, DMSO-$d_6$) 2.41 (s, 3H), 7.70 (s, 1H), 9.98 (s, 1H).

Step 2: 6-Bromo-2-methylpyridin-3-ol

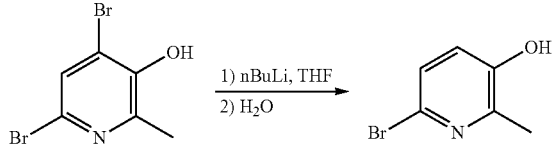

4,6-Dibromo-2-methylpyridin-3-ol (15.8 g, 59.4 mmol) was dissolved in THF (200 mL). The solution was cooled to −78° C. and n-BuLi (50 mL, 125 mmol, 2.5 M in hexane) was added drop-wise keeping the temperature at −78° C. The mixture was allowed to stir at that temperature for 2 h. The mixture was quenched with water (50 mL) and was neutralized with 2 N HCl. The aqueous mixture was extracted with dichloromethane (2×). The combined organic layers were dried (Na$_2$SO$_4$) and concentrated to give 6-bromo-2-methylpyridin-3-ol (10.5 g, 95%) as a yellow oil. $^1$H-NMR (300 MHz, DMSO-$d_6$) 2.29 (s, 3H), 7.08 (d, 1H), 7.26 (d, 1H), 10.08 (s, 1H).

Step 3: 6-Bromo-3-isopropoxy-2-methylpyridine

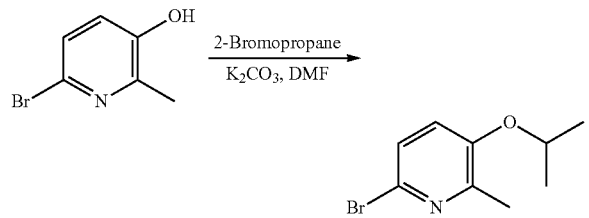

6-Bromo-2-methylpyridin-3-ol (10.5 g, 55.9 mmol) was dissolved in DMF (100 mL). K$_2$CO$_3$ (19.3 g, 139.6 mmol) and 2-bromopropane (13.1 ml, 139.6 mmol) were added to the solution and the mixture was heated at 100° C. overnight. The mixture was poured into a mixture of water and EtOAc (200 mL). The layers were separated and the aqueous layer was extracted with EtOAc (2×). The combined organic layers were dried (Na$_2$SO$_4$) and concentrated. The crude oil was purified by column chromatography (0-20% ethyl acetate/heptanes) to give 6-bromo-3-isopropoxy-2-methylpyridine (10.9 g, 85) as a yellow oil. $^1$H-NMR (300 MHz, CDCl$_3$) 1.42 (d, 6H), 2.48 (s, 3H), 4.65 (m, 1H), 7.20 (d, 1H), 8.04 (d, 1H).

Step 4: Methyl 5-isopropoxy-6-methylpicolinate

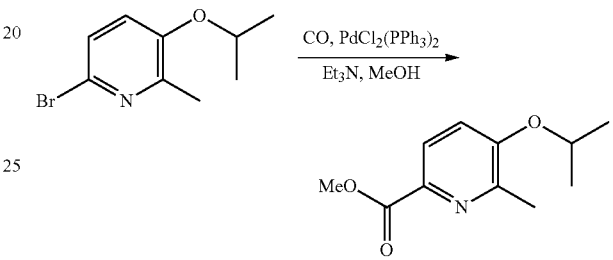

6-Bromo-3-isopropoxy-2-methylpyridine (2.00 g, 8.70 mmol), PdCl$_2$(PPh$_3$)$_2$ (0.18 g, 0.26 mmol) and Et$_3$N (1.8 ml, 13.04 mmol) were added to MeOH (5.2 mL) and acetonitrile (20 mL) in a Berghoff reactor. The reactor was charged with 10 bar CO (g) and was heated at 60° C. overnight. The mixture was concentrated and the residue was partitioned between DCM and water. The layers were separated and the organic layer was washed with brine and dried (Na$_2$SO$_4$). The mixture was concentrated and purified by column chromatography to give methyl 5-isopropoxy-6-methylpicolinate (1.3 g, 71%) as a yellow oil. $^1$H-NMR (300 MHz, CDCl$_3$) 1.40 (d, 6H), 2.53 (s, 3H), 3.98 (s, 3H), 4.62 (m, 1H), 7.12 (d, 1H), 7.98 (d, 1H).

Step 5: 5-Isopropoxy-6-methylpicolinic Acid

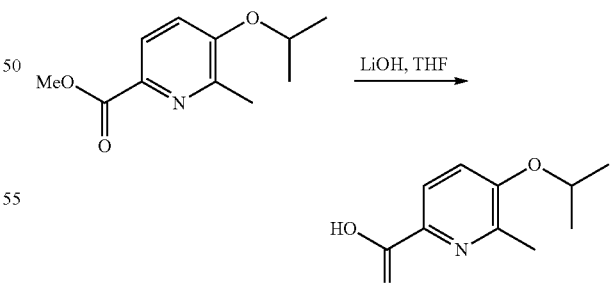

Methyl 5-isopropoxy-6-methylpicolinate (1.3 g, 6.22 mmol) was dissolved in THF/water 2:1 (9 mL). LiOH*H$_2$O (0.26 g, 6.22 mmol) was added and the mixture was stirred at room temperature overnight. The mixture was poured into a mixture of water and EtOAc and the layers were separated. The aqueous layer was acidified to pH 4 with 2 N HCl and was extracted with EtOAc (2×). The combined organics were dried (Na₂SO₄) and concentrated to give 5-isopropoxy-6-methylpicolinic acid (860 mg, 74%) as a beige solid.

4-(2-Hydroxypropan-2-yl)-3-methoxybenzoic Acid

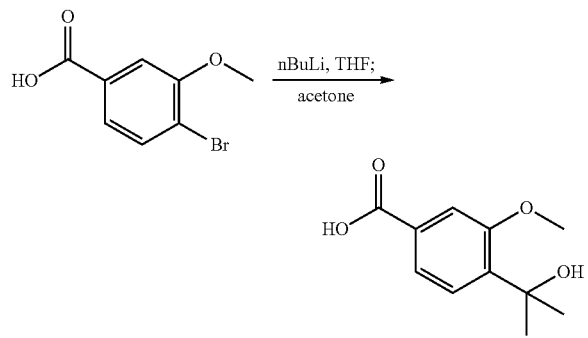

4-Bromo-3-methoxy-benzoic acid (2.00 g, 8.67 mmol) was dissolved in THF (50 mL) and the solution was cooled to −78° C. n-BuLi in hexanes (7.6 mL of 2.5 M, 19 mmol) was added dropwise over 15 minutes. The reaction mixture was allowed to stir for 30 minutes at −78° C. and then acetone (640 μL, 8.9 mmol) was added in a dropwise manner. The reaction mixture was allowed to stir for 30 minutes at −78° C., and then it was allowed to warm to room temperature. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography utilizing a gradient of 0-5% methanol in dichloromethane to give 4-(2-hydroxypropan-2-yl)-3-methoxybenzoic acid (618 mg, 34%). ESI-MS m/z calc. 210.1, found 209.1 (M−1)⁻; Retention time: 0.68 minutes (3 min run).

4-(Isopropylsulfonyl)-3-methylbenzoic Acid

Step 1: 4-(Isopropylthio)-3-methylbenzoic Acid

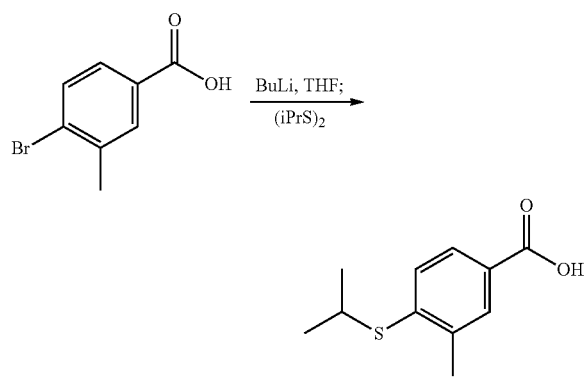

Butyllithium (16 mL of 1.6 M, 26 mmol) was added drop-wise to a mixture of 4-bromo-3-methyl-benzoic acid (2.5 g, 12 mmol) and THF (63 mL) at −78° C. The mixture was allowed to stir at −78° C. for 30 minutes before a solution of 2-isopropyldisulfanylpropane (1.7 g, 12 mmol) in THF (2 mL) was added drop-wise. The mixture was allowed to stir at −78° C. for 30 min, then 30 min at rt. The reaction mixture was then diluted with 100 mL of 1M aqueous sodium hydroxide. The organic layer was discarded and the aqueous layer was made acidic with 4M aqueous hydrochloric acid. The aqueous layer was then extracted 3 times with ethyl acetate. The combined extracts were dried over sodium sulfate and then evaporated to dryness. The crude material was purified by column chromatography using a gradient of 0-5% MeOH in dichloromethane to give 4-(isopropylthio)-3-methylbenzoic acid (870 mg, 18%). MS m/z calc. 210.3, found 211.2 (M+1)⁺. Retention time: 2.32 minutes (3 min run).

Step 2: 4-(Isopropylsulfonyl)-3-methylbenzoic Acid

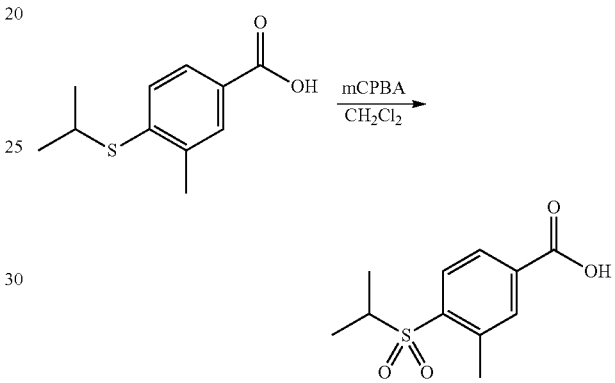

3-Chlorobenzenecarboperoxoic acid (930 mg, 4.2 mmol) was added to a mixture of 4-(isopropylthio)-3-methylbenzoic acid (250 mg, 1.2 mmol) and dichloromethane (5.0 mL) at 25° C. The mixture was allowed to stir at 25° C. for 2 h before it was concentrated in vacuo. The white solid material was taken up in dichloromethane and was subjected to column chromatography (0-2% MeOH/dichloromethane) to give 4-isopropylsulfonyl-3-methyl-benzoic acid (90 mg, 31%) as a white solid. ESI-MS m/z calc. 242.3, found 243.2 (M+1)⁺. Retention time: 1.57 minutes (3 min run). ¹H NMR (400 MHz, DMSO) δ 13.50 (s, 1H), 8.50-7.66 (m, 3H), 3.50-3.47 (m, 1H), 2.67 (s, 3H), 1.19 (d, J=1.16 Hz, 6H).

4-(tert-Butylsulfonyl)benzoic Acid

Step 1: 4-(tert-Butylthio)benzoic Acid

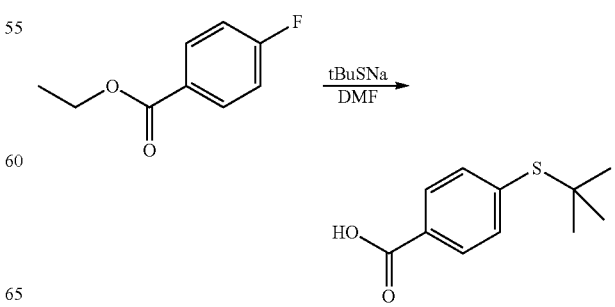

Ethyl 4-fluorobenzoate (1.5 g, 8.9 mmol) and tert-butylsulfanylsodium (2.00 g, 17.8 mmol) were combined in N,N-dimethylformamide (10 mL). The reaction mixture was heated at 80° C. for 2 hours. A large amount of precipitate formed and an additional 15 mL of N,N-dimethylformamide was added and the reaction mixture was stirred for an additional 20 hours at 80° C. The reaction mixture was partitioned between ethyl acetate (100 mL) and water (100 mL). The organic layer was discarded, and the water layer was made acidic with 4M hydrochloric acid. The water layer was extracted two times with ethyl acetate. The combined extracts were dried over sodium sulfate, filtered, and evaporated to dryness to yield 4-(tert-butylthio)benzoic acid as a colorless oil. ESI-MS m/z calc. 210.3, found 211.1 (M+1)+. Retention time: 1.74 minutes (3 min run).

Step 2: 4-(tert-Butylsulfonyl)benzoic Acid

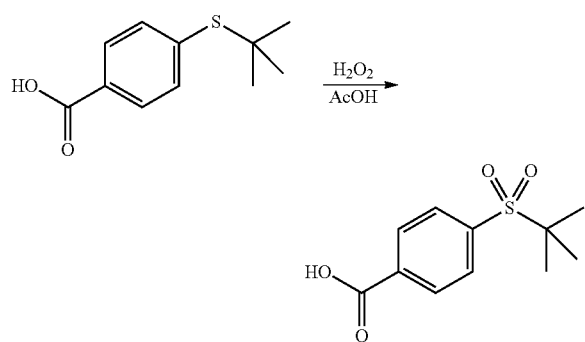

4-(tert-Butylthio)benzoic acid (from Step 1) was dissolved in AcOH (10 mL) and hydrogen peroxide (5.0 mL of 30% w/w, 52 mmol) was added to the reaction mixture. The resulting mixture was heated at 80° C. for 2 hours. The reaction mixture was then allowed to cool to room temperature, and was diluted with 50 mL of water and 100 mL of ethyl acetate. The layers were separated and the aqueous layer was extracted with ethyl acetate. The combined ethyl acetate extracts were dried over sodium sulfate, filtered, and evaporated to dryness to yield a white solid. The white solid was then dissolved in dichloromethane and was evaporated to dryness. The solid was then dried under vacuum for 16 hours to give 4-tert-butylsulfonylbenzoic acid (2.2 g, 92%) as a white solid. ESI-MS m/z calc. 242.1, found 243.1 (M+1)+. Retention time: 1.15 minutes (3 min run). $^1$H NMR (400 MHz, DMSO) δ 8.18 (d, J=8.0 Hz, 2H), 7.94 (d, J=7.6 Hz, 2H), 1.25 (s, 9H).

4-(Ethylsulfonyl)benzoic acid and 4-(2-propylsulfonyl) benzoic acid were also synthesized using the procedures described above.

3-Formyl-4-isopropoxybenzoic Acid

Step 1: Methyl 3-formyl-4-isopropoxybenzoate

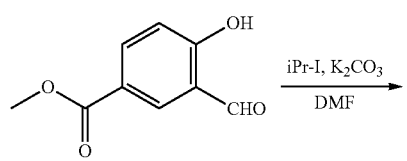

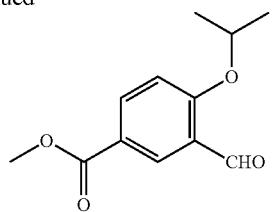

To methyl 3-formyl-4-hydroxy-benzoate (10.0 g, 55.5 mmol), potassium carbonate (30.7 g, 222 mmol) and N,N-dimethylformamide (63 mL) was added 2-iodopropane (11.1 mL, 111 mmol). The mixture was heated at 60° C. for 18 hours. The mixture was filtered using ethyl acetate (200 mL) and the solvent was evaporated under reduced pressure. The residue was dissolved in ethyl acetate (150 mL) and was washed with water (3×75 mL) and a saturated aqueous solution of sodium chloride (1×75 mL). The organic layer was dried over sodium sulfate, filtered and the solvent was evaporated under reduced pressure to yield methyl 3-formyl-4-isopropoxy-benzoate (98%) as a yellow viscous liquid. ESI-MS m/z calc. 222.2, found 223.3 (M+1)+; Retention time: 1.51 minutes (3 min run). $^1$H NMR (400 MHz, DMSO) δ 10.35 (s, 1H), 8.23 (d, J=2.3 Hz, 1H), 8.17 (dd, J=8.8, 2.3 Hz, 1H), 7.39 (d, J=8.9 Hz, 1H), 4.98-4.83 (m, 1H), 3.85 (s, 3H), 1.38 (d, J=6.0 Hz, 6H).

Step 2: 3-Formyl-4-isopropoxybenzoic Acid

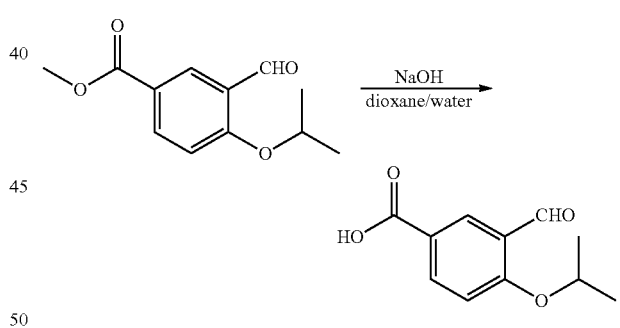

To a solution of the ester (from previous step) in dioxane (4 mL) was added 2 mL of sodium hydroxide solution (5N). The reaction mixture was heated at 65° C. for 4 hours. The reaction mixture was cooled to room temperature and was diluted with 20 mL of water. The water layer was extracted with 20 mL portion of ethyl acetate (2×). The organic extracts were discarded and the aqueous layer was made acidic with 1M HCl. The resulting product was then extracted into ethyl acetate, dried over MgSO₄, filtered, and evaporated to dryness to yield 3-formyl-4-isopropoxy-benzoic acid (320 mg, 55% over 2 steps) as a white solid. $^1$H NMR (400 MHz, DMSO) δ 10.36 (s, 1H), 8.23 (d, J=2.5 Hz, 1H), 8.15 (dd, J=2.5, 8.9 Hz, 1H), 7.37 (d, J=8.9 Hz, 1H), 4.96-4.87 (m, 1H), 1.37 (d, J=5.6 Hz, 6H).

3-(Hydroxymethyl)-4-isopropoxy-benzoic Acid

Step 1: Methyl 3-formyl-4-isopropoxy-benzoate

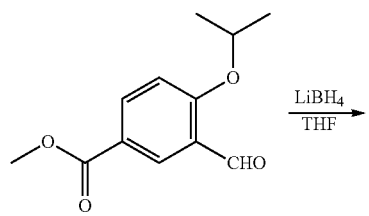

Methyl 3-formyl-4-isopropoxy-benzoate (180 mg, 0.81 mmol) was dissolved in tetrahydrofuran (4.8 mL) and LiBH$_4$ (35 mg, 1.6 mmol) was added. The reaction was stirred at room temperature for 30 minutes before it was quenched with methanol (3 mL). The reaction was neutralized by the addition of a saturated aqueous solution of sodium bicarbonate (3 mL) and was then extracted with ethyl acetate (3×10 mL). The combined organics were washed with a saturated aqueous solution of sodium chloride (1×10 mL), dried over sodium sulfate, filtered and the solvent was evaporated under reduced pressure to yield methyl 3-(hydroxymethyl)-4-isopropoxy-benzoate (99%) as a viscous liquid. ESI-MS m/z calc. 224.3, found 225.3 (M+1)$^+$; Retention time: 1.26 minutes (3 min run). $^1$H NMR (400 MHz, DMSO) δ 8.09 (s, 1H), 7.89 (d, J=8.6 Hz, 1H), 7.13 (d, J=8.6 Hz, 1H), 5.25 (t, J=5.6 Hz, 1H), 4.86-4.68 (m, 1H), 4.54 (d, J=5.6 Hz, 2H), 3.87 (s, 3H), 1.35 (d, J=6.0 Hz, 6H).

Step 2: 3-(Hydroxymethyl)-4-isopropoxy-benzoic Acid

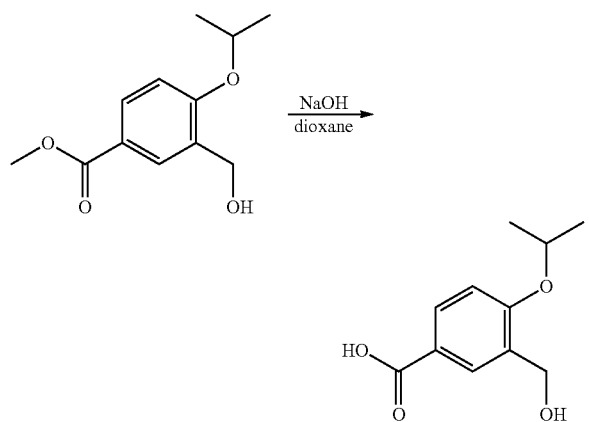

To methyl 3-(hydroxymethyl)-4-isopropoxy-benzoate (180 mg, 0.80 mmol) and 1,4-dioxane (1.895 mL) was added sodium hydroxide (2.1 mL of 1.0 M, 2.1 mmol) and the mixture was heated at 80° C. for 50 minutes. The solvent was evaporated under reduced pressure. The crude mixture was dissolved in water (10 mL) and was washed with ethyl acetate (3×10 mL) which was discarded. The aqueous layer was acidified with hydrochloric acid. The aqueous layer was extracted with ethyl acetate (3×10 mL). The combined organics were dried over sodium sulfate, filtered and the solvent was evaporated under reduced pressure to yield 3-(hydroxymethyl)-4-isopropoxy-benzoic acid (89%) as a white solid. ESI-MS m/z calc. 210.2, found 211.3 (M+1)$^+$; Retention time: 1.01 minutes (3 min run).

3-Methyl-4-methylsulfonyl-benzoic Acid

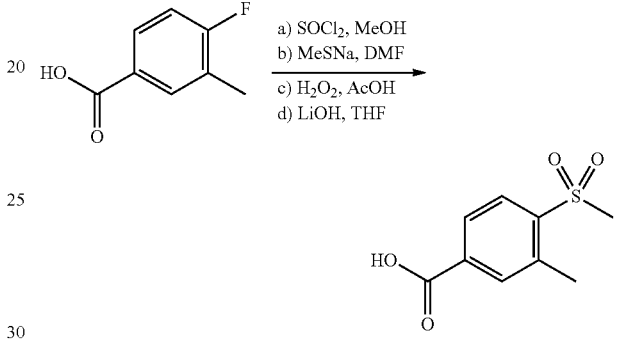

Thionyl chloride (3.55 mL, 48.7 mmol) was added dropwise to a solution of 4-fluoro-3-methyl-benzoic acid (2.50 g, 16.2 mmol) in methanol (102 mL) at 0° C. The mixture was stirred at 50° C. for 2 hours. The reaction mixture was evaporated to dryness and the crude ester was then dissolved in N,N-dimethylformamide (10 mL). Sodium thiomethoxide (2.50 g, 35.7 mmol) was added and the reaction mixture was heated at 80° C. for 15 hours. The reaction mixture was then partitioned between 1M hydrochloric acid and ethyl acetate. The layers were separated and the organic layer was washed with 1M hydrochloric acid. The ethyl acetate layer was then dried over sodium sulfate, filtered, and evaporated to dryness. The resultant acid and ester mixture was suspended in acetic acid (20 mL). Hydrogen peroxide (5.0 mL of 30% w/w) was added and the reaction mixture was heated at 80° C. for 2 hours. The reaction mixture was diluted with water (20 mL) and the resulting mixture was extracted three times with 50 mL portions of ethyl acetate. The combined organics were evaporated to dryness and the residue was dissolved in tetrahydrofuran (10 mL). Water (10 mL) and lithium hydroxide (1.17 g, 48.7 mmol) were then added and the reaction mixture was heated at 65° C. for 4 hours. The reaction mixture was diluted with water (20 mL) and the resulting mixture was extracted three times with 20 mL portions of ethyl acetate. The aqueous layer was then made acidic with aqueous 6M hydrochloric acid and was extracted 3 times with 50 mL portions of ethyl acetate. The combined ethyl acetate extracts were dried over sodium sulfate, filtered, and evaporated to dryness to yield 3-methyl-4-methylsulfonyl-benzoic acid (2.25 g, 72%) as a white solid. ESI-MS m/z calc. 214.0, found 215.0 (M+1)$^+$; Retention time: 0.97 minutes (3 min run). $^1$H NMR (400 MHz, DMSO) δ 13.48 (s, 1H), 8.07-7.94 (m, 3H), 3.27 (s, 3H), 2.70 (s, 3H).

2-(Difluoromethoxy)-4-isopropoxy-benzoic Acid

Step 1: Isopropyl 2-hydroxy-4-isopropoxy-benzoate

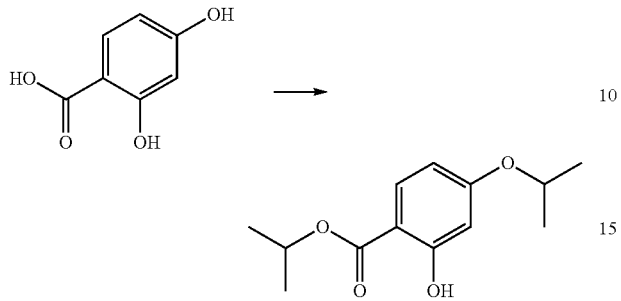

To a solution of 2,4-dihydroxybenzoic acid (5.0 g, 32.4 mmol) in DMF (50 mL) was added 2-bromopropane (7.98 g, 6.1 mL, 64.9 mmol) followed by finely ground potassium carbonate (8.97 g, 64.9 mmol). Substantial bubbling was observed. The reaction mixture was allowed to stir at 60° C. overnight. The reaction mixture was concentrated under reduced pressure to a brown solid. It was taken up in a mixture of EtOAc (75 mL) and water (75 mL). Layers were mixed well, and the organic layer was washed with saturated sodium bicarbonate (1×75 mL) and brine (1×75 mL). The organic layer was dried over sodium sulfate, filtered and concentrated under reduced pressure to provide 4.73 grams of brown oil. It was purified by silica gel column chromatography: 80 gram silica gel column, 0-20% EtOAc/hexane gradient over 25 minutes. Pure fractions were combined and concentrated to provide isopropyl 2-hydroxy-4-isopropoxy-benzoate (3.1 g, 40%) as a clear colorless oil. $^1$H NMR (400 MHz, CDCl$_3$) δ 11.12 (s, 1H), 7.72 (d, J=8.8 Hz, 1H), 6.44-6.36 (m, 2H), 5.26 (dq, J=12.5, 6.2 Hz, 1H), 4.58 (dt, J=12.1, 6.1 Hz, 1H), 1.36 (dd, J=7.7, 6.2 Hz, 12H). ESI-MS m/z calc. 238.12051, found 239.2 (M+1)$^+$; Retention time: 2.05 minutes.

Step 2: Isopropyl 2-(difluoromethoxy)-4-isopropoxy-benzoate

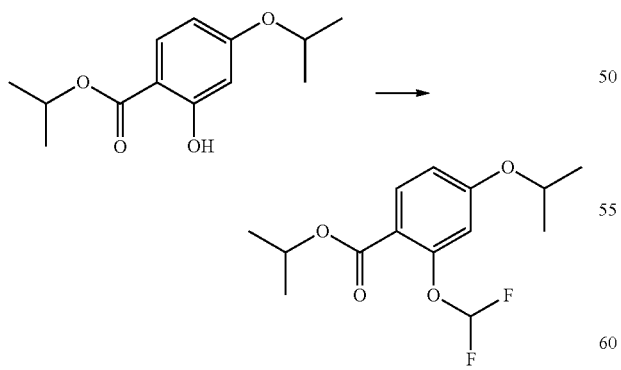

To a solution of sodium 2-chloro-2,2-difluoro-acetate (2.4 g, 15.7 mmol) in water (2.25 mL) and DMF (7.5 mL) was added isopropyl 2-hydroxy-4-isopropoxy-benzoate (1.5 g, 6.29 mmol). The reaction mixture was allowed to stir at 100° C. for 2 days. The reaction mixture was diluted with EtOAc (75 mL) and washed with water (1×75 mL) and brine (1×75 mL). The organic layer was dried over sodium sulfate, filtered and concentrated under reduced pressure. The resulting oil was purified by silica gel column chromatography: 24 gram silica gel column, 0-5% EtOAc/hexanes gradient over 15 minutes; product eluted at 5%. Pure fractions were combined and concentrated to provide isopropyl 2-(difluoromethoxy)-4-isopropoxy-benzoate (148 mg, 8%) as a clear colorless oil. ESI-MS m/z calc. 288.1173, found 289.1 (M+1)$^+$; Retention time: 1.84 minutes.

Step 3: 2-(difluoromethoxy)-4-isopropoxy-benzoic Acid

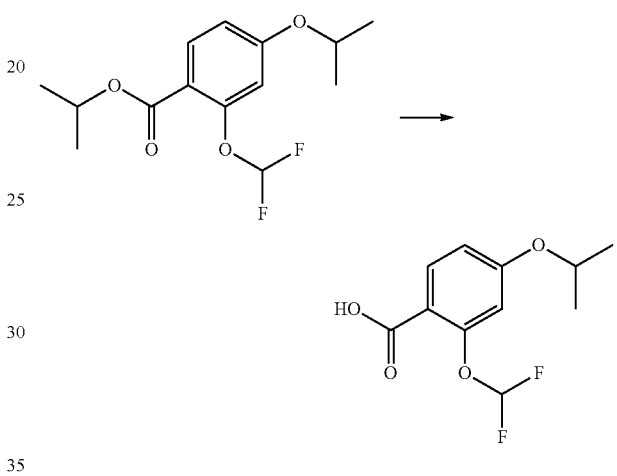

To a solution of isopropyl 2-(difluoromethoxy)-4-isopropoxy-benzoate (148 mg, 0.51 mmol) in methanol (2.5 mL) was added an aqueous solution of sodium hydroxide (2.6 mL of 1 M, 2.6 mmol). The reaction mixture was allowed to stir at 70° C. for 2 hours. The mixture was then diluted with EtOAc (75 mL) and washed with 1 N HCl (2×75 mL). The organic layer was dried over sodium sulfate, filtered and concentrated under reduced pressure. The obtained clear oil was purified by UV-triggered HPLC: 1-99% ACN/water gradient with no modifier to afford 2-(difluoromethoxy)-4-isopropoxy-benzoic acid (26 mg, 21%) as a white solid. $^1$H NMR (400 MHz, CDCl$_3$) δ 8.03 (d, J=8.8 Hz, 1H), 6.93-6.72 (m, 2H), 6.51 (d, J=74.5 Hz, 1H), 4.64 (dd, J=12.0, 6.0 Hz, 1H), 1.38 (d, J=6.1 Hz, 6H). ESI-MS m/z calc. 246.1, found 247.5 (M+1)$^+$; Retention time: 1.3 minutes.

5-(Cyclobutylmethylsulfonyl)pyridine-2-carboxylic Acid

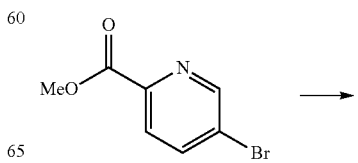

-continued

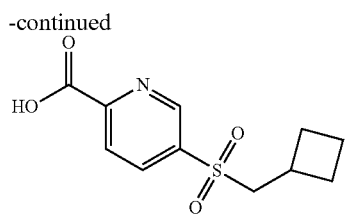

To a 100 mL round bottom flask was added methyl 5-bromopyridine-2-carboxylate (0.5 g, 2.3 mmol) followed by DMF (5 mL) and sodium sulfanide (259 mg, 4.6 mmol). The reaction was heated at 65° C. overnight and was found to contain the product by lcms. Bromomethylcyclobutane (260 µL, 2.3 mmol) was added and the reaction was allowed to stir for 30 minutes while cooling to rt. The reaction showed the thioether product by lcms. The reaction was then quenched with brine and extracted with EtOAc 3 times. The organic layers were combined and dried over sodium sulfate and the solvent was evaporated. The crude reaction mixture was then treated with 50 mL of Clorox® bleach and allowed to stir for 30 minutes. LiOH (5 mL of 3M) was added and the reaction was allowed to stir for 1 h. The reaction was extracted with ethyl acetate and the organic layer was discarded. The aqueous layer was acidified to pH 2 and extracted with ethyl acetate 3 times. The organic layers were combined and dried over sodium sulfate. The crude product was purified via HPLC (1-99%) ACN:$H_2O$ with a 0.1% TFA modifier. 5-(cyclobutylmethylsulfonyl)pyridine-2-carboxylic acid (39 mg) was isolated as a white solid. $^1$H NMR (400 MHz, MeOD) δ 9.11 (dd, J=2.2, 0.8 Hz, 1H), 8.47 (dd, J=8.2, 2.2 Hz, 1H), 8.35 (dd, J=8.2, 0.8 Hz, 1H), 3.47 (d, J=7.3 Hz, 2H), 2.80-2.66 (m, 1H), 2.11-2.00 (m, 2H), 1.97-1.75 (m, 4H).

The following compound was prepared following the procedure described above:
5-(cyclopropylmethylsulfonyl)pyridine-2-carboxylic acid.

5-Isopropylsulfonylpyridine-2-carboxylic Acid

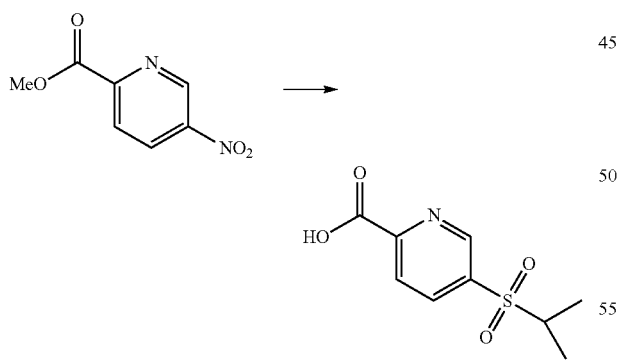

To a 250 mL round bottom flask was added methyl 5-nitropyridine-2-carboxylate (2.37 g, 13.0 mmol) and DMF (20 mL) followed by isopropylsulfanylsodium (3.2 g, 32.5 mmol) and the reaction was heated overnight at 55° C. The reaction was found to be complete by lcms. The reaction was removed from the oil bath and quenched with brine. Ethyl acetate was added and the reaction mixture was extracted and the aqueous layer was kept. The aqueous layer was then treated with bleach (100 mL) and the reaction was allowed to stir for 10 minutes. 1N HCl was then added until the solution was pH 1. The reaction was then extracted with EtOAc and the organic layer was further washed with brine 3 times. The organic layer was then dried over sodium sulfate and the solvent was removed. 5-Isopropylsulfonylpyridine-2-carboxylic acid (1.53 g, 51%) was isolated as a white solid. $^1$H NMR (400 MHz, CDCl$_3$) δ 9.14 (s, 1H), 8.46 (s, 2H), 3.31 (dt, J=13.7, 6.8 Hz, 1H), 1.36 (t, J=19.0 Hz, 6H). ESI-MS m/z calc. 229.0, found 230.2 (M+1)$^+$; Retention time: 0.87 minutes (3 min run).

3-Cyano-4-isopropylsulfonyl-benzoic Acid

Step 1: Methyl 3-cyano-4-fluoro-benzoate

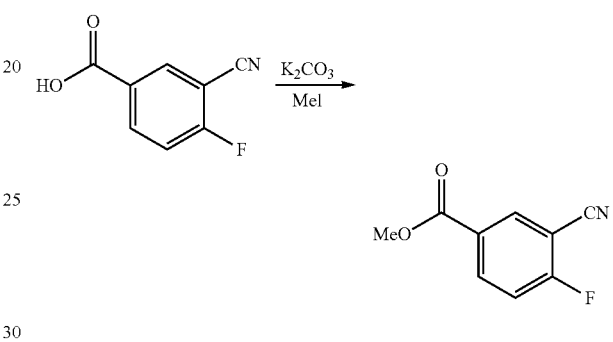

To a 100 mL round bottom flask was added 3-cyano-4-fluoro-benzoic acid (2.6 g, 15.9 mmol), potassium carbonate (6.6 g, 47.6 mmol), and DMF (30 mL) and the reaction was allowed to stir for 10 minutes. Iodomethane (1.1 mL, 17.5 mmol) was added dropwise and the reaction was allowed to stir for 1 h. The reaction was complete by lcms. The reaction was quenched with brine and extracted with ethyl acetate. The organic layer was washed with brine 3 times and the organic layer was dried over sodium sulfate and evaporated. Methyl 3-cyano-4-fluoro-benzoate (2.5 g, 62%) was isolated as a white solid. ESI-MS m/z calc. 179.0, found 180.0 (M+1)$^+$; Retention time: 1.15 minutes (3 min run).

Step 2: 3-Cyano-4-isopropylsulfonyl-benzoic Acid

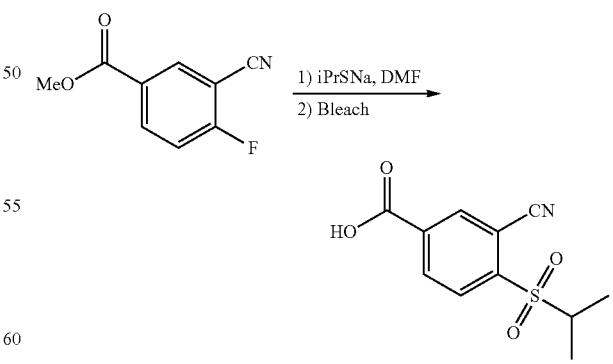

To a 100 mL round bottom flask was added methyl 3-cyano-4-fluoro-benzoate (2.5 g, 14.0 mmol) followed by DMF (20 mL). Isopropylsulfanylsodium (3.8 g, 39.7 mmol) was added and the reaction was placed in a preheated 65° C. oil bath and allowed to stir overnight. The reaction was quenched with brine and extracted 3 times with EtOAc. The aqueous layer was then treated with bleach (100 mL) and the reaction was allowed to stir for 10 minutes. 1N HCl was then added until pH 1. The reaction was then extracted with EtOAc and the organic layer was further washed with brine 3 times. The organic layer was then dried over sodium sulfate and the solvent was removed. 3-Cyano-4-isopropyl-sulfonyl-benzoic acid (2.24 g) was isolated as a white solid. $^{1}$H NMR (400 MHz, CDCl$_3$) δ 8.59 (d, J=1.4 Hz, 1H), 8.47 (dd, J=8.2, 1.7 Hz, 1H), 8.28 (d, J=8.2 Hz, 1H), 3.64 (s, 1H), 1.39 (d, J=6.8 Hz, 6H).

Table 2 below recites the analytical data for the compounds of Table 1.

TABLE 2

| Cmpd. No. | LC/MS M + 1 | LC/RT Min | NMR |
|---|---|---|---|
| 1 | 470.11 | 2.73 | |
| 2 | 468.60 | 2.14 | |
| 3 | 514.40 | 1.92 | |
| 4 | 508.40 | 5.72 | 1H NMR (400 MHz, CDCl3) δ 8.08-8.00 (m, 1H), 7.38 (d, J = 6.4 Hz, 2H), 6.84 (d, J = 8.6 Hz, 1H), 6.78 (ddd, J = 11.0, 8.4, 2.9 Hz, 1H), 4.51 (d, J = 8.2 Hz, 2H), 3.84 (dt, J = 12.2, 6.1 Hz, 1H), 3.67-3.38 (m, 2H), 3.30 (dd, J = 32.6, 13.1 Hz, 1H), 3.16 (q, J = 7.4 Hz, 2H), 2.72 (s, 3H), 2.31-1.49 (m, 7H), 1.36-1.25 (m, 6H), 1.23 (s, 3H). |
| 5 | 490.20 | 1.92 | |
| 6 | 454.50 | 1.88 | |
| 7 | 516.20 | 2.16 | 1H NMR (400 MHz, MeOD) δ 8.19 (d, J = 8.2 Hz, 2H), 7.83 (d, J = 8.5 Hz, 2H), 7.02 (dd, J = 9.0, 2.9 Hz, 1H), 6.92 (td, J = 8.5, 3.2 Hz, 1H), 6.84 (dd, J = 9.0, 4.8 Hz, 1H), 4.67-4.55 (m, 1H), 4.43 (s, 1H), 3.94 (dt, J = 12.3, 6.1 Hz, 1H), 3.61-3.45 (m, 1H), 3.36 (t, J = 10.6 Hz, 2H), 2.19-2.12 (m, 1H), 2.05-1.67 (m, 5H), 1.28 (d, J = 6.0 Hz, 3H), 1.22 (s, 3H). |
| 8 | 471.20 | 1.60 | |
| 9 | 490.20 | 5.62 | 1H NMR (400 MHz, MeOD) δ 8.03 (d, J = 8.1 Hz, 1H), 7.48 (d, J = 7.1 Hz, 2H), 7.02 (d, J = 9.1 Hz, 1H), 6.91 (d, J = 8.4 Hz, 1H), 6.84 (dd, J = 9.0, 4.8 Hz, 1H), 4.62 (s, 1H), 4.48-4.33 (m, 1H), 3.98-3.89 (m, 1H), 3.49 (dd, J = 9.6, 8.0 Hz, 2H), 3.25 (d, J = 7.3 Hz, 2H), 3.16-3.09 (m, 1H), 2.71 (s, 3H), 2.14 (s, 2H), 1.94 (s, 2H), 1.82-1.71 (m, 2H), 1.28 (d, J = 6.0 Hz, 3H), 1.22 (t, J = 7.4 Hz, 6H). |
| 10 | 472.20 | 1.93 | |
| 11 | 504.20 | 5.71 | 1H NMR (400 MHz, MeOD) δ 7.80 (d, J = 10.9 Hz, 2H), 7.59-7.42 (m, 1H), 7.02 (dt, J = 9.2, 2.7 Hz, 1H), 6.95-6.87 (m, 1H), 6.84 (dd, J = 8.9, 4.7 Hz, 1H), 4.60 (dt, J = 12.2, 6.4 Hz, 1H), 4.47 (s, 1H), 3.94 (dt, J = 12.1, 6.1 Hz, 1H), 3.54-3.36 (m, 2H), 3.22 (s, 1H), 2.38 (s, 3H), 2.16 (ddd, J = 14.0, 8.4, 5.7 Hz, 2H), 2.03-1.88 (m, 2H), 1.88-1.55 (m, 3H), 1.26 (t, J = 7.5 Hz, 12H). |
| 12 | 440.50 | 1.92 | |
| 13 | 504.20 | 5.90 | 1H NMR (400 MHz, MeOD) δ 8.00 (d, J = 7.9 Hz, 1H), 7.49 (s, 2H), 7.02 (dd, J = 9.0, 2.7 Hz, 1H), 6.91 (td, J = 8.6, 3.0 Hz, 1H), 6.87-6.80 (m, 1H), 4.61 (d, J = 12.0 Hz, 1H), 4.43 (s, 1H), 3.94 (dt, J = 12.2, 6.1 Hz, 1H), 3.46 (ddd, J = 20.4, 14.8, 10.6 Hz, 3H), 2.71 (s, 3H), 2.13 (t, J = 17.4 Hz, 2H), 2.02-1.88 (m, 2H), 1.75 (d, J = 12.5 Hz, 3H), 1.29-1.20 (m, 12H). |
| 14 | 417.13 | 2.88 | |
| 15 | 485.60 | 1.64 | |
| 16 | 456.60 | 1.65 | |
| 17 | 547.10 | 2.97 | |
| 18 | 444.10 | 2.83 | H NMR (400.0 MHz, CDCl3) δ 7.27-7.16 (m, 2H), 7.12-7.04 (m, 4H), 6.94-6.92 (m, 2H), 6.81 (dd, J = 8.3, 19.2 Hz, 2H), 6.70 (dd, J = 7.6, 14.3 Hz, 2H), 4.42-4.30 (m, 1H), 4.05 (q, J = 7.1 Hz, 1H), 3.83 (s, 3H), 3.65-3.54 (m, 2H), 2.00-1.96 (m, 2H), 1.80 (dd, J = 6.8, 13.9 Hz, 1H), 1.70-1.52 (m, 2H), 1.24-1.14 (m, 2H). |
| 19 | 505.10 | 2.04 | |
| 20 | 410.29 | 2.07 | |
| 21 | 452.20 | 2.04 | |

TABLE 2-continued

| Cmpd. No. | LC/MS M + 1 | LC/RT Min | NMR |
|---|---|---|---|
| 22 | 515.40 | 5.87 | 1H NMR (400 MHz, MeOD) δ 8.21 (d, J = 8.1 Hz, 1H), 8.15 (d, J = 1.3 Hz, 1H), 7.96 (dd, J = 8.1, 1.6 Hz, 1H), 7.02 (dd, J = 9.1, 3.0 Hz, 1H), 6.92 (td, J = 8.5, 3.1 Hz, 1H), 6.85 (d, J = 4.8 Hz, 1H), 4.68-4.54 (m, 1H), 4.42 (s, 1H), 3.94 (s, 1H), 3.68-3.57 (m, 1H), 3.57-3.46 (m, 1H), 3.37 (dd, J = 23.2, 11.4 Hz, 2H), 2.24-2.05 (m, 2H), 2.04-1.89 (m, 2H), 1.81 (d, J = 22.5 Hz, 2H), 1.33 (d, J = 6.8 Hz, 6H), 1.28 (d, J = 6.0 Hz, 3H), 1.22 (t, J = 6.6 Hz, 3H). |
| 23 | 490.50 | 2.13 | |
| 24 | 488.50 | 4.40 | 1H NMR (400 MHz, DMSO) δ 7.83 (d, J = 7.8 Hz, 1H), 7.77-7.66 (m, 1H), 7.66-7.50 (m, 2H), 7.06-6.88 (m, 3H), 4.79-4.69 (m, 1H), 4.68-4.51 (m, 1H), 4.34-3.59 (m, 7H), 3.54-3.35 (m, 2H), 2.83-2.70 (m, 1H), 2.57-2.51 (m, 1H), 2.07-1.71 (m, 4H), 1.26 (d, J = 6.0 Hz, 6H), 1.20 (t, J = 13.1, 6.2 Hz, 3H). |
| 25 | 472.20 | 2.05 | 1H NMR (400 MHz, CDCl3) δ 7.31-7.25 (m, 1H), 7.00 (d, J = 1.9 Hz, 1H), 6.96 (dd, J = 8.2, 1.9 Hz, 1H), 6.88 (d, J = 8.3 Hz, 1H), 6.65 (td, J = 8.4, 2.6 Hz, 1H), 6.57 (dd, J = 10.2, 2.5 Hz, 1H), 4.57 (dt, J = 12.2, 6.1 Hz, 1H), 4.50 (t, J = 5.6 Hz, 1H), 3.92-3.78 (m, 4H), 3.40 (s, 2H), 2.26-2.06 (m, 1H), 2.06-1.92 (m, 2H), 1.92-1.73 (m, 2H), 1.67 (s, 2H), 1.39 (dd, J = 11.7, 6.1 Hz, 6H), 1.26 (t, J = 7.3 Hz, 4H), 1.21 (d, J = 6.2 Hz, 3H). |
| 26 | 438.40 | 1.89 | |
| 27 | 522.40 | 6.06 | 1H NMR (400 MHz, CDCl3) δ 8.02 (d, J = 8.5 Hz, 1H), 7.37 (d, J = 7.5 Hz, 2H), 6.84 (d, J = 8.6 Hz, 1H), 6.78 (ddd, J = 11.0, 8.4, 3.0 Hz, 1H), 4.52 (s, 2H), 3.84 (dt, J = 12.2, 6.2 Hz, 1H), 3.63-3.21 (m, 4H), 2.71 (s, 3H), 2.24 (s, 1H), 2.16-1.92 (m, 3H), 1.76 (d, J = 18.5 Hz, 2H), 1.54 (s, 4H), 1.31 (d, J = 6.8 Hz, 6H), 1.28 (d, J = 6.0 Hz, 3H), 1.23 (s, 3H). |
| 28 | 406.21 | 1.59 | |
| 29 | 515.40 | 5.83 | 1H NMR (400 MHz, MeOD) δ 8.21 (d, J = 8.1 Hz, 1H), 8.16 (d, J = 1.4 Hz, 1H), 7.97 (s, 1H), 7.02 (dd, J = 9.1, 3.0 Hz, 1H), 6.92 (td, J = 8.5, 3.1 Hz, 1H), 6.85 (d, J = 4.8 Hz, 1H), 4.68-4.54 (m, 1H), 4.41 (s, 1H), 3.93 (dq, J = 12.2, 6.1 Hz, 1H), 3.62 (s, 1H), 3.57-3.33 (m, 3H), 2.19-2.11 (m, 1H), 2.04-1.89 (m, 2H), 1.81 (d, J = 22.7 Hz, 3H), 1.33 (d, J = 6.8 Hz, 6H), 1.28 (d, J = 6.0 Hz, 3H), 1.22 (s, 3H). |
| 30 | 503.20 | 1.85 | |
| 31 | 442.40 | 1.83 | |
| 32 | 476.20 | 1.79 | |
| 33 | 476.40 | 5.18 | |
| 34 | 500.30 | 2.07 | |
| 35 | 438.40 | 1.88 | |
| 36 | 396.29 | 1.83 | |
| 37 | 439.40 | 1.41 | 1H NMR (400 MHz, CDCl3) δ 8.18 (s, 1H), 8.10 (d, J = 4.7 Hz, 1H), 7.17 (dd, J = 13.9, 6.0 Hz, 3H), 6.75 (d, J = 8.1 Hz, 1H), 4.58-4.38 (m, 2H), 3.80 (dt, J = 12.2, 6.1 Hz, 1H), 3.39 (d, J = 44.0 Hz, 2H), 2.14 (s, 3H), 2.10-1.83 (m, 4H), 1.68 (s, 6H), 1.30 (t, J = 12.9 Hz, 7H), 1.22 (d, J = 6.0 Hz, 3H), 1.17 (d, J = 6.1 Hz, 4H). |
| 38 | 511.70 | 1.43 | |
| 39 | 414.50 | 1.71 | |
| 40 | 380.40 | 3.10 | |
| 41 | 498.14 | 2.98 | |
| 42 | 454.80 | 1.92 | |
| 43 | 463.50 | 1.90 | |
| 44 | 454.50 | 2.08 | 1H NMR (400 MHz, DMSO) δ 7.05-6.83 (m, 7H), 5.81 (s, 1H), 5.13 (s, 2H), 4.59 (hept, J = 6.0 Hz, 1H), 4.45-4.06 (m, 1H), 3.77 (s, 3H), 3.53-3.04 (m, 6H), 1.94-1.76 (m, 4H), 1.26 (d, J = 6.0 Hz, 6H). |
| 45 | 439.50 | 4.01 | 1H NMR (400 MHz, DMSO) δ 8.14-8.03 (m, 1H), 7.70 (d, J = 6.8 Hz, 1H), 7.27-7.18 (m, 2H), 7.07-6.90 (m, 2H), 4.71-4.56 (m, 2H), 4.35-3.18 (m, 5H), 2.26-2.15 (m, 1H), 2.14 (s, 3H), 1.99-1.65 (m, 5H), 1.29 (d, J = 6.0 Hz, 6H), 1.22 (d, J = 6.0 Hz, 3H), 1.15 (d, J = 6.1 Hz, 3H). |
| 46 | 442.40 | 1.57 | |
| 47 | 453.50 | 1.23 | |

TABLE 2-continued

| Cmpd. No. | LC/MS M + 1 | LC/RT Min | NMR |
|---|---|---|---|
| 48 | 460.40 | 1.88 | 1H NMR (400 MHz, MeOD) δ 7.72 (t, J = 8.1 Hz, 1H), 7.22 (dd, J = 8.0, 1.6 Hz, 1H), 7.14 (dd, J = 11.9, 1.5 Hz, 1H), 7.02 (dd, J = 9.1, 3.0 Hz, 1H), 6.91 (td, J = 8.5, 3.1 Hz, 1H), 6.83 (dd, J = 9.0, 4.8 Hz, 1H), 4.60 (s, 1H), 4.37 (s, 1H), 3.93 (hept, J = 6.1 Hz, 1H), 3.51 (d, J = 25.9 Hz, 2H), 3.30 (dt, J = 3.3, 1.6 Hz, 2H), 2.20-1.82 (m, 4H), 1.81-1.68 (m, 2H), 1.58 (d, J = 0.7 Hz, 6H), 1.28 (d, J = 6.0 Hz, 3H), 1.21 (d, J = 5.7 Hz, 3H). |
| 49 | 468.60 | 1.95 | |
| 50 | 424.20 | 2.18 | |
| 51 | 454.50 | 1.99 | 1H NMR (400 MHz, DMSO) δ 7.13-7.05 (m, 2H), 7.02-6.90 (m, 3H), 6.88-6.77 (m, 2H), 4.59 (hept, J = 6.1 Hz, 1H), 4.52-4.07 (m, 1H), 3.83-3.65 (m, 4H), 3.59 (t, J = 5.0 Hz, 1H), 3.51-3.04 (m, 3H), 2.97 (dd, J = 16.6, 3.9 Hz, 1H), 2.67 (dd, J = 17.0, 5.6 Hz, 1H), 1.95-1.38 (m, 4H), 1.26 (d, J = 6.0 Hz, 6H), 1.13-1.03 (m, 6H). |
| 52 | 470.40 | 1.58 | |
| 53 | 458.20 | 2.28 | |
| 54 | 482.15 | 3.08 | |
| 55 | 508.40 | 7.18 | 1H NMR (400 MHz, MeOD) δ 7.37-7.21 (m, 1H), 7.01 (dd, J = 9.1, 3.0 Hz, 1H), 6.98-6.76 (m, 4H), 6.75 (s, 1H), 4.85 (s, 2H), 4.62 (dtd, J = 18.1, 12.1, 6.1 Hz, 2H), 4.40 (d, J = 12.2 Hz, 1H), 3.93 (dt, J = 12.1, 6.0 Hz, 1H), 3.53-3.22 (m, 8H), 2.10 (s, 2H), 1.92 (dd, J = 13.8, 6.9 Hz, 2H), 1.70 (d, J = 47.5 Hz, 3H), 1.32 (d, J = 6.0 Hz, 6H), 1.28 (d, J = 6.0 Hz, 3H), 1.21 (dd, J = 8.0, 6.3 Hz, 3H). |
| 56 | 454.30 | 1.97 | |
| 57 | 454.50 | 1.80 | |
| 58 | 517.20 | 1.98 | |
| 59 | 504.20 | 1.98 | |
| 60 | 452.50 | 2.37 | |
| 61 | 482.15 | 3.53 | |
| 62 | 468.70 | 1.90 | |
| 63 | 476.30 | 2.09 | |
| 64 | 456.15 | 3.13 | |
| 65 | 406.21 | 1.58 | |
| 66 | 456.15 | 3.12 | |
| 67 | 468.12 | 3.12 | |
| 68 | 490.20 | 5.68 | 1H NMR (400 MHz, MeOD) δ 7.98 (d, J = 8.3 Hz, 2H), 7.73-7.66 (m, 2H), 7.02 (dd, J = 9.1, 3.0 Hz, 1H), 6.91 (td, J = 8.5, 3.1 Hz, 1H), 6.84 (dd, J = 9.0, 4.8 Hz, 1H), 4.68-4.54 (m, 1H), 4.43 (s, 1H), 3.94 (dt, J = 12.2, 6.1 Hz, 1H), 3.60-3.42 (m, 2H), 3.37 (dd, J = 13.7, 6.9 Hz, 2H), 2.21-2.08 (m, 2H), 1.92 (d, J = 26.3 Hz, 2H), 1.88-1.66 (m, 2H), 1.27 (t, J = 6.6 Hz, 9H), 1.22 (t, J = 6.9 Hz, 3H). |
| 69 | 411.18 | 3.53 | |
| 70 | 462.20 | 2.00 | |
| 71 | 468.70 | 5.81 | |
| 72 | 438.40 | 2.25 | |
| 73 | 501.00 | 1.86 | |
| 74 | 442.40 | 2.16 | |
| 75 | 468.15 | 3.12 | |
| 76 | 449.50 | 1.98 | |
| 77 | 414.40 | 1.86 | |
| 78 | 490.20 | 1.80 | 1H NMR (400 MHz, CDCl3) δ 7.94 (d, J = 8.3 Hz, 2H), 7.60 (d, J = 8.3 Hz, 2H), 7.09 (d, J = 7.8 Hz, 1H), 7.04-6.92 (m, 1H), 6.86 (td, J = 7.9, 4.9 Hz, 1H), 4.54 (s, 2H), 3.86 (dt, J = 12.2, 6.1 Hz, 1H), 3.68-3.26 (m, 3H), 3.21 (dt, J = 13.7, 6.8 Hz, 1H), 2.34 (d, J = 13.8 Hz, 1H), 2.19-1.93 (m, 3H), 1.91-1.65 (m, 2H), 1.59 (s, 2H), 1.38-1.17 (m, 13H). |
| 79 | 480.20 | 2.05 | |
| 80 | 439.50 | 1.91 | |
| 81 | 502.20 | 1.68 | 1H NMR (400 MHz, CDCl3) δ 7.94 (dd, J = 7.1, 4.1 Hz, 1H), 7.69-7.55 (m, 2H), 7.51 (dd, J = 10.8, 7.2 Hz, 1H), 7.05-6.93 (m, 2H), 6.87 (dd, J = 8.2, 4.1 Hz, 1H), 4.89-4.76 (m, 1H), 4.65-4.50 (m, 1H), 3.92 (dd, J = 11.1, 5.1 Hz, 1H), 3.87 (d, J = 4.1 Hz, 3H), 3.40 (dd, J = 13.7, 9.9 Hz, 2H), 2.67-2.54 (m, 1H), 2.53-2.40 (m, 1H), 2.40-2.16 (m, J = 39.2 Hz, 2H), 1.90 (s, 1H), 1.70 (s, 1H), 1.58 (d, J = 5.0 Hz, 2H), 1.38 (dd, J = 6.0, 4.1 Hz, 6H), 1.35-1.22 (m, 6H). |

TABLE 2-continued

| Cmpd. No. | LC/MS M + 1 | LC/RT Min | NMR |
|---|---|---|---|
| 82 | 488.20 | 1.86 | 1H NMR (400 MHz, MeOD) δ 8.01 (d, J = 8.3 Hz, 2H), 7.68 (d, J = 8.5 Hz, 2H), 7.02 (d, J = 9.7 Hz, 1H), 6.96-6.87 (m, 1H), 6.84 (dd, J = 8.9, 4.8 Hz, 1H), 4.61 (s, 1H), 4.44 (s, 1H), 4.00-3.85 (m, 1H), 3.43 (d, J = 40.6 Hz, 3H), 2.71 (s, 1H), 2.15 (s, 2H), 1.95 (s, 2H), 1.77 (s, 3H), 1.28 (d, J = 6.0 Hz, 3H), 1.24 (dd, J = 10.8, 5.1 Hz, 4H), 1.08 (dd, J = 7.9, 2.4 Hz, 2H). |
| 83 | 456.50 | 0.84 | |
| 84 | 455.70 | 3.05 | 1H NMR (400 MHz, DMSO) δ 8.15-8.04 (m, 1H), 7.70 (d, J = 7.4 Hz, 1H), 7.06-6.89 (m, 4H), 4.67-4.50 (m, 2H), 4.34-3.81 (m, 2H), 3.77 (s, 3H), 3.67-3.21 (m, 3H), 2.25-2.12 (m, 1H), 2.04-1.67 (m, 5H), 1.26 (d, J = 6.0 Hz, 6H), 1.22 (d, J = 6.0 Hz, 3H), 1.15 (d, J = 6.1 Hz, 3H). |
| 85 | 476.20 | 5.08 | 1H NMR (400 MHz, MeOD) δ 7.87 (d, J = 16.0 Hz, 2H), 7.57-7.40 (m, 1H), 7.02 (d, J = 8.7 Hz, 1H), 6.92 (t, J = 8.3 Hz, 1H), 6.84 (dd, J = 8.9, 4.6 Hz, 1H), 4.60 (dt, J = 16.2, 6.3 Hz, 1H), 4.49 (s, 1H), 3.94 (dt, J = 12.3, 6.1 Hz, 1H), 3.53-3.36 (m, 2H), 3.22 (s, 1H), 3.13 (d, J = 1.1 Hz, 3H), 2.42 (d, J = 27.9 Hz, 3H), 2.21-2.02 (m, 2H), 1.94 (dt, J = 13.7, 6.7 Hz, 2H), 1.77 (d, J = 36.7 Hz, 2H), 1.28 (dd, J = 5.9, 2.5 Hz, 3H), 1.22 (dd, J = 10.4, 6.0 Hz, 3H). |
| 86 | 518.10 | 1.63 | |
| 87 | 471.30 | 1.88 | |
| 88 | 432.50 | 1.92 | |
| 89 | 439.40 | 1.41 | 1H NMR (400 MHz, CDCl3) δ 8.49 (s, 1H), 8.30 (d, J = 5.4 Hz, 1H), 7.25-7.19 (m, 2H), 6.82 (d, J = 8.2 Hz, 1H), 6.77 (d, J = 5.7 Hz, 1H), 4.57 (dt, J = 18.3, 6.0 Hz, 2H), 3.88 (dt, J = 12.2, 6.1 Hz, 1H), 3.54-3.20 (m, 2H), 2.20 (s, 4H), 2.04 (dd, J = 4.1, 1.7 Hz, 3H), 1.92-1.56 (m, 4H), 1.35 (d, J = 6.0 Hz, 7H), 1.31-1.18 (m, 7H). |
| 90 | 504.40 | 1.88 | 1H NMR (400 MHz, CDCl3) δ 8.02 (d, J = 8.6 Hz, 1H), 7.38 (d, J = 7.4 Hz, 2H), 7.10 (d, J = 7.8 Hz, 1H), 7.03-6.95 (m, 1H), 6.86 (td, J = 7.9, 4.9 Hz, 1H), 4.53 (t, J = 14.2 Hz, 2H), 3.91-3.80 (m, 1H), 3.67-3.20 (m, 4H), 2.71 (s, 3H), 2.32 (d, J = 13.4 Hz, 1H), 2.18-1.94 (m, 3H), 1.79 (dd, J = 25.7, 10.1 Hz, 2H), 1.57 (d, J = 10.4 Hz, 2H), 1.31 (d, J = 6.8 Hz, 6H), 1.28 (d, J = 5.9 Hz, 3H), 1.22 (s, 3H). |
| 91 | 440.00 | 1.89 | |
| 92 | 470.40 | 2.01 | |
| 93 | 498.14 | 3.15 | |
| 94 | 468.50 | 2.06 | |
| 95 | 482.08 | 2.72 | |
| 96 | 380.50 | 2.17 | |
| 97 | 485.16 | 2.32 | |
| 98 | 430.50 | 1.60 | |
| 99 | 472.20 | 1.76 | 1H NMR (400 MHz, CDCl3) δ 7.94 (d, J = 7.9 Hz, 1H), 7.64-7.54 (m, 2H), 7.50 (t, J = 7.4 Hz, 1H), 7.37 (d, J = 8.5 Hz, 2H), 6.88 (d, J = 8.5 Hz, 2H), 4.80 (t, J = 6.5 Hz, 1H), 4.58 (dt, J = 12.1, 6.0 Hz, 1H), 3.91 (dt, J = 12.1, 6.1 Hz, 1H), 3.50-3.31 (m, 2H), 2.58 (dd, J = 14.7, 5.9 Hz, 1H), 2.45 (dd, J = 14.6, 7.0 Hz, 1H), 2.33 (s, 1H), 2.23 (s, 1H), 1.88 (s, 1H), 1.69 (s, 1H), 1.58 (s, 2H), 1.34 (d, J = 6.0 Hz, 6H), 1.29 (dd, J = 18.1, 6.0 Hz, 6H). |
| 100 | 440.50 | 1.95 | 1H NMR (400 MHz, DMSO) δ 7.13-7.05 (m, 2H), 7.02-6.91 (m, 3H), 6.88-6.77 (m, 2H), 4.59 (hept, J = 6.2 Hz, 1H), 4.44-4.08 (m, 1H), 3.76 (s, 3H), 3.73-3.60 (m, 1H), 3.53 (t, J = 5.0 Hz, 1H), 3.48-3.36 (m, 1H), 3.38-3.03 (m, 3H), 2.97 (dd, J = 17.1, 4.5 Hz, 1H), 2.74 (dd, J = 17.1, 5.3 Hz, 1H), 1.94-1.49 (m, 4H), 1.26 (d, J = 6.0 Hz, 6H), 1.10 (t, J = 7.0 Hz, 3H). |
| 101 | 505.20 | 1.84 | |
| 102 | 436.17 | 2.77 | |
| 103 | 518.05 | 2.80 | |
| 104 | 442.20 | 1.72 | 1H NMR (400 MHz, CDCl3) δ 7.25-7.17 (m, 2H), 6.94 (s, 1H), 6.81 (d, J = 8.3 Hz, 1H), 4.64 (t, J = 4.6 Hz, 1H), 4.55 (dt, J = 12.1, 6.0 Hz, 1H), 4.38 (s, 1H), 4.04 (dt, J = 12.2, 6.1 Hz, 1H), 3.82 (s, 3H), 3.65 (s, 1H), 3.37 (s, 2H), 2.20 (s, 3H), 2.01 (qd, J = 14.5, 4.6 Hz, 2H), 1.82 (s, 1H), 1.70 (s, 3H), 1.34 (d, J = 6.0 Hz, 6H), 1.21 (t, J = 7.0 Hz, 6H). |

TABLE 2-continued

| Cmpd. No. | LC/MS M + 1 | LC/RT Min | NMR |
|---|---|---|---|
| 105 | 503.50 | 1.44 | |
| 106 | 470.33 | 1.61 | |
| 107 | 439.40 | 1.91 | |
| 108 | 468.60 | 2.01 | |
| 109 | 474.30 | 3.90 | 1H NMR (400 MHz, DMSO) δ 7.84 (d, J = 7.9 Hz, 1H), 7.78-7.67 (m, 1H), 7.67-7.57 (m, 2H), 7.07-6.91 (m, 3H), 4.73-4.51 (m, 2H), 4.27-3.64 (m, 5H), 3.56-3.37 (m, 5H), 2.84-2.71 (m, 1H), 2.57-2.52 (m, 1H), 2.13-1.68 (m, 4H), 1.26 (d, J = 6. |
| 110 | 498.00 | 2.00 | 1H NMR (400 MHz, DMSO) δ 7.84 (d, J = 7.9 Hz, 1H), 7.78-7.67 (m, 1H), 7.67-7.57 (m, 2H), 7.07-6.91 (m, 3H), 4.73-4.51 (m, 2H), 4.27-3.64 (m, 5H), 3.56-3.37 (m, 5H), 2.84-2.71 (m, 1H), 2.57-2.52 (m, 1H), 2.13-1.68 (m, 4H), 1.26 (d, J = 6.0 Hz, 6H). |
| 111 | 413.40 | 1.82 | |
| 112 | 460.20 | 2.15 | 1H NMR (400 MHz, MeOD) δ 7.25-7.11 (m, 3H), 7.02 (dd, J = 9.1, 3.1 Hz, 1H), 6.91 (td, J = 8.5, 3.1 Hz, 1H), 6.83 (dd, J = 9.0, 4.8 Hz, 1H), 4.67 (dt, J = 12.1, 6.1 Hz, 1H), 4.60 (dd, J = 11.6, 5.5 Hz, 1H), 4.34 (s, 1H), 3.93 (hept, J = 6.1 Hz, 1H), 3.75-3.37 (m, 2H), 3.31 (dt, J = 3.3, 1.6 Hz, 2H), 2.14 (dd, J = 13.9, 5.7 Hz, 1H), 1.95-1.68 (m, 4H), 1.34 (d, J = 6.1 Hz, 6H), 1.28 (d, J = 6.0 Hz, 3H), 1.20 (t, J = 8.3 Hz, 3H). |
| 113 | 368.30 | 1.65 | |
| 114 | 454.50 | 1.96 | |
| 115 | 424.33 | 1.73 | |
| 116 | 470.32 | 1.70 | |
| 117 | 474.40 | 1.68 | |
| 118 | 460.40 | 1.88 | 1H NMR (400 MHz, CDCl3) δ 7.62 (t, J = 8.0 Hz, 1H), 7.28 (dd, J = 8.4, 6.7 Hz, 1H), 7.15 (dd, J = 8.0, 1.5 Hz, 1H), 7.09 (dd, J = 11.9, 1.5 Hz, 1H), 6.65 (td, J = 8.4, 2.5 Hz, 1H), 6.56 (dd, J = 10.2, 2.5 Hz, 1H), 4.50 (s, 2H), 3.84 (dt, J = 12.2, 6.1 Hz, 1H), 3.51 (d, J = 32.4 Hz, 2H), 3.28 (d, J = 12.0 Hz, 1H), 2.80 (s, 1H), 2.54 (d, J = 69.0 Hz, 1H), 2.23 (s, 1H), 1.98 (dd, J = 35.9, 14.3 Hz, 3H), 1.87-1.66 (m, 2H), 1.63 (s, 7H), 1.27 (t, J = 4.2 Hz, 4H), 1.22 (t, J = 5.9 Hz, 3H). |
| 119 | 472.40 | 2.60 | |
| 120 | 486.40 | 6.13 | |
| 121 | 484.40 | 1.90 | |
| 122 | 414.40 | 1.86 | |
| 123 | 420.21 | 1.75 | |
| 124 | 425.14 | 3.75 | |
| 125 | 428.20 | 2.03 | |
| 126 | 442.40 | 2.23 | |
| 127 | 452.50 | 1.95 | |
| 128 | 468.30 | 1.99 | |
| 129 | 429.40 | 1.86 | |
| 130 | 460.40 | 1.73 | 1H NMR (400 MHz, CDCl3) δ 7.62 (t, J = 8.0 Hz, 1H), 7.32-7.24 (m, 2H), 7.17 (d, J = 8.0 Hz, 1H), 7.11 (d, J = 11.9 Hz, 1H), 6.66 (td, J = 8.4, 2.4 Hz, 1H), 6.57 (dd, J = 10.1, 2.5 Hz, 1H), 4.50 (s, 2H), 3.84 (dt, J = 12.0, 6.0 Hz, 1H), 3.49 (s, 4H), 3.31 (s, 1H), 2.24 (s, 1H), 2.01 (s, 4H), 1.69 (s, 2H), 1.65 (s, 7H), 1.61-1.34 (m, 4H), 1.27 (d, J = 6.0 Hz, 4H), 1.25-1.17 (m, 4H). |
| 131 | 468.20 | 2.15 | |
| 132 | 482.15 | 3.53 | |
| 133 | 410.29 | 2.07 | 1H NMR (400 MHz, DMSO) δ 7.30-7.20 (m, 3H), 7.19-7.13 (m, 1H), 6.96 (d, J = 8.4 Hz, 1H), 6.89 (td, J = 7.5, 1.1 Hz, 1H), 6.81 (dd, J = 8.2, 0.9 Hz, 1H), 4.54 (t, J = 5.9 Hz, 1H), 3.87 (dt, J = 12.1, 6.1 Hz, 1H), 3.82 (s, 3H), 2.16 (s, 3H), 2.15-2.05 (m, 3H), 1.90 (dd, J = 13.8, 6.6 Hz, 2H), 1.71 (s, 3H), 1.21 (d, J = 6.0 Hz, 3H), 1.14 (d, J = 6.1 Hz, 3H). |
| 134 | 414.40 | 1.43 | |
| 135 | 456.70 | 1.90 | |
| 136 | 412.40 | 4.49 | |
| 137 | 420.21 | 1.72 | |
| 138 | 414.60 | 1.86 | |
| 139 | 443.40 | 1.96 | |
| 140 | 442.40 | 2.11 | |
| 141 | 438.50 | 2.24 | |
| 142 | 426.30 | 1.81 | |
| 143 | 476.50 | 1.92 | |

TABLE 2-continued

| Cmpd. No. | LC/MS M + 1 | LC/RT Min | NMR |
|---|---|---|---|
| 144 | 412.25 | 1.73 | |
| 145 | 489.40 | 1.38 | |
| 146 | 472.70 | 2.08 | 1H NMR (400 MHz, MeOD) δ 7.06-6.98 (m, 4H), 6.91 (td, J = 8.4, 3.1 Hz, 1H), 6.83 (dd, J = 9.0, 4.8 Hz, 1H), 4.67-4.54 (m, 2H), 3.94 (dt, J = 12.2, 6.1 Hz, 1H), 3.85 (s, 3H), 3.80-3.34 (m, 3H), 2.15 (dd, J = 13.9, 5.7 Hz, 1H), 2.03 (s, 1H), 1.93 (dd, J = 13.9, 7.0 Hz, 2H), 1.76 (s, 3H), 1.32 (d, J = 6.1 Hz, 6H), 1.28 (d, J = 6.0 Hz, 3H), 1.21 (d, J = 6.1 Hz, 3H). |
| 147 | 504.40 | 2.01 | |
| 148 | 472.40 | 1.98 | |
| 149 | 396.29 | 1.81 | |
| 150 | 454.70 | 2.00 | |
| 151 | 482.50 | 2.14 | |
| 152 | 513.40 | 2.01 | |
| 153 | 508.20 | 5.71 | 1H NMR (400 MHz, CDCl3) δ 7.98-7.92 (m, 2H), 7.63-7.56 (m, 2H), 6.84 (d, J = 8.7 Hz, 1H), 6.78 (ddd, J = 11.0, 8.4, 3.0 Hz, 1H), 4.51 (s, 2H), 3.84 (dt, J = 12.1, 6.1 Hz, 1H), 3.66-3.26 (m, 3H), 3.21 (dt, J = 13.7, 6.9 Hz, 1H), 2.28 (d, J = 13.8 Hz, 1H), 2.16-1.94 (m, 3H), 1.88-1.67 (m, 2H), 1.51 (d, J = 25.1 Hz, 2H), 1.31 (d, J = 6.9 Hz, 6H), 1.28 (d, J = 6.0 Hz, 3H), 1.23 (s, 3H). |
| 154 | 460.20 | 1.73 | 1H NMR (400 MHz, CDCl3) δ 7.62 (t, J = 8.0 Hz, 1H), 7.32-7.25 (m, 1H), 7.17 (dd, J = 8.0, 1.4 Hz, 1H), 7.11 (d, J = 11.9 Hz, 1H), 6.66 (td, J = 8.4, 2.5 Hz, 1H), 6.57 (dd, J = 10.2, 2.5 Hz, 1H), 4.50 (s, 2H), 3.84 (dt, J = 12.3, 6.1 Hz, 1H), 3.53 (d, J = 28.8 Hz, 2H), 3.28 (s, 1H), 2.24 (s, 1H), 2.03 (d, J = 19.5 Hz, 4H), 1.65 (s, 8H), 1.55 (s, 2H), 1.27 (d, J = 6.0 Hz, 4H), 1.22 (d, J = 6.1 Hz, 3H). |
| 155 | 500.40 | 1.88 | |
| 156 | 476.40 | 5.38 | 1H NMR (400 MHz, MeOD) δ 8.07 (d, J = 8.5 Hz, 1H), 7.47 (d, J = 7.4 Hz, 2H), 7.02 (dd, J = 9.1, 3.0 Hz, 1H), 6.91 (td, J = 8.6, 3.2 Hz, 1H), 6.84 (dd, J = 9.0, 4.8 Hz, 1H), 4.69-4.52 (m, 1H), 4.40 (s, 1H), 3.94 (dt, J = 12.2, 6.1 Hz, 1H), 3.49 (dd, J = 9.6, 7.9 Hz, 2H), 3.16 (s, 3H), 2.74 (s, 3H), 2.15 (dd, J = 13.6, 5.2 Hz, 2H), 2.04-1.89 (m, 2H), 1.89-1.62 (m, 3H), 1.28 (d, J = 6.0 Hz, 3H), 1.25-1.18 (m, 3H). |
| 157 | 450.30 | 2.03 | |
| 158 | 466.30 | 2.02 | |
| 159 | 471.33 | 1.87 | |
| 160 | 468.60 | 5.85 | |
| 161 | 474.20 | 1.77 | 1H NMR (400 MHz, MeOD) δ 7.73 (d, J = 8.4 Hz, 2H), 7.68-7.62 (m, 2H), 7.02 (dd, J = 9.1, 2.9 Hz, 1H), 6.91 (td, J = 8.5, 3.1 Hz, 1H), 6.84 (dd, J = 9.0, 4.8 Hz, 1H), 4.61 (s, 1H), 4.42 (s, 1H), 3.94 (hept, J = 6.2 Hz, 1H), 3.49 (d, J = 11.4 Hz, 2H), 3.33 (d, J = 4.7 Hz, 1H), 3.01 (dq, J = 13.5, 6.8 Hz, 1H), 2.14 (s, 1H), 1.90 (d, J = 33.6 Hz, 2H), 1.77 (s, 3H), 1.33-1.26 (m, 6H), 1.22 (s, 3H), 1.09 (d, J = 6.8 Hz, 3H). |
| 162 | 396.50 | 1.91 | |
| 163 | 468.60 | 1.98 | |
| 164 | 467.50 | 2.06 | |
| 165 | 426.50 | 1.82 | 1H NMR (400 MHz, DMSO) δ 7.12-7.06 (m, 2H), 7.01-6.91 (m, 3H), 6.87-6.78 (m, 2H), 4.59 (hept, J = 6.0 Hz, 1H), 4.47-4.07 (m, 1H), 3.76 (s, 3H), 3.44 (t, J = 5.0 Hz, 1H), 3.32 (s, 3H), 3.38-3.05 (m, 3H), 2.98 (dd, J = 17.1, 4.4 Hz, 1H), 2.78 (dd, J = 17.2, 5.3 Hz, 1H), 1.96-1.48 (m, 4H), 1.26 (d, J = 6.0 Hz, 6H). |
| 166 | 454.60 | 1.88 | |
| 167 | 449.40 | 2.11 | |
| 168 | 440.50 | 1.86 | |
| 169 | 438.40 | 2.16 | |
| 170 | 412.28 | 1.73 | |
| 171 | 454.50 | 1.96 | |
| 172 | 466.30 | 2.05 | |
| 173 | 499.50 | 1.63 | |
| 174 | 456.60 | 1.57 | |

TABLE 2-continued

| Cmpd. No. | LC/MS M + 1 | LC/RT Min | NMR |
|---|---|---|---|
| 175 | 491.20 | 1.83 | 1H NMR (400 MHz, MeOD) δ 9.03 (t, J = 1.5 Hz, 1H), 8.40 (dd, J = 8.2, 2.2 Hz, 1H), 7.84 (dd, J = 8.2, 0.6 Hz, 1H), 7.02 (dd, J = 9.1, 3.0 Hz, 1H), 6.92 (td, J = 8.5, 3.1 Hz, 1H), 6.85 (d, J = 4.8 Hz, 1H), 4.61 (dt, J = 12.5, 6.2 Hz, 1H), 4.50-4.36 (m, 1H), 4.00-3.88 (m, 1H), 3.54 (s, 2H), 3.49-3.41 (m, 1H), 3.41-3.34 (m, 1H), 2.16 (dd, J = 8.9, 5.0 Hz, 1H), 2.03-1.76 (m, 5H), 1.29 (dd, J = 9.8, 4.1 Hz, 9H), 1.25-1.18 (m, 3H). |
| 176 | 498.14 | 3.25 | |
| 177 | 472.20 | 1.98 | 1H NMR (400 MHz, CDCl3) δ 7.10 (d, J = 7.7 Hz, 1H), 6.98 (ddd, J = 10.1, 6.9, 1.9 Hz, 3H), 6.90-6.82 (m, 2H), 4.56 (dt, J = 6.2, 5.0 Hz, 2H), 3.91-3.81 (m, 4H), 3.45 (s, 2H), 2.13 (d, J = 25.3 Hz, 1H), 2.09-1.97 (m, 2H), 1.88 (s, 1H), 1.68 (s, 2H), 1.56 (s, 5H), 1.38 (d, J = 6.1 Hz, 6H), 1.28 (d, J = 6.0 Hz, 3H), 1.22 (d, J = 6.1 Hz, 3H). |
| 178 | 442.40 | 1.62 | |

Assays for Detecting and Measuring NaV Inhibition Properties of Compound
E-VIPR Optical Membrane Potential Assay Method with Electrical Stimulation Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

24 hours before the assay on E-VIPR, HEK cells expressing human NaV subtype, like NaV 1.7, are seeded in 384-well poly-lysine coated plates at 15,000-20,000 cells per well. Other subtypes are performed in an analogous mode in a cell line expressing the NaV of interest. HEK cells are grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

Reagents and Solutions 100 mg/mL Pluronic F-127 (Sigma #P2443), in dry DMSO
Compound Plates: 384-well round bottom plate, e.g. Corning 384-well Polypropylene Round Bottom #3656
Cell Plates: 384-well tissue culture treated plate, e.g. Greiner #781091-1B
10 mM $DiSBAC_6(3)$ (Aurora #00-100-010) in dry DMSO
10 mM CC2-DMPE (Aurora #00-100-008) in dry DMSO
200 mM ABSC1 in $H_2O$
Bath1 buffer. Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (make this prior to use, Sigma #C4767), 8 μM CC2-DMPE+ 2.5 μM $DiSBAC_6(3)$. To make the solution Add volume of 10% Pluronic F127 stock equal to volumes of CC2-DMPE+ $DiSBAC_6(3)$. The order of preparation is first mix Pluronic and CC2-DMPE, then add $DiSBAC_6(3)$ while vortexing, then add Bath1+β-Cyclodextrin.

Assay Protocol

1) Pre-spot compounds (in neat DMSO) into compound plates. Vehicle control (neat DMSO), the positive control (20 mM DMSO stock tetracaine, 125 μM final in assay) and test compounds are added to each well at 160× desired final concentration in neat DMSO. Final compound plate volume will be 80 μL (80-fold intermediate dilution from 1 μL DMSO spot; 160-fold final dilution after transfer to cell plate). Final DMSO concentration for all wells in assay is 0.625%.

2) Prepare Hexyl Dye Solution.

3) Prepare cell plates. On the day of the assay, medium is aspirated and cells are washed three times with 100 μL of Bath1 Solution, maintaining 25 μL residual volume in each well.

4) Dispense 25 μL per well of Hexyl Dye Solution into cell plates. Incubate for 20-35 minutes at room temp or ambient conditions.

5) Dispense 80 μL per well of Bath1 into compound plates. Acid Yellow-17 (1 mM) is added and Potassium Chloride can be altered from 4.5 to 20 mM depending on the NaV subtype and assay sensitivity.

6) Wash cell plates three times with 100 μL per well of Bath1, leaving 25 μL of residual volume. Then transfer 25 uL per well from Compound Plates to Cell Plates. Incubate for 20-35 minutes at room temp/ambient condition 7) Read Plate on E-VIPR. Use the current-controlled amplifier to deliver stimulation wave pulses for typically 9 seconds and a scan rate of 400 Hz. A pre-stimulus recording is performed for 0.5 seconds to obtain the un-stimulated intensities baseline. The stimulatory waveform is applied for 9 seconds followed by 0.5 seconds of post-stimulation recording to examine the relaxation to the resting state. The stimulatory waveform of the electrical stimulation is specific for each cell type and can vary the magnitude, duration and frequency of the applied current to provide an optimal assay signal.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - background_{460\,nm})}{(intensity_{580\,nm} - background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated and reported as a function of time.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R - P}{N - P} * 100.$$

where R is the ratio response of the test compound

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

IonWorks Assays.

Sodium currents were recorded using the automated patch clamp system, IonWorks (Molecular Devices Corporation, Inc.). Cells expressing Nav subtypes are harvested from tissue culture and placed in suspension at 0.5-4 million cells per mL Bath1. The IonWorks instrument measures changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents are measured at the test potential.

1-Benzazepin-2-One Binding Assay

The sodium channel inhibiting properties of the compounds of the invention can also be determined by assay methods described in Williams, B. S. et al., "Characterization of a New Class of Potent Inhibitors of the Voltage-Gated Sodium Channel NaV 1.7," *Biochemistry*, 2007, 46, 14693-14703, the entire contents of which are incorporated herein by reference.

The exemplified compounds of Table 1 herein are active against one or more sodium channels as measured using the assays described herein above as presented in Table 3.

TABLE 3

| IC50: +++ <= 2.0 µM < ++ <= 5.0 µM < + | |
|---|---|
| Cmpd. No. | Binned Activity Data |
| 1 | +++ |
| 2 | +++ |
| 3 | +++ |
| 4 | ++ |
| 5 | +++ |
| 6 | +++ |
| 7 | +++ |
| 8 | + |
| 9 | +++ |
| 10 | +++ |
| 11 | +++ |
| 12 | +++ |
| 13 | +++ |
| 14 | +++ |
| 15 | + |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | +++ |
| 28 | ++ |
| 29 | +++ |
| 30 | ++ |
| 31 | +++ |
| 32 | ++ |
| 33 | +++ |
| 34 | +++ |
| 35 | +++ |
| 36 | +++ |
| 37 | +++ |
| 38 | + |
| 39 | + |
| 40 | + |
| 41 | +++ |
| 42 | +++ |
| 43 | +++ |
| 44 | +++ |
| 45 | +++ |
| 46 | +++ |
| 47 | + |
| 48 | +++ |
| 49 | +++ |
| 50 | +++ |
| 51 | +++ |
| 52 | +++ |
| 53 | +++ |
| 54 | +++ |
| 55 | +++ |

TABLE 3-continued

IC50: +++ <= 2.0 μM < ++ <= 5.0 μM < +

| Cmpd. No. | Binned Activity Data |
|---|---|
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | ++ |
| 66 | +++ |
| 67 | +++ |
| 68 | +++ |
| 69 | +++ |
| 70 | ++ |
| 71 | +++ |
| 72 | +++ |
| 73 | ++ |
| 74 | +++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | ++ |
| 86 | + |
| 87 | +++ |
| 88 | +++ |
| 89 | ++ |
| 90 | +++ |
| 91 | +++ |
| 92 | +++ |
| 93 | +++ |
| 94 | +++ |
| 95 | +++ |
| 96 | +++ |
| 97 | + |
| 98 | +++ |
| 99 | +++ |
| 100 | +++ |
| 101 | + |
| 102 | + |
| 103 | + |
| 104 | +++ |
| 105 | +++ |
| 106 | +++ |
| 107 | +++ |
| 108 | +++ |
| 109 | + |
| 110 | +++ |
| 111 | + |
| 112 | +++ |
| 113 | +++ |
| 114 | +++ |
| 115 | ++ |
| 116 | ++ |
| 117 | +++ |
| 118 | +++ |
| 119 | +++ |
| 120 | +++ |
| 121 | + |
| 122 | +++ |
| 123 | ++ |
| 124 | + |
| 125 | +++ |
| 126 | +++ |
| 127 | +++ |
| 128 | +++ |
| 129 | ++ |
| 130 | ++ |

TABLE 3-continued

IC50: +++ <= 2.0 μM < ++ <= 5.0 μM < +

| Cmpd. No. | Binned Activity Data |
|---|---|
| 131 | +++ |
| 132 | +++ |
| 133 | +++ |
| 134 | +++ |
| 135 | +++ |
| 136 | +++ |
| 137 | +++ |
| 138 | +++ |
| 139 | +++ |
| 140 | +++ |
| 141 | +++ |
| 142 | +++ |
| 143 | +++ |
| 144 | +++ |
| 145 | +++ |
| 146 | +++ |
| 147 | +++ |
| 148 | +++ |
| 149 | +++ |
| 150 | +++ |
| 151 | +++ |
| 152 | +++ |
| 153 | ++ |
| 154 | +++ |
| 155 | +++ |
| 156 | +++ |
| 157 | +++ |
| 158 | +++ |
| 159 | +++ |
| 160 | +++ |
| 161 | +++ |
| 162 | ++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | +++ |

Many modifications and variations of the embodiments described herein may be made without departing from the scope, as is apparent to those skilled in the art. The specific embodiments described herein are offered by way of example only.

We claim:

1. A compound of formula I:

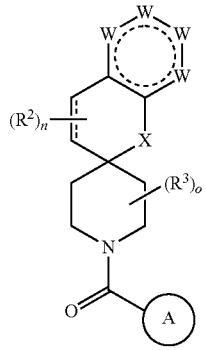

or a pharmaceutically acceptable salt thereof,
wherein, independently for each occurrence:
W is $CR^1$;
a dashed circle denotes unsaturation;
$R^1$ is H or halo;
$R^2$ is C1-C6 alkoxy, halo, CN, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $CH_2OCHF_2$, $CH_2OCH_2CHF_2$, C3-C8 cycloalkyl, or heterocycloalkyl, a straight chain or branched (C1-C8)-H wherein up to two $CH_2$ units are replaced with O, CO, S, SO, $SO_2$ or $NR^7$;
$R^7$ is C1-C6 alkyl or fluoroalkyl, or C3-C8 cycloalkyl, or 2 $R^7$ taken together with the atoms to which they are attached form a ring;
$R^8$ is H, $CF_3$, $CO_2R^7$, OH, an optionally substituted aryl, heteroaryl, C3-C8 cycloalkyl, heterocycloalkyl, $N(R^7)_2$, $NR^7COR^7$, $CON(R^7)_2$, CN, or $SO_2R^7$;
A is aryl optionally substituted with one or more of C1-C6 alkyl, C3-C8 cycloalkoxy, C1-C6 alkoxy, halo, $OR^7$, $NR^7SO_2R^7$, $SOR^7$, $SR^7$, $NR^7CO_2R^7$, $SO_2N(R^7)_2$, $OCF_3$, $OCHF_2$, $R^8$, heterocycloalkoxy, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$; or wherein two adjacent groups on the aryl ring form a heterocyclic ring comprising up to 2 heteroatoms and which is optionally substituted with a methyl group;
X is O;
n is 1 or 2; and
o is 0.

2. The compound of claim 1, wherein all W's are CH.

3. The compound of claim 1, wherein $R^1$ is halo.

4. The compound of claim 1, wherein $R^1$ is F.

5. The compound of claim 1, wherein $R^2$ is C1-C6 alkoxy, $OR^7$, or $N(R^7)_2$.

6. The compound of claim 1, wherein $R^2$ is $OCH_3$, $CH_2OCHF_2$, $CH_2OCH_3$, $OCH_2CH_3$, $CH_3$, $CH(CH_3)_2$, $OCH(CH_3)_2$, $CH_2OCH_2CH_3$, $CH(CH_3)OCH_3$, $CH_2SCH_3$,

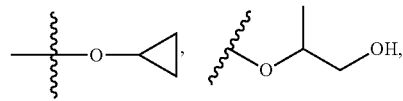

$OCH_2CH_2SO_2CH_3$, $NHCH(CH_3)_2$, OtBu,

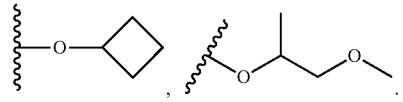

7. The compound of claim 1, wherein A is

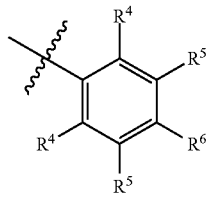

wherein:
$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CHF_2$, $CF_3$, $OCF_3$, $OCHF_2$, heterocycloalkyl, heterocycloalkoxy, an optionally substituted aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, CO, S, SO, $SO_2$, or $NR^7$;
$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, an optionally substituted aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, CO, S, SO, $SO_2$, or $NR^7$;
$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, an optionally substituted aryl, heteroaryl, a straight chain (C1-C8)-$R^8$, branched, or cyclic (C3-C8)-$R^8$ wherein up to three $CH_2$ units of the straight chain (C1-C8)-$R^8$ and branched or cyclic (C3-C8)-$R^8$ may be replaced with O, CO, S, SO, $SO_2$, or $NR^7$; or
two occurrences of $R^4$ and $R^5$, or $R^5$ and $R^6$ together with the carbons to which they are attached form an optionally substituted ring comprising up to 2 heteroatoms.

8. The compound of claim 7, wherein $R^4$ is H, C1-C6 alkyl, C1-C6 alkoxy, halo, CN, OH, $CHF_2$, $CF_3$, $OCHF_2$, $OCF_3$, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, CO, S, SO, $SO_2$, or $NR^7$.

9. The compound of claim 7, wherein $R^4$ is H, $OCH_3$, $OCHF_2$, $OCF_3$, F, $CH_3$, or $CH_2OCH_3$.

10. The compound of claim 7, wherein $R^5$ is H, C1-C6 alkyl, C1-C6 alkoxy, CN, a straight chain (C1-C8)-$R^8$, branched, or cyclic (C3-C8)-$R^8$ wherein up to three $CH_2$ units of the straight chain (C1-C8)-$R^8$ and branched or cyclic (C3-C8)-$R^8$ may be replaced with O, CO, S, SO, $SO_2$, or $NR^7$.

11. The compound of claim 7, wherein $R^5$ is H, F, $CH_3$, $OCH_3$, $CH_2OH$, OH, $CH_2NH_2$, $CH_2NHCH_3$, $CH_2N(CH_3)_2$, or CN.

12. The compound of claim 7, wherein $R^6$ is H, C1-C6 alkyl, C1-C6 alkoxy, $SO_2R^7$, $SO_2N(R^7)_2$, a straight chain (C1-C8)-$R^8$, or branched or cyclic (C3-C8)-$R^8$, wherein up to three $CH_2$ units of the straight chain (C1-C8)-$R^8$ and branched or cyclic (C3-C8)-$R^8$ may be replaced with O, S, SO, $SO_2$, or $NR^7$.

13. The compound of claim 7, wherein $R^6$ is H, $OCH_3$, OH, $OCH(CH_3)_2$,

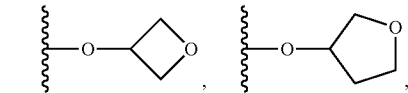

$C(CH_3)_2OH$,

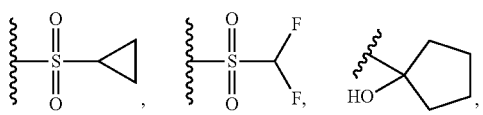

$SO_2CH_3$, $OCH_2CH_2OH$, $OCH_2CH_2CH_2OH$, $SO_2CH_3$, $SO_2CH_2CH_3$, $SO_2CF_3$, $SO_2CH(CH_3)_2$, $SO_2tBu$,

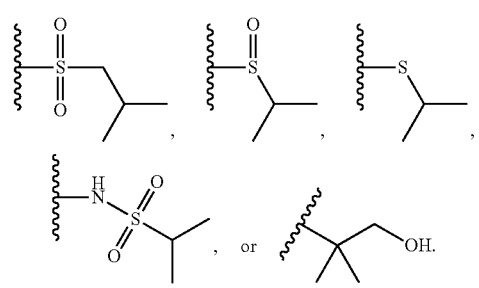

$SO_2NHCH(CH_3)_2$, tBu, $OCHF_2$, $CH_2CH_3$, $OCH_2CH_3$,

14. The compound of claim 7, wherein

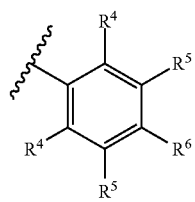

is selected from:

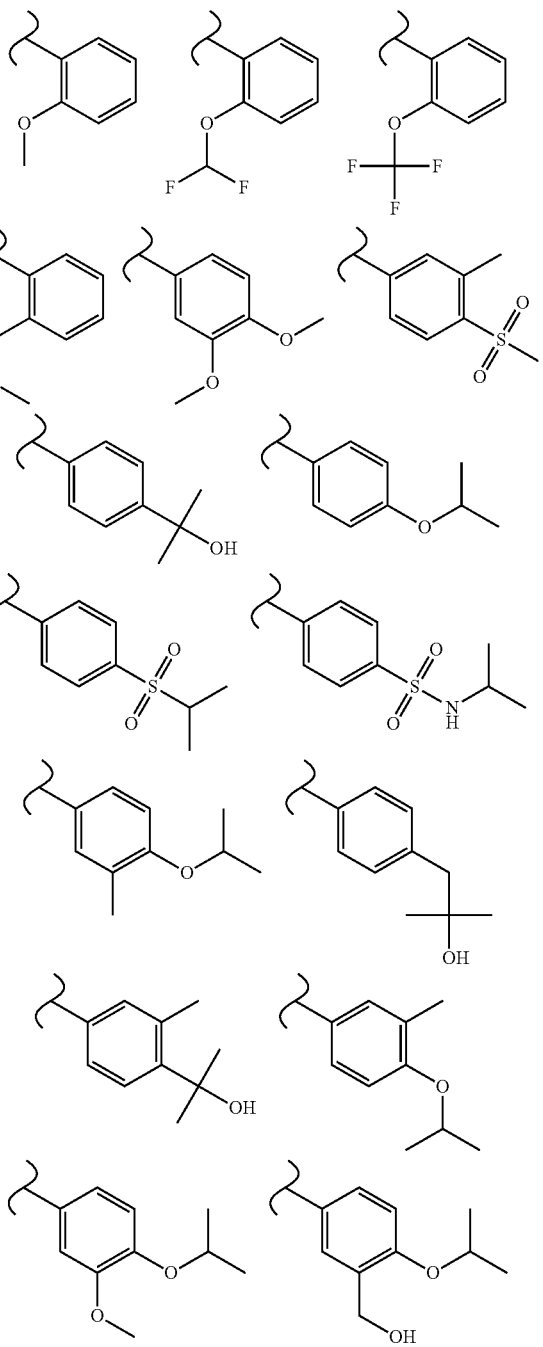

223
-continued
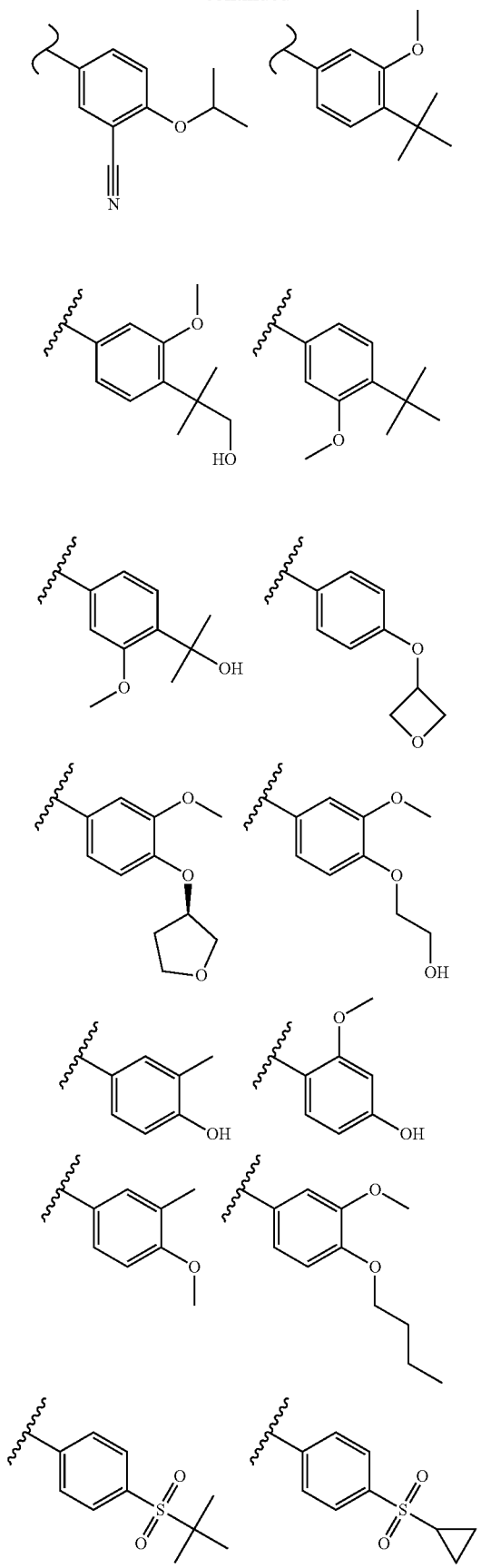
224
-continued
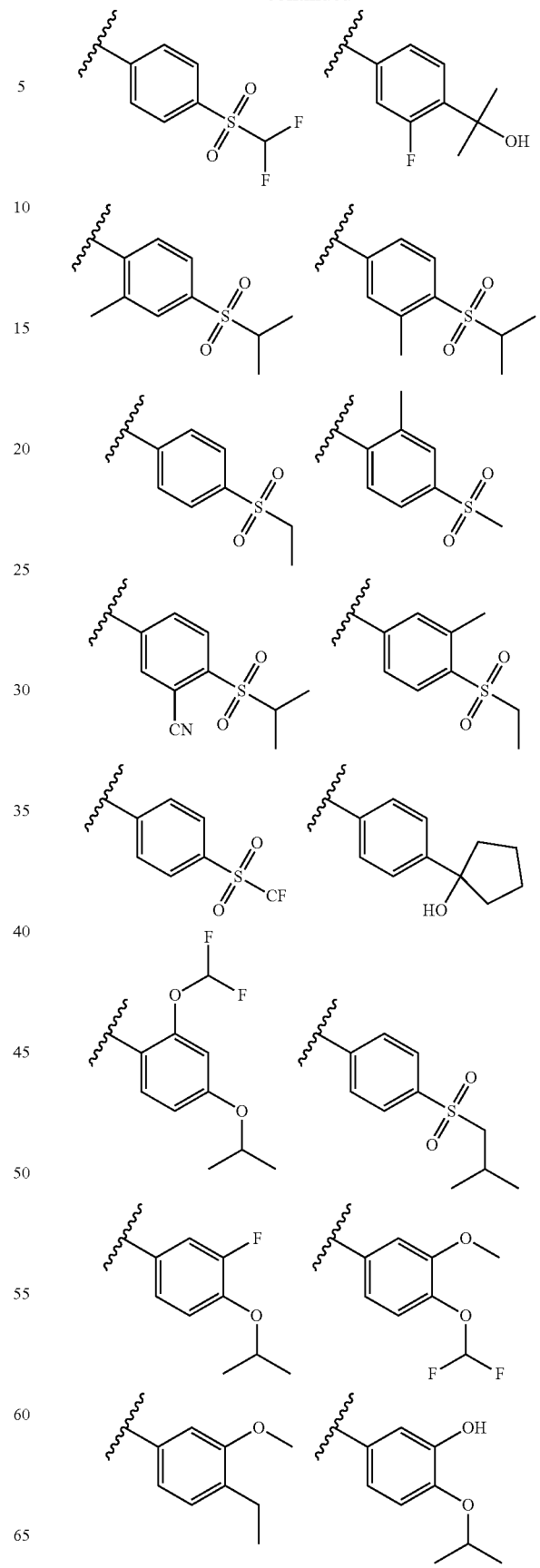

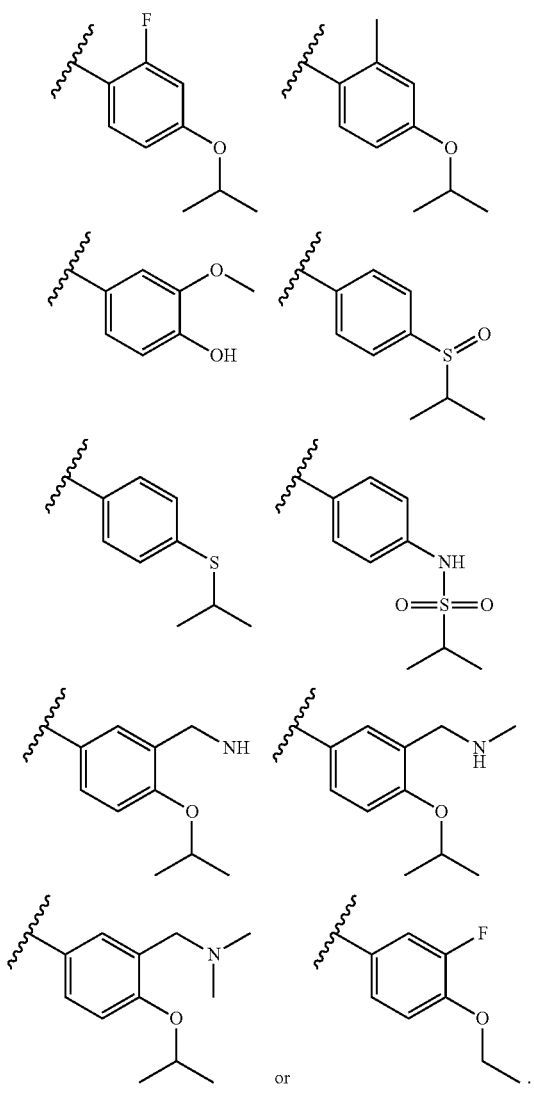

15. The compound of claim 1, wherein the compound has formula IA:

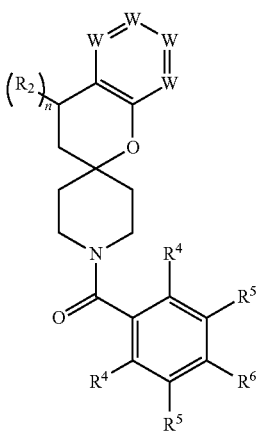

or a pharmaceutically acceptable salt thereof,
wherein, independently for each occurrence:
$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, an optionally substituted aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$; or two occurrences of $R^4$ and $R^5$, or $R^5$ and $R^6$ together with the carbons to which they are attached form an optionally substituted ring comprising up to 2 heteroatoms; and n is 1 or 2.

16. The compound of claim 15, wherein $R^1$ is halo.
17. The compound of claim 15, wherein $R^1$ is F.
18. The compound of claim 15, wherein $R^2$ is C1-C6 alkoxy, $N(R^7)_2$, a straight chain or branched (C1-C8)-H wherein up to two $CH_2$ units are replaced with O, S, SO, $SO_2$ or $NR^7$.
19. The compound of claim 15, wherein $R^2$ is $OCH_3$, $CH_2OCH_3$, $OCH_2CH_3$, $CH_3$, $CH(CH_3)_2$, $OCH(CH_3)_2$, $CH_2OCH(CH_3)_2$, $CH_2OCHF_2$, $CH_2OCH_2CH_3$, $CH(CH_3)OCH_3$,

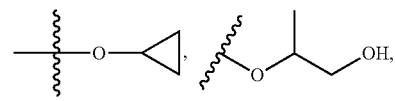

$CH_2SCH_3$, $OCH_2CH_2SO_2CH_3$, $NHCH(CH_3)_2$, OtBu,

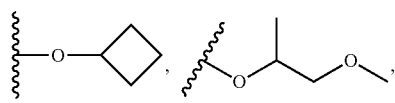

or $OCH_2CH_2N(C_2H_5)_2$, $OCH_2Ph$.

20. The compound of claim 15, wherein $R^4$ is H, C1-C6 alkyl, C1-C6 alkoxy, halo, CN, OH, $OR^7$, $CHF_2$, $CF_3$, $OCHF_2$, $OCF_3$, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$.

21. The compound of claim 15, wherein $R^4$ is H, $OCH_3$, $OCHF_2$, $OCF_3$, F, $CH_3$, or $CH_3$.

22. The compound of claim 15, wherein $R^5$ is H, C1-C6 alkyl, C1-C6 alkoxy, CN, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$.

23. The compound of claim 15, wherein $R^5$ is H, $CH_3$, $OCH_3$, $CH_2OH$, F, OH, $CH_2NH_2$, $CH_2NHCH_3$, $CH_2N(CH_3)_2$, or CN.

24. The compound of claim 15, wherein $R^6$ is H, C1-C6 alkyl, C1-C6 alkoxy, $SO_2R^7$, $SO_2N(R^7)_2$, a straight chain (C1-C8)-$R^8$, or branched or cyclic (C3-C8)-$R^8$, wherein up to three $CH_2$ units of the straight chain (C1-C8)-$R^8$ and branched or cyclic (C3-C8)-$R^8$ may be replaced with O, S, SO, $SO_2$, or $NR^7$.

25. The compound of claim 15, wherein $R^6$ is H, OH, $OCH_3$, $OCH(CH_3)_2$, $OCH_2CH_2OH$, $OCH_2CH_2CH_2OH$,

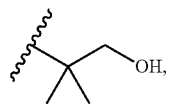 [SMILES: *C(C)(C)CO]

$SO_2CH_3$, $SO_2CH_2CH_3$, $SO_2CF_3$, $SO_2CH(CH_3)_2$, $SO_2tBu$, $SO_2CHF_2$, tBu,

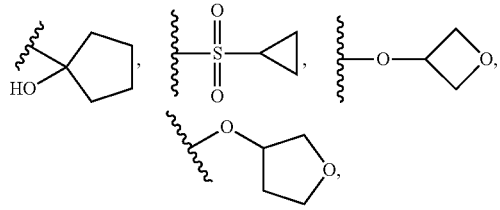

$OCHF_2$, $CH_2CH_3$, $OCH_2CH_3$,

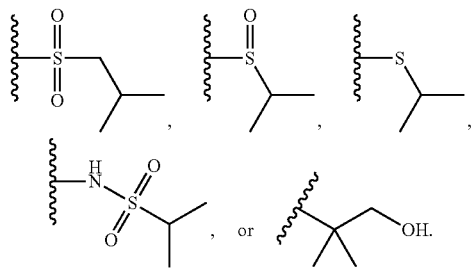

, or 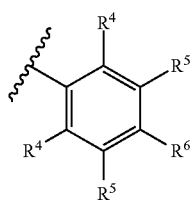

26. The compound of claim 15, wherein n is 1.

27. The compound of claim 15, wherein is selected from:

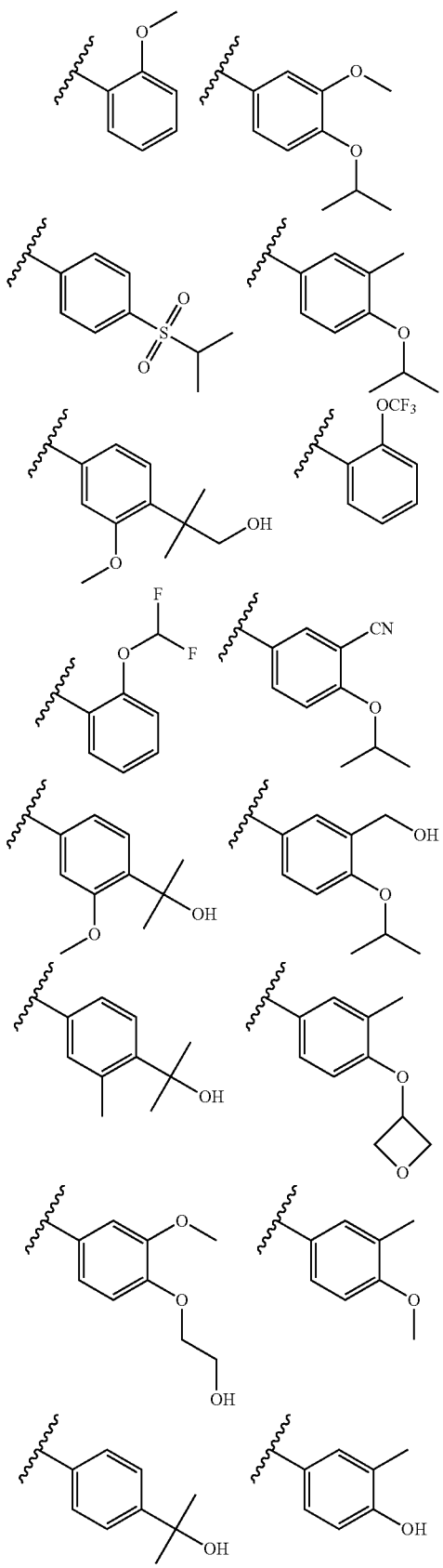

-continued

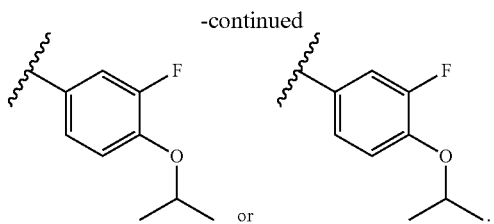

28. A compound having formula IB:

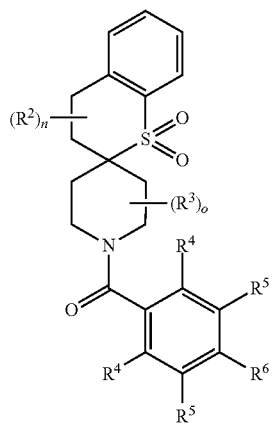

or a pharmaceutically acceptable salt thereof,
wherein, independently for each occurrence:

$R^2$ is C1-C6 alkoxy, halo, CN, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, $CH_2OCHF_2$, $CH_2OCH_2CHF_2$, C3-C8 cycloalkyl, or heterocycloalkyl, a straight chain or branched (C1-C8)-H wherein up to two $CH_2$ units are replaced with O, CO, S, SO, $SO_2$ or $NR^7$;

n is 0, 1, or 2;

o is zero;

$R^4$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$;

$R^5$ is H, C1-C6 alkyl, C3-C8 cycloalkyl, C1-C6 alkoxy, C3-C8 cycloalkoxy, halo, CN, OH, $OR^7$, $N(R^7)_2$, $NR^7SO_2R^7$, $SO_2R^7$, $SR^7$, $SOR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$;

$R^6$ is H, C1-C6 alkyl, C3-C8 cycloalkyl, C1-C6 alkoxy, halo, CN, OH, $OR^7$, $N(R^7)_2$, $NR^7SO_2R^7$, $SO_2R^7$, $SOR^7$, $SR^7$, $CO_2R^7$, $NR^7COR^7$, $NR^7CO_2R^7$, $CON(R^7)_2$, $SO_2N(R^7)_2$, $CF_3$, $OCF_3$, $OCHF_2$, heterocycloalkyl, heterocycloalkoxy, aryl, heteroaryl, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$;

$R^7$ is C1-C6 alkyl or fluoroalkyl, or C3-C8 cycloalkyl, or 2 $R^7$ taken together with the atoms to which they are attached form a ring;

$R^8$ is H, $CF_3$, $CO_2R^7$, OH, an optionally substituted aryl, heteroaryl, C3-C8 cycloalkyl, heterocycloalkyl, $N(R^7)_2$, $NR^7COR^7$, $CON(R^7)_2$, CN, or $SO_2R^7$; or two occurrences of $R^4$ and $R^5$, or $R^5$ and $R^6$ together with the carbons to which they are attached form an optionally substituted ring comprising up to 2 heteroatoms.

29. The compound of claim 28, wherein $R^2$ is C1-C6 alkoxy.

30. The compound of claim 28, wherein $R^2$ is $OCH_3$, $OC_2H_5$, or $OCH(CH_3)_2$.

31. The compound of claim 28, wherein $R^4$ is H, C1-C6 alkyl, C1-C6 alkoxy.

32. The compound of claim 28, wherein $R^4$ is H or $OCHF_2$.

33. The compound of claim 28, wherein $R^5$ is H, C1-C6 alkyl, C3-C8 cycloalkyl, C1-C6 alkoxy, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$.

34. The compound of claim 28, wherein $R^5$ is H, $CH_3$ or $OCH_3$.

35. The compound of claim 28, wherein $R^6$ is H, C1-C6 alkyl, C3-C8 cycloalkyl, C1-C6 alkoxy, a straight chain (C1-C8)-$R^8$, or branched or cyclic (C3-C8)-$R^8$ wherein up to three $CH_2$ units of the straight chain (C1-C8)-$R^8$ and branched or cyclic (C3-C8)-$R^8$ may be replaced with O, S, SO, $SO_2$, or $NR^7$.

36. The compound of claim 28, wherein $R^6$ is $OCH(CH_3)_2$.

37. The compound of claim 28, wherein n is 1.

38. The compound of claim 28, wherein o is 0.

39. The compound of claim 28, wherein

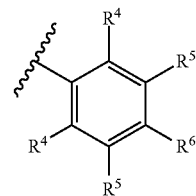

is selected from:

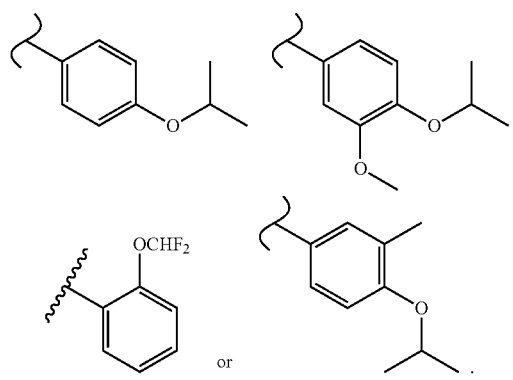

40. A compound selected from the following table:
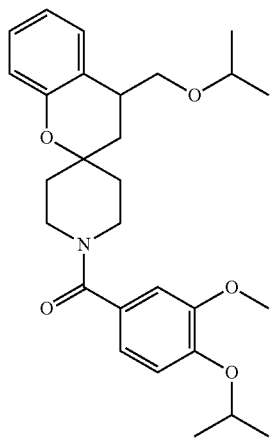 [SMILES: COc1cc(C(=O)N2CCC3(CC2)CC(COC(C)C)c2ccccc2O3)ccc1OC(C)C]
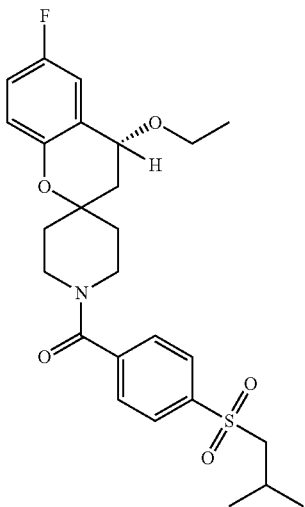
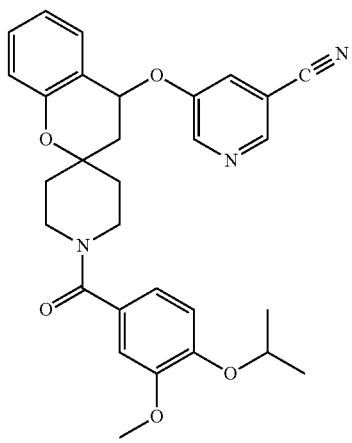 [SMILES: COc1cc(C(=O)N2CCC3(CC2)CC(Oc2cncc(C#N)c2)c2ccccc2O3)ccc1OC(C)C]
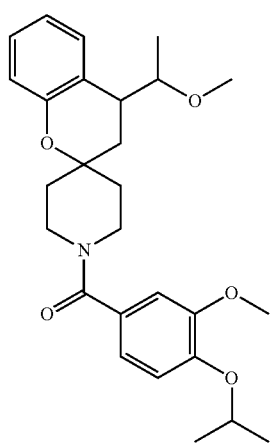
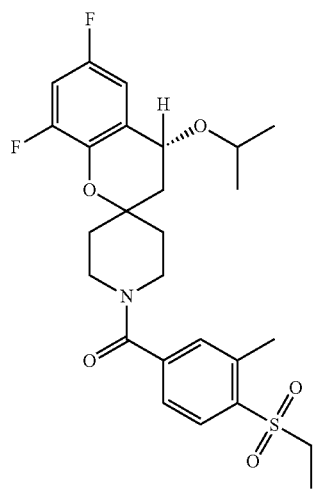 [SMILES: CCS(=O)(=O)c1ccc(C(=O)N2CCC3(CC2)C[C@@H](OC(C)C)c2cc(F)cc(F)c2O3)cc1C]
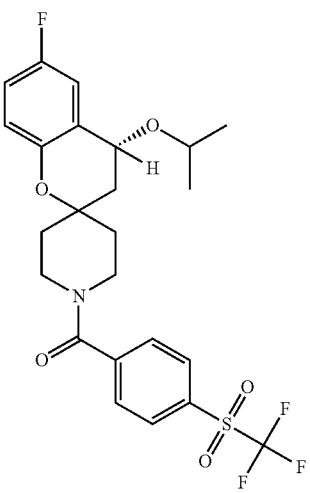 [SMILES: CC(C)O[C@@H]1CC2(CCN(C(=O)c3ccc(S(=O)(=O)C(F)(F)F)cc3)CC2)Oc2ccc(F)cc21]

| 235 -continued | 236 -continued |
|---|---|
| 8 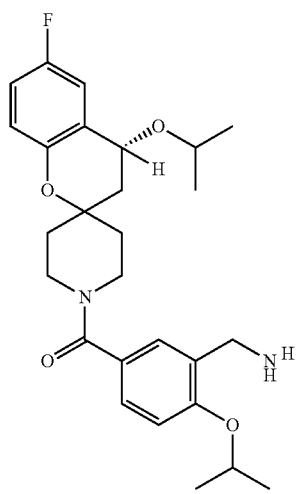 | 11 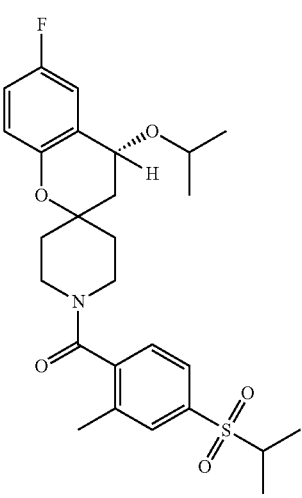 |
| 9 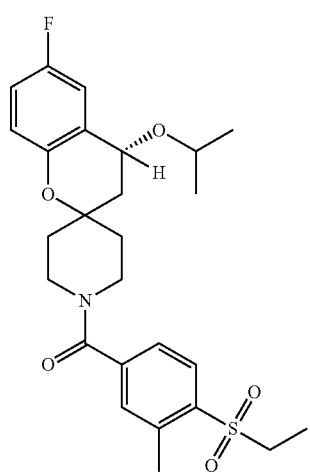 [SMILES: CCS(=O)(=O)c1ccc(C(=O)N2CCC3(CC2)C[C@@H](OC(C)C)c2cc(F)ccc2O3)cc1C] | 12 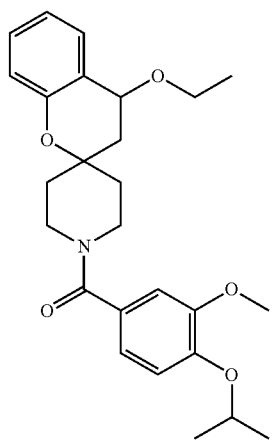 |
| 10 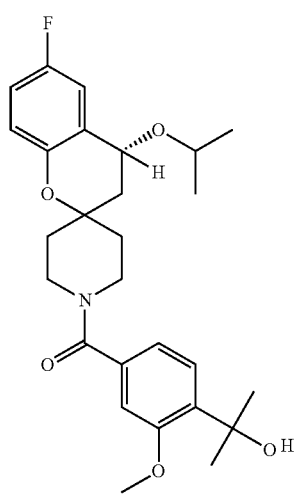 | 13 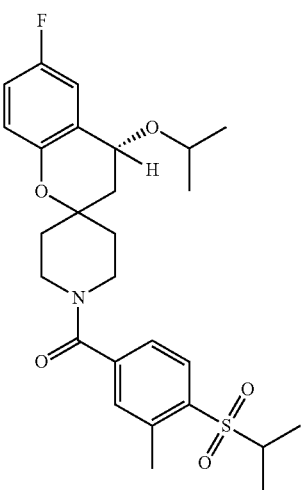 [SMILES: Cc1cc(C(=O)N2CCC3(CC2)C[C@@H](OC(C)C)c2cc(F)ccc2O3)ccc1S(=O)(=O)C(C)C] |

14
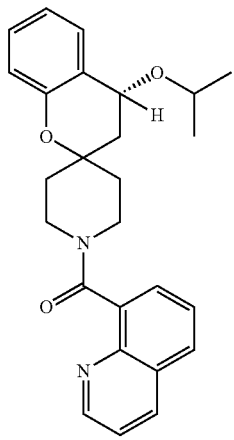 [SMILES: CC(C)O[C@@H]1CC2(CCN(C(=O)c3cccc4cccnc34)CC2)Oc2ccccc21]
15
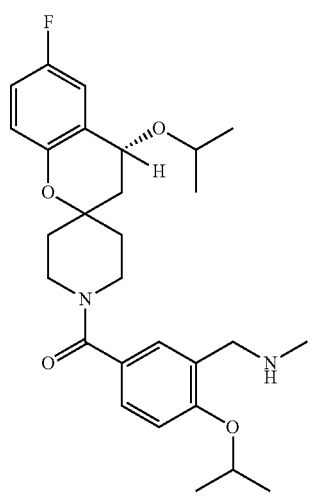
18
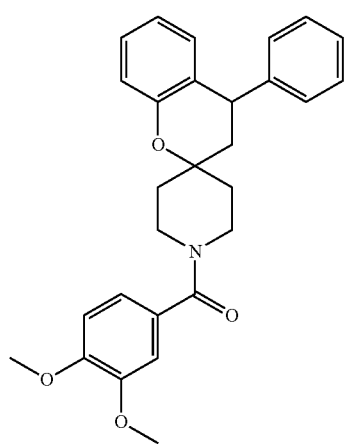 [SMILES: COc1ccc(C(=O)N2CCC3(CC2)CC(c2ccccc2)c2ccccc2O3)cc1OC]
19
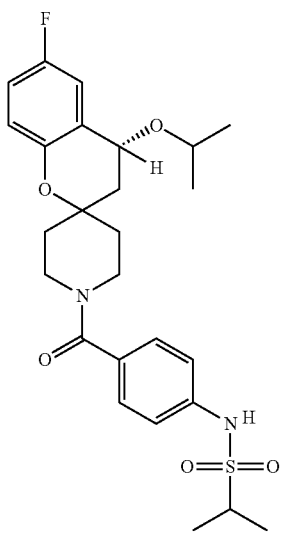
20
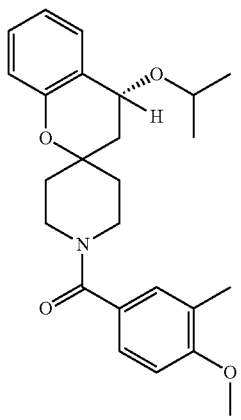 [SMILES: COc1ccc(C(=O)N2CCC3(CC2)C[C@@H](OC(C)C)c2ccccc2O3)cc1C]
21
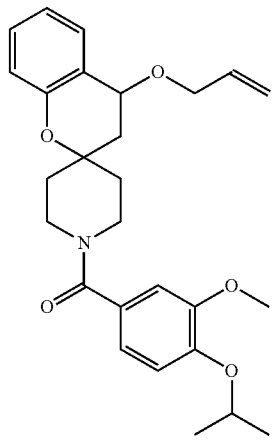 [SMILES: C=CCOC1CC2(CCN(C(=O)c3ccc(OC(C)C)c(OC)c3)CC2)Oc2ccccc21]

| 22 | 25 |
|---|---|
| 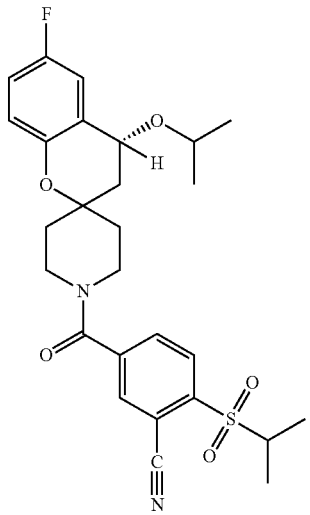 [SMILES: CC(C)O[C@@H]1CC2(CCN(C(=O)c3ccc(S(=O)(=O)C(C)C)c(C#N)c3)CC2)Oc2ccc(F)cc21] | 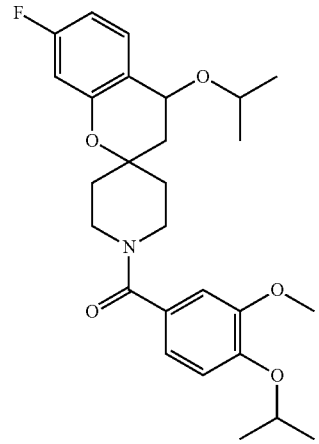 |
| 23 | 26 |
| 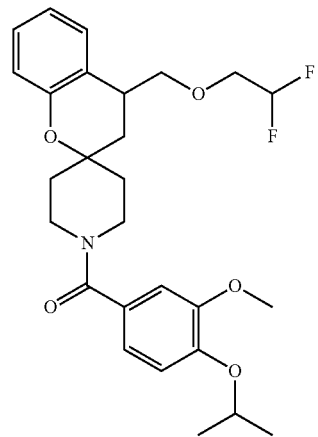 [SMILES: COc1cc(C(=O)N2CCC3(CC2)CC(COCC(F)F)c2ccccc2O3)ccc1OC(C)C] | 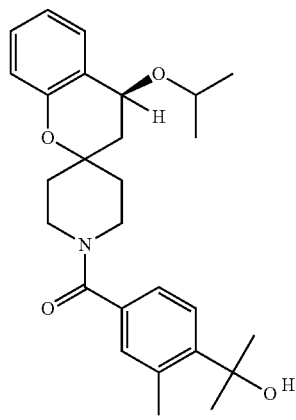 |
| 24 | 27 |
| 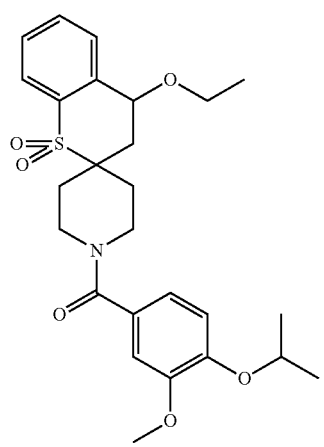 [SMILES: CCOC1CC2(CCN(C(=O)c3ccc(OC(C)C)c(OC)c3)CC2)S(=O)(=O)c2ccccc21] | 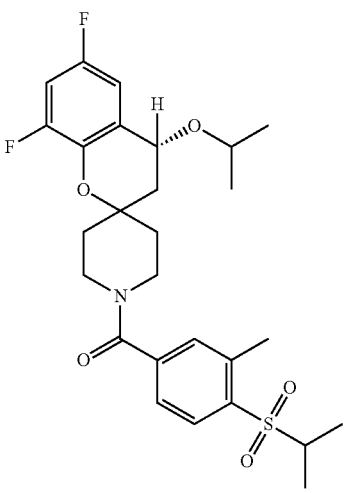 [SMILES: Cc1cc(C(=O)N2CCC3(CC2)C[C@@H](OC(C)C)c2cc(F)cc(F)c2O3)ccc1S(=O)(=O)C(C)C] |

28 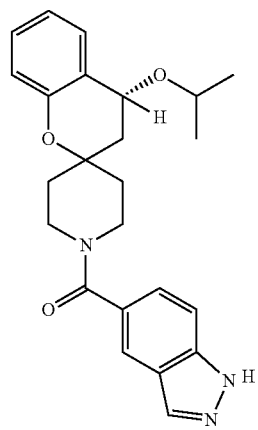
29 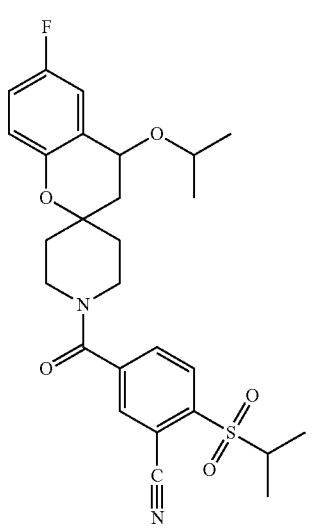 [SMILES: CC(C)OC1CC2(CCN(C(=O)c3ccc(S(=O)(=O)C(C)C)c(C#N)c3)CC2)Oc2ccc(F)cc21]
31 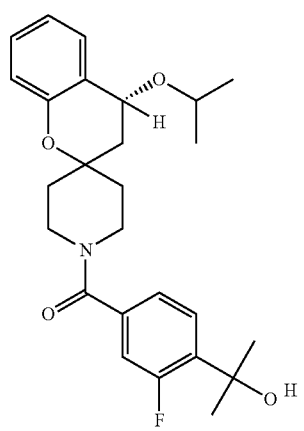
32 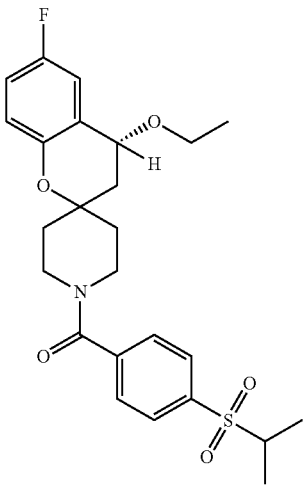 [SMILES: CCO[C@@H]1CC2(CCN(C(=O)c3ccc(S(=O)(=O)C(C)C)cc3)CC2)Oc2ccc(F)cc21]
33 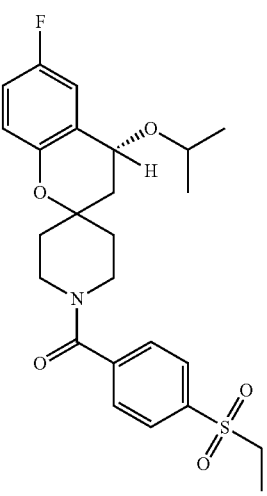 [SMILES: CCS(=O)(=O)c1ccc(C(=O)N2CCC3(CC2)C[C@@H](OC(C)C)c2cc(F)ccc2O3)cc1]
34 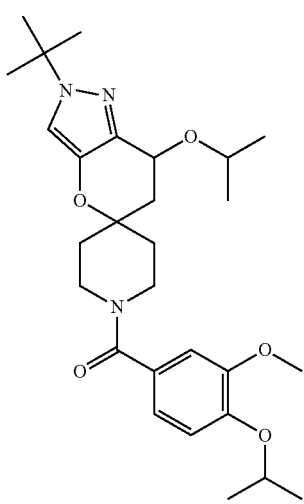 [SMILES: COc1cc(C(=O)N2CCC3(CC2)CC(OC(C)C)c2nn(C(C)(C)C)cc2O3)ccc1OC(C)C]

35 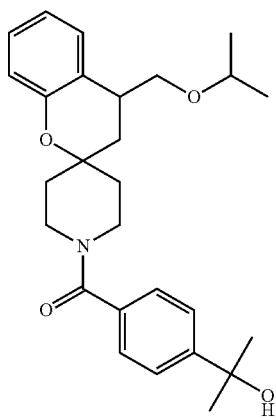 [SMILES: CC(C)OCC1CC2(CCN(C(=O)c3ccc(C(C)(C)O)cc3)CC2)Oc2ccccc21]
36 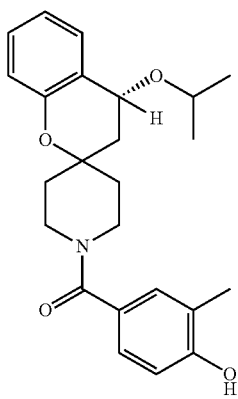 [SMILES: Cc1cc(C(=O)N2CCC3(CC2)C[C@@H](OC(C)C)c2ccccc2O3)ccc1O]
37 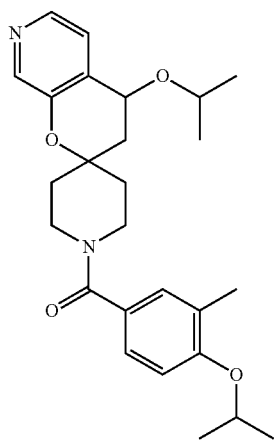 [SMILES: Cc1cc(C(=O)N2CCC3(CC2)CC(OC(C)C)c2ccncc2O3)ccc1OC(C)C]
38 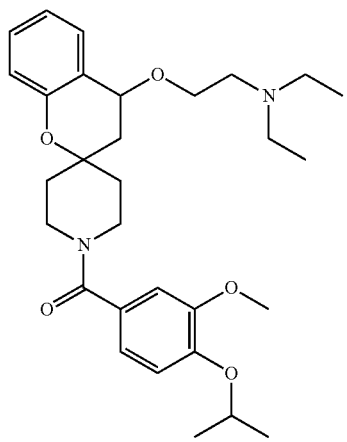 [SMILES: CCN(CC)CCOC1CC2(CCN(C(=O)c3ccc(OC(C)C)c(OC)c3)CC2)Oc2ccccc21]
40 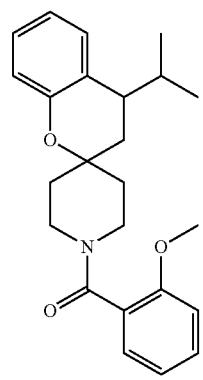 [SMILES: COc1ccccc1C(=O)N1CCC2(CC1)CC(C(C)C)c1ccccc1O2]
42 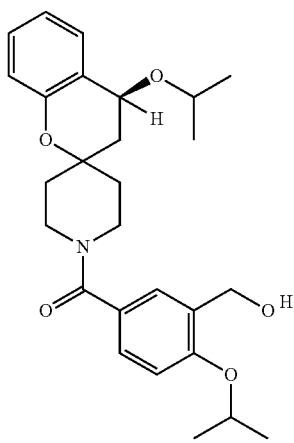

43
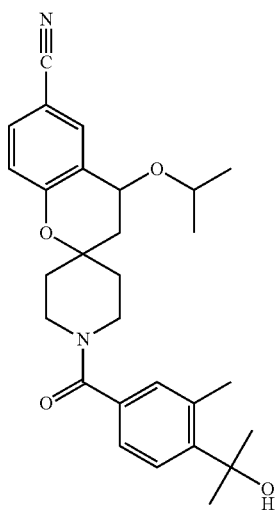 [SMILES: Cc1cc(C(=O)N2CCC3(CC2)CC(OC(C)C)c2cc(C#N)ccc2O3)ccc1C(C)(C)O]
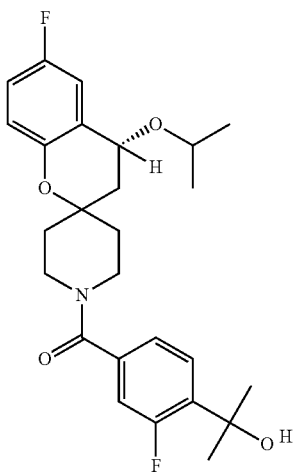
48
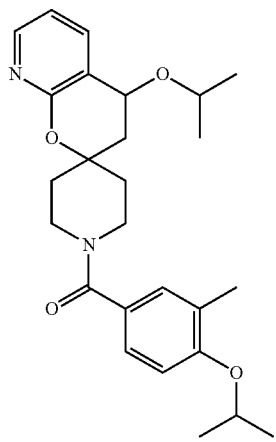 [SMILES: Cc1cc(C(=O)N2CCC3(CC2)CC(OC(C)C)c2cccnc2O3)ccc1OC(C)C]
47
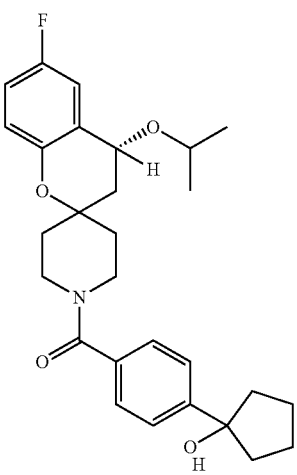
49
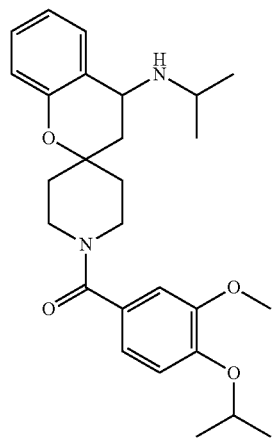 [SMILES: COc1cc(C(=O)N2CCC3(CC2)CC(NC(C)C)c2ccccc2O3)ccc1OC(C)C]
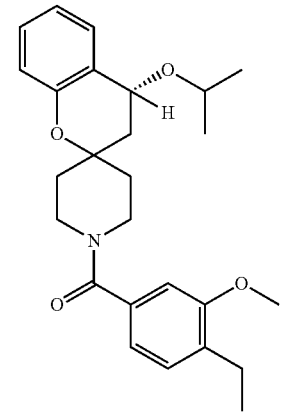 [SMILES: CCc1ccc(C(=O)N2CCC3(CC2)C[C@@H](OC(C)C)c2ccccc2O3)cc1OC]
50

247
-continued
51
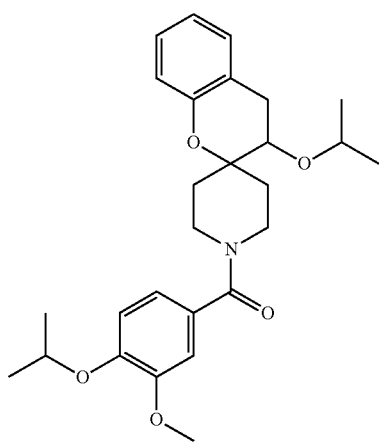
53
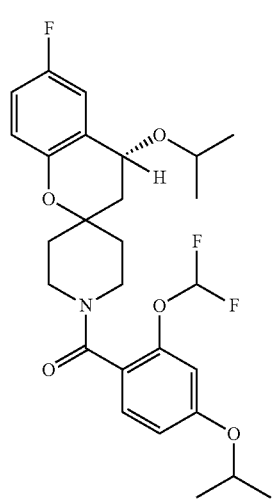 [SMILES: CC(C)Oc1ccc(C(=O)N2CCC3(CC2)C[C@@H](OC(C)C)c2cc(F)ccc2O3)c(OC(F)F)c1]
55
248
-continued
56
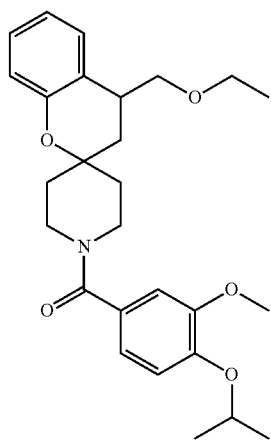 [SMILES: CCOCC1CC2(CCN(C(=O)c3ccc(OC(C)C)c(OC)c3)CC2)Oc2ccccc21]
57
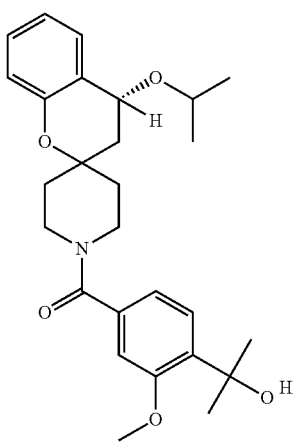
59
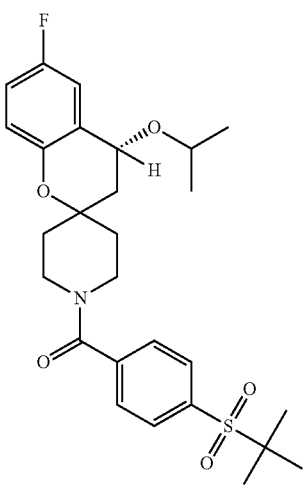 [SMILES: CC(C)O[C@@H]1CC2(CCN(C(=O)c3ccc(S(=O)(=O)C(C)(C)C)cc3)CC2)Oc2ccc(F)cc21]

-continued
60
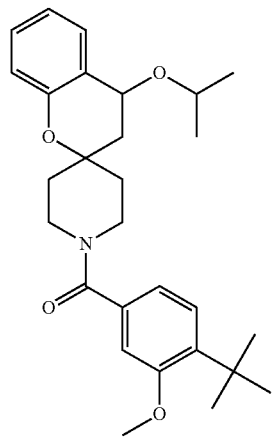 [SMILES: COc1cc(C(=O)N2CCC3(CC2)CC(OC(C)C)c2ccccc2O3)ccc1C(C)(C)C]
62
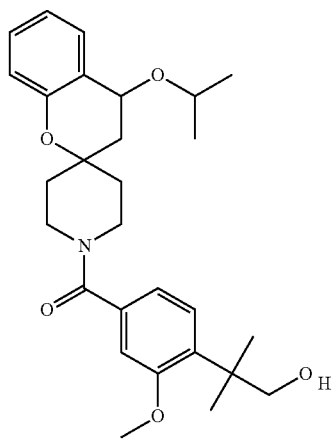
63
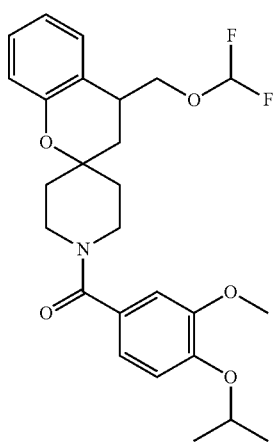 [SMILES: COc1cc(C(=O)N2CCC3(CC2)CC(COC(F)F)c2ccccc2O3)ccc1OC(C)C]
-continued
65
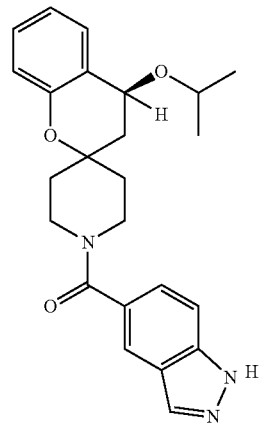
68
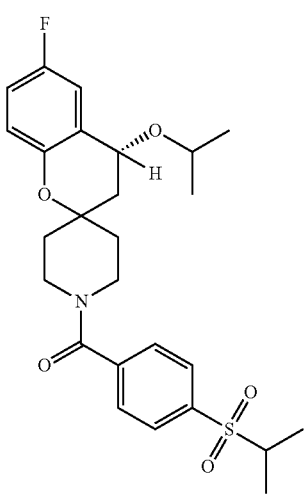
70
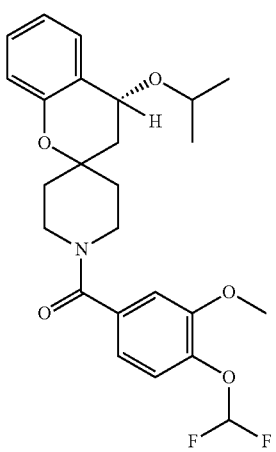 [SMILES: COc1cc(C(=O)N2CCC3(CC2)C[C@@H](OC(C)C)c2ccccc2O3)ccc1OC(F)F]

| 251 -continued | 252 -continued |
|---|---|
| 71 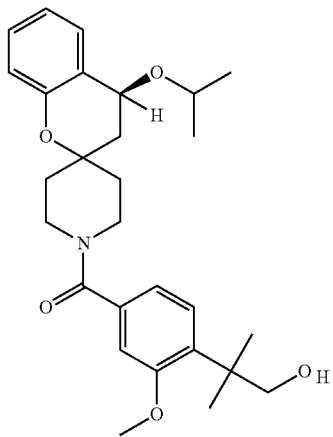 | 74 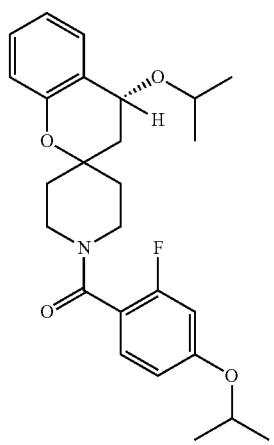 |
| 72 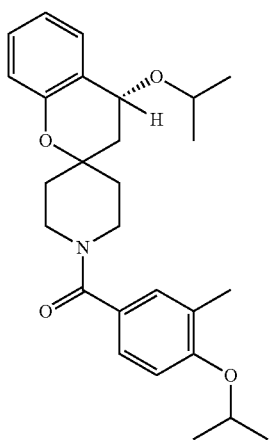 [SMILES: Cc1cc(C(=O)N2CCC3(CC2)C[C@@H](OC(C)C)c2ccccc2O3)ccc1OC(C)C] | 76 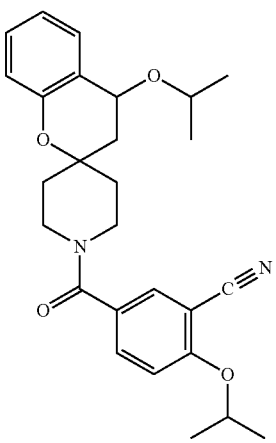 [SMILES: CC(C)Oc1ccc(C(=O)N2CCC3(CC2)CC(OC(C)C)c2ccccc2O3)cc1C#N] |
| 73 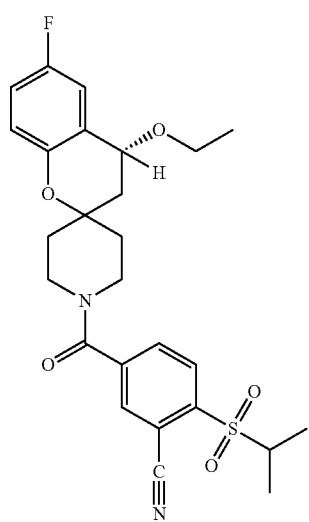 | 77 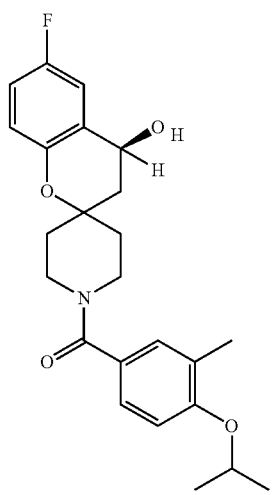 |

| 253 -continued | 254 -continued |
|---|---|
| 78 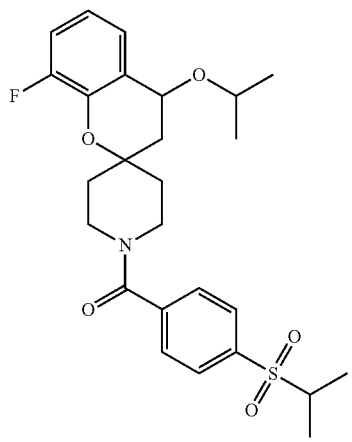 [SMILES: CC(C)OC1CC2(CCN(C(=O)c3ccc(S(=O)(=O)C(C)C)cc3)CC2)Oc2c(F)cccc21] | 82 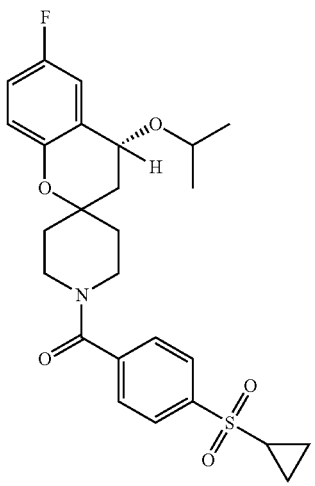 |
| 79 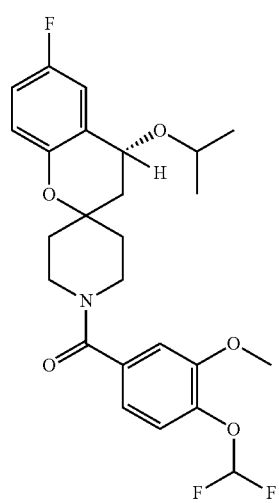 [SMILES: COc1cc(C(=O)N2CCC3(CC2)C[C@@H](OC(C)C)c2cc(F)ccc2O3)ccc1OC(F)F] | 83 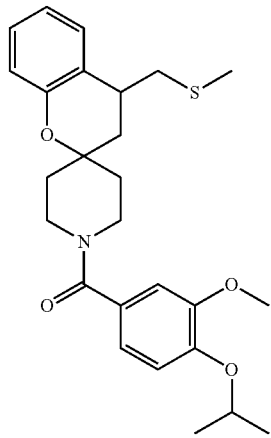 |
| 81 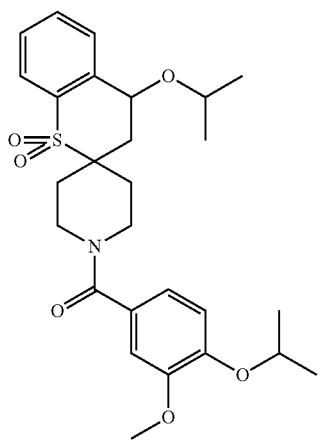 [SMILES: COc1cc(C(=O)N2CCC3(CC2)CC(OC(C)C)c2ccccc2S3(=O)=O)ccc1OC(C)C] | 84 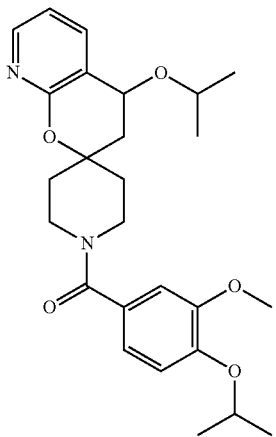 [SMILES: COc1cc(C(=O)N2CCC3(CC2)CC(OC(C)C)c2cccnc2O3)ccc1OC(C)C] |

| 85 | 86 |
|---|---|
| 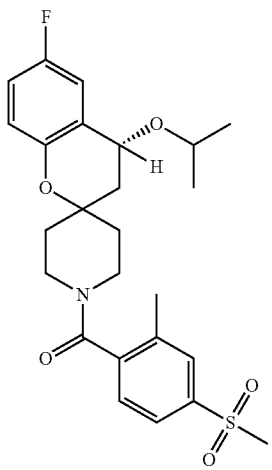 [SMILES: Cc1cc(S(C)(=O)=O)ccc1C(=O)N1CCC2(CC1)C[C@@H](OC(C)C)c1cc(F)ccc1O2] | 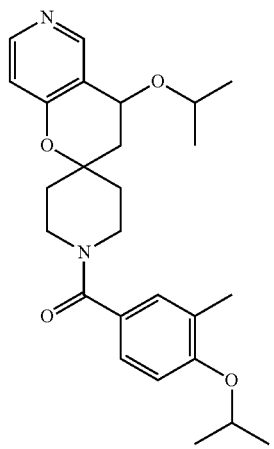 |
| 87 | 89 |
| 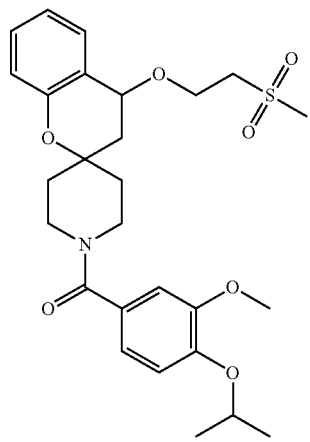 [SMILES: COc1cc(C(=O)N2CCC3(CC2)CC(OCCS(C)(=O)=O)c2ccccc2O3)ccc1OC(C)C] | 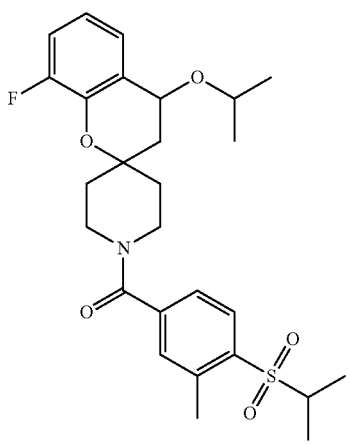 |
| 88 | 90 |
| 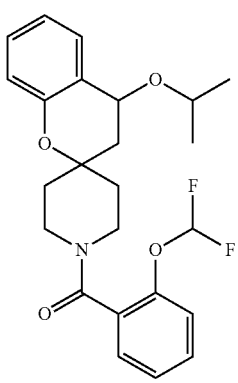 [SMILES: CC(C)OC1CC2(CCN(C(=O)c3ccccc3OC(F)F)CC2)Oc2ccccc21] | 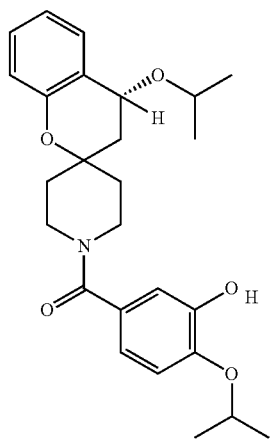 |

| 257 -continued | 258 -continued |
|---|---|
| 92 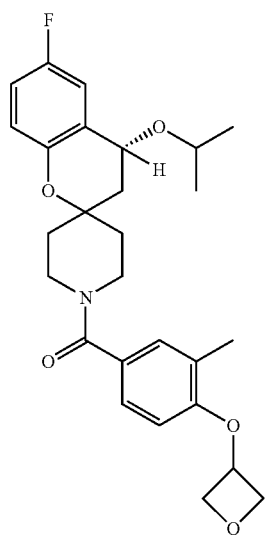 [SMILES: Cc1cc(C(=O)N2CCC3(CC2)C[C@@H](OC(C)C)c2cc(F)ccc2O3)ccc1OC1COC1] | 99 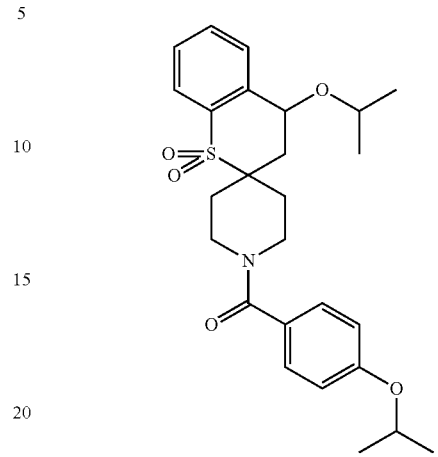 |
| 94 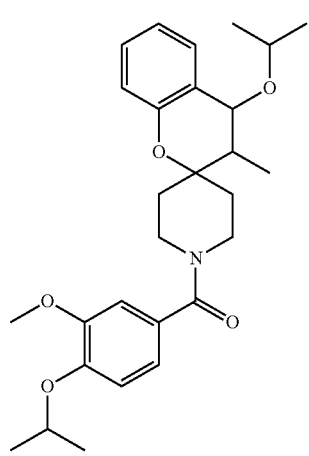 [SMILES: COc1cc(C(=O)N2CCC3(CC2)Oc2ccccc2C(OC(C)C)C3C)ccc1OC(C)C] | 100 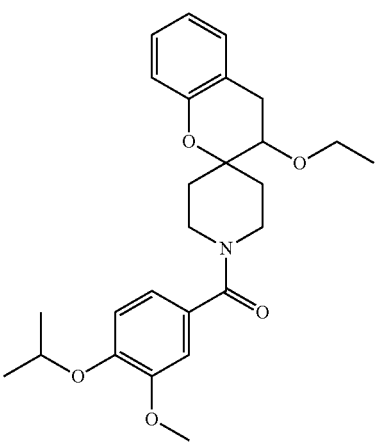 |
| 98 | 104 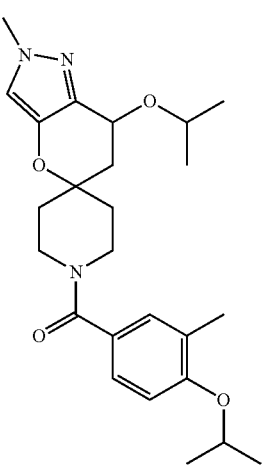 [SMILES: Cc1cc(C(=O)N2CCC3(CC2)CC(OC(C)C)c2nn(C)cc2O3)ccc1OC(C)C] |

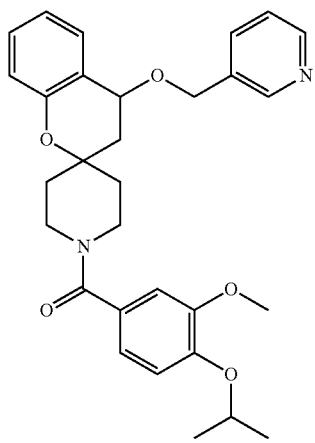 [SMILES: COc1cc(C(=O)N2CCC3(CC2)CC(OCc2cccnc2)c2ccccc2O3)ccc1OC(C)C]
105
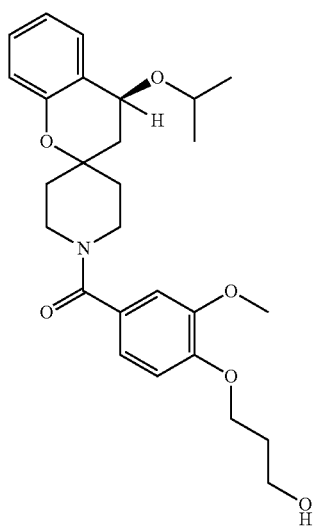 [SMILES: COc1cc(C(=O)N2CCC3(CC2)C[C@H](OC(C)C)c2ccccc2O3)ccc1OCCCO]
106
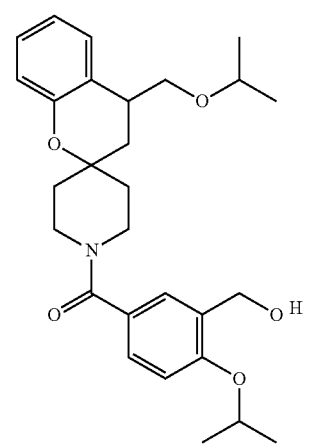
108
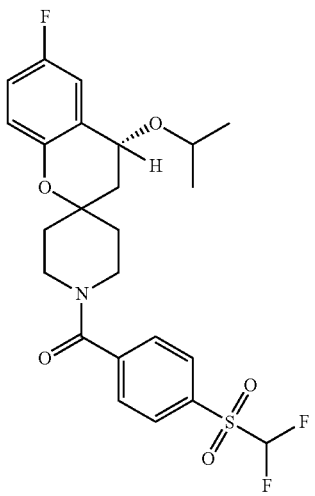 [SMILES: CC(C)O[C@@H]1CC2(CCN(C(=O)c3ccc(S(=O)(=O)C(F)F)cc3)CC2)Oc2ccc(F)cc21]
110
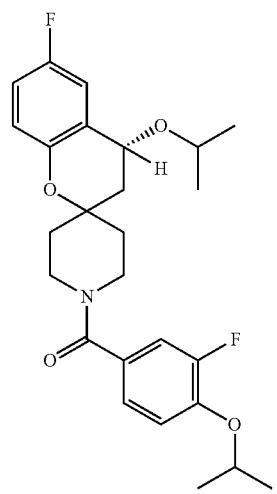 [SMILES: CC(C)Oc1ccc(C(=O)N2CCC3(CC2)C[C@@H](OC(C)C)c2cc(F)ccc2O3)cc1F]
112
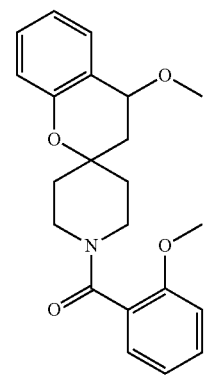 [SMILES: COc1ccccc1C(=O)N1CCC2(CC1)CC(OC)c1ccccc1O2]
113

114
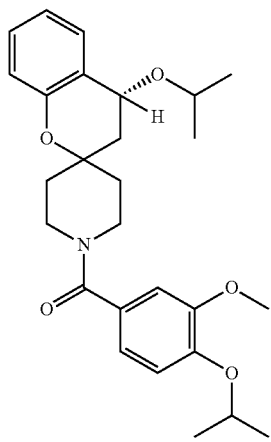 [SMILES: COc1cc(C(=O)N2CCC3(CC2)C[C@@H](OC(C)C)c2ccccc2O3)ccc1OC(C)C]
115
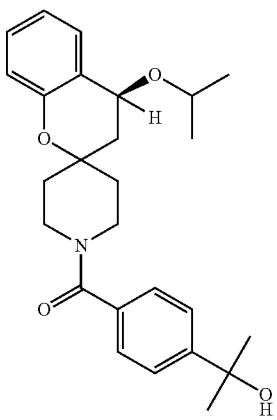 [SMILES: CC(C)O[C@H]1CC2(CCN(C(=O)c3ccc(C(C)(C)O)cc3)CC2)Oc2ccccc21]
116
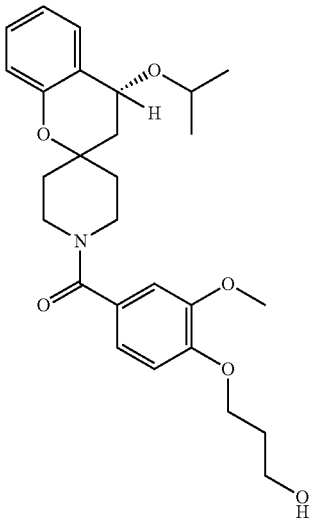 [SMILES: COc1cc(C(=O)N2CCC3(CC2)C[C@@H](OC(C)C)c2ccccc2O3)ccc1OCCCO]
117
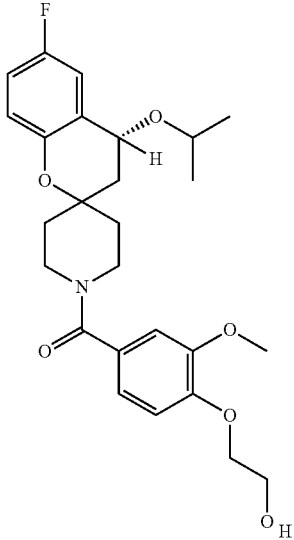
118
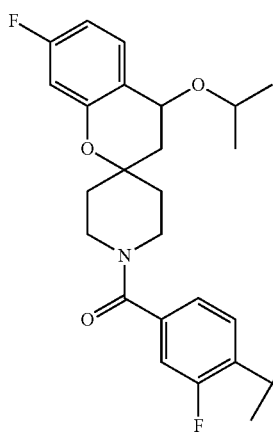
119
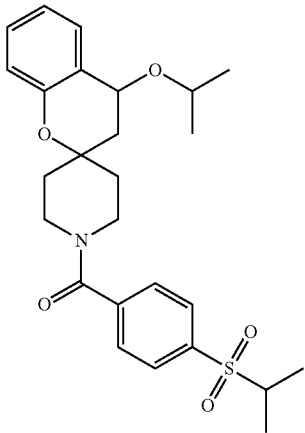 [SMILES: CC(C)OC1CC2(CCN(C(=O)c3ccc(S(=O)(=O)C(C)C)cc3)CC2)Oc2ccccc21]

| 263 -continued | 264 -continued |
|---|---|
| 120 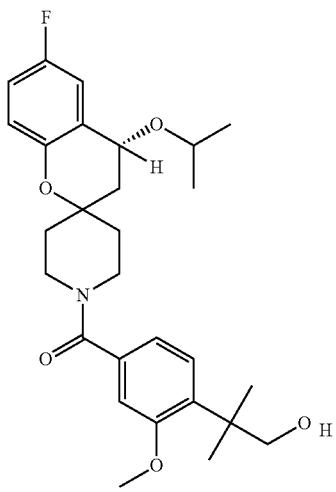 | 123 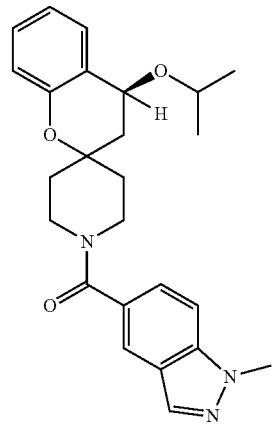 |
| 121 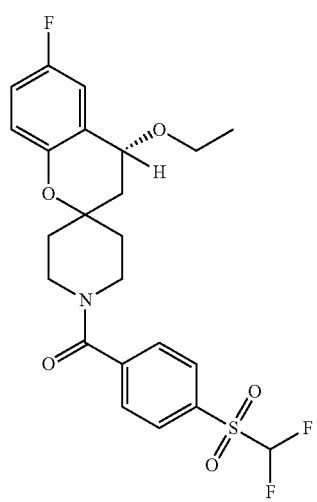 [SMILES: CCO[C@@H]1CC2(CCN(C(=O)c3ccc(S(=O)(=O)C(F)F)cc3)CC2)Oc2ccc(F)cc21] | 125 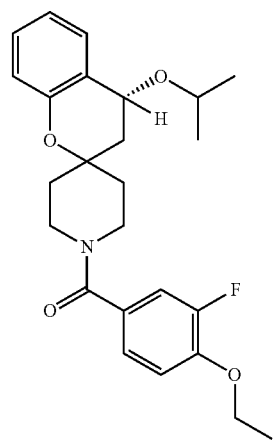 |
| 122 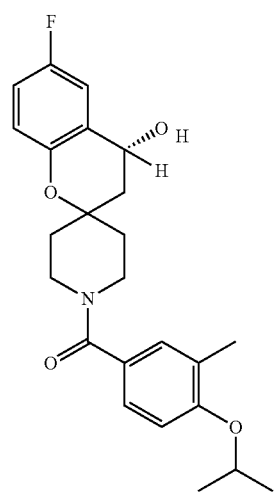 | 126 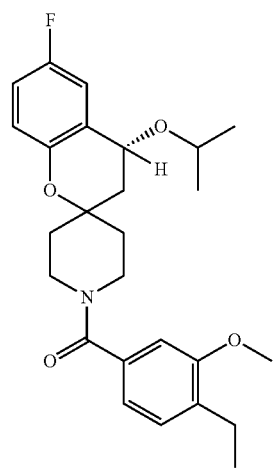 [SMILES: CCc1ccc(C(=O)N2CCC3(CC2)C[C@@H](OC(C)C)c2cc(F)ccc2O3)cc1OC] |

| 127 | 131 |
|---|---|
| 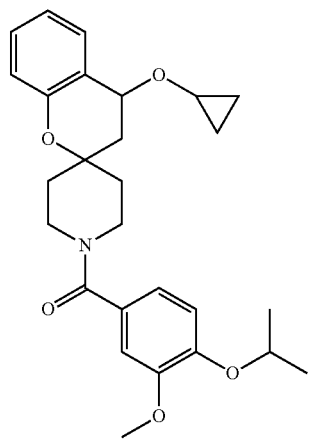 [SMILES: COc1cc(C(=O)N2CCC3(CC2)CC(OC2CC2)c2ccccc2O3)ccc1OC(C)C] | 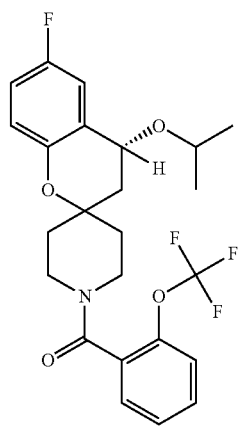 |
| 128 | 133 |
|---|---|
| 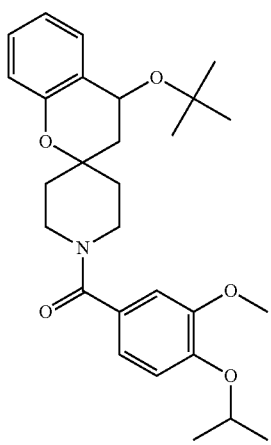 [SMILES: COc1cc(C(=O)N2CCC3(CC2)CC(OC(C)(C)C)c2ccccc2O3)ccc1OC(C)C] | 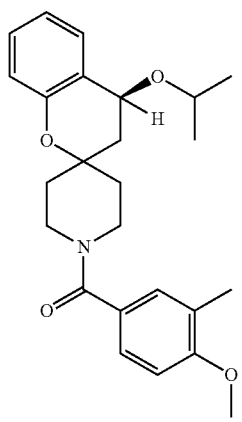 |
| 130 | 134 |
|---|---|
| 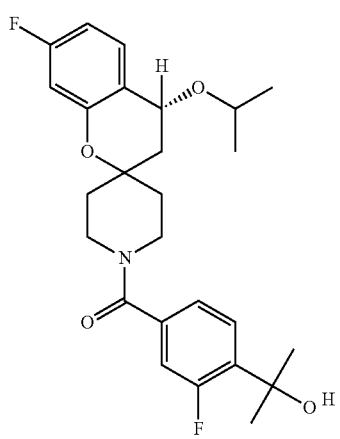 | 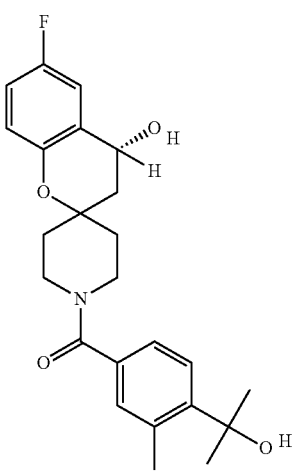 |

| 267 -continued | 268 -continued |
|---|---|
| 135 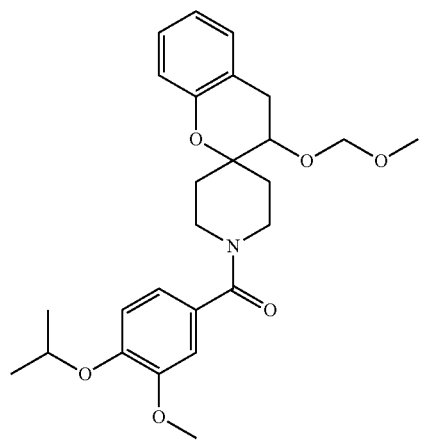 [SMILES: COCOC1Cc2ccccc2OC12CCN(C(=O)c1ccc(OC(C)C)c(OC)c1)CC2] | 138 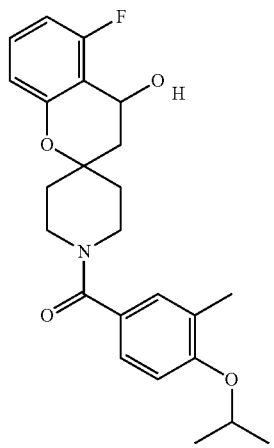 |
| 136 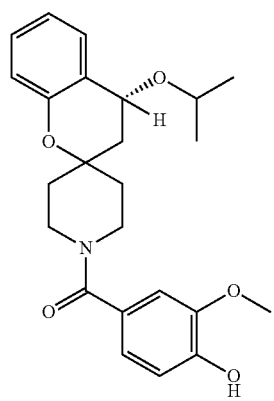 [SMILES: COc1cc(C(=O)N2CCC3(CC2)C[C@@H](OC(C)C)c2ccccc2O3)ccc1O] | 140 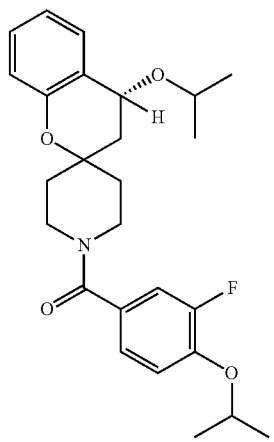 |
| 137 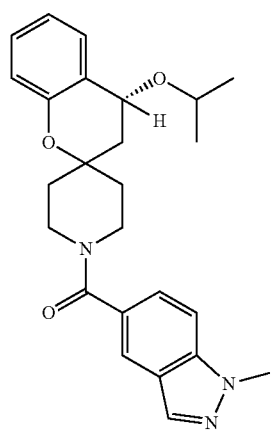 | 141 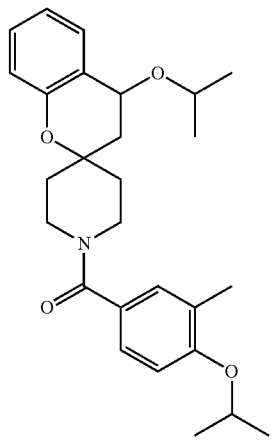 [SMILES: Cc1cc(C(=O)N2CCC3(CC2)CC(OC(C)C)c2ccccc2O3)ccc1OC(C)C] |

142
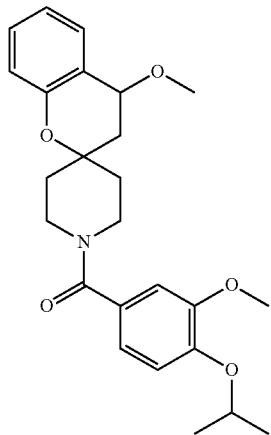 [SMILES: COc1cc(C(=O)N2CCC3(CC2)CC(OC)c2ccccc2O3)ccc1OC(C)C]
143
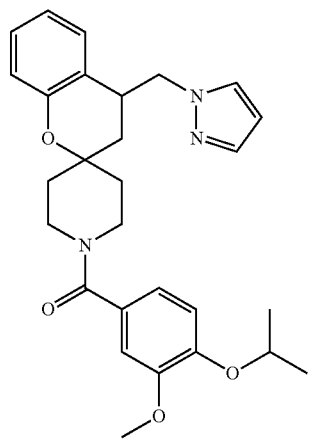 [SMILES: COc1cc(C(=O)N2CCC3(CC2)CC(Cn2cccn2)c2ccccc2O3)ccc1OC(C)C]
144
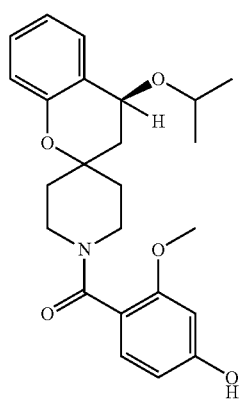 [SMILES: COc1cc(O)ccc1C(=O)N1CCC2(CC1)C[C@H](OC(C)C)c1ccccc1O2]
145
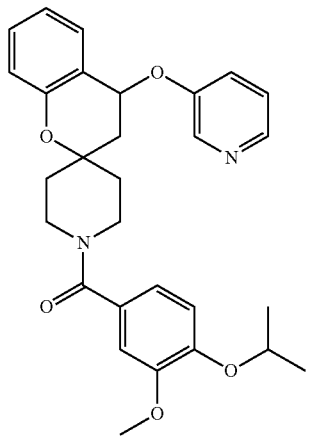 [SMILES: COc1cc(C(=O)N2CCC3(CC2)CC(Oc2cccnc2)c2ccccc2O3)ccc1OC(C)C]
146
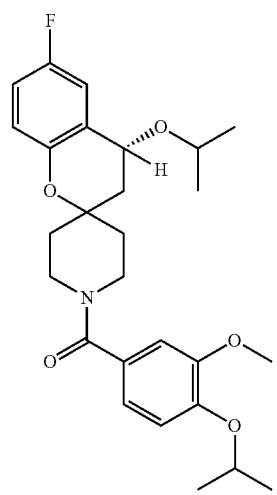 [SMILES: COc1cc(C(=O)N2CCC3(CC2)C[C@@H](OC(C)C)c2cc(F)ccc2O3)ccc1OC(C)C]
147
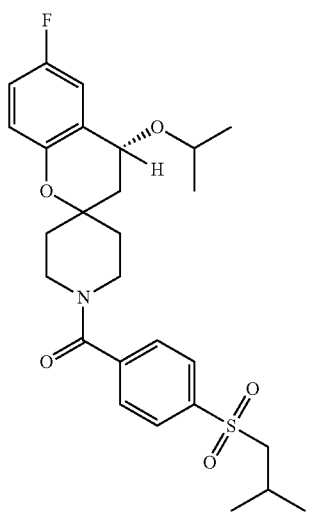 [SMILES: CC(C)CS(=O)(=O)c1ccc(C(=O)N2CCC3(CC2)C[C@@H](OC(C)C)c2cc(F)ccc2O3)cc1]

148
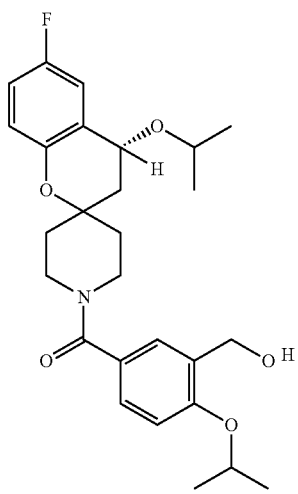
149
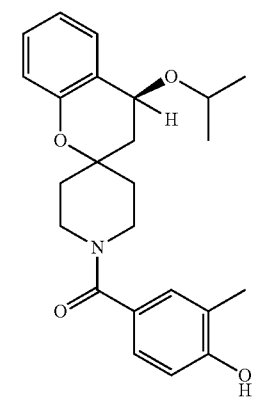 [SMILES: Cc1cc(C(=O)N2CCC3(CC2)C[C@H](OC(C)C)c2ccccc2O3)ccc1O]
150
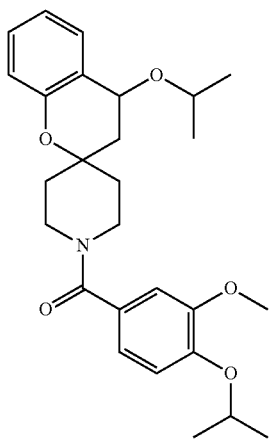 [SMILES: COc1cc(C(=O)N2CCC3(CC2)CC(OC(C)C)c2ccccc2O3)ccc1OC(C)C]
151
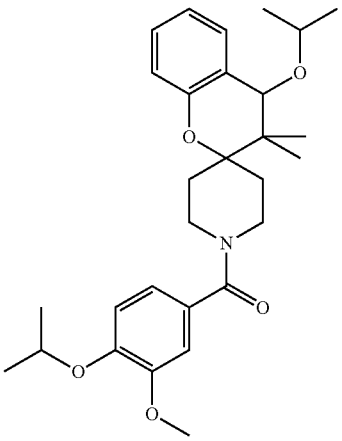 [SMILES: COc1cc(C(=O)N2CCC3(CC2)Oc2ccccc2C(OC(C)C)C3(C)C)ccc1OC(C)C]
152
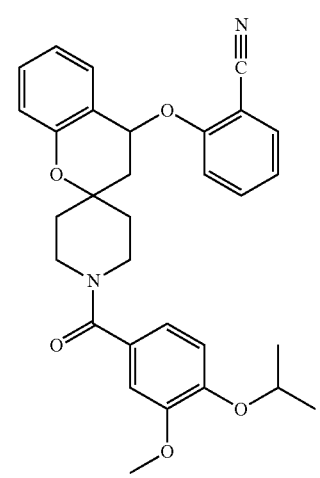 [SMILES: COc1cc(C(=O)N2CCC3(CC2)CC(Oc2ccccc2C#N)c2ccccc2O3)ccc1OC(C)C]
153
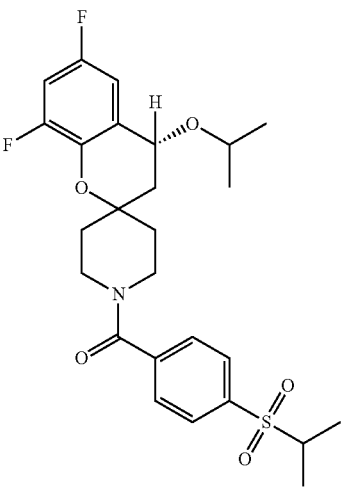 [SMILES: CC(C)O[C@@H]1CC2(CCN(C(=O)c3ccc(S(=O)(=O)C(C)C)cc3)CC2)Oc2c(F)cc(F)cc21]

154 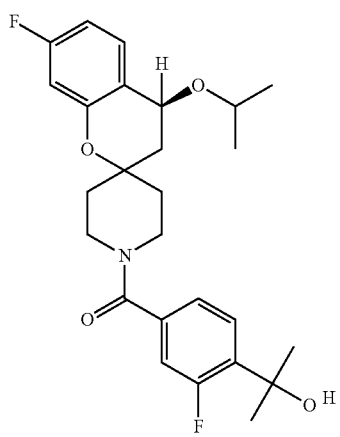
155 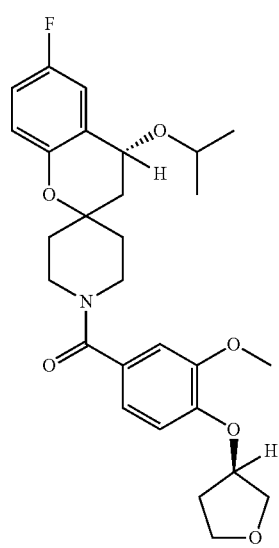 [SMILES: COc1cc(C(=O)N2CCC3(CC2)C[C@@H](OC(C)C)c2cc(F)ccc2O3)ccc1O[C@@H]1CCOC1]
156 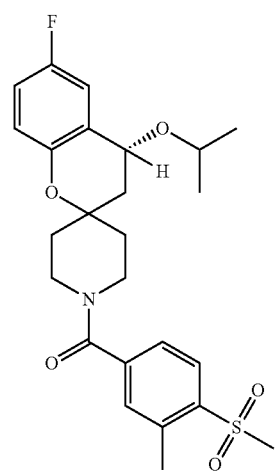 [SMILES: Cc1cc(C(=O)N2CCC3(CC2)C[C@@H](OC(C)C)c2cc(F)ccc2O3)ccc1S(C)(=O)=O]
157 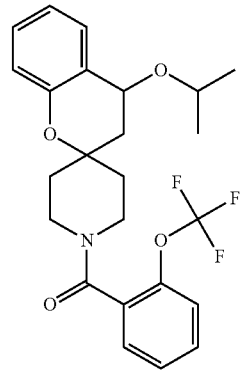 [SMILES: CC(C)OC1CC2(CCN(C(=O)c3ccccc3OC(F)(F)F)CC2)Oc2ccccc21]
158 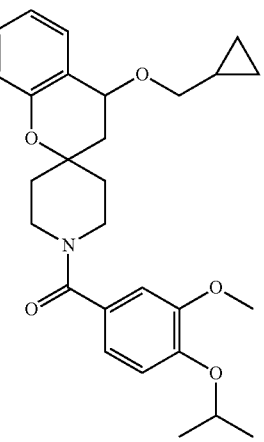
160 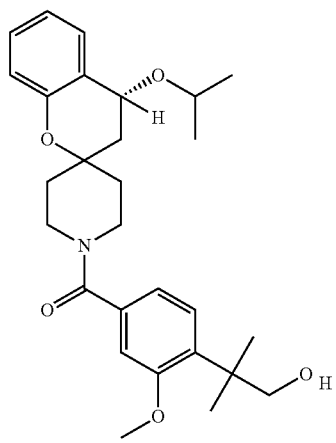

| 275 -continued | 276 -continued |
|---|---|
| 161 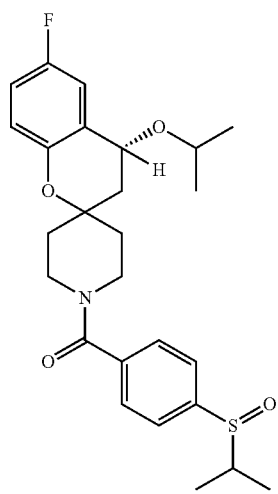 [SMILES: CC(C)O[C@@H]1CC2(CCN(C(=O)c3ccc(S(=O)C(C)C)cc3)CC2)Oc2ccc(F)cc21] | 165 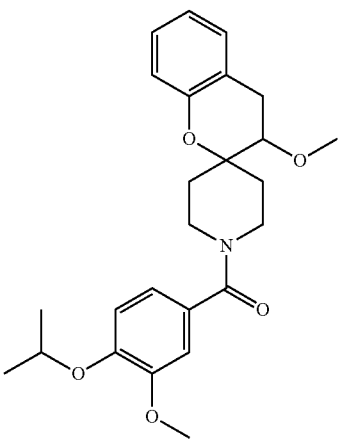 |
| 163 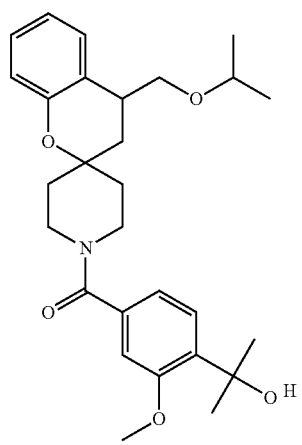 | 166 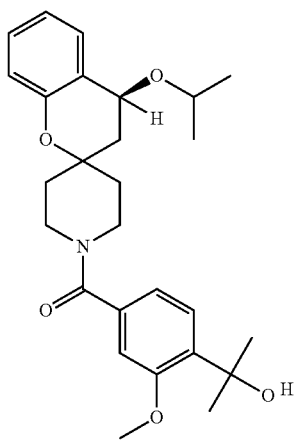 |
| 164 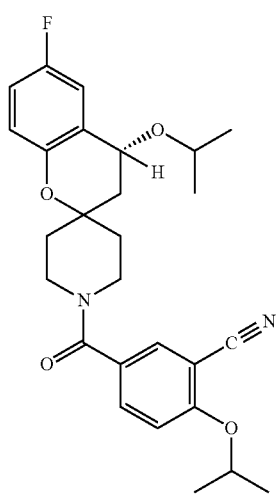 [SMILES: CC(C)Oc1ccc(C(=O)N2CCC3(CC2)C[C@@H](OC(C)C)c2cc(F)ccc2O3)cc1C#N] | 167 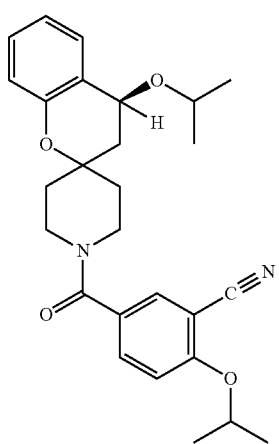 [SMILES: CC(C)Oc1ccc(C(=O)N2CCC3(CC2)C[C@H](OC(C)C)c2ccccc2O3)cc1C#N] |

168
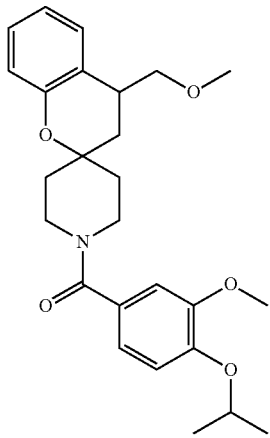 [SMILES: COCC1CC2(CCN(C(=O)c3ccc(OC(C)C)c(OC)c3)CC2)Oc2ccccc21]
169
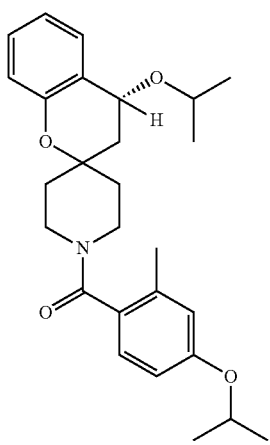 [SMILES: Cc1cc(OC(C)C)ccc1C(=O)N1CCC2(CC1)C[C@@H](OC(C)C)c1ccccc1O2]
170
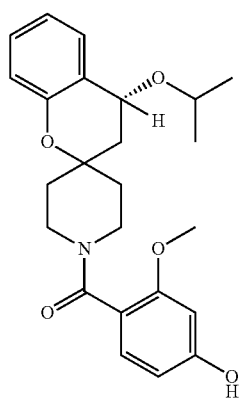 [SMILES: COc1cc(O)ccc1C(=O)N1CCC2(CC1)C[C@@H](OC(C)C)c1ccccc1O2]
171
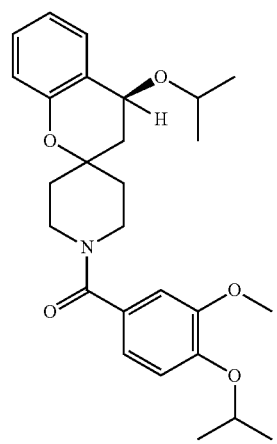 [SMILES: COc1cc(C(=O)N2CCC3(CC2)C[C@H](OC(C)C)c2ccccc2O3)ccc1OC(C)C]
172
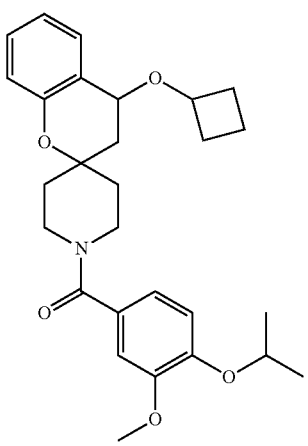 [SMILES: COc1cc(C(=O)N2CCC3(CC2)CC(OC2CCC2)c2ccccc2O3)ccc1OC(C)C]
173
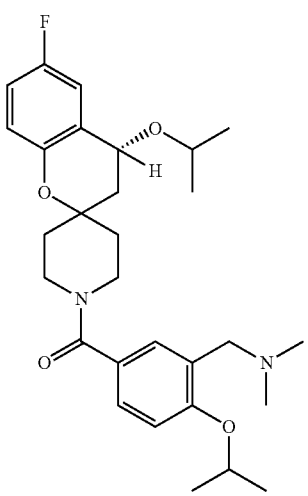 [SMILES: CC(C)Oc1ccc(C(=O)N2CCC3(CC2)C[C@@H](OC(C)C)c2cc(F)ccc2O3)cc1CN(C)C]

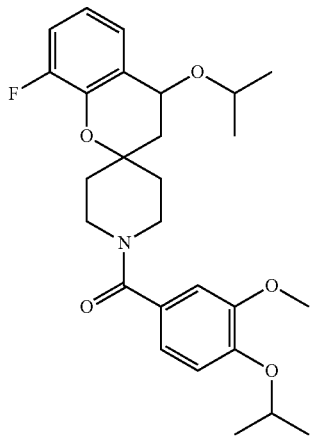

177

41. A pharmaceutical composition comprising the compound of claim 1 and a pharmaceutically acceptable carrier.

42. A method of inhibiting a voltage-gated sodium ion channel in:
 a patient; or
 a biological sample;
 comprising administering to the patient, or contacting the biological sample, with the compound of claim 1.

43. The method of claim 42, wherein the voltage-gated sodium ion channel is NaV 1.7.

* * * * *